(12) United States Patent
Chen et al.

(10) Patent No.: US 10,941,132 B2
(45) Date of Patent: Mar. 9, 2021

(54) PYRAZOLE DERIVATIVES

(71) Applicant: HUA MEDICINE (SHANGHAI) Ltd., Shanghai (CN)

(72) Inventors: Li Chen, Shanghai (CN); Xiaowei Jin, Shanghai (CN)

(73) Assignee: Hua Medicine (Shanghai) Ltd., Shanghai (CN)

( * ) Notice: Subject to any disclaimer, the term of this patent is extended or adjusted under 35 U.S.C. 154(b) by 0 days.

(21) Appl. No.: 16/068,272

(22) PCT Filed: Jan. 5, 2016

(86) PCT No.: PCT/CN2016/070115
§ 371 (c)(1),
(2) Date: Jul. 5, 2018

(87) PCT Pub. No.: WO2017/117708
PCT Pub. Date: Jul. 13, 2017

(65) Prior Publication Data
US 2019/0002432 A1    Jan. 3, 2019

(51) Int. Cl.
| | | |
|---|---|---|
| *C07D 401/06* | (2006.01) | |
| *C07D 401/14* | (2006.01) | |
| *C07D 231/12* | (2006.01) | |
| *C07D 403/06* | (2006.01) | |

(52) U.S. Cl.
CPC ......... *C07D 401/06* (2013.01); *C07D 231/12* (2013.01); *C07D 401/14* (2013.01); *C07D 403/06* (2013.01)

(58) Field of Classification Search
CPC .. C07D 401/04; C07D 401/06; C07D 401/14; C07D 231/10; C07D 231/12; C07D 231/14
See application file for complete search history.

(56) References Cited

U.S. PATENT DOCUMENTS

| | | | |
|---|---|---|---|
| 6,255,333 B1 * | 7/2001 | Banks ................... | A01N 43/56 514/406 |
| 8,455,477 B2 * | 6/2013 | Katz ....................... | A61P 1/00 514/210.18 |
| 8,835,472 B2 * | 9/2014 | Roth ..................... | C07C 233/05 514/365 |
| 8,877,754 B2 * | 11/2014 | Roth ..................... | C07C 235/34 514/247 |
| 2006/0030559 A1 | 2/2006 | Buettelmann et al. | |
| 2012/0214782 A1 * | 8/2012 | Roth ..................... | C07C 235/34 514/210.2 |
| 2012/0214785 A1 * | 8/2012 | Roth ..................... | C07C 233/05 514/210.17 |
| 2016/0280660 A1 * | 9/2016 | Ahmad ................ | C07D 401/04 |
| 2018/0228776 A1 * | 8/2018 | Saitoh .................. | A61K 31/436 |

FOREIGN PATENT DOCUMENTS

| | | | |
|---|---|---|---|
| JP | 2014015447 A | * | 1/2014 |
| WO | 2002/046166 A1 | | 6/2002 |
| WO | 2004/080998 A1 | | 9/2004 |
| WO | WO2014124560 | | 8/2014 |

OTHER PUBLICATIONS

CAS Registry No. 1638760-76-5 (2014) (Year: 2014).*
CAS Registry No. 1638760-76-5 (Dec. 15, 2014) (Year: 2014).*
E. Arbačiauskienė et al., 65 Tetrahedron Letters, 7817-7824 (2009) (Year: 2009).*
G.A. Eller et al., 41 Synthetic Communications, 541-547 (2011) (Year: 2011).*
CAS Abstract and Indexed Compound, JP 2014015447 (2014) (Year: 2014).*
English-Language Machine Translation of JP 2014015447 (2014) (Year: 2014).*
Egle, Arbaciauskiene, et al., "Pd-catalyzed cross-coupling reactions of halogenated 1-phenylpyrazol-3-ols and related triflates", Tetrahedron, vol. 65:7817-7824 (2009).
Li, et al., "Metabotropic glutamate recepter 5-negative allosteric modulators for the treatment of psychiatric and neurological disorders" Pharm. Pat. Anal. 2(6): 767-802 (2013).
Chinchilla et al., "Recent advances in Sonogashira reactions" Chem. Soc. Rev. 40(10): 5084-5121 (2011).
Corey et al., "A synthetic method for formyl -> ethynyl conversion" Tetrahedron Lett. 13(36): 3769-3772 (1972).
Dekundy et al., "Effects of dopamine uptake inhibitor MRZ-9547 in animal models of Parkinson's disease" J. Neural Transm. 122(6):809-819 (2015).
Dutta et al., "Aerobic oxynitration of alkynes with t-BuONO and TEMPO" Organic Lett. 16(24): 6302-6305 (2014).
Emmitte et al., "mGlu5 negative allostereic modulators: a patent review (2010-2012)" Expert Opin. Ther. Pat. 23(4): 393-408 (2013).

(Continued)

*Primary Examiner* — Paul V Ward
(74) *Attorney, Agent, or Firm* — McDonnell Boehnen Hulbert & Berghoff LLP

(57) ABSTRACT

Provided herein are compounds of the formula I: as well as pharmaceutically acceptable salts thereof, wherein the substituents are as those disclosed in the specification. These compounds, and the pharmaceutical compositions containing them, are useful for the treatment or prevention of mGluR5 mediated disorders, such as acute and/or chronic neurological disorders, cognitive disorders and memory deficits, as well as acute and chronic pain.

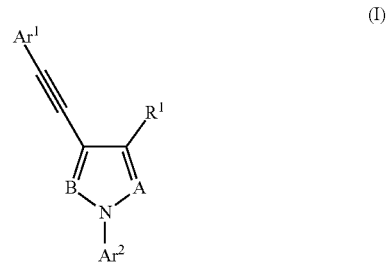

(I)

14 Claims, No Drawings

(56) References Cited

OTHER PUBLICATIONS

Gasparini et al., "mGluR5 anatagonists: discovery, characterization and drug development" Curr. Opin. Drug Discov. Devel. 11(5): 655-665 (2008).

Han, "Name reactions for homologations" John Wiley and Sons Pt 1: 393-403 (2009).

Holmes et al., "Efficient synthesis of a complete donor/acceptor bis(aryl)diyne family" Synthetic Communications 33(14): 2447-2461 (2003).

Illa et al., "Reaction of C-silylated alpha-diazophosphines as nucleophiles toward carbonyl compounds: a mechanistic study and application to the synthesis of alkynes and alpha-hydroxyphosphonamides" J. Org. Chem. 71: 5320-5327 (2006).

Jaeschke et al., "Metabotropic glutamate receptor 5 negative allosteric modulators: discovery of 2-chloro-4-[1-(4-fluoropheny)-2,5,-dimethyl-1H-imidazol-4-ylethynyl]pyridine (basimglurant, RO4917523), a promising novel medicine for psychiatric diseases" 58(3): 1358-1371 (2015).

King et al., "Palladium-catalyzed cross-coupling reactions in the synthesis of pharmaceuticals organometallics in process chemistry" Top. Organ. Met. 6: 205-245 (2004).

Knorr, "Synthese von Pyroolderivaten" Berichte der deutschen chemischen Gesellschaft 17(2): 1635-1642 (1884).

Lam et al., "New aryl/heteroaryl CN bond cross-coupling reactions via arylboronic acid/cupris acetate arylation" Tetrahedron Lett. 39(19): 2941-2944 (1998).

Salanouve et al., "3-Methoxypyrazoles from 1,1-dimethoxyethene, few original results" Tetrahedron 68(15): 3165-3171.

Negishi et al., "Direct synthesis of heteroarylethynes via palladium-catalyzed coupling of heteroaryl halide with ethynylzinc halides" 46(1): 209-214 (1997).

Niswender et al., "Metabotropic glutamate receptors: physiology, pharamacology, and disease" Ann. Rev. Pharmacol. Toxicol. 50: 295-322 (2010).

Rocher et al., "mGluR5 negative allosteric modulators overview: a medicinal chemistry approach towards a series of novel therapeutic agents" Curr. Top. Med. Chem. 11(6): 680-695 (2011).

Rodriguez-Franco et al., "A mild and efficient method for the regioselective iodination of pyrazoles" Tetrahedron Lett. 42(5): 863-865 (2001).

Shigemoto et al., "Immunohistochemical localization of a metabotropic glutamate receptor, mGluR5, in the rat brain" Neuroscience Lett 163(1): 53-57 (1993).

Sonogashira, "Development of Pd—Cu catalyzed cross-coupling of terminal acetylenes with sp2-carbon halides" J. Organomet. Chem. 653: 46-69 (2002).

The International Search Report (ISR) for PCT/CN2016/070115, 4 pages, dated Jul. 13, 2016.

Supplementary European Search Report for EP16882855, 3 pages, completed Apr. 12, 2019.

International Preliminary Report on Patentability for PCT/CN2016/070115, 6 pages, dated Jul. 10, 2018.

* cited by examiner

PYRAZOLE DERIVATIVES

FIELD OF THE INVENTION

This invention relates generally to compounds of formula I:

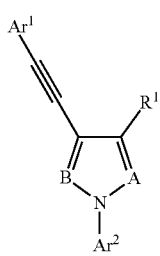

or a pharmaceutically acceptable salt thereof, and to pharmaceutical compositions comprising said compounds or a pharmaceutically acceptable salt thereof, wherein the definitions of $Ar^1$, $Ar^2$, $R^1$, A and B are as defined below. The compounds and compositions disclosed herein are mGlu5 receptor antagonists useful for the treatment or prevention of mGluR5 mediated disorders, such as acute and/or chronic neurological disorders, cognitive disorders and memory deficits, as well as acute and chronic pain.

All documents cited or relied upon below are expressly incorporated herein by reference.

BACKGROUND OF THE INVENTION

Glutamate is the most prominent neurotransmitter in the body, being present in over 50% of nervous tissue. Glutamate mediates its effects through two major groups of receptors: ionotropic and metabotropic. Ionotropic glutamate receptors are ion channel receptors which are often responsible for fast excitatory transmission. They are generally divided into N-methyl-D-aspartate (NMDA), α-amino-3-hydroxy-5-methyl-4-isoxazole propionic acid (AMPA) and kainite receptors. By contrast, metabotropic glutamate receptors (mGluRs) belong to the class C G-protein-coupled receptor (GPCR) protein family and are mainly involved in the modulation of fast excitatory transmission. As such, they are attractive therapeutic targets for treatment of disorders involving malfunction of glutamate signaling. The mGluRs are further divided into three groups (Group I, II and III) based on amino acid sequence homology, signal transduction mechanism and pharmacological properties. Group I receptors include mGluR1 and mGluR5, Group II includes mGluR2 and mGluR3 and Group III includes mGluR4, mGluR6, mGluR7 and mGluR8. The Group I mGluR1 and mGluR5 receptors couple to G-proteins of the Gq family, Gq and G11, and their activation leads to activation of phospholipase C, resulting in the hydrolysis of membrane phosphatidylinositol (4, 5)-bisphosphate to diacylglycerol, which subsequently activates protein kinase C, and inositol trisphosphate, which in turn activates the inositol trisphosphate receptor to promote the release of intracellular calcium.

Anatomical studies demonstrate a broad and selective distribution of mGluRs in the mammalian nervous system. For example, mGlu5 receptors are abundantly expressed in the striatum, cortex, hippocampus, caudate-putamen and nucleus accumbens; see for example: Shigemoto, R., Nomura, S., Hidemitsu, S., et al. Neuroscience Lett 1993, 163, 53-57. As these brain areas have been shown to be involved in emotion, motivational processes, learning and memory, as well as motor control, mGluR5 modulators have long been regarded as possessing therapeutic potential for a wide range of indications.

mGlu5 receptor antagonists can be used for modulating the activity of the mGlu5 receptor and for use in the treatment or prevention of mGluR5 mediated disorders, such as acute and/or chronic neurological disorders, cognitive disorders and memory deficits, acute and chronic pain, protection against drug or disease induced liver damage or failure, urinary inconsistence. Other diseases contemplated include cerebral ischemia, chronic neurodegeneration including Huntington's chorea, amyotrophic lateral sclerosis, Alzheimer's disease, Parkinson's disease, levodopa-induced dyskinesia in Parkinson's disease (PD-LID), psychiatric disorders, schizophrenia, mood disorders, emotion disorders, disorders of extrapyramidal motor function, obesity, disorders of pulmonary system and respiration, motor control and function, attention deficit disorders, concentration disorders, mental retardation (including mental retardation related to Fragile X syndrome), autism spectrum disorders (ASDs), pain disorders, neurodegenerative disorders, epilepsy, convulsive disorders, migraine, dyskinesia, eating disorders, vomiting, muscle spasms, urinary inconsistence, sleep disorders, sexual disorders, circadian disorders, drug withdrawal, drug addiction, compulsive disorders, anxiety, panic disorders, depression disorders, skin disorders, retinal ischemia, retinal degeneration, glaucoma, disorders associated with organ transplantation, asthma, ischemia and astrocytomas, diseases of the cardiovascular system, diseases of the gastrointestinal system such as gastroesophageal reflux disease (GERD) and irritable bowel syndrome, diseases of the endocrine system, diseases of the exocrine system, diseases of the skin, cancer and diseases of the ophthalmic system. The development and use of mGLuR5 antagonists has been summarized in numerous review articles for example: Gasparini, F., Bilbe, G., Gomez-Mancilla, G., and Spooren, W., *Current Opinion in Drug Discovery & Development.* 11 (5), 655-665, 2008; Rocher, J.-P., Bonnet, B., Boléa, C., et al., *Current Topics in Medicinal Chemistry.* 11, 680-695, 2011; Dekundy, A., Gravius, A., Hechenberger, M, et al., *J. Neural Transm.* 118, 1703-1716, 2011; Niswender, C. M. and Conn, P. J., *Annu Rev Pharmacol Toxicol.* 50, 295-322, 2010; Emmitte K A. mGluR5 negative allosteric modulators, a patent review (2010-2012). Expert Opin Ther Pat. 2013 April; 23 (4):393-408 and Guiying Li, Morten Jørgensen and Brian M Campbell. Metabotropic glutamate receptor 5-negative allosteric modulators for the treatment of psychiatric and neurological disorders (2009-July 2013), *Pharmaceutical Patent Analyst.* 2 (6), 767-802.

SUMMARY OF THE INVENTION

The present invention is directed to compounds of the formula I, or a pharmaceutically acceptable salt thereof, pharmaceutical compositions containing them and to methods of treating diseases and disorders. The compounds and compositions disclosed herein are mGlu5 receptor antagonists useful for the treatment of mGluR5 mediated disorders, including acute and/or chronic neurological disorders, cognitive disorders and memory deficits, as well as acute and chronic pain.

DETAILED DESCRIPTION OF THE INVENTION

In an embodiment, the present invention provides a novel compound of formula I:

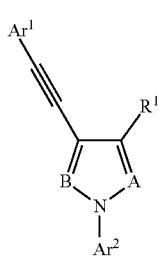

(I)

or a pharmaceutical accepted salt thereof, wherein:
one of A and B is CR, and the other is N;
R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;
R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;
Ar$^1$ is a 5- to 10-membered mono- or bicyclic heteroaryl ring that contains 1-3 heteroatoms selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form an optionally substituted 5-7 membered fused carbacyclic or heterocyclic ring, or
a 5- to 10-membered mono- or bicyclic aryl ring, wherein the 5- to 10-membered mono- or bicyclic aryl ring is optionally substituted with 1-3 substituents independently selected from the group consisting of alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form a 5-7 membered fused and optionally substituted carbacyclic or heterocyclic ring;

Ar$^2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)— heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring, or
a 5- to 10-membered mono- or bicyclic aryl ring, wherein the 5- to 10-membered mono- or bicyclic aryl ring is optionally substituted with 1-3 substituents independently selected from the group consisting of -alkyl, -halogen, —OH, —CN, nitro, —CF$_3$, —O—CF, —O-alkyl, -so O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring.

In an embodiment, the present invention provides a novel compound of formula I:

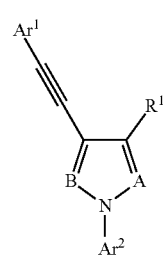

(I)

or a pharmaceutical accepted salt thereof, wherein:
one of A and B is CR, and the other is N;
R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;

$R^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, and —O-alkyl, or a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, and —O-alkyl:

Ar$^2$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, —O-alkyl, —S-alkyl, —S(O)— alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$, or a 6-membered aryl ring, wherein the 6-membered aryl is optionally substituted with 1-3 substituents independently selected from the group consisting of -alkyl, -halogen. —OH, —CN, nitro, —CF$_3$, —O—CF$_3$, —O-alkyl, —S-alkyl, —S(O)-alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$;

In a further embodiment of the present invention, provided is a compound according to formula I:

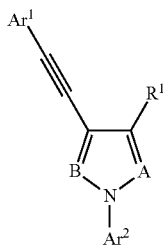

(I)

or a pharmaceutically acceptable salt thereof,
wherein:
one of A and B is CR, and the other is N,
R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;

$R^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 6-membered aryl ring or a 5- or 6-membered mono-heteroaryl ring that contains 1, 2, or 3 heteroatoms independently selected from the group consisting of N, O and S, wherein the 6-membered aryl or the 5- or 6-membered mono-heteroaryl ring is optionally substituted with 1, 2 or 3 substituents independently selected from the group consisting of lower alkyl, and halogen, wherein the halogen is preferably chloro;

wherein the 6-membered aryl ring is preferably phenyl, and the 5- or 6-membered mono-heteroaryl ring is preferably pyridinyl including 2-pyridinyl, 3-pyridinyl, and 4-pyridinyl, pyrimidinyl including 2-pyrimidinyl, 4-pyrimidinyl, and 5-pyrimidinyl; or pyrazinyl.

Ar$^2$ is a 6-membered aryl ring or a 5- or 6-membered mono-heteroaryl ring that contains 1, 2, or 3 heteroatoms independently selected from the group consisting of N, O and S, wherein the 6-membered aryl ring or the 5- or 6-membered mono-heteroaryl ring is optionally substituted with 1, 2 or 3 substituents independently selected from the group consisting of —C$_1$-C$_4$alkyl, —F, —Cl, —Br, —OH, —CN, nitro, —CF$_3$, —OCF$_3$, —O—C$_1$-C$_4$alkyl, —SCH$_3$, —S(O)—CH$_3$, —S(O$_2$)—CH$_3$, —O—C$_1$-C$_4$alkyl-O—C$_1$-C$_4$alkyl, —C(O)OCH$_3$, —C(O)NH$_2$, —C(O)NH(CH$_3$), —C(O)N(CH$_3$)$_2$, phenyl, wherein the —C$_1$-C$_4$alkyl is preferably methyl, ethyl, n-propyl, iso-propyl, n-butyl, iso-butyl, tert-butyl; the —O—C$_1$-C$_4$alkyl is preferably methoxy, ethoxy, n-propoxy, iso-propoxy, n-butoxy, iso-butoxy, tert-butoxy, In a further embodiment of the present invention, provided is a compound according to formula Ia:

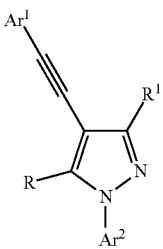

(Ia)

or a pharmaceutically acceptable salt thereof, wherein:
R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;

$R^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 5- to 10-membered mono- or bicyclic heteroaryl ring that contains 1-3 heteroatoms selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)—alkyl, —C(O)-cycloalkyl, —C(O)-heterocycloalkyl, —C(O)-aryl, —C(O)-heteroaryl, —C(O)O— alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form an optionally substituted 5-7 membered fused carbacyclic or heterocyclic ring, or a 5- to 10-membered mono- or bicyclic aryl ring, wherein the 5- to 10-membered mono- or bicyclic aryl ring is optionally substituted with 1-3 substituents independently selected from the group consisting of alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form a 5-7 membered fused and optionally substituted carbacyclic or heterocyclic ring;

Ar$^2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)— heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring, or a 5- to 10-membered mono- or bicyclic aryl ring, wherein the 5- to 10-membered mono- or bicyclic aryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH— cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring.

In a further embodiment, provided is a compound according to formula Ia, or a pharmaceutically acceptable salt thereof, wherein:

R is —H, -halogen, -alkyl, -cycloalkyl, -haloalkyl, —OR$^2$, or —N(lower alkyl)$_2$, wherein R$^2$ is lower alkyl which may be optionally substituted with 1-2 substituents selected from the group consisting of —OH and -alkoxy;

R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, and —O-alkyl, or a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, and —O-alkyl;

Ar$^2$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, —O-alkyl, —S-alkyl, —S(O)— alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$, or a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, —O-alkyl, —S-alkyl, —S(O)-alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$;

In a further embodiment, provided is a compound according to formula Ia, or a pharmaceutically acceptable salt thereof, wherein:

R is —H, -halogen, -alkyl, -cycloalkyl, -haloalkyl, —OR$^2$, or —N(lower alkyl)$_2$, wherein R$^2$ is lower alkyl which may be optionally substituted with 1-2 substituents selected from the group consisting of —OH and -alkoxy;

R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 6-membered aryl ring or a 5- or 6-membered mono-heteroaryl ring that contains 1, 2, or 3 heteroatoms independently selected from the group consisting of N, O and S, wherein the 6-membered aryl or the 5- or 6-membered mono-heteroaryl ring is optionally substituted with 1, 2 or 3 substituents independently selected from the group consisting of lower alkyl, and halogen;

Ar$^2$ is a 6-membered aryl ring or a 5- or 6-membered mono-heteroaryl ring that contains 1, 2, or 3 heteroatoms independently selected from the group consisting of N, O and S, wherein the 6-membered aryl ring or the 5- or 6-membered mono-heteroaryl ring is optionally substituted with 1, 2 or 3 substituents independently selected from the group consisting of —C$_1$-C$_4$alkyl, —F, —Cl, —Br, —OH, —CN, nitro, —CF$_3$, —OCF$_3$, —O—C$_1$-

$C_4$alkyl, —$SCH_3$, —$S(O)$—$CH_3$, —$S(O_2)$—$CH_3$, —O—$C_1$-$C_4$alkyl-O—$C_1$-$C_4$alkyl, —$C(O)OCH_3$, —$C(O)NH_2$, —$C(O)NH(CH_3)$, —$C(O)N(CH_3)_2$, phenyl.

In a further embodiment, provided is a compound according to formula Ia, or a pharmaceutically acceptable salt thereof, wherein:

R is —H, -halogen, —$C_1$-$C_4$alkyl, —$CF_3$, —O—$C_1$-$C_4$alkyl, or —O—$C_1$-$C_4$alkyl-O—$C_1$-$C_4$alkyl;

$R^1$ is —H, -halogen, —$C_1$-$C_4$alkyl, —$C_3$-$C_6$cycloalkyl, -halo-$C_1$-$C_4$alkyl, —$OR^{2'}$, or —$N(C_1$-$C_4$alkyl$)_2$, wherein $R^{2'}$ is $C_1$-$C_4$alkyl which may be optionally substituted with 1-2 substituents selected from the group consisting of -halogen, —OH, —$C_1$-$C_4$alkoxy, and —$N(CH_3)_2$;

$Ar^1$ is optionally substituted pyridinyl, pyrimidinyl, pyrazinyl, or phenyl, wherein the pyridinyl, pyrimidinyl, pyrazinyl, or phenyl is optionally substituted with a substituent selected from the group consisting of —$C_1$-$C_4$alkyl, and halogen, wherein the halogen is preferably chloro;

$Ar^2$ is optionally substituted pyridinyl, or phenyl, wherein the pyridinyl, or phenyl is optionally substituted with 1-2 substituents independently selected from the group consisting of —$C_1$-$C_4$alkyl, -halogen, —CN, —$CF_3$, —O—$CF_3$, —$S(O_2)$—$C_1$-$C_4$alkyl, and —O—$C_1$-$C_4$alkyl-O—$C_1$-$C_4$alkyl.

In another embodiment of the present invention, provided is a compound according to formula Ib:

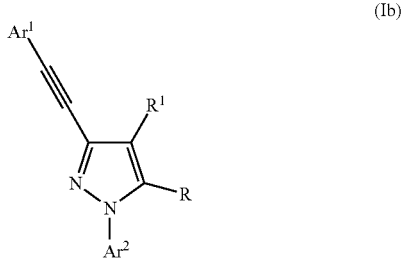

(Ib)

or a pharmaceutically acceptable salt thereof, wherein:

R is —H, -halogen, -alkyl, -cycloalkyl, -haloalkyl, —$OR^2$, or —N(lower alkyl$)_2$, wherein $R^2$ is lower alkyl which may be optionally substituted with 1-3 substituents selected from the group consisting of -halogen, —OH, -alkoxy, and —$N(CH_3)_2$;

$R^1$ is —H, -halogen, -alkyl, -cycloalkyl, -haloalkyl, —$OR^{2'}$, or —N(lower alkyl$)_2$, wherein $R^{2'}$ is lower alkyl which may be optionally substituted with 1-3 substituents selected from the group consisting of -halogen, —OH, -alkoxy, and —$N(CH_3)_2$;

$Ar^1$ is a 5- to 10-membered mono- or bicyclic heteroaryl ring that contains 1-3 heteroatoms selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —$S(O_2)$-alkyl, —$S(O_2)$-aryl, —$CH_2$-aryl, aryl, heteroaryl, —O—$CH_2$-aryl, —$N(CH_3)_2$, cycloalkyl, heterocycloalkyl, —C(O)—alkyl, —C(O)-cycloalkyl, —C(O)-heterocycloalkyl, —C(O)-aryl, —C(O)-heteroaryl, —C(O)O— alkyl, —C(O)O-cycloalkyl, —C(O)O-heterocycloalkyl, —C(O)O-aryl, —C(O)O-heteroaryl, —$C(O)NH_2$, —C(O)NH-alkyl, —C(O)N(alkyl$)_2$, —C(O)NH-cycloalkyl, —C(O)N(cycloalkyl$)_2$, —C(O)NH-heterocycloalkyl, —C(O)N(heterocycloalkyl$)_2$, —C(O)NH-aryl, —C(O)N(aryl$)_2$, —C(O)NH-heteroaryl, —C(O)N(heteroaryl$)_2$, and substituted lower alkyl, wherein the substituents may combine to form an optionally substituted 5-7 membered fused carbacyclic or heterocyclic ring, or a 5- to 10-membered mono- or bicyclic aryl ring, wherein the 5- to 10-membered mono- or bicyclic aryl ring is optionally substituted with 1-3 substituents independently selected from the group consisting of alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —$S(O_2)$-alkyl, —$S(O_2)$-aryl, —$CH_2$-aryl, aryl, heteroaryl, —O—$CH_2$-aryl, —$N(CH_3)_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —$C(O)NH_2$, —C(O)NH-alkyl, —C(O)N(alkyl$)_2$, —C(O)NH-cycloalkyl, —C(O)N(cycloalkyl$)_2$, —C(O)NH-heterocycloalkyl, —C(O)N(heterocycloalkyl$)_2$, —C(O)NH-aryl, —C(O)N(aryl$)_2$, —C(O)NH-heteroaryl, —C(O)N(heteroaryl$)_2$, and substituted lower alkyl, wherein the substituents may combine to form a 5-7 membered fused and optionally substituted carbacyclic or heterocyclic ring;

$Ar^2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —$S(O_2)$-alkyl, —$S(O_2)$-aryl, —O-alkyl-OH, —O-alkyl-O-alkyl, —$CH_2$-aryl, aryl, heteroaryl, —O—$CH_2$-aryl, —$N(CH_3)_2$, cycloalkyl, heterocycloalkyl, —C(O)-alkyl, —C(O)-cycloalkyl, —C(O)— heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —$C(O)NH_2$, —C(O)NH-alkyl, —C(O)N(alkyl$)_2$, —C(O)NH-cycloalkyl, —C(O)N(cycloalkyl$)_2$, —C(O)NH-heterocycloalkyl, —C(O)N(heterocycloalkyl$)_2$, —C(O)NH-aryl, —C(O)N(aryl$)_2$, —C(O)NH-heteroaryl, —C(O)N(heteroaryl$)_2$, and substituted lower alkyl wherein the substituents may combine to form an optionally substituted the 5-7 membered fused carbacyclic or heterocyclic ring, or a 5- to 10-membered mono- or bicyclic aryl ring, wherein the 5- to 10-membered mono- or bicyclic aryl ring is optionally substituted with 1-3 substituents independently selected from the group consisting of -alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —$S(O_2)$-alkyl, —$S(O_2)$-aryl, —O-alkyl-OH, —O-alkyl-O-alkyl, —$CH_2$-aryl, aryl, heteroaryl, —O—$CH_2$-aryl, —$N(CH_3)_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —$C(O)NH_2$, —C(O)NH-alkyl, —C(O)N(alkyl$)_2$, —C(O)NH— cycloalkyl, —C(O)N(cycloalkyl$)_2$, —C(O)NH-heterocycloalkyl, —C(O)N(heterocycloalkyl$)_2$, —C(O)NH-aryl, —C(O)N(aryl$)_2$, —C(O)NH-heteroaryl, —C(O)N(heteroaryl$)_2$, and substituted lower alkyl wherein the substituents may combine to form an optionally substituted 5-7 membered fused carbacyclic or heterocyclic ring.

In a further embodiment, provided is a compound according to formula Ib, or a pharmaceutically acceptable salt thereof, wherein:

R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;

R$^1$ is —H, -halogen, -alkyl, -cycloalkyl, -haloalkyl, —OR$^{2*}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 5- or 6-membered mono-heteroaryl ring that contains 1-3 heteroatoms selected from so the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, and —O-alkyl, or
 a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, and —O-alkyl;

Ar$^2$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, —O-alkyl, —S-alkyl, —S(O)— alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$, or
 a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, —O-alkyl, —S-alkyl, —S(O)-alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$.

In a further embodiment, provided is a compound according to formula Ib, or a pharmaceutically acceptable salt thereof, wherein:

R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;

R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 6-membered aryl ring or a 5- or 6-membered mono-heteroaryl ring that contains 1, 2, or 3 heteroatoms independently selected from the group consisting of N, O and S, wherein the 6-membered aryl or the 5- or 6-membered mono-heteroaryl ring is optionally substituted with 1, 2 or 3 substituents independently selected from the group consisting of lower alkyl, and halogen;

Ar$^2$ is a 6-membered aryl ring or a 5- or 6-membered mono-heteroaryl ring that contains 1, 2, or 3 heteroatoms independently selected from the group consisting of N, O and S, wherein the 6-membered aryl ring or the 5- or 6-membered mono-heteroaryl ring is optionally substituted with 1, 2 or 3 substituents independently selected from the group consisting of —C$_1$-C$_4$alkyl, —F, —Cl, —Br, —OH, —CN, nitro, —CF$_3$, —OCF$_3$, —O—C$_1$-C$_4$alkyl, —SCH$_3$, —S(O)—CH$_3$, —S(O$_2$)—CH$_3$, —O—C$_1$-C$_4$alkyl-O—C$_1$-C$_4$alkyl, —C(O)OCH$_3$, —C(O)NH$_2$, —C(O)NH(CH$_3$), —C(O)N(CH$_3$)$_2$, phenyl.

In a further embodiment, provided is a compound according to formula Ib, or a pharmaceutically acceptable salt thereof, wherein:

R is —H, -halogen, —C$_1$-C$_4$alkyl;

R$^1$ is —H, -halogen, —C$_1$-C$_4$alkyl;

Ar$^1$ is optionally substituted pyridinyl, pyrimidinyl, pyrazinyl, or phenyl, wherein the pyridinyl, pyrimidinyl, pyrazinyl, or phenyl is optionally substituted with a substituent selected from the group consisting of —C$_1$-C$_4$alkyl, and halogen, wherein the halogen is preferably chloro;

Ar$^2$ is optionally substituted pyridinyl, or phenyl, wherein the pyridinyl, or phenyl is optionally substituted with 1-2 substituents independently selected from the group consisting of —C$_1$-C$_4$alkyl, -halogen, —CN, —CF$_3$, —O—CF$_3$, —S(O$_2$)—C$_1$-C$_4$alkyl, and —O—C$_1$-C$_4$alkyl-O—C$_1$-C$_4$alkyl.

In a still further embodiment of the present invention, provided is a pharmaceutical composition, comprising a therapeutically effective amount of a compound according to formula I or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, for simplicity, the term "C$_x$-C$_y$" denotes the number of atoms, including to carbon atoms and heteroatoms where present, where x and y are integers. So, for example, C$_1$-C$_4$alkyl refers to an alkyl group having 1 to 4 carbon atoms, C$_5$-C$_{12}$heterocyclyl refers to a 5 to 12 membered ring system having at least one heteroatom but not a ring system containing 5 to 12 annular carbon atoms.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten, one to eight, one to six, one to five or one to four carbon atoms.

As used herein, the term "alkenyl", alone or in combination with other groups, refers to a straight-chain or branched hydrocarbon residue having an olefinic bond of two to twenty carbon atoms, preferably two to sixteen carbon atoms, more preferably two to ten, two to eight, two to six, two to five or two to four carbon atoms.

The term "cycloalkyl" refers to a mono- or polycarbocyclic saturated aliphatic hydrocarbonyl radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the understanding that said substituents are not, in turn, substituted further unless indicated otherwise in the Examples or claims below. Each substituent can independently be, alkyl, alkoxy, halogen, amino, hydroxyl or oxygen (O═) unless otherwise specifically indicated. Examples of cycloalkyl moieties include, but are not limited to, optionally substituted cyclopropyl, optionally substituted cyclobutyl, optionally substituted cyclopentyl, optionally substituted cyclohexyl, optionally substituted cycloheptyl, and the like or those which are specifically exemplified herein.

The term "heterocycloalkyl" denotes a mono- or polycyclic alkyl ring of three to ten, preferably three to six ring atoms, wherein one, two or three of the ring atoms is a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms, more preferably one to five carbon atoms or one to four carbon atoms. This term is further exemplified by radicals such as methyl, ethyl, n-propyl, iso-propyl, n-butyl, s-butyl, iso-butyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonloxy) and ureas (e.g. mono- or di-alkylaminutesocarbonylamino or arylaminutesocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl", refers to an aromatic mono- or polycyclic radical of 5 to 12 atoms having at least one aromatic ring containing one, two, or three ring heteroatoms selected from N, O, and S, with the remaining ring atoms being C, preferably an aromatic monocyclic radical of 5 to 6 atoms, and preferably an aromatic bicyclic radical of 11 to 12 atoms. One or two ring carbon atoms of the heteroaryl group may be replaced with a carbonyl group. Examples of such groups include, but are not limited to, pyrimidinyl, pyridyl, indoyl, quinolinyl, pyridon-2-yl, isoquinolinyl, 5,6,7,8-tetrahydroquinolinyl, thienyl, furanyl, imidazolyl, pyrazolyl, thiazolyl, isothiazolyl, oxazolyl, oxadiazolyl, thiadiazolyl, pyrazolidinyl, pyrazinyl, pyridazinyl, thianaphthyl, benzofuranyl, isobenzofuranyl, oxyindolyl, isoindolyl, indazolyl, indolinyl, 7-azaindolyl, benzopyranyl, coumarinyl, isocoumarinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and the like.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as so alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means —O-alkyl; and "alkanoyl" means —CO-alkyl, wherein the alkyl moiety contains 1 to 8 carbon atoms, preferably 1 to 6 carbon atoms, more preferably 1 to 5 carbon atoms, or 1 to 4 carbon atoms. Alkoxy substituent groups or alkoxy-containing substituent groups may be substituted by, for example, one or more alkyl groups, with the understanding that said substituents are not, in turn, substituted further unless indicated otherwise in the Examples or claims below.

As used herein, the term "halogen" or "halo" means a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula Ia and Ib. Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction so with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions or of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Reminutesgton's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster.

The present compounds of formula I can be prepared by the methods described below, by the methods given in the schemes or in the examples. Appropriate reaction conditions for the individual reaction steps are known to a person skilled in the art. The reaction sequence is not limited to the one displayed in the schemes, however, depending on the starting materials and their respective reactivity, the sequence of reaction steps can be freely altered. Starting materials are either commercially available or can be prepared by methods analogous to the methods given below, by methods described in the examples, or by methods known in the art.

The present compounds of formula I can be prepared by the following schemes described below.

Scheme 1

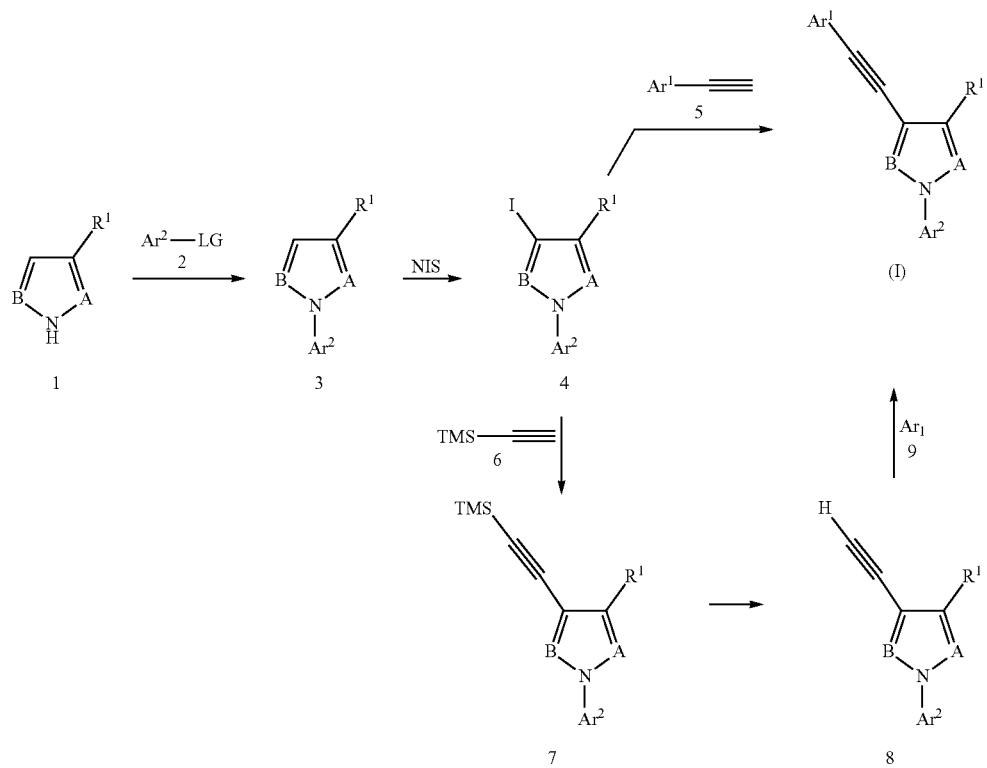

In scheme 1 compounds of formula 1 are known, and in many cases, commercially available compounds or can be prepared using well established methodology. For example, B═C—CH$_3$ or C—CF$_3$, A is N and R$^1$ is CH$_3$ are commercial available from several suppliers including Sigma-Aldrich. In case compound 1 are not commercially available, it can be synthesized through Knorr pyrazole synthesis. The Knorr pyrazole synthesis is an organic reaction used to convert a 1, 3-dicarbonyl compound and a hydrazine or its derivatives to a pyrazole. Knorr, L. (1884), *Berichte der deutschen chemischen Gesellschaft* 17: 1635.

In scheme 1 compounds 5, for example, Ar$^1$=2-pyridinyl or 3-pyridinyl are available from several suppliers including Sigma-Aldrich. In the case that commercial supplies are not readily available, aryl- and heteroaryl alkynes can be prepared from the corresponding aryl or heteroaryl carboxaldehydes using the Corey-Fuchs procedure (Corey, E. J. and Fuchs, P. L., *Tetrahedron Lett.* 1972, 3769; reviewed in: Han, Xiaojun. Editor(s): Li, Jie Jack. *Name Reactions for Homologations* (2009), (Pt. 1), 393-403. Publisher: John Wiley & Sons, Inc.). Alternatively, aryl and heteroaryl carboxaldehydes may be converted to aryl or heteroaryl alkynes by treatment with C-silylated-diazophosphines under neutral conditions (Ona, I., Xavier, B., Cazoria, A. M., et al., *Journal of Organic Chemistry*, 2006, 71, 5320).

In cases where the appropriate carboxaldehydes are not readily available, aryl or heteroaryl aryl alkynes may also be prepared from aryl or heteroaryl compounds functionalized with groups capable of undergoing transition metal catalyzed cross-coupling reactions with alkynes. Those skilled in the art will appreciate how to select the appropriate reaction partners.

For example 3-alkynyl pyridine can be synthesized from either 3-bromopyridine or 3-trifluoromethanesulfonyl pyridine through reactions with suitably functionalized alkynes catalyzed by transition metals, followed by deprotection of terminal alkynes bearing a protecting group at the terminal position. In the event the protecting group is trimethylsilyl (TMS), the compound may be treated with an aqueous base, for example potassium hydroxide or tetrabutylammonium fluoride (TBAF) in methanol to effect its removal. In the case where the alkyne is formed through a transition metal catalyzed reaction between an aryl or heteroaryl ring bearing a suitable functionality for cross coupling reactions, for example a bromide, and 2-methyl-3-butyne-2-ol, deprotection to give a terminal alkyne can be achieved through heating in a suitable solvent, for example toluene, in the presence of catalytic amounts of a base, for example sodium hydride. The following references are among the many examples of such transformations in the published literature: Uttam Dutta, Soham Maity, Rajesh Kancherla, and Debabrata Maiti, *Organic Letters*. 2014, 16 (24), 6302-6305; Holmes, B. T., Pennington, W. T., Hanks, T. W., *Synthetic Communications*, 2003, 33, 2447-2461; Negishi, E.-i., Xu, C., Tan, Z., Kotora, M., *Heterocycles*, 1997, 46, 209-214. One common variant is known as the Sonogashira coupling reaction, reviewed in Chinchilla, R., Nájera, C., Recent Advances in Sonogashira reactions, *Chemical Society Reviews*, 2011, 40, 5084-5121.

In scheme 1 compound of structure 2 in which LG is a leaving group, which can be B(OH)$_2$ or halogen like F, Cl, Br and I. Reaction condition for compounds 1 and 2 to form compound 3 depending on the LG types, 1) for example, when LG is B(OH)$_2$, compound 1 and 2 go through Chan-Lam Coupling reaction in an suitable inert solvent, such as DCM in the presence of catalyst copper (II) like Cu(OAC)$_2$ at a suitable temperature, for example room temperature in air, after reaction is complete the newly formed compound 3 can be isolated using conventional technics, for example by filtering and concentrating under vacuo, the reaction residue was purified through chromatography over silica gel (P. Y. S. Lam., C. G. Clark, S. Saubern, J. Adams, M. P. Winters, D. M. T. Chan, A. Combs, *Tetrahedron Lett.*, 1998, 39, 2941-2944); 2) for example, when LG is halogen like F, Cl, Br and I, compound 1 and 2 go through SNAr reaction in an suitable inert solvent, such as DMF with a base like Cs$_2$CO$_3$ or NaH at a suitable temperature, for example 90° C., after reaction is complete and the newly formed compound 3 can be isolated using conventional technics, for example by quenching the reaction with an aqueous solution followed by extraction of the products into an organic solvent, washing with brine, drying and chromatography over silica gel, if necessary.

Conversion of compounds of structure 3 to the iodides 4 can be achieved by nucleophilic substitution reaction, like combination of a solution of 3 to a iodination reagent, for example N-iodosuccinimide (NIS) in a suitable inert solvent, for example, chloroform at a medium temperature, for example 60° C. Such reactions may be worked up using common procedures, for example, the reaction mixture was concentrated under vacuo and the residue was purified by silica gel chromatography, if necessary to obtain the nuclear substituted products 4 (*Tetrahedron Letters*, 42 (15), 863-865, 2001; *Tetrahedron Letters*, 68 (15), 3165-3171, 2012).

Compound 4 could go through two pathways to get the final product of formula I.
1) Reaction of compounds 4 and aryl alkyne 5 to form final product of formula I can be achieved by Sonogashira coupling of the alkyne 5 and halohydrocarbon 4 in a suitable inert solvent, for example THF, by adding Pd(PPH$_3$)$_2$Cl$_2$, Et$_3$N and CuI, then the reaction mixture microwaved at a medium temperature, for example 90C, after reaction is complete and the newly formed compound I can be isolated using conventional technics, for example The reaction mixture was concentrated to dryness and the residue was purified by pre-HPLC to afford the final product I (Sonogashira, K. (2002), "Development of Pd—Cu catalyzed cross-coupling of terminal acetylenes with sp$^2$-carbon halides", *J. Organomet. Chem.* 653: 46-49; King, A. O.; Yasuda, N. (2004), "Palladium-Catalyzed Cross-Coupling Reactions in the Synthesis of Pharmaceuticals Organometallics in Process Chemistry", *Top. Organomet. Chem.* 6: 205-245).
2) Reaction of compounds 4 and ethynyltrimethylsilane 6 to form compound 7 can be achieved by Sonogashira coupling of the alkyne 6 and halohydrocarbon 4 in a suitable inert solvent, for example THF, by adding Pd(PPH$_3$)$_2$Cl$_2$, Et$_3$N and CuI, then the reaction mixture was stirred at a medium temperature, for example 90° C., after reaction is complete and the newly formed compound 7 can be isolated using conventional technics, for example reaction mixture was concentrated under vacuo and the residue was added organic solvent like EtOAc, followed by washing with brine, drying and chromatography over silica gel. Compound 7 may be treated with an aqueous base, for example potassium hydroxide or tetrabutylammonium fluoride (TBAF) so in MeOH to effect the removal of protecting group trimethylsilyl (TMS) to afford compound 8.

Then, reaction of compound 8 and compound 9 to form final product of formula I can be achieved by Sonogashira coupling of the alkyne 8 and compound 9 in a suitable inert solvent, for example CH$_3$CN, by adding Pd(PPH$_3$)$_2$Cl$_2$, Et$_3$N and CuI, then the reaction mixture was stirred at appropriate temperature, for example 120° C., after reaction is complete and the newly formed compound I can be isolated using conventional technics, for example The reaction mixture was concentrated to dryness and the residue was purified by prep-HPLC to afford the final product I.

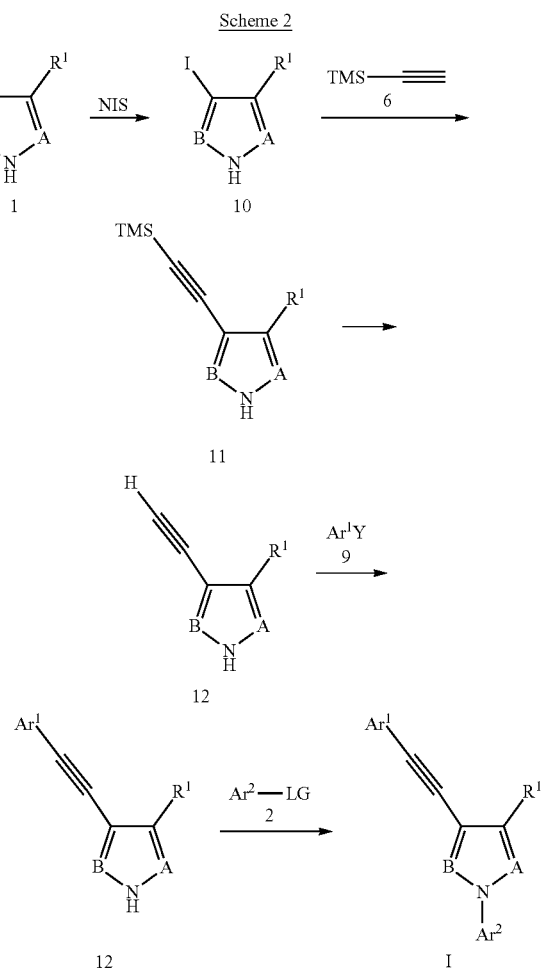

Scheme 2

An alternative method for the preparation of compounds of formula I is shown in Scheme 2. Iodides like 3-iodopyrazole and 4-iodopyrazole are commercially available, in case it's not commercially available, iodides 10 can be achieved by nucleophilic substitution reaction, like combination of a solution of 1 to a iodination reagent, for example N-iodosuccinimide (NIS) in a suitable inert solvent, for example, chloroform at appropriate temperature, for example 60° C. Such reactions may be worked up using common procedures, for example, the reaction mixture was concentrated under vacuo and the residue was purified by silica gel chromatography, if necessary.

Reaction of compounds 10 and ethynyltrimethylsilane 6 to form compound 11 can be achieved by Sonogashira coupling of the alkyne 6 and halohydrocarbon 10 in a suitable inert solvent, for example THF, by adding Pd(PPH$_3$)$_2$ Cl$_2$, Et$_3$N and CuI then reaction at a medium temperature, for example 70° C., after reaction is complete and the newly formed compound 11 can be isolated using conventional technics, for example the reaction mixture was filtered and concentrated then purified by chromatograph column. Compound 11 may be treated with an aqueous base, for example potassium hydroxide or tetrabutylammonium fluoride (TBAF) in MeOH to effect the removal of protecting group trimethylsilyl (TMS) to afford compound 12, which reacted with compound 9 through Sonogashira coupling in a suitable inert solvent, for example CH$_3$CN, by adding Pd(PPH$_3$)$_2$Cl$_2$, Et$_3$N and CuI, then the reaction mixture was stirred at appropriate temperature, for example 90° C., after reaction is complete and the newly formed compound 13 can be isolated using conventional technics, the mixture was filtered and concentrated by vacuo to give the crude product which was purified by silica gel chromatography. As described in Scheme 1, reaction condition of compound 13 and compound 2 to form the final product of formula I depending on the LG types, a) for example when LG is B(OH)$_2$, compound 13 and 2 go through Chan-Lam Coupling reaction in an suitable inert solvent, such as DCM in the presence of catalyst copper (II) like Cu(OAC)$_2$ at a suitable temperature, for example room temperature in air, after reaction is complete the final compound of formula I can be isolated using conventional technics, for example by filtering and concentrating under vacuo, the reaction residue was purified by prep-TLC; b) for example when LG is halogen like F, Cl, Br and I, compound 13 and 2 go through SNAr reaction in an suitable inert solvent, such as DMF with a base like Cs$_2$CO$_3$ at a suitable temperature, for example 110° C., after reaction is complete and the final compound of formula I can be isolated using conventional technics, for example by filtering and concentrating under vacuo, the reaction residue was purified by prep-HPLC.

The invention will now be further described in the Examples below, which are intended as an illustration only and do not limit the scope of the invention.

EXAMPLES

Example 1

Procedure for Preparation of 2-ethynyl-pyrimidine

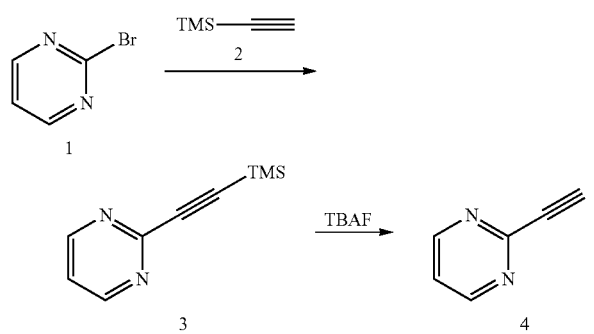

To a solution of 1 (5.0 g, 31.45 mmol) and 2 (3.40 g, 34.6 mmol) in 30 mL of Et$_3$N was added CuI (0.6 g, 3.15 mmol) and Pd(PPh$_3$)$_4$ (1.8 g, 1.55 mmol). The resulting mixture was protected with N$_2$ atmosphere, and then was stirred for 48 hours at room temperature. TLC showed the starting material was consumed. The reaction mixture was then concentrated in vacuo. The crude product was purified by silica gel column chromatography to give product 3 (3.5 g, yield: 63.1%).

To a solution of 3 (3.0 g, 17.02 mmol) in 10 mL THF was added 1M of TBAF over 3 minutes. TLC showed the starting material was consumed. The reaction mixture was then concentrated in vacuo. The crude product was purified by silica gel column chromatography to give product 4 (1.2 g, yield: 67.4%).

LCMS: m/z, 105 (M+H)$^+$.

Example 2

Procedure for Preparation of 2-chloro-4-ethynyl-pyridine

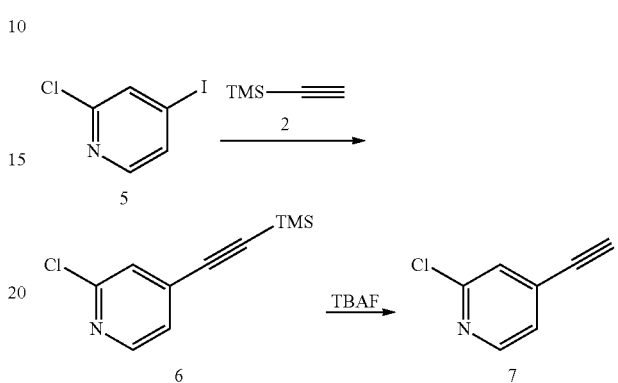

To a solution of 5 (3.3 g, 13.78 mmol) and 2 (1.49 g, 15.16 mmol) in Et$_3$N was added CuI (0.26 g, 1.38 mmol) and Pd(PPh$_3$)$_2$Cl$_2$ (0.48 g, 0.69 mmol). The resulting mixture was protected with N$_2$ atmosphere, and then was heated at 70° C. for 4 hours. The reaction mixture was filtered, and concentrated in vacuo. The residue was purified by flash chromatography to give product 6 (2.0 g, yield: 69.2%).

To a solution of 6 (0.4 g, 1.91 mmol) in 10 mL THF was added 1M TBAF over 3 minutes. TLC showed the starting material was consumed. The reaction mixture was then concentrated in vacuo. The crude product was purified by silica gel column chromatography to give product 7 (0.15 g, yield: 57.2%).

LCMS: m/z 138 (M+H)$^+$.

Example 3

Procedure for Preparation of 2-ethynyl-pyrazine

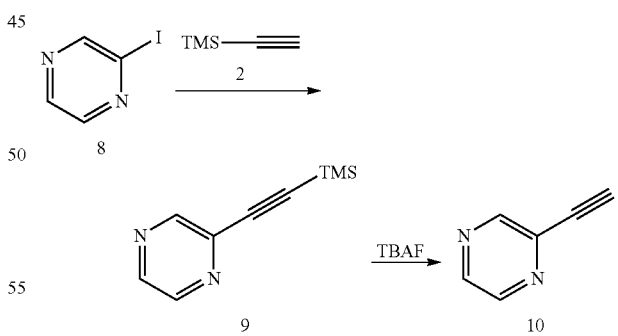

To a solution of 8 (5.0 g, 24.39 mmol) and 2 (2.82 g, 26.8 mmol) in 100 mL of Et$_3$N was added Pd(PPh$_3$)$_4$ (1.4 g, 1.22 mmol) and CuI (0.46 g, 2.44 mmol). The reaction mixture was protected by N$_2$ atmosphere, and was stirred at room temperature for 48 hours. TLC showed the starting material was consumed. The reaction mixture was then concentrated in vacuum. The resulting crude product was purified by silica gel column chromatography to give product 9 (3.2 g, yield: 74.4%).

To a solution of 9 (3.0 g, 17.02 mmol) in 10 mL THF was added 1M of TBAF over 3 minutes. TLC analysis showed complete conversion of starting material to a major product. The reaction mixture was then concentrated in vacuo. The crude product was purified by silica gel column chromatography to give product 10 (1.0 g, yield: 56.5%).

LCMS: m/z 105 (M+H)+.

Example 4

Procedure for Preparation of 4-ethynyl-pyridine

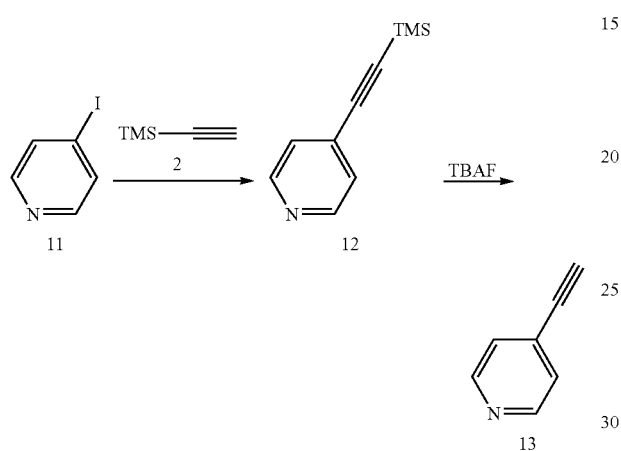

To a solution of 11 (5.0 g, 24.39 mmol) and 2 (2.64 g, 26.8 mmol) in 100 mL of Et₃N was added Pd(PPh₃)₄ (1.40 g, 1.22 mmol) and CuI (0.46 g, 2.44 mmol). The reaction mixture was protected by N₂ atmosphere, and was stirred at room temperature for 48 hours. TLC showed that the starting material was consumed. The reaction mixture was then concentrated in vacuo. The resulting crude product was purified by silica gel column chromatography to give the target product 12 (3.0 g, yield: 70.4%).

To a solution of 12 (3.0 g, 17.14 mmol) in 10 mL THF was added 1M of TBAF over 3 minutes. TLC analysis showed complete conversion of starting material to a major product. The reaction mixture was then concentrated in vacuo. The crude product was purified by silica gel column chromatography to give product 13 (1.0 g, yield: 56.8%).

LCMS: m/z 104 (M+H)+.

Example Compound 1

Preparation of 2-((1-(4-fluorophenyl)-3,5-dimethyl-1H-pyrazol-4-yl ethynyl) pyridine

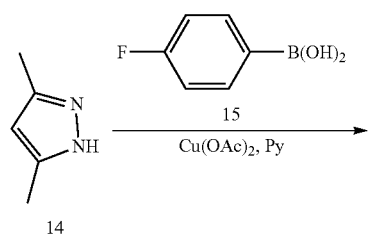

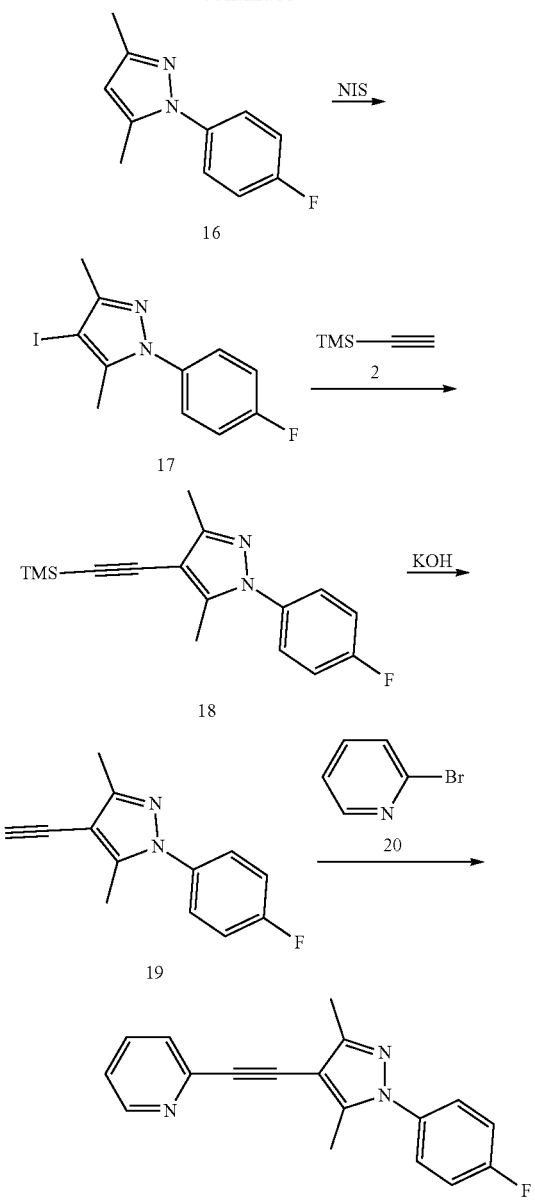

Experimental Section

Procedure for Preparation of 16

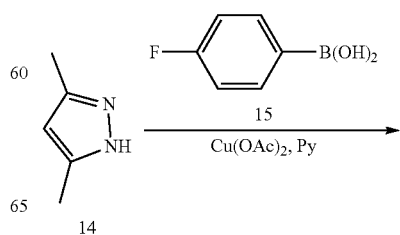

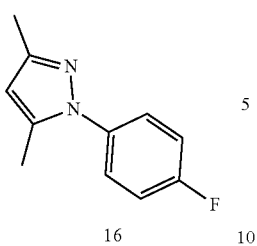

16

To a solution of 14 (1.00 g, 10.40 mmol) in 60 mL of degassed DCM, 15 (2.91 g, 20.81 mmol), Cu(OAc)$_2$ (3.78 mg, 20.81 mmol), and pyridine (2.49 g, 31.21 mmol) were added successively. The mixture was then degassed for 1 minute under O$_2$ atmosphere and stirred at room temperature overnight. The reaction mixture was filtered and the filtrate was evaporated to give crude product, which was purified by chromatography column to give the title product 16 (1.7 g, yield: 86%).
LCMS: m/z 191 (M+H)$^+$.

Procedure for Preparation of 17

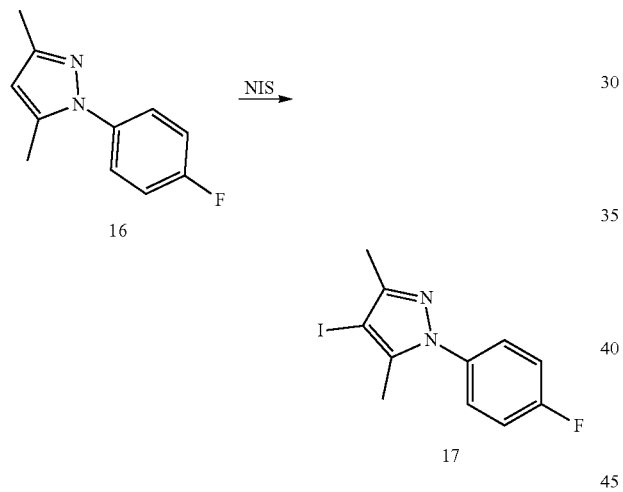

To a solution of 16 (1.00 g, 5.26 mmol) in CHCl$_3$ (50 mL) was added NIS (1.18 g, 5.26 mmol). Then the reaction mixture was stirred at reflux for 2 hours. LCMS showed that the reaction was complete, then the reaction mixture was concentrated and purified by chromatograph column to give the title product 17 (1.4 g, yield: 84%).
LCMS: n/z 317 (M+H)+.

Procedure for Preparation of 18

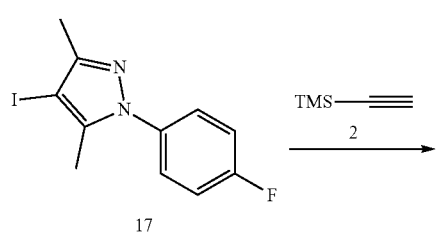

To a solution of 17 (1.00 g, 3.16 mmol) in 50 mL of degassed CH$_3$CN was added successively CuI (60 mg, 0.32 mmol), 2 (620 mg, 6.33 mmol), and Pd(PPh$_3$)$_2$Cl$_2$ (220 mg, 0.32 mmol) and Et$_3$N (630 mg, 9.49 mmol). The reaction mixture was stirred at 70° C. for 18 hours. LCMS showed that the reaction was complete, then the reaction mixture was filtered and the filtrate was concentrated to give the crude product, which was purified by chromatograph column to give the title product 18 (780 mg, yield 85%).
LCMS: m/z 287 (M+H)$^+$.

Procedure for Preparation of 19

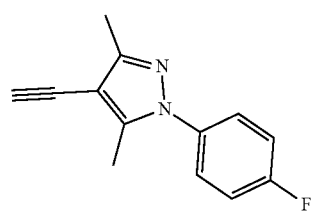

To a solution of 18 (780 mg, 2.72 mmol) in MeOH (50 mL) was added KOH (306 mg, 5.45 mmol). Then the reaction mixture was stirred at room temperature for 1 hour. LCMS showed that the reaction was complete, then the reaction mixture was quenched with water, extracted with DCM (3×50 mL). The combined organic layer was dried over Na$_2$SO$_4$, concentrated to give the title product 19 (500 mg, yield: 86%).
LCMS: m/z 215 (M+H)$^+$.

Procedure for Preparation of Compound 1

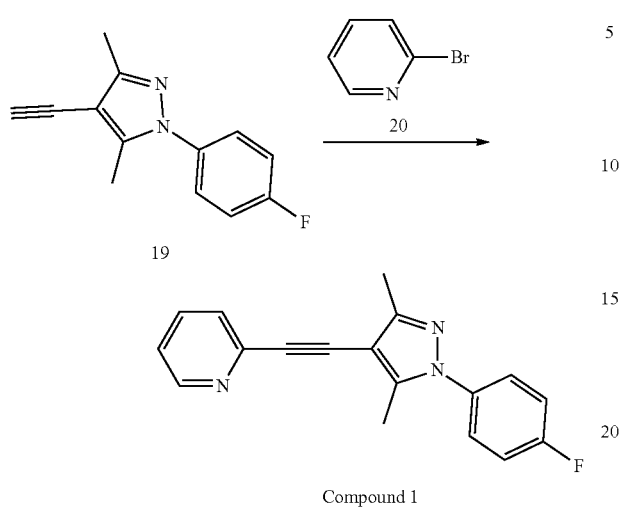

Compound 1

To a solution of 19 (100 mg, 0.47 mmol) in 3 mL of degassed CH$_3$CN was added successively CuI (8 mg, 0.046 mmol), 20 (222 mg, 1.40 mmol), and Pd(PPh$_3$)$_2$Cl$_2$ (32 mg, 0.046 mmol) and Et$_3$N (142 mg, 1.40 mmol). The reaction vessel was sealed and heated in microwave at 120° C. for 1 hour. LCMS showed that the reaction was complete, then the reaction mixture was filtered and the filtrate was concentrated to give the crude product, which was purified by prep-TLC to give the desired product Compound 1 (18 mg, yield: 13%). LCMS: m/z 292 (M+H)$^+$;

$^1$H NMR (400 MHz, CDCl3): δ 8.61 (d, J=4.8 Hz, 1H), 7.68-7.66 (m, 1H), 7.50-7.39 (m, 3H), 7.18-7.14 (m, 3H), 2.42 (s, 3H), 2.41 (s, 3H).

Example Compound 2

Preparation of 2-((1-(4-fluorophenyl)-3, 5-dimethyl-1H-pyrazol-4-yl) ethynyl) pyrimidine

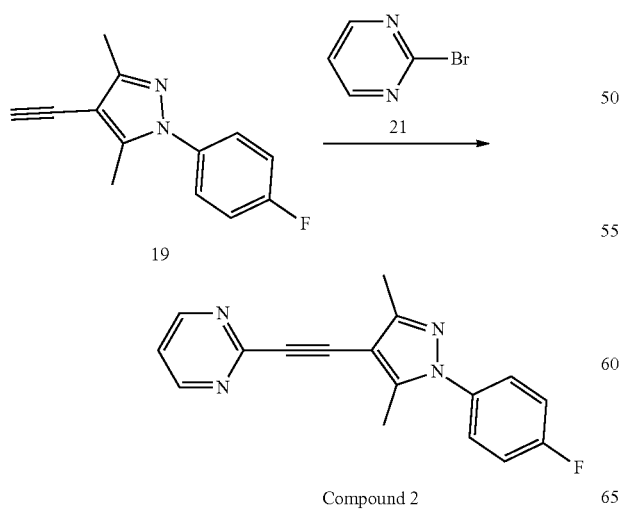

Compound 2

Experimental Section

Procedure for Preparation of Compound 2

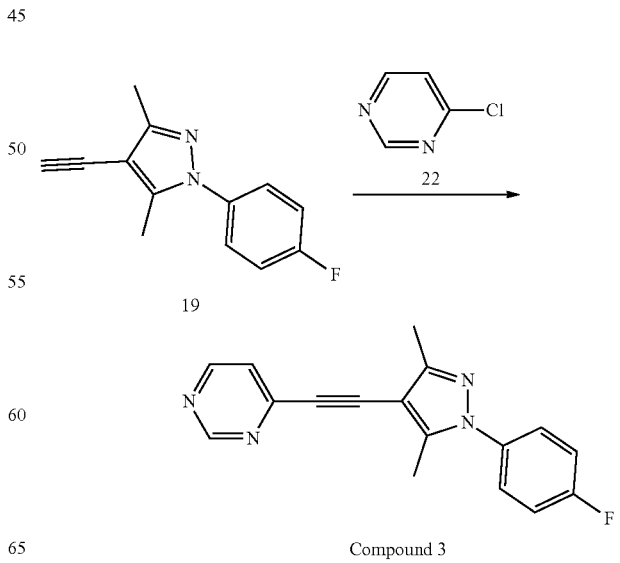

Compound 2

To a solution of 19 (100 mg, 0.47 mmol) in 3 mL of degassed CH$_3$CN was added successively CuI (8 mg, 0.046 mmol), 21 (223 mg, 1.40 mmol), and Pd(PPh$_3$)$_2$Cl$_2$ (32 mg, 0.046 mmol) and Et$_3$N (142 mg, 1.40 mmol). The reaction vessel was sealed and heated by microwave at 120° C. for 1 hour. LCMS showed that the reaction was completed, then the reaction mixture was filtered and the filtrate was concentrated to give the crude product, which was purified by prep-TLC to give the desired product Compound 2 (18 mg, yield: 13%).

LCMS: m/z 293 (M+H)$^+$;

$^1$H NMR (400 MHz, CDCl3): δ8.74 (d, J=4.8 Hz, 2H), 7.43-7.39 (m, 2H), 7.20-7.14 (m, 3H), 2.45 (s, 3H), 2.44 (s, 3H).

Example Compound 3

Preparation of 4-((1-(4-fluorophenyl)-3, 5-dimethyl-1H-pyrazol-4-yl) ethynyl) pyrimidine

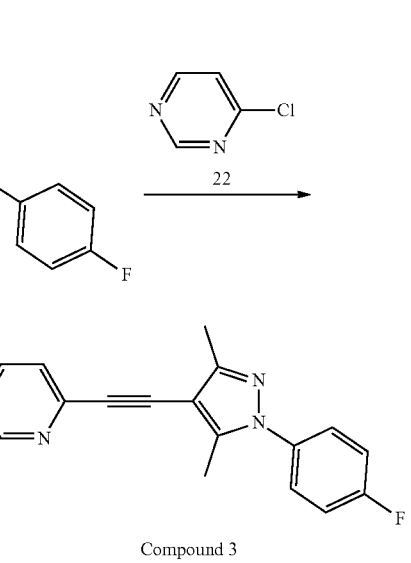

Compound 3

Experimental Section

Procedure for Preparation Compound 3

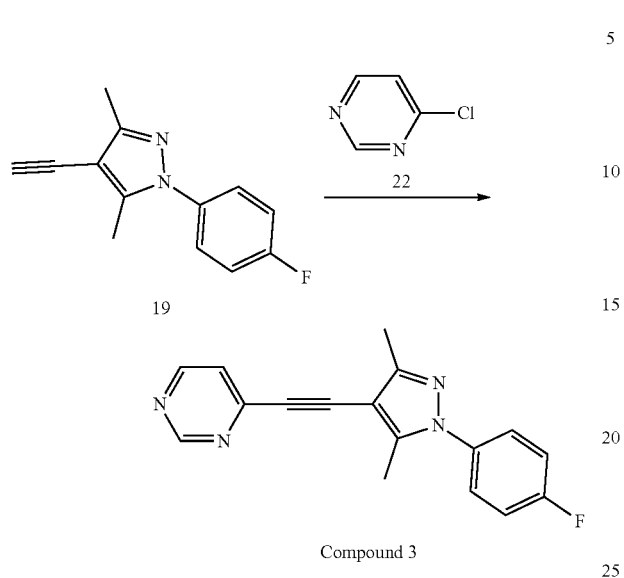

Compound 3

To a solution of 19 (100 mg, 0.47 mmol) in 3 mL of degassed CH₃CN was added successively CuI (8 mg, 0.046 mmol), 22 (160 mg, 1.40 mmol), and Pd(PPh₃)₂Cl₂ (32 mg, 0.046 mmol) and Et₃N (142 mg, 1.40 mmol). The reaction vessel was sealed and heated by microwave at 120° C. for 1 hour. LCMS showed that the reaction was complete. The reaction mixture was filtered and the filtrate was concentrated to give the crude product, which was purified by prep-TLC to give the desired product compound 3 (9 mg, yield: 7%).

LCMS: m/z 292 (M+H)$^+$;

$^1$H NMR (400 MHz, CDCl3): δ 9.19 (s, 1H), 8.69 (s, 1H), 7.43-7.39 (m, 3H), 7.19-7.15 (m, 2H), 2.43 (s, 3H), 2.42 (s, 3H).

Example Compound 4

Preparation of 2-((3,5-dimethyl-1-(4-(trifluoromethoxy)phenyl)-H-pyrazol-4-yl) ethynyl)pyridine

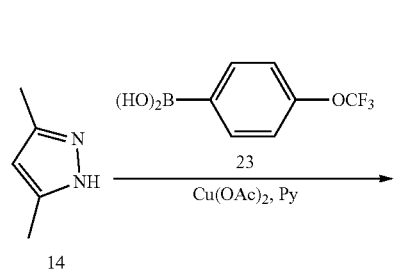

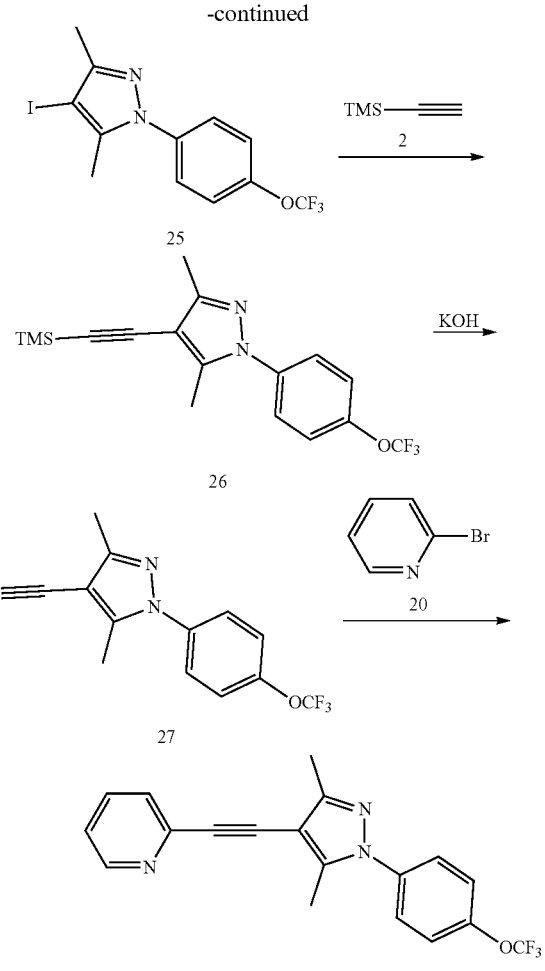

Compound 4

Experimental Section

Procedure for Preparation of 24

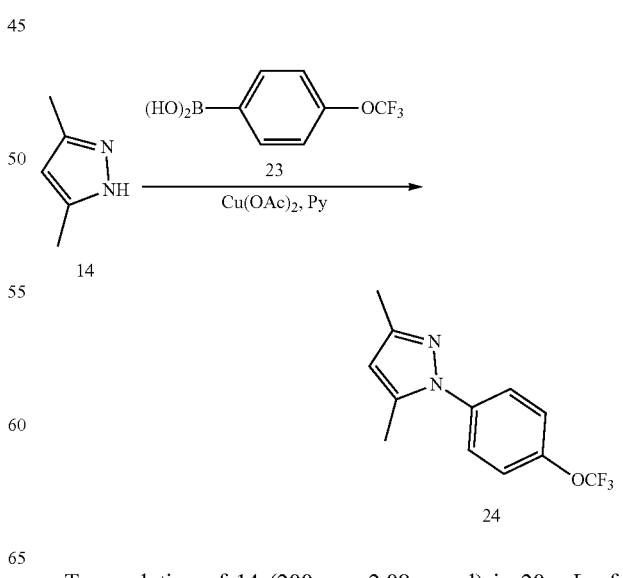

To a solution of 14 (200 mg, 2.08 mmol) in 20 mL of degassed DCM was added successively 23 (857 mg, 4.16 mmol), Cu(OAc)₂ (756 mg, 4.16 mmol), and pyridine (493 mg, 6.24 mmol). The mixture was then degassed for 1 minute under O₂ atmosphere and stirred at room temperature overnight. The reaction mixture was filtered and the filtrate was concentrated and purified by chromatograph column to give the product 24 (460 mg, yield: 86%).

LCMS: m/z 257 (M+H)⁺.

Procedure for Preparation of 2

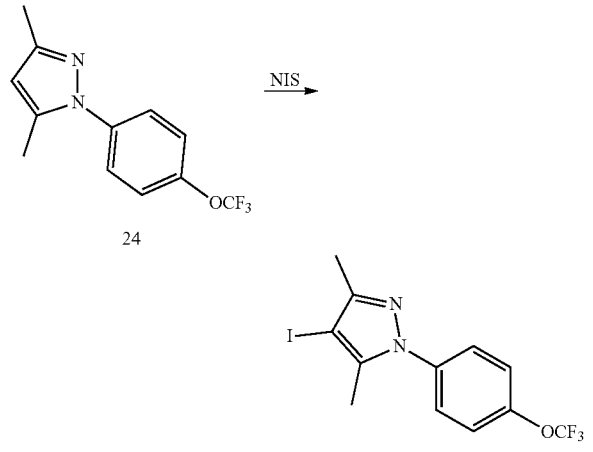

To a solution of 24 (320 mg, 1.25 mmol) in CHCl₃ (50 mL) was added NIS (309 mg, 1.37 mmol). Then the reaction mixture was stirred at reflux for 2 hours. LCMS showed that the reaction was complete, then the reaction mixture was concentrated and purified by chromatograph column to give the product 25 (340 mg, yield: 71%).

LCMS: m/z 383 (M+H)⁺.

Procedure for Preparation of 26

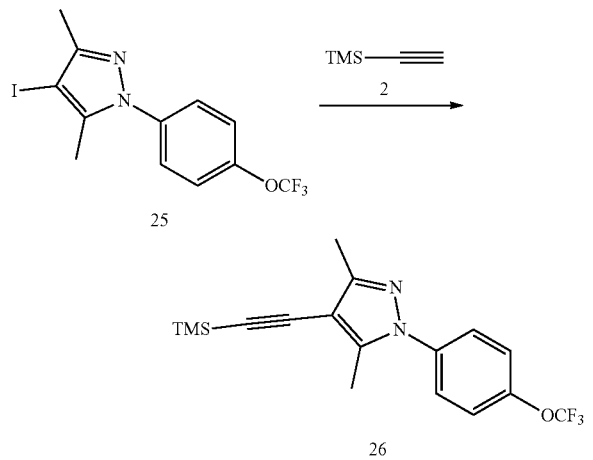

To a solution of 25 (340 mg, 0.89 mmol) in 50 mL of degassed CH₃CN was added successively CuI (17 mg, 0.089 mmol), 2 (175 mg, 1.78 mmol), Pd(PPh₃)₂Cl₂ (62 mg, 0.089 mmol) and Et₃N (270 mg, 2.67 mmol). The mixture was stirred at 70° C. for 18 hours. LCMS showed that the reaction was complete, then the reaction mixture was filtered and the filtrate was concentrated to give the crude product, which was purified by chromatograph column to give the product 26 (280 mg, yield: 89%).

LCMS: m/z 353 (M+H)⁺.

Procedure for Preparation of 27

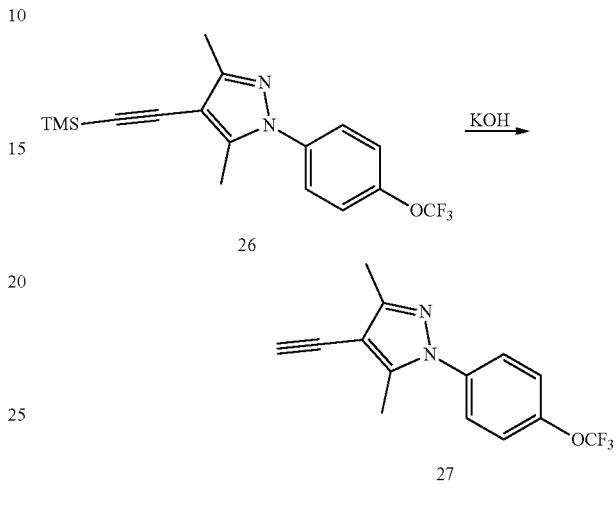

To a solution of 26 (300 mg, 0.85 mmol) in MeOH (10 mL) was added KOH (96 mg, 1.70 mmol). Then the reaction mixture was stirred at room temperature for 1 hour. LCMS showed that the reaction was complete, then the reaction mixture was quenched with water, extracted with DCM (3×20 mL). The combined organic layer was dried over Na₂SO₄, concentrated to give the desired product 27 (500 mg, yield: 86%).

LCMS: m/z 281 (M+H)⁺.

Procedure for Preparation of Compound 4

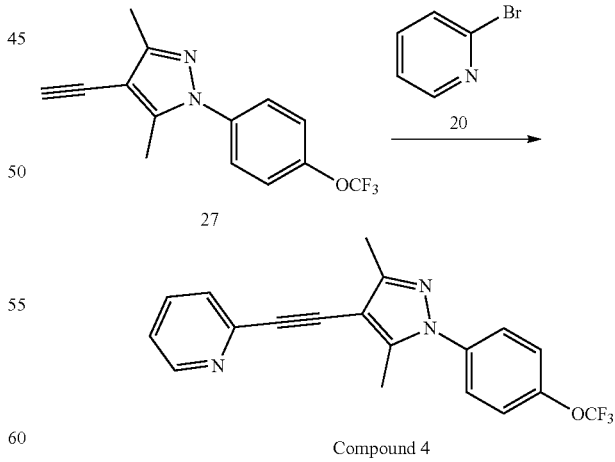

To a solution of 27 (100 mg, 0.36 mmol) in 10 mL of degassed THF (10 ml) was added successively CuI (7 mg, 0.036 mmol), 20 (113 mg, 0.71 mmol), Pd(PPh₃)₂Cl₂ (25 mg, 0.036 mmol) and Et₃N (108 mg, 1.07 mmol). The mixture was stirred at 80° C. for 18 hours. LCMS showed that the reaction was completed, then the reaction mixture was filtered and the filtrate was concentrated and purified by prep-TLC to give the desired product Compound 4 (30 mg, yield: 24%).

LCMS: m/z 358 (M+H)+;

$^1$H NMR (400 MHz, CDCl3): δ8.61 (d, J=4.8 Hz, 1H), 7.68-7.67 (m, 1H), 7.50-7.48 (m, 3H), 7.33-7.31 (m, 2H), 7.23-7.22 (m, 1H), 2.47 (s, 3H), 2.42 (s, 3H).

Example Compound 5

Preparation of 3-(3, 5-dimethyl-4-(2-(pyridin-2-yl)ethyl)-1H-pyrazol-1-yl)-5-fluorobenzonitrile

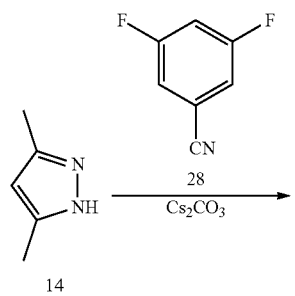

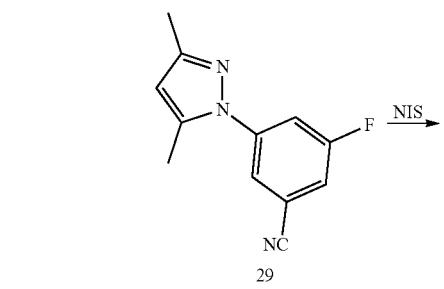

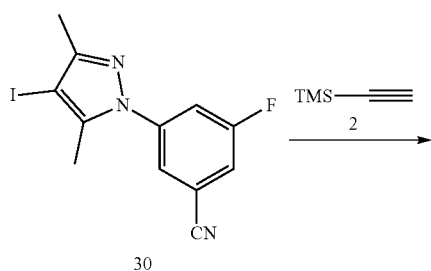

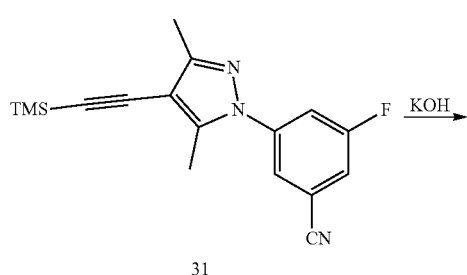

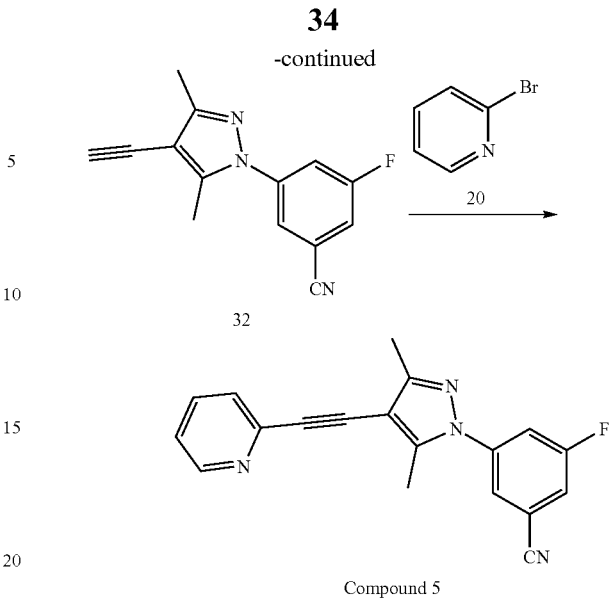

Compound 5

Experimental Section

Procedure for Preparation of 29

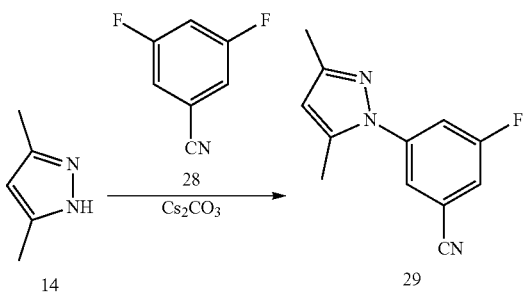

To a solution of 14 (500 mg, 5.20 mmol) in 20 mL of degassed DMF was added successively 28 (1.09 g, 7.80 mmol) and Cs$_2$CO$_3$ (3.39 g, 10.40 mmol). The mixture was heated to 120° C. and stirred for 2 hours. LCMS showed that the reaction was completed, then the reaction mixture was filtered and the filtrate was concentrated to give the product 29, which was purified by chromatograph column (800 mg, yield: 74%).

LCMS: n/z 216 (M+H)+.

Procedure for Preparation of 30

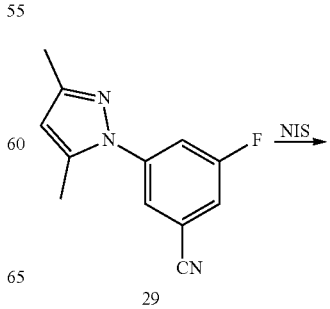

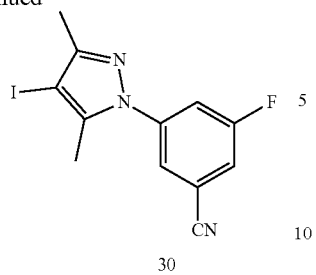

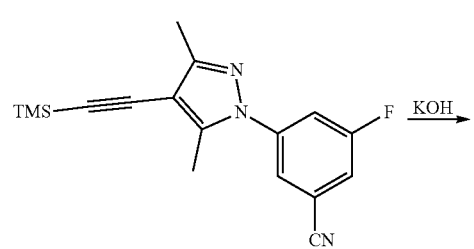

To a solution of 29 (730 mg, 3.39 mmol) in CHCl₃ (50 mL) was added NIS (839 mg, 3.73 mmol). Then the reaction mixture was stirred at reflux for 2 hours. LCMS showed that the reaction was complete, then the reaction mixture was concentrated and purified by chromatograph column to give the desired product 30 (700 mg, yield: 61%).

LCMS: n/z 342 (M+H)⁺.

Procedure for Preparation of 31

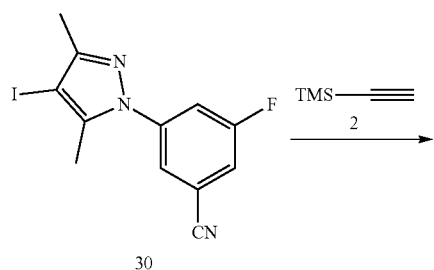

To a solution of 31 (700 mg, 2.05 mmol) in 50 mL of degassed CH₃CN was added successively CuI (39 mg, 0.205 mmol), 2 (403 mg, 4.10 mmol), and Pd(PPh₃)₂Cl₂ (144 mg, 0.205 mmol) and Et₃N (623 mg, 6.16 mmol). The mixture was stirred at 70° C. for 18 hours. LCMS showed that the reaction was completed, then the reaction mixture was filtered and the filtrate was concentrated to give the crude product, which was purified by chromatograph column to give the product 31 (600 mg, yield 94%).

LCMS: m/z 312 (M+H)⁺.

Procedure for Preparation of 32

To a solution of 31 (600 mg, 1.93 mmol) in MeOH (10 mL) was added KOH (216 mg, 3.85 mmol). Then the reaction mixture was stirred at room temperature for 1 h. LCMS showed that the reaction was completed, then the reaction mixture was quenched with water, extracted with DCM (3×20 mL). The combined organic layer was dried over Na₂SO₄, concentrated to give the desired product 32 (310 mg, yield 67%).

LCMS: m/z 240 (M+H)⁺.

Procedure for Preparation of Compound 5

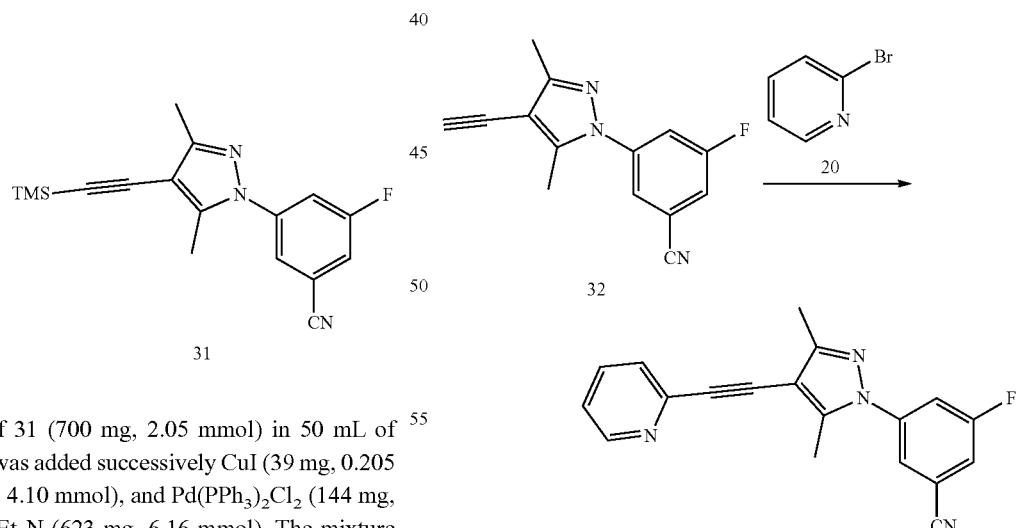

To a solution of 32 (100 mg, 0.42 mmol) in 10 mL of degassed THF (10 ml) was added successively CuI (8 mg, 0.042 mmol), compound 20 (132 mg, 0.84 mmol), Pd(PPh₃)₂ Cl₂ (29 mg, 0.042 mmol) and Et₃N (127 mg, 1.25 mmol). The mixture was stirred at 80° C. for 18 hours.

LCMS showed that the reaction was completed, then the reaction mixture was filtered and the filtrate was concentrated and purified by prep-TLC to give the product Compound 5 (35 mg, yield: 26%).

LCMS: m/z 317 (M+H)+;

1H NMR (400 MHz, CDCl3): δ 8.61 (d, J=4.4 Hz, 1H), 7.67-7.62 (m, 2H), 7.53-7.48 (m, 2H), 7.35-7.33 (m, 1H), 7.24-7.22 (m, 1H), 2.54 (s, 3H), 2.40 (s, 3H);

Example Compound 6

Preparation of 3-fluoro-5-(5-methoxy-3-methyl-4-(2-(pyridin-2-yl) ethynyl)-1H-pyrazol-1-yl) benzonitrile

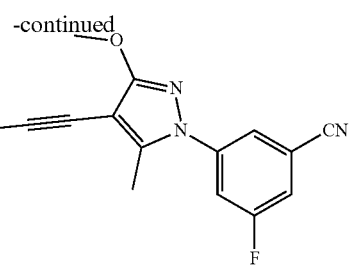

Compound 6

Experimental Section

Procedure for Preparation of 36

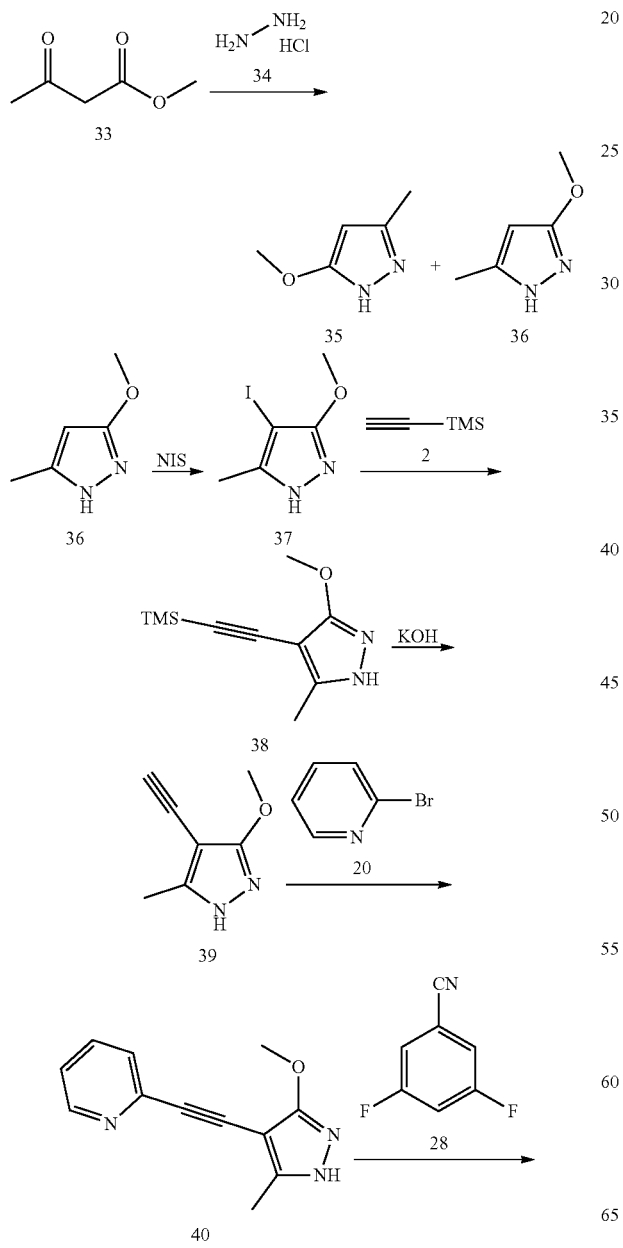

To a solution of 33 (10.00 g, 86.12 mmol) in MeOH (150 mL) was added 34 (9.49 g, 90.43 mmol). Then the reaction mixture was stirred at reflux for 18 hours. The reaction mixture was concentrated and the obtained residue was treated with saturated NaHCO3 solution (200 mL), extracted with DCM (3×150 mL), the combined organic layer was dried over Na2SO4, filtered and concentrated to give two products 35 and 36, by separating them to get the desired product 36 (3.32 g, yield 34%).

1H NMR (400 MHz, CDCl3): δ 5.48 (s, 1H), 3.86 (s, 3H), 2.23 (s, 3H).

Procedure for Preparation of 37

To a solution of 36 (3.32 g, 29.61 mmol) in CHCl3 (50 mL) was added NIS (7.33 g, 32.57 mmol). Then the reaction mixture was stirred at reflux for 2 hours. LCMS showed that the reaction was complete, then the reaction mixture was concentrated to give the desired product 37, which was used in the next step without further purification (7.1 g, crude).

LCMS: m/z 239 (M+H)+.

Procedure for Preparation of 38

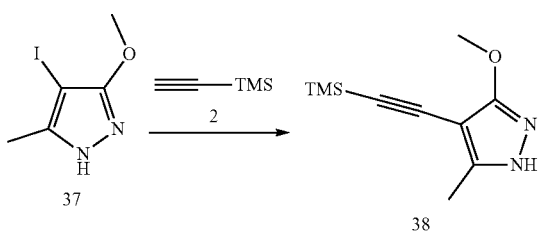

To a solution of compound 37 (3.20 g, 13.44 mmol) in 60 mL of degassed CH$_3$CN was added successively CuI (0.26 g, 1.34 mmol), 2 (2.64 g, 26.89 mmol), and Pd(PPh$_3$)$_2$Cl$_2$ (0.94 g, 1.34 mmol) and Et$_3$N (4.08 g, 40.33 mmol). The mixture was stirred at 70° C. for 18 hours. LCMS showed that the reaction was completed, then the reaction mixture was filtered and the filtrate was concentrated to give the product 38, which was purified by chromatograph column (910 mg, yield 32%).

LCMS: m/z 209 (M+H)$^+$.

Procedure for Preparation of 39

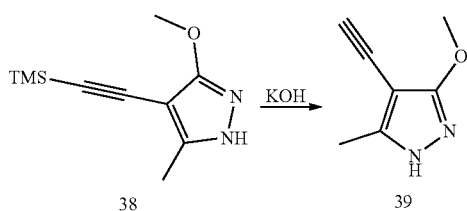

To a solution of 38 (900 mg, 4.37 mmol) in MeOH (20 mL) was added KOH (490 mg, 8.74 mmol). Then the reaction mixture was stirred at room temperature for 1 hour. LCMS showed that the reaction was completed, then the reaction mixture was quenched with water, extracted with DCM (3×20 mL). The combined organic layer was dried over Na$_2$SO$_4$, concentrated to give the desired product 39 (380 mg, yield 64%).

LCMS: m/z 273 (M+H)$^+$.

Procedure for Preparation of 40

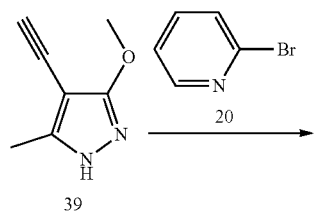

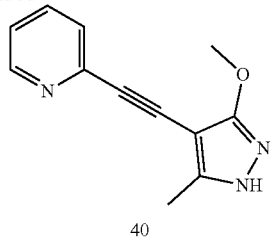

To a solution of 39 (380 mg, 2.79 mmol) in 20 mL of degassed THF was added successively CuI (53 mg, 0.28 mmol), compound 20 (882 mg, 5.58 mmol), and Pd(PPh$_3$)$_2$Cl$_2$ (196 mg, 0.28 mmol) and Et$_3$N (847 mg, 8.37 mmol). The mixture was stirred at 80° C. for 18 hours. LCMS showed that the reaction was completed, then the reaction mixture was filtered and the filtrate was concentrated and purified by prep-TLC to give the product 40 (320 mg, yield 54%).

LCMS: m/z 214 (M+H)$^+$.

Procedure for Preparation of Compound 6

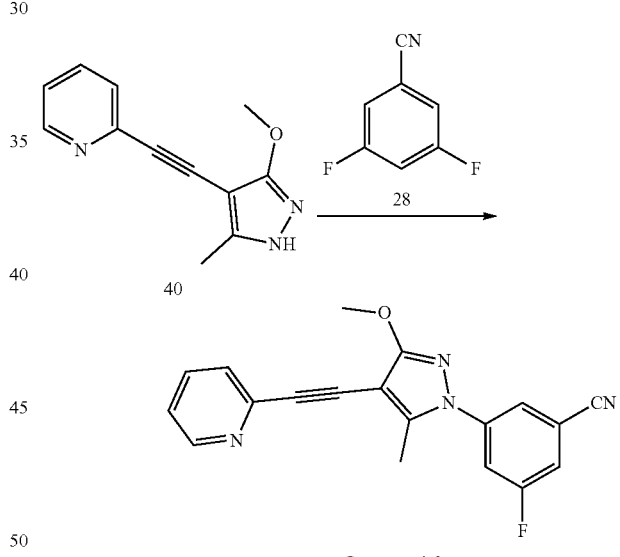

Compound 6

To a solution of 40 (100 mg, 0.47 mmol) in 5 mL of degassed DMF was added successively compound 28 (98 mg, 0.70 mmol) and Cs$_2$CO$_3$ (458 mg, 1.41 mmol). The mixture was heated to 120° C. and stirred for 2 hours. LCMS showed that the reaction was completed, then the reaction mixture was filtered and the filtrate was concentrated to give the product Compound 6, which was purified by prep-HPLC (36 mg, yield 23%).

LCMS: m/z 333 (M+H)$^+$;

$^1$H NMR (400 MHz, CDCl3): δ 8.61 (d, J=3.2 Hz, 1H), 7.66-7.63 (m, 2H), 7.53-7.50 (m, 2H), 7.28-7.25 (m, 1H), 7.24-7.22 (m, 1H), 4.01 (s, 3H), 2.54 (s, 3H).

Example Compound 7

Preparation of 2-((3-methoxy-5-methyl-1-(4-(trifluoromethoxy) phenyl)-1H-pyrazol-4-yl) ethynyl) pyridine

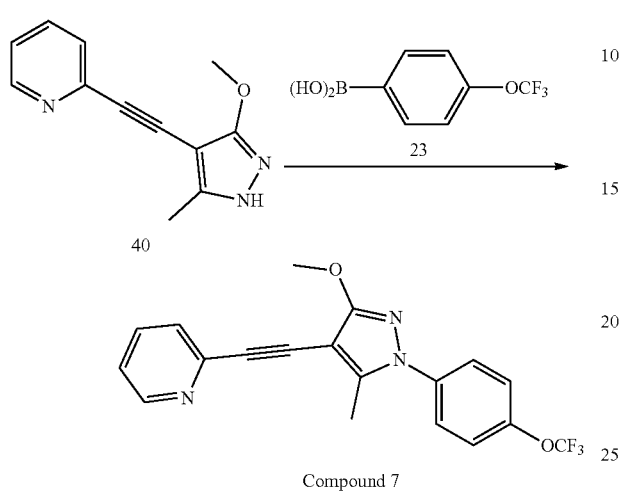

Compound 7

Experimental Section

Procedure for Preparation of Compound 7

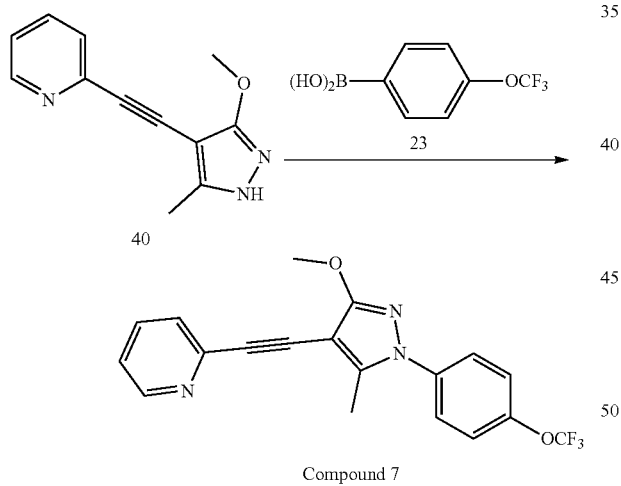

Compound 7

To a solution of 40 (100 mg, 0.47 mmol) in 10 mL of DCM was added successively compound 23 (193 mg, 0.94 mmol), Cu(OAc)$_2$ (170 mg, 0.94 mmol), and pyridine (111 mg, 1.41 mmol). The mixture was then degassed for 1 minute under O$_2$ atmosphere and stirred at room temperature overnight. After the reaction was complete, the reaction mixture was filtered and the filtrate was concentrated and purified by chromatograph column to give the desired product Compound 7 (42 mg, yield 24%).

LCMS: m/z 374 (M+H)$^+$;

$^1$H NMR (400 MHz, CDCl3): δ 8.58 (d, J=4.4 Hz, 1H), 7.71-7.63 (m, 3H), 7.43-7.41 (m, 1H), 7.24-7.16 (m, 3H), 4.40 (s, 3H), 2.37 (s, 3H).

Example Compound 8

Preparation 2-((1-(4-fluorophenyl)-3-methoxy-5-methyl-1H-pyrazol-4-yl)ethynyl)pyridine

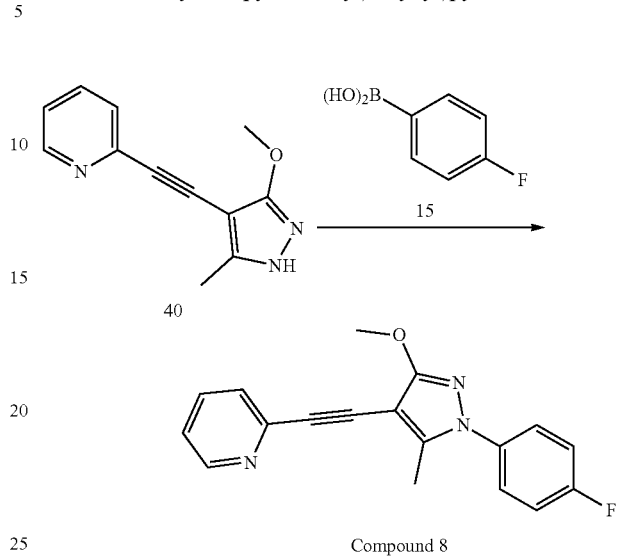

Compound 8

Experimental Section

Procedure for Preparation of Compound 8

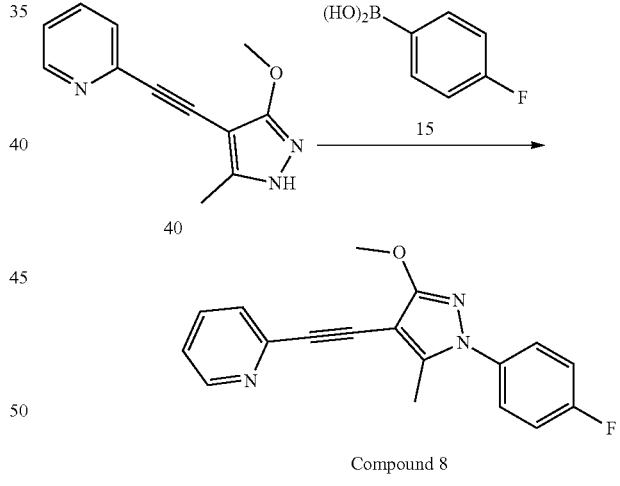

Compound 8

To a solution of 40 (100 mg, 0.47 mmol) in 10 mL of DCM was added successively 15 (131 mg, 0.94 mmol), Cu(OAc)$_2$ (170 mg, 0.94 mmol), and pyridine (111 mg, 1.41 mmol). The mixture was then degassed for 1 minute under O$_2$ atmosphere and stirred at room temperature overnight. After the reaction was complete, the reaction mixture was filtered and the filtrate was concentrated and purified by chromatograph column to give the desired product Compound 8 (50 mg, yield 35%).

LCMS: m/z 308 (M+H)$^+$;

$^1$H NMR (400 MHz, CDCl3): δ 8.58 (s, 1H), 7.63-7.61 (m, 1H), 7.49-7.39 (m, 3H), 7.17-7.13 (m, 3H), 3.99 (s, 3H), 2.39 (s, 3H).

Example Compound 9

Preparation 2-((1-(4-fluorophenyl)-5-methoxy-3-methyl-1H-pyrazol-4-yl)ethynyl)pyridine

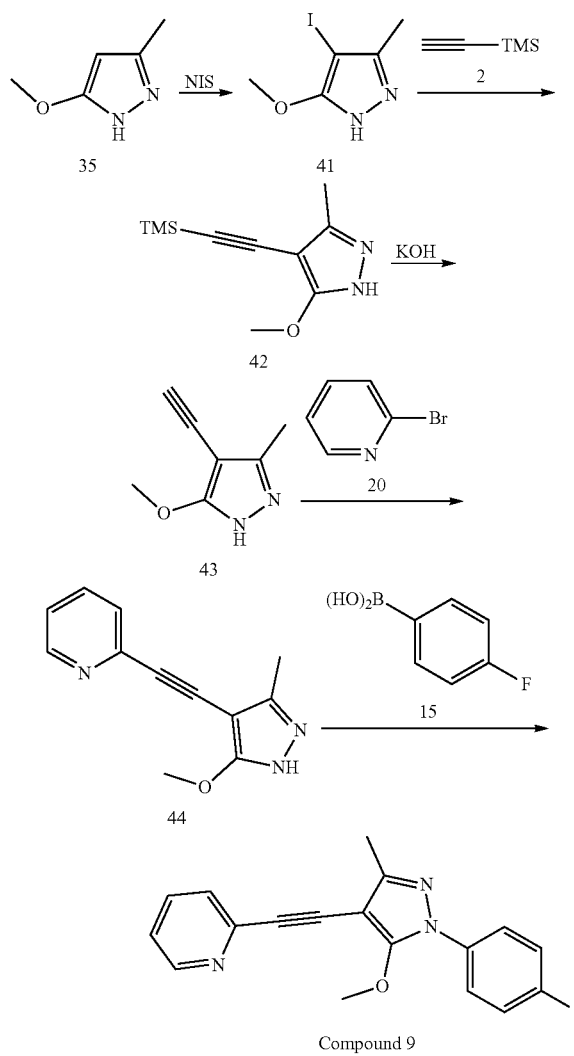

Experimental Section

Procedure for Preparation of 41

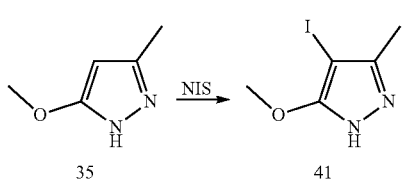

To a solution of compound 35 (3.32 g, 29.61 mmol) in CHCl$_3$ (50 mL) was added NIS (7.33 g, 32.57 mmol). Then the reaction mixture was stirred at reflux for 2 hours. LCMS showed that the reaction was completed. The reaction mixture was concentrated to give the desired product 41, which was used in the next step without further purification (7.1 g, crude).

LCMS: m/z 239 (M+H)$^+$.

Procedure for Preparation of 42

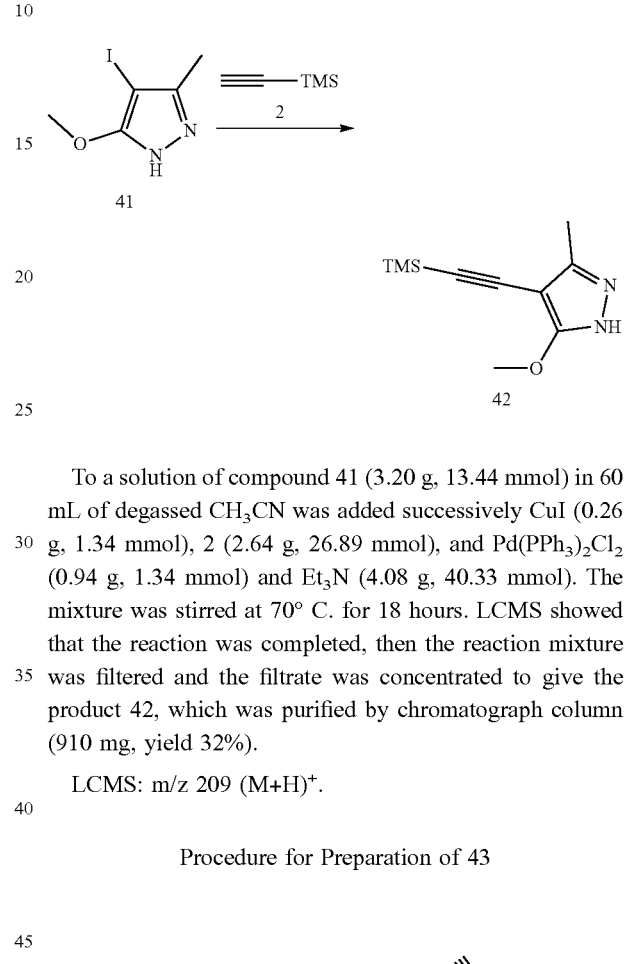

To a solution of compound 41 (3.20 g, 13.44 mmol) in 60 mL of degassed CH$_3$CN was added successively CuI (0.26 g, 1.34 mmol), 2 (2.64 g, 26.89 mmol), and Pd(PPh$_3$)$_2$Cl$_2$ (0.94 g, 1.34 mmol) and Et$_3$N (4.08 g, 40.33 mmol). The mixture was stirred at 70° C. for 18 hours. LCMS showed that the reaction was completed, then the reaction mixture was filtered and the filtrate was concentrated to give the product 42, which was purified by chromatograph column (910 mg, yield 32%).

LCMS: m/z 209 (M+H)$^+$.

Procedure for Preparation of 43

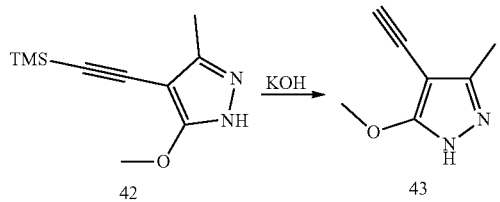

To a solution of compound 42 (900 mg, 4.37 mmol) in MeOH (20 mL) was added KOH (490 mg, 8.74 mmol). Then the reaction mixture was stirred at room temperature for 1 hour. LCMS showed that the reaction was completed. The reaction mixture was quenched with water, extracted with DCM (3×20 mL). The combined organic layer was dried over Na$_2$SO$_4$, concentrated to give the desired product 43 (380 mg, yield 64%).

LCMS: m/z 273 (M+H)$^+$.

Procedure for Preparation of 44

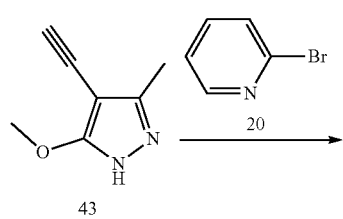

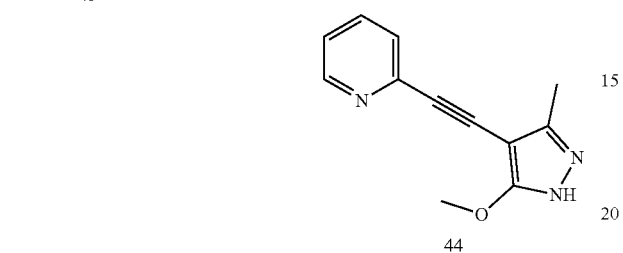

To a solution of compound 43 (380 mg, 2.79 mmol) in 20 mL of degassed THF was added successively CuI (53 mg, 0.28 mmol), 20 (882 mg, 5.58 mmol), and Pd(PPh₃)₂Cl₂ (196 mg, 0.28 mmol) and Et₃N (847 mg, 8.37 mmol). The mixture was stirred at 80° C. for 18 hours. LCMS showed that the reaction was completed, then the reaction mixture was filtered and the filtrate was concentrated and purified by prep-TLC to give the product 44 (320 mg, yield 54%).

LCMS: m/z 214 (M+H)⁺.

Procedure for Preparation of Compound 9

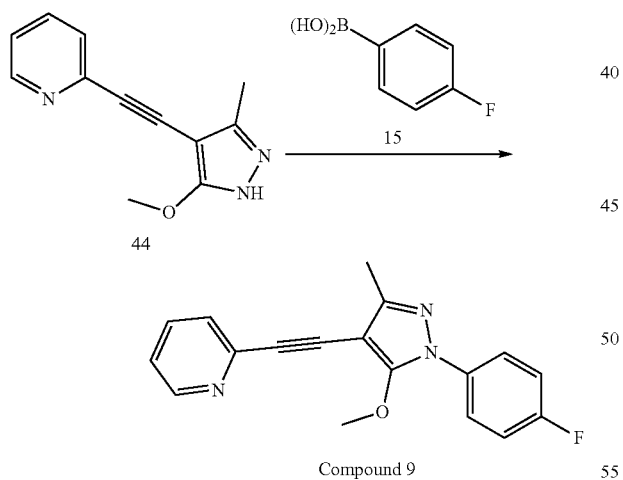

To a solution of 44 (100 mg, 0.47 mmol) in 10 mL of DCM was added successively 15 (131 mg, 0.94 mmol), Cu(OAc)₂ (170 mg, 0.94 mmol), and pyridine (111 mg, 1.41 mmol). The mixture was then degassed for 1 minute under O₂ atmosphere and stirred at room temperature overnight. After the reaction was complete, the reaction mixture was filtered and the filtrate was concentrated and purified by chromatograph column to give the desired product Compound 9 (32 mg, yield 22%).

LCMS: m/z 308 (M+H)⁺;

¹H NMR (400 MHz, CDCl3): δ 8.58 (s, 1H), 7.63-7.61 (m, 1H), 7.49-7.39 (m, 3H), 7.17-7.13 (m, 3H), 4.37 (s, 3H), 2.36 (s, 3H).

Example Compound 10

Preparation of 2-((3-methyl-5-methoxy-1-(4-(trifluoromethoxy) phenyl)-1H-pyrazol-4-yl) ethynyl) pyridine

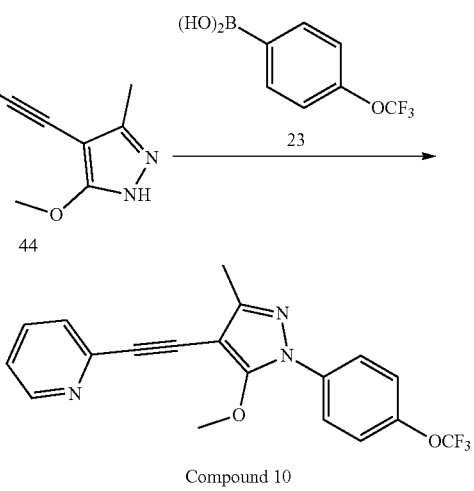

Experimental Section

Procedure for Preparation of Compound 10

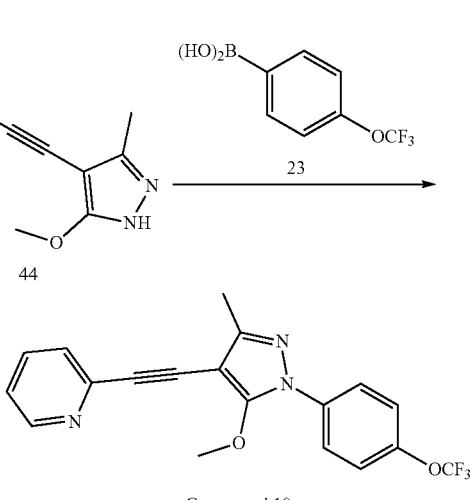

To a solution of 4-((100 mg, 0.47 mmol) in 10 mL of DCM was added successively 23 (193 mg, 0.94 mmol), Cu(OAc)₂ (170 mg, 0.94 mmol), and pyridine (111 mg, 1.41 mmol). The mixture was then degassed for 1 minute under O₂ atmosphere and stirred at room temperature overnight. After the reaction was completed, the reaction mixture was filtered and the filtrate was concentrated and purified by chromatograph column to give the desired product Compound 10 (30 mg, yield 17%).

LCMS: m/z 374 (M+H)+;

$^1$H NMR (400 MHz, CDCl3): δ 8.58 (d, J=4.4 Hz, 1H), 7.64-7.62 (m, 1H), 7.50-7.47 (m, 3H), 7.30-7.29 (m, 2H), 7.18-7.16 (m, 1H), 4.00 (s, 3H), 2.44 (s, 3H).

Example Compound 11

Preparation of 3-fluoro-5-(3-methyl-4-(pyridin-2-ylethynyl)-5-(trifluoromethyl)-1H-pyrazol-1-yl)benzonitrile

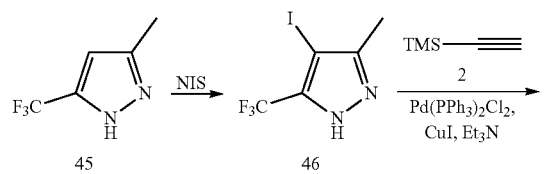

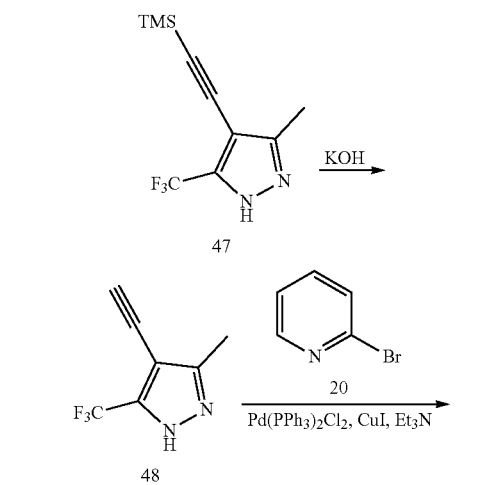

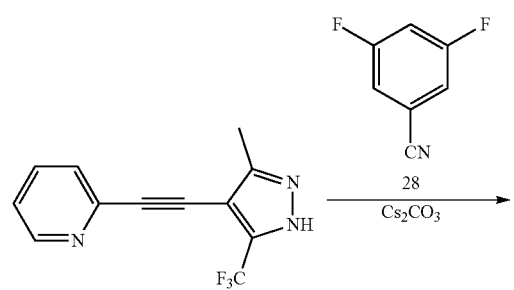

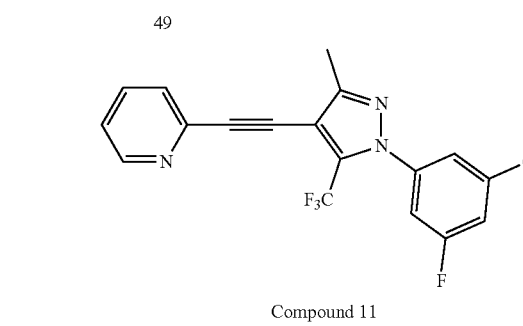

Compound 11

Experimental Section

Procedure for Preparation of 46

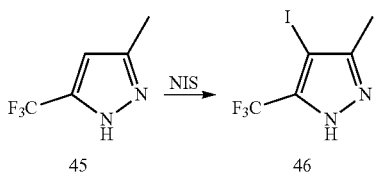

To a solution of compound 45 (1 g, 6.66 mmol) in CHCl$_3$ (10 mL) was added NIS (1.82 g, 7.99 mmol). The mixture was stirred at 60° C. for 2 hours, then reaction mixture was quenched with water and extracted with DCM (2×20 mL). The combined organic layer was concentrated under vacuo and the residue was purified by silica gel chromatography to give the product 46 (1.55 g, 84%).

LCMS: m/z, 277.0 (M+H)+.

Procedure for Preparation of 47

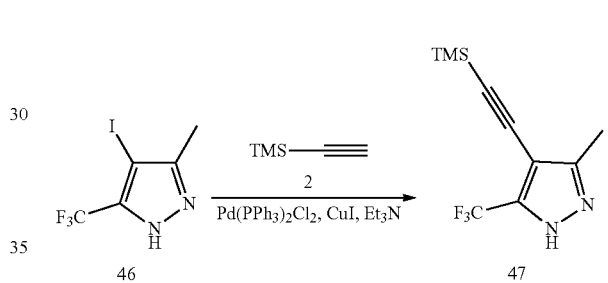

To a solution of compound 46 (1.55 g, 5.62 mmol) in CH$_3$CN (20 mL) was added successively CuI (0.107 g, 0.562 mmol), 2 (1.10 g, 11.23 mmol), and Pd(PPh$_3$)$_2$Cl$_2$ (0.197 g, 0.281 mmol). The mixture was then degassed for 1 minute under N$_2$ atmosphere and was heated at 70° C. for 4 hours. The reaction mixture was filtered, 60 mL of H$_2$O was added into the filtrate, and extracted with EtOAc (3×50 mL). The organic layer was washed with brine (2×30 mL) and dried over anhydrous Na$_2$SO$_4$, filtered and evaporated to give the product 47 (1.3 g, 94%), which was used the next step without further purification.

LCMS: m/z, 247.1 (M+H)+.

Procedure for Preparation of 48

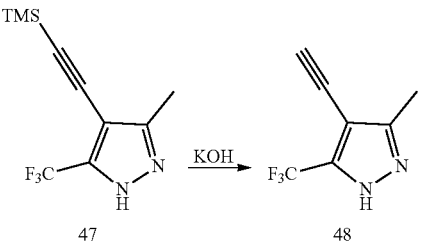

compound 47 (1.5 g, 6.09 mmol) was dissolved in MeOH/CH$_2$Cl$_2$ (20 mL/10 mL), after cooled to 0° C., KOH (0.535 g, 9.54 mmol) was added. The reaction mixture stirred at room temperature for 2 hours, and then quenched with H$_2$O, extracted with EtOAc (3×30 mL). The combined organic layers were dried over anhydrous Na$_2$SO$_4$, filtered and concentrated to give product 48 (1 g, crude).

LCMS: m/z, 175.1 (M+H)$^+$.

Procedure for Preparation of 49

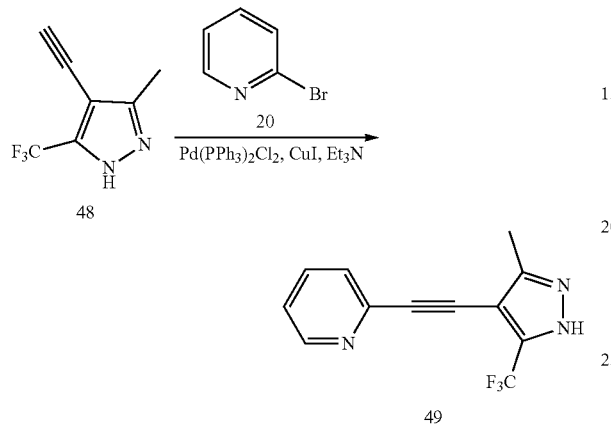

To a solution of 48 (1 g, 5.74 mmol), 20 (1.98 g, 11.49 mmol), CuI (109 mg, 0.574 mmol), Et$_3$N (1.74 g, 17.23 mmol) in THF (30 mL) was added Pd(PPh$_3$)$_2$Cl$_2$ (202 mg, 0.288 mmol). The reaction mixture was stirred at 90° C. overnight, then the mixture was filtered and concentrated by vacuo to give the crude product which was purified by silica gel chromatography to give the product 49 (700 mg, 49%).

LCMS: m/z, 252.1 (M+H)$^+$.

Procedure for Preparation of Compound 11

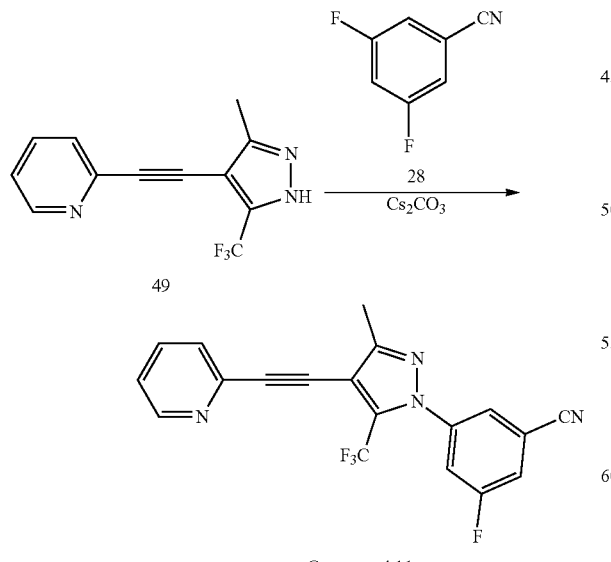

To a solution of 49 (100 mg, 0.398 mmol) in DMF (5 mL) was added 28 (11 mg, 0.796 mmol) and Cs$_2$CO$_3$ (259 mg, 0.796 mmol). The reaction mixture was heated at 110° C. for 2 hours, then filtered and concentrated under vacuo. The residue was purified by prep-TLC to give the desired product Compound 11 (50 mg, 34%).

LCMS: m/z, 371.1 (M+H)$^+$;

$^1$H NMR (400 MHz, CDCl3): δ 8.65-8.64 (s, 1H), 7.72 (m, 1H), 7.67 (m, 1H), 7.59-7.57 (m, 2H), 7.56 (m, 1H), 7.26 (m, 1H), 2.60 (s, 3H).

Example Compound 12

Preparation of 2-((1-(4-fluorophenyl)-3-methyl-5-(trifluoromethyl)-1H-pyrazol-4-yl) ethyny) pyridine

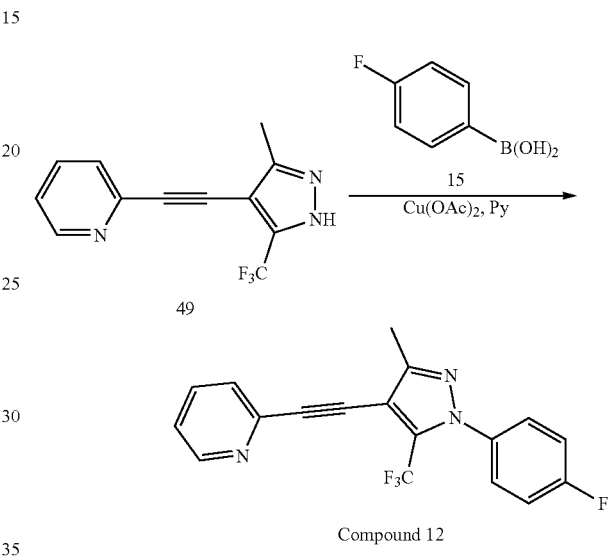

Experimental Section

Procedure for Preparation of Compound 12

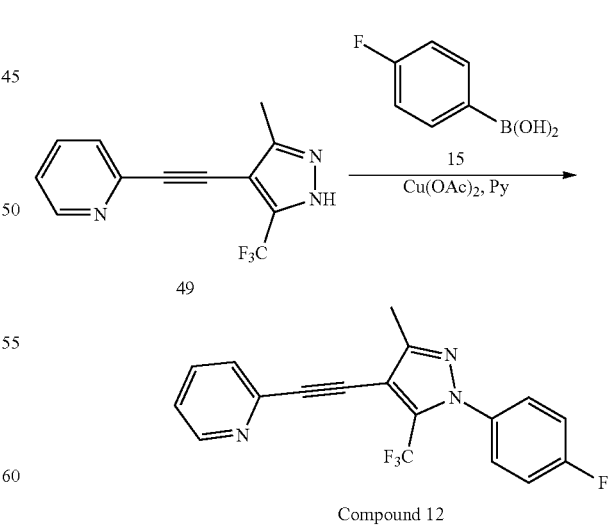

To a solution of compound 49 (100 mg, 0.398 mmol) in DCM (10 mL) was added 15 (111 mg, 0.796 mmol), Cu(OAc)$_2$ (145 mg, 0.796 mmol), pyridine (94 mg, 19 mmol). The reaction mixture was stirred at room temperature overnight under O₂ atmosphere. The mixture was filtered and concentrated under vacuo. The residue was purified by prep-TLC to give the desired product Compound 12 (50 mg, 36%).

LCMS: m/z, 346.1 (M+H)⁺;

¹H NMR (400 MHz, CDCl3): δ 8.57-8.56 (m, 1H), 7.63 (m, 1H), 7.47 (m, 1H), 7.39-7.37 (m, 2H), 7.19-7.13 (m, 3H), 2.41 (s, 3H).

Example Compound 13

Preparation of 2-((3-methyl-1-(4-(trifluoromethoxy) phenyl)-5-(trifluoromethyl)-1H-pyrazol-4-yl) ethynyl) pyridine

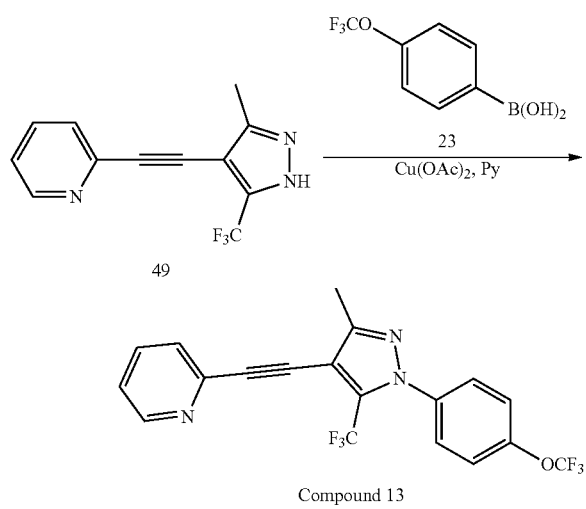

Experimental Section

Procedure for Preparation of Compound 13

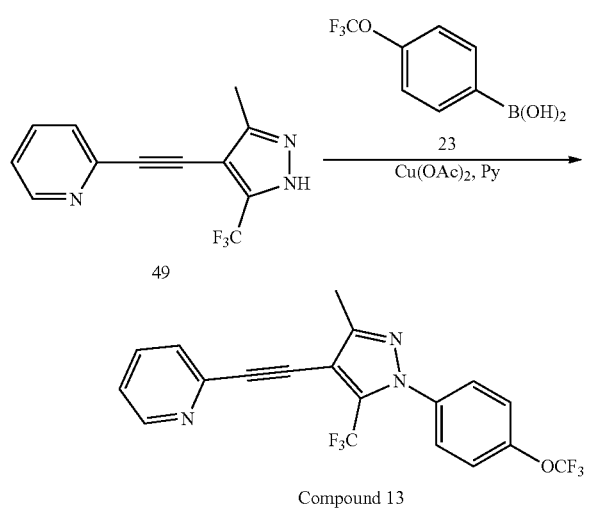

To a solution of 49 (100 mg, 0.398 mmol) in DCM (10 mL) was added 23 (164 mg, 0.796 mmol), Cu(OAc)₂ (145 mg, 0.796 mmol), pyridine (94 mg, 1.19 mmol). The reaction mixture was stirred at room temperature overnight under O₂, then the mixture was filtered and concentrated under vacuo, residue was purified by prep-TLC to give the desired product Compound 13 (50 mg, 31%).

LCMS: m/z, 412.0 (M+H)⁺;

¹H NMR (400 MHz, CDCl3): δ 8.57-8.56 (m, 1H), 7.65-7.62 (m, 1H), 7.48-7.45 (m, 3H), 7.32-7.30 (m, 2H), 7.20-7.19 (m, 1H), 2.45 (s, 3H).

Example Compound 14

Preparation of 2-((3, 5-dimethyl-1-(4-(trifluoromethoxy) phenyl)-1H-pyrazol-4-yl) ethynyl) pyrimidine

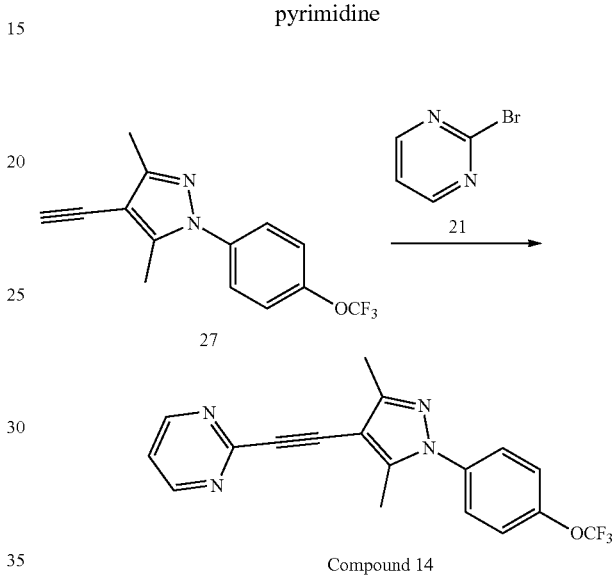

Experimental Section

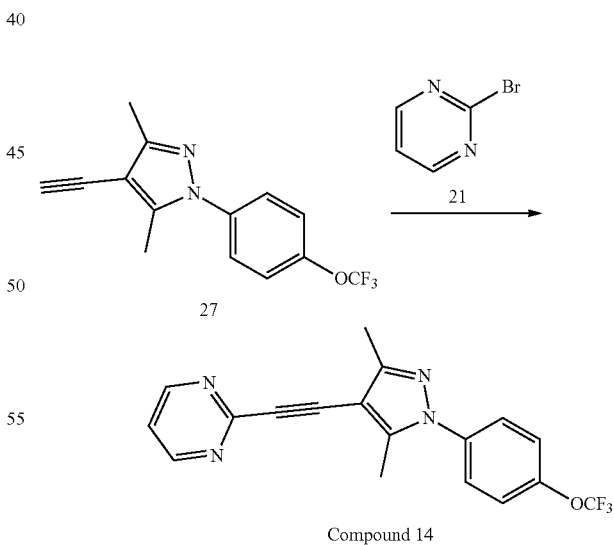

To a solution of 27 (100 mg, 0.36 mmol) in 10 mL of degassed THF (10 ml) was added successively CuI (7 mg, 0.036 mmol), 21 (113 mg, 0.71 mmol), and Pd(PPh₃)₂Cl₂ (25 mg, 0.036 mmol) and Et₃N (108 mg, 1.07 mmol). The mixture was stirred at 80° C. for 18 hours. LCMS showed that the reaction was completed, then the reaction mixture was filtered and the filtrate was concentrated and purified by prep-TLC to give the product Compound 14 (6 mg, yield 5%).
LCMS: m/z 359 (M+H)+;
$^1$H NMR (400 MHz, CDCl3): δ 8.74 (d, J=4.8 Hz, 2H), 7.50-7.48 (m, 2H), 7.34-7.32 (m, 2H), 7.23-7.21 (m, 1H), 2.50 (s, 3H), 2.45 (s, 3H).
Example Compound 15
Preparation of 3-(3-(dimethylaminuteso)-5-methyl-4-(2-(pyridin-2-yl) ethynyl)-1H-pyrazol-1-yl)-5-fluorobenzonitrile
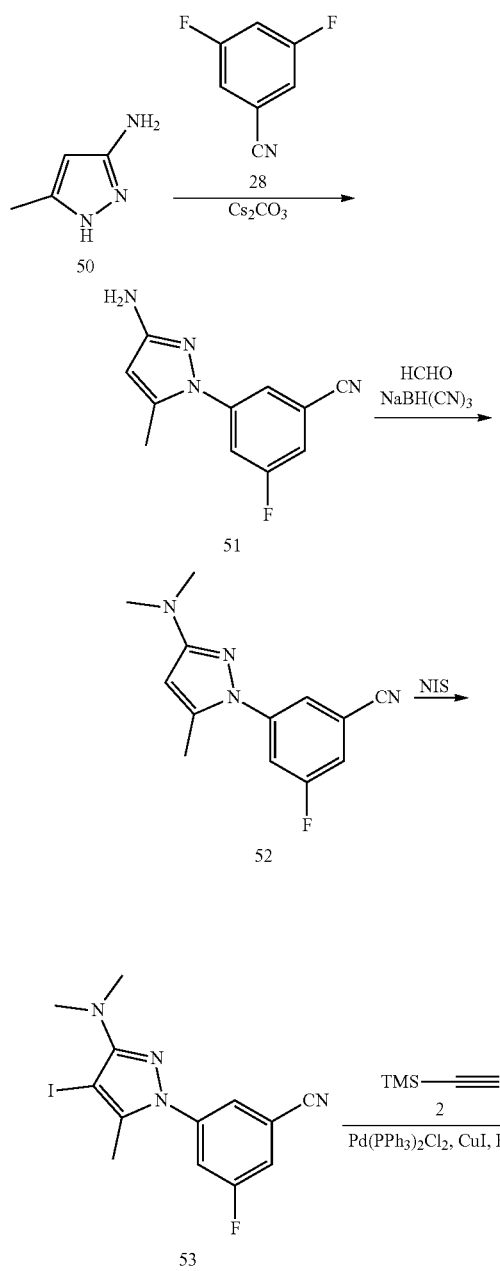
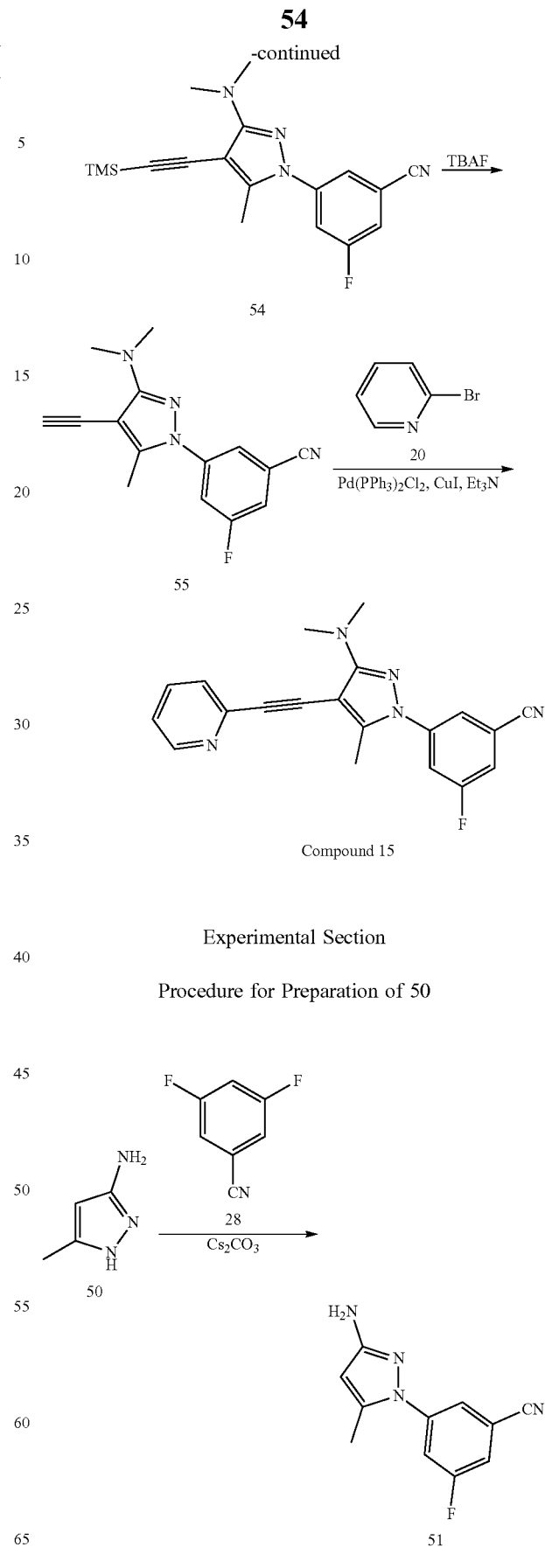
Compound 15
Experimental Section
Procedure for Preparation of 50
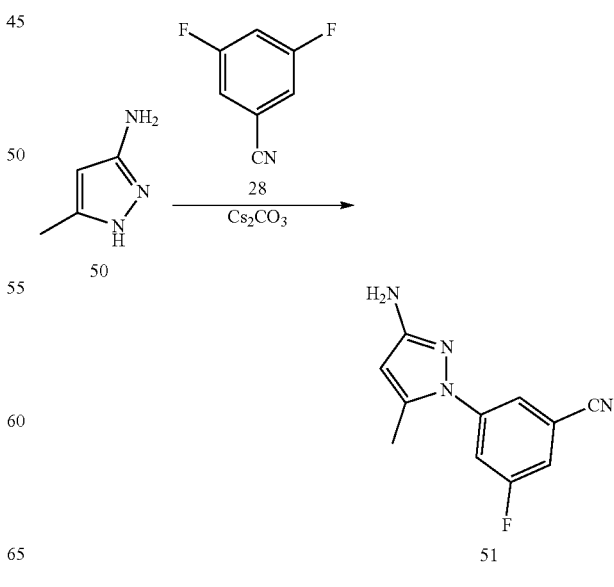

To a solution of 50 (500 mg, 5.15 mmol) in DMF (10 mL) was added 28 (1430 mg, 10.30 mmol) and $Cs_2CO_3$ (3350 g, 10.30 mmol). The reaction mixture was heated at 110° C. for 2 hours, then the mixture was filtered and concentrated under vacuo. The residue was purified by silica gel chromatography to give product 51 (350 mg, 31%).

LCMS: m/z, 217.1 (M+H)⁺.

Procedure for Preparation of 52

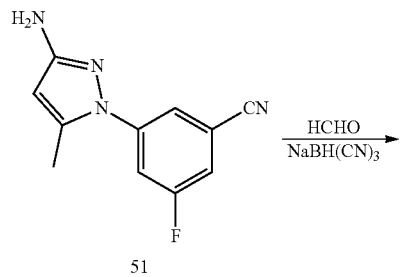

51

To a solution of 51 (500 mg, 2.31 mmol) in MeOH (15 mL) was added HCHO (37% in $H_2O$) (15 mL) and AcOH (1 mL). The mixture was stirred at room temperature overnight, then $NaBH(CN)_3$ (783 mg, 6.94 mmol) was added to the mixture which was stirred for another 1 hour. The mixture was diluted with DCM, the organic layer was separated, concentrated and purified by silica gel chromatography to give product 52 (150 mg, 27%).

$^1$H NMR (400 MHz, CDCl3): δ 7.62 (s, 1H), 7.54-7.51 (m, 1H), 7.19-7.17 (m, 1H), 5.72 (s, 1H), 2.90 (s, 6H), 2.40 (s, 3H).

Procedure for Preparation of 53

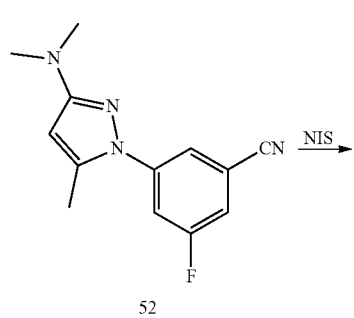

52

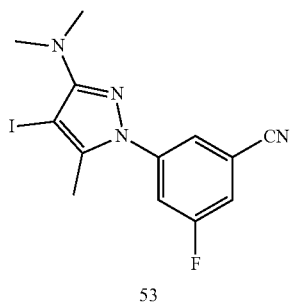

53

To a solution of 52 (100 mg, 0.410 mmol) in $CHCl_3$ (10 mL) was added NIS (110 mg, 0.492 mmol). The reaction mixture was stirred at 60° C. for 2 hours, then the mixture was quenched with water and extracted with DCM (2×20 mL). The combined organic layer was concentrated under vacuo and the residue was purified by prep-TLC to give product 53 (120 mg, 79%).

LCMS: m/z, 371.0 (M+H)⁺.

Procedure for Preparation of 54

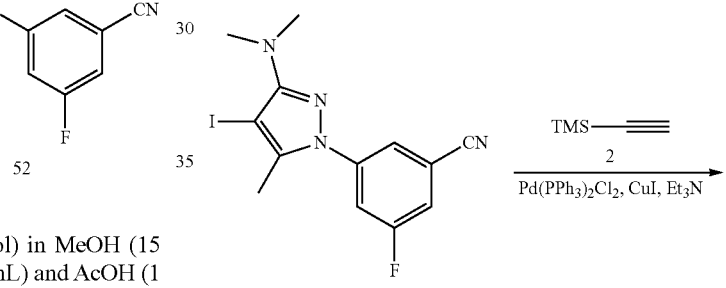

53

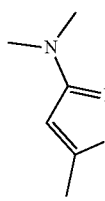

54

To a solution of 53 (120 mg, 0.324 mmol) in $CH_3CN$ (10 mL) was added successively CuI (6 mg, 0.032 mmol), 2 (64 mg, 0.648 mmol), $Pd(PPh_3)_2Cl_2$ (11 mg, 0.016 mmol) and $Et_3N$ (98 mg, 0.972 mmol). The mixture was then degassed for 1 minute under $N_2$ atmosphere and was heated at 70° C. for 7 hours. The reaction mixture was filtered and concentrated by vacuo and the residue was purified prep-TLC to give product 54 (110 mg, 100%).

LCMS: m/z, 341.1 (M+H)⁺.

Procedure for Preparation of 55

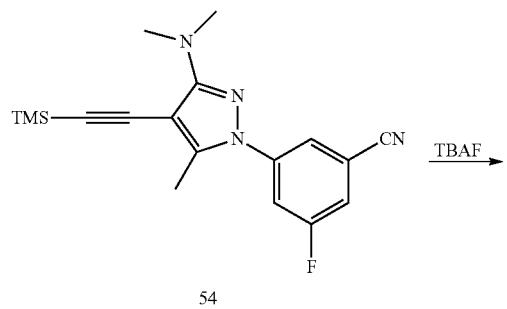

Compound 54 (100 mg, 0.294 mmol) was dissolved in THF (8 mL). TBAF (1M in THF) (0.44 mL, 0.44 mmol) was added to the solution dropwise. The reaction mixture stirred at room temperature for 1 hour. The mixture was extracted with EA. The combined organic layer was concentrated by vacuo and purified with prep-TLC to give product 55 (70 mg, 89%).

Procedure for Preparation of Compound 15

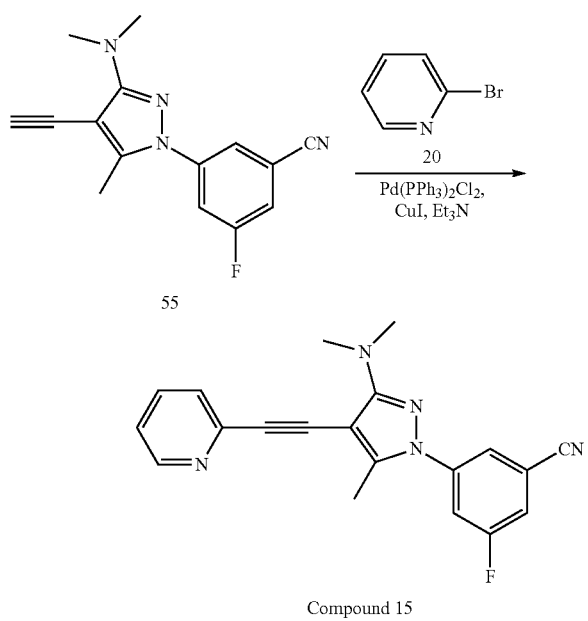

To a solution of 55 (70 mg, 0.261 mmol), 20 (82 mg, 0.522 mmol), CuI (5 mg, 0.026 mmol), Et₃N (79 mg, 0.783 mmol) in THF (5 mL) Pd(PPh₃)₂Cl₂ (9 mg, 0.013 mmol) was added. The mixture was microwaved at 90° C. for 1 hour, then the mixture was filtered and concentrated under vacuo. The residue was purified by prep-TLC to give the desired product Compound 15 (20 mg, 22%).

LCMS: m/z, 346.2 (M+H)⁺;
¹H NMR (400 MHz, CDCl3): δ 8.61-8.60 (m, 1H), 7.66-7.64 (m, 2H), 7.54-7.52 (m, 1H), 7.45-7.43 (m, 1H), 7.24-7.21 (m, 2H), 3.12 (s, 6H), 2.54 (s, 3H).

Example Compound 16

Preparation of 2-(3-(dimethylaminuteso)-5-methyl-1-(4-(trifluoromethoxy)phenyl)-1H-pyrazol-4-yl) ethynyl)pyridine

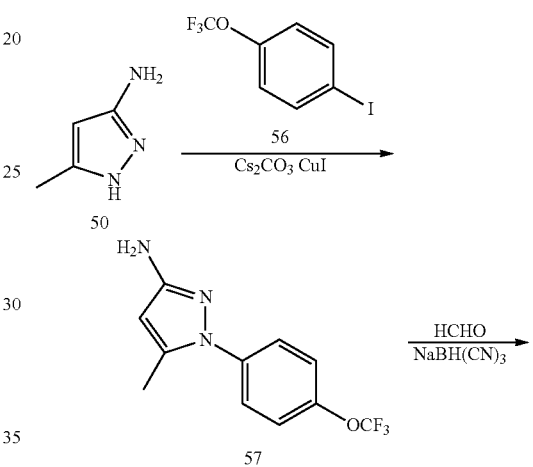

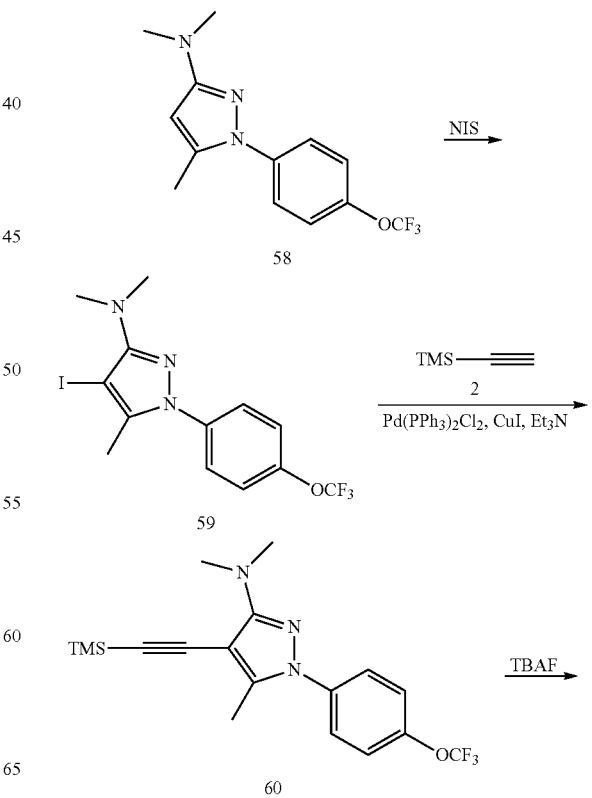

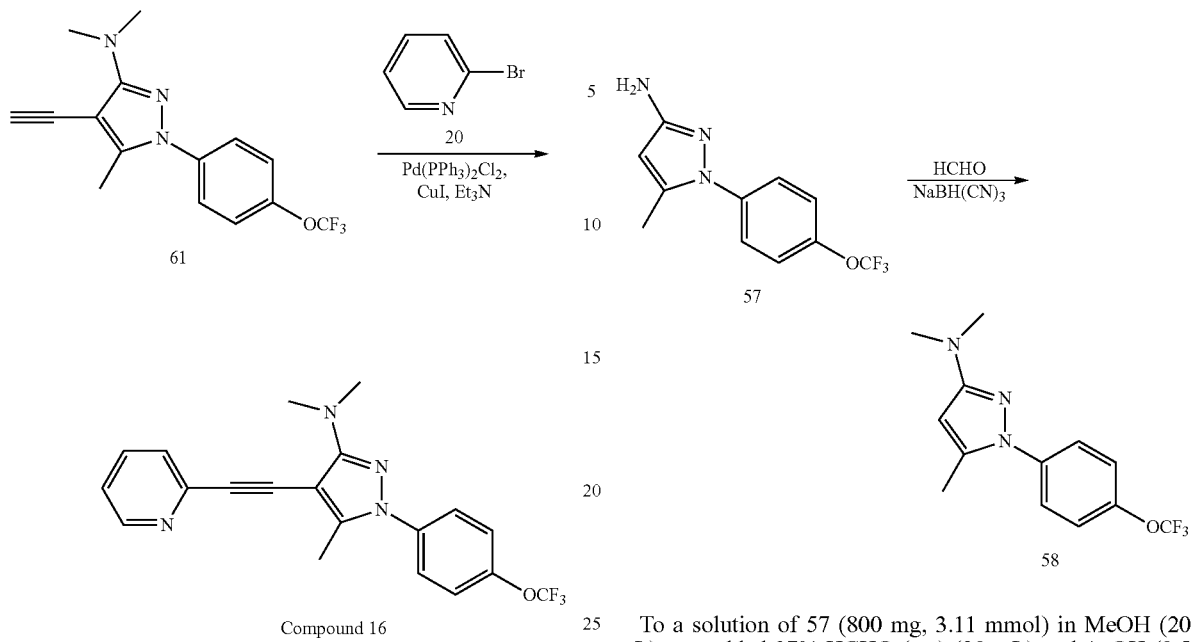

Experimental Section

Procedure for Preparation of 57

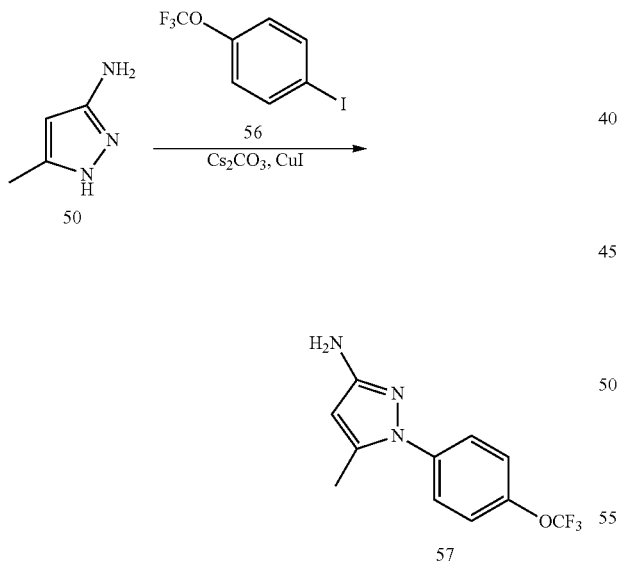

To a solution of 50 (1.56 g, 16.06 mmol) in DMF (50 mL) was added 56 (5.09 g, 17.67 mmol), CuI (306 mg, 1.61 mmol), Cs$_2$CO$_3$ (10.47 g, 32.13 mmol). The mixture was stirred at 110° C. for 5 hours under N$_2$ atmosphere, then the mixture was filtered and concentrated to give the crude product which was purified by silica gel chromatography to give product 57 (800 mg, 19%).

LCMS: r/z, 259.1 (M+H)$^+$.

Procedure for Preparation of 58

To a solution of 57 (800 mg, 3.11 mmol) in MeOH (20 mL) was added 37% HCHO (aq.) (20 mL) and AcOH (0.5 mL). The mixture was stirred at room temperature overnight, then NaBH(CN)$_3$ (1050 mg, 9.33 mmol) was added to the mixture which was stirred for another 1 hours. The mixture was diluted with DCM, the organic layer was separated, concentrated and purified by silica gel chromatography to give product 58 (130 mg, 15%).

LCMS: r/z, 286.1 (M+H)$^+$.

Procedure for Preparation of 59

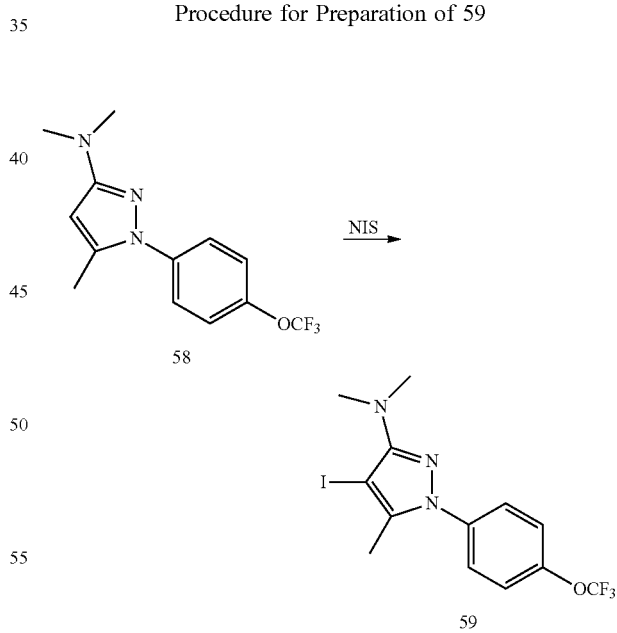

To a solution of 58 (130 mg, 0.456 mmol) in CHCl$_3$ (10 mL) was added NIS (123 mg, 0.547 mmol). The mixture was stirred at 60° C. for 2 hours, then the mixture was quenched with water and extracted with DCM (2×20 mL). The combined organic layer was concentrated under vacuo and the residue was purified by prep-TLC to give the product 59 (130 mg, 69%).

LCMS: r/z, 412.0 (M+H)$^+$.

Procedure for Preparation of 60

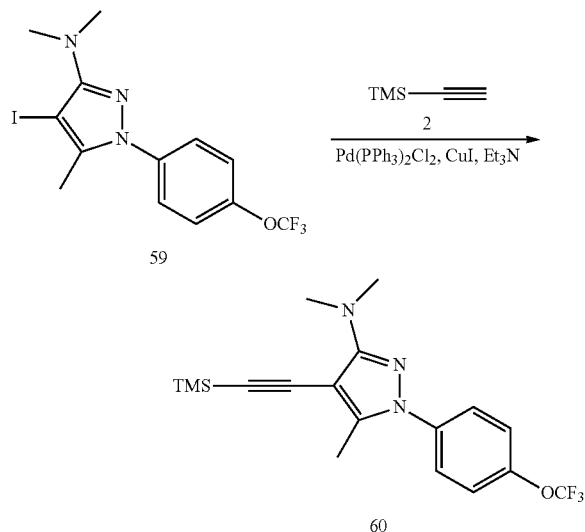

To a solution of 59 (130 mg, 0.316 mmol) in CH$_3$CN (5 mL) was added successively CuI (6 mg, 0.032 mmol), 2 (62 mg, 0.632 mmol), Pd(PPh$_3$)$_2$Cl$_2$ (11 mg, 0.016 mmol) and Et$_3$N (96 mg, 0.949 mmol). The mixture was degassed for 1 minute under N$_2$ atmosphere and was heated at 95° C. for 1 hour under microwave. Then the reaction mixture was filtered and concentrated by vacuo and the residue was purified by prep-TLC to give product 60 (50 mg, 42%).

LCMS: m/z, 382.1 (M+H)$^+$.

Procedure for Preparation of 61

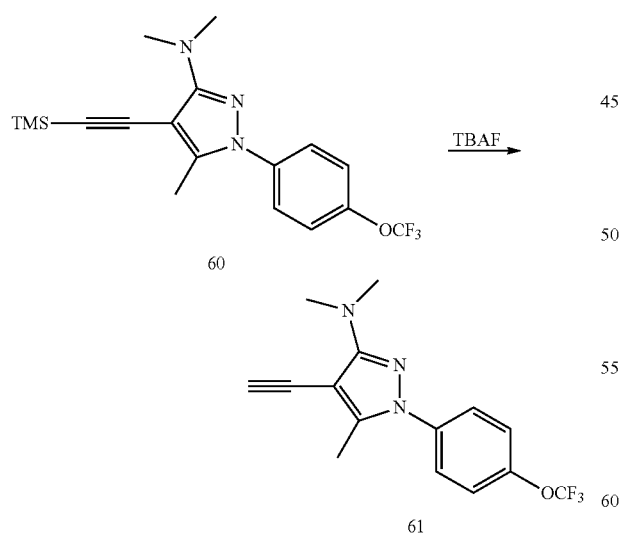

A solution of 60 (50 mg, 0.2131 mmol) in THF (5 mL), TBAF (1M in THF) (0.197 mL, 0.197 mmol) was added to the solution dropwise. The reaction mixture was stirred at room temperature for 1 hour, then the mixture was extracted with EA. The combined organic layer was concentrated by vacuo and purified with prep-TLC to give product 61 (30 mg, 74%).

LCMS: m/z, 310.1 (M+H)$^+$.

Procedure for Preparation of Compound 16

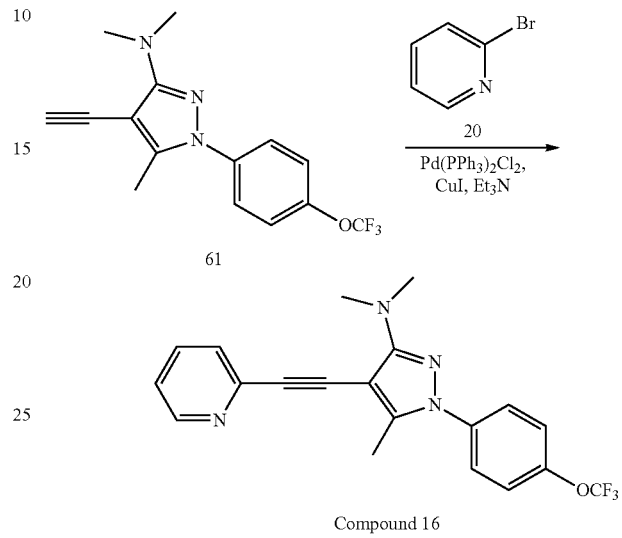

To a solution of 61 (30 mg, 0.097 mmol), 20 (31 mg, 0.194 mmol), CuI (2 mg, 0.010 mmol), and Et$_3$N (29 mg, 0.291 mmol) in THF (3 mL) Pd(PPh$_3$)$_2$Cl$_2$ (3 mg, 0.004 mmol) was added. The mixture was stirred at 90° C. under microwave for 1 hour, then the mixture was filtered and concentrated under vacuo. The residue was purified by prep-HPLC to give the desired product Compound 16 (5 mg, 14%).

LCMS: m/z, 387.1 (M+H)$^+$;
$^1$H NMR (400 MHz, CDCl3): δ 8.62 (s, 1H), 7.65-7.63 (m, 1H), 7.49-7.48 (m, 2H), 7.47-7.46 (m, 1H), 7.28-7.25 (m, 2H), 7.24-7.23 (m, 1H), 3.10 (s, 6H), 2.48 (s, 3H).

Example Compound 17

Preparation of 2-((5-chloro-1-(4-fluorobenzyl)-1H-pyrazol-4-yl) ethynyl) pyrimidine

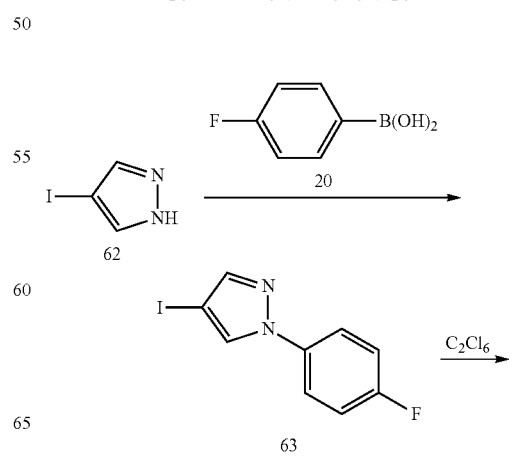

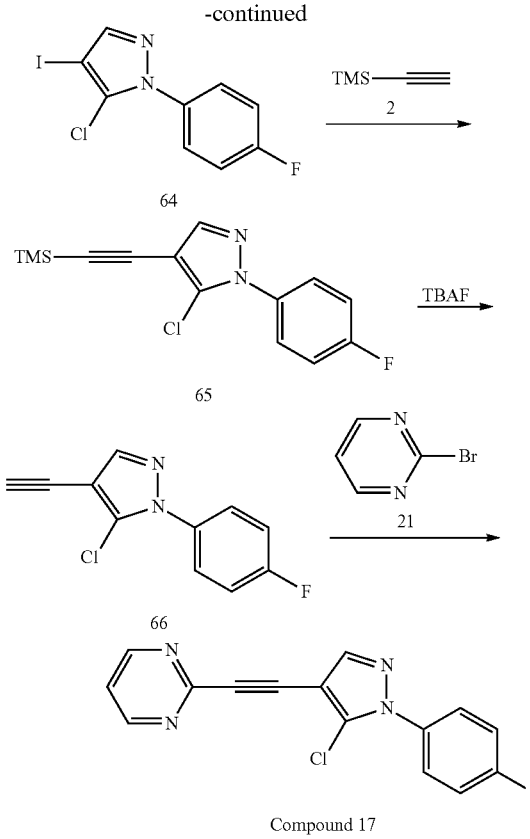

Compound 17

Experimental Section

Procedure for Preparation of 63

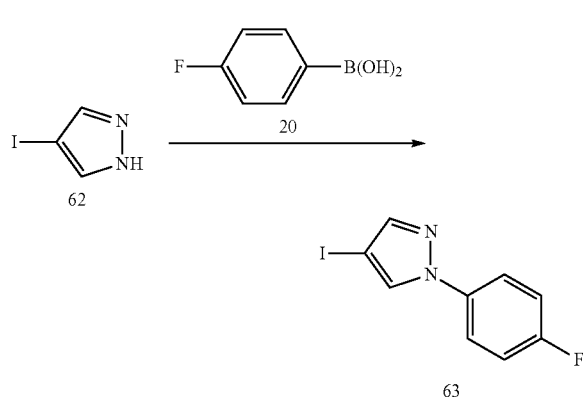

To a solution of 62 (1 g, 5.16 mmol) and 20 (1.08 g, 7.73 mmol) in DCM (20 ml) was added Cu(OAc)₂ (1.87 g, 10.3 mmol) and pyridine (1.22 g, 15.5 mmol) at room temperature under 02 atmosphere. The reaction mixture was stirred at room temperature overnight, then the mixture was filtered and filter cake was washed with DCM (20 ml), The combined organic layers were washed with brine and dried over Na₂SO₄. The crude product was purified by silica gel chromatography to give product 63 (1.1 g, yield: 74%).

¹HNMR (400 MHz, CDCl3): δ7.06~7.10 (m, 2H), 7.49-7.51 (m, 2H), 7.68 (s, 1H), 7.83 (s, 1H).

Procedure for Preparation of 64

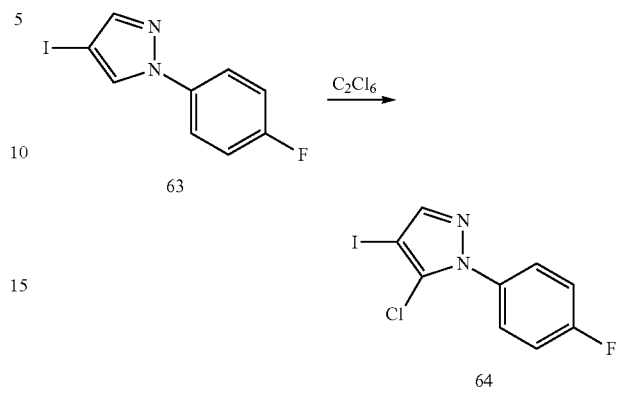

To a solution of 63 (1 g, 3.47 mmol) in 30 mL of degassed THF was added successively, LDA (2.1 mL, 4.17 mmol) at −78° C. After stirring 30 minutes, perchloroethane (0.99 mg, 4.17 mmol) was added. The reaction mixture was stirred at −78° C. for 30 minutes. An aqueous solution of NH₄Cl (5 mL) was added drop-wise into the reaction mixture once the reaction mixture was warmed to room temperature. The mixture was extracted with ethyl acetate (30 mL), organic layer was washed with water, dried over (Na₂SO₄) and evaporated to dryness, which was purified by Prep-TLC to give title product 64 (700 mg, yield: 63%).

¹HNMR (400 MHz, CDCl₃): δ7.06~7.11 (m, 2H), 7.35~7.47 (m, 2H), 7.63 (s, 1H).

Procedure for Preparation of 65

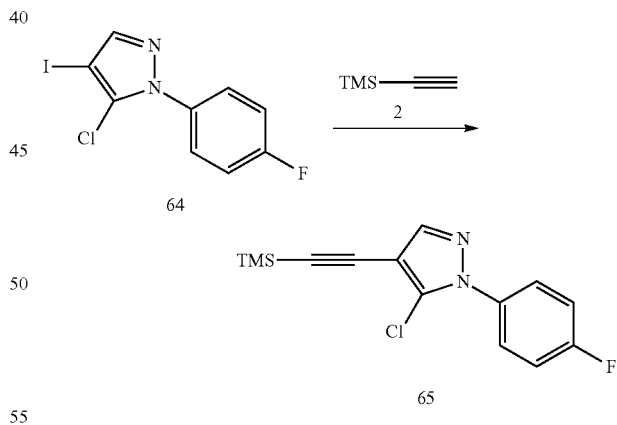

To a solution of 64 (0.7 g, 2.17 mmol), 2 (1.28 g, 13.0 mmol), CuI (41 mg, 0.217 mmol), Et₃N (0.66 g, 6.54 mmol) in THF (20 mL) was added Pd(PPh₃)₂Cl₂ (152 mg, 0.217 mmol). The suspension was degassed under vacuum and purged with N₂ several times. After stirring at 90° C. for 6 hours under N₂ atmosphere, the mixture was filtered and concentrated under vacuo. The residue was purified by prep-TLC to give the product 65 (300 mg, 47%).

¹HNMR (400 MHz, CDCl3): δ₀.₂₁ (s, 9H), 7.12~7.17 (m, 2H), 7.45~7.51 (m, 2H), 7.67 (s, 1H).

Procedure for Preparation of 66

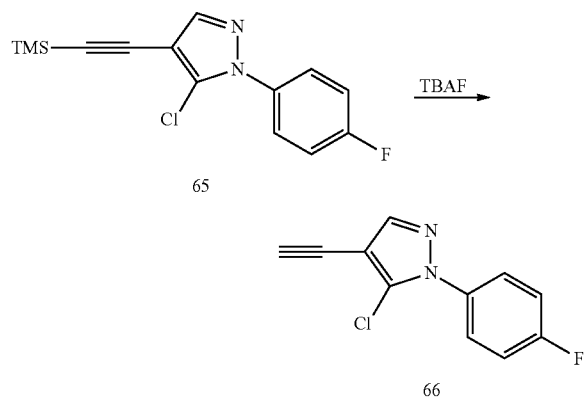

To a solution of 65 (300 mg, 1.02 mmol) in 10 mL of degassed THF was added TBAF (1.54 mL, 1.54 mmol) at room temperature. After stirring 2 hours, the solvent was removed. It was extracted with DCM (20 mL) and washed with brine. The organic layer was dried over $Na_2SO_4$ and purified by Prep-TLC to give title product 66 (200 mg, yield: 88%).

Procedure for Preparation of Compound 17

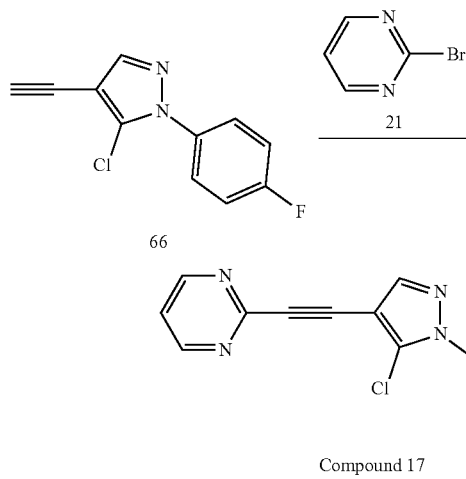

To a solution of 66 (100 mg, 0.45 mmol) and 21 (108 mg, 0.68 mmol), CuI (9 mg, 0.045 mmol), $Et_3N$ (136 mg, 1.35 mmol) in degassed THF (5 mL) was added $Pd(PPh_3)_2Cl_2$ (31 mg, 0.045 mmol). The suspension was degassed under vacuo and purged with $N_2$ several times. The mixture was stirred at 90° C. for 6 hours under $N_2$ atmosphere. The mixture was filtered and concentrated under vacuo to afford crude product, which was purified by prep-HPLC to give the desired product Compound 17 (20 mg, yield: 15%).

LCMS: m/z, 299.1 $(M+H)^+$;

$^1$HNMR (400 MHz, CDCl3): δ7.17~7.25 (m, 3H), 7.51~7.53 (m, 2H), 7.72 (s, 1H), 8.71~8.75 (m, 2H).

Example Compound 18

Preparation of 5-((5-chloro-4-(pyridin-2-ylethynyl)-1H-pyrazol-1-yl)-2-fluoropyridine

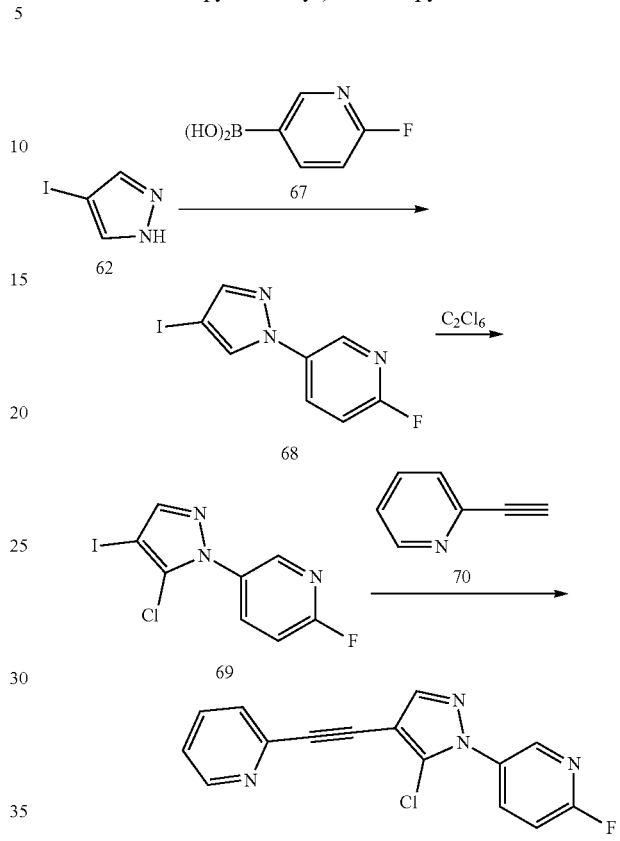

Compound 18

Experimental Section

Procedure for Preparation of 68

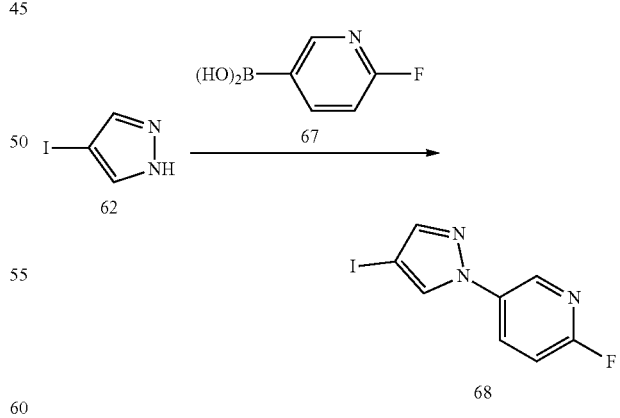

To a solution of compound 62 (1 g, 5.16 mmol) and compound 67 (1.09 g, 7.73 mmol) in DCM (20 ml) was added $Cu(OAc)_2$ (1.87 g, 10.3 mmol) and pyridine (1.22 g, 15.5 mmol) at room temperature under $O_2$ atmosphere, the mixture was stirred at room temperature overnight. The suspension was filtered and filter cake was washed with DCM (20 ml). The combined organic layers were washed with water and dried over Na$_2$SO$_4$. The crude product was purified by silica gel chromatography to give product 68 (0.6 g, 40%).

LCMS: m/z, 290.9 (M+H)$^+$.

Procedure for Preparation of 69

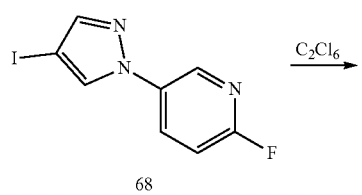

To a solution of 68 (500 mg, 1.75 mmol) in 20 mL of degassed THF was added a solution of LDA (1.05 mL, 2.1 mmol) at −78° C. After stirring 30 minutes, a solution of perchloroethane (500 mg, 2.1 mmol) in THF (2 mL) was added, and the reaction mixture was stirred at the same condition for another 30 minutes. The reaction mixture was quenched with sat.NH$_4$Cl, extracted with DCM and water, the organic layer was dried and purified by prep-TLC to give the title product 69 (400 mg, 35%).

LCMS: m/z, 323.9 (M+H)$^+$.

Procedure for Preparation of Compound 18

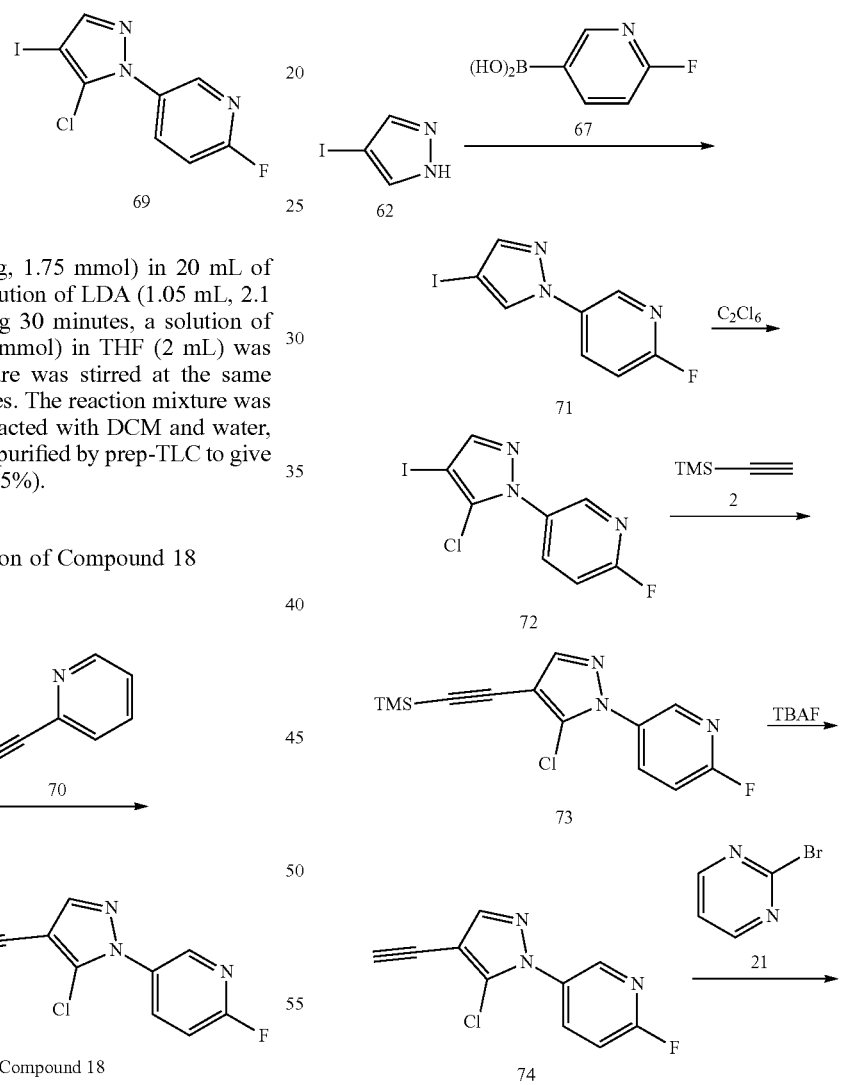

To a solution of 69 (50 mg, 0.15 mmol) in 4 mL of degassed THF was added solid CuI (1.5 mg, 0.008 mmol), 70 (24 mg, 0.24 mmol), Et$_3$N (45.5 mg, 0.45 mmol) and Pd(PPh$_3$)$_2$Cl$_2$ (5.6 mg, 0.008 mmol). The mixture was then degassed for 2 minutes under N$_2$ atmosphere and stirred at 90° C. for 1 hour under microwave. Most of the solvent was removed, the residue was dissolved in EtOAc (30 mL), then washed with brine (2×20 mL) and dried over anhydrous Na$_2$SO$_4$, filtered to and evaporated to give the residue which was purified by prep-HPLC to afford the desired product Compound 18 (5 mg, 11%).

LCMS: m/z, 298.9 (M+H)$^+$;

$^1$H NMR (400 MHz, CDCl$_3$): δ7.11-7.14 (m, 1H), 7.27-7.31 (m, 1H), 7.54-7.56 (m, 1H), 7.70-7.72 (m, 1H), 7.94 (s, 1H), 7.95-8.05 (m, 1H), 8.54 (s, 1H), 8.65 (d, J=4.0 Hz, 1H).

Example Compound 19

Preparation of 2-((5-chloro-1-(6-fluoropyridin-3-yl)-1H-pyrazol-4-yl)ethynyl)pyrimidine

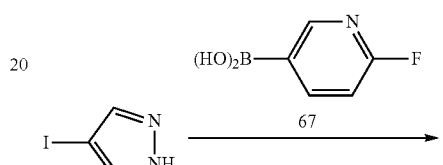

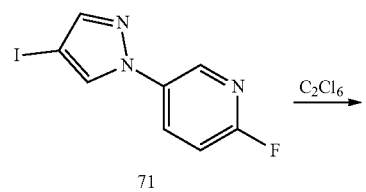

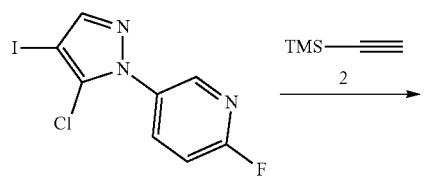

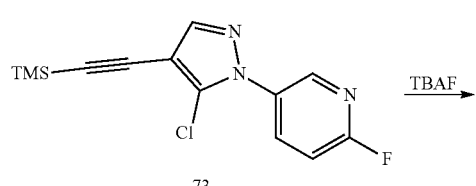

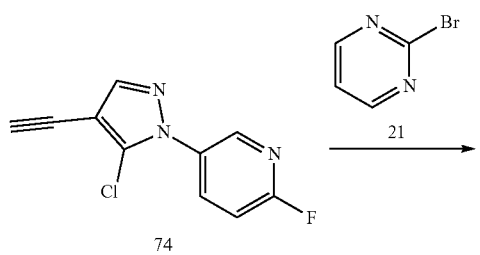

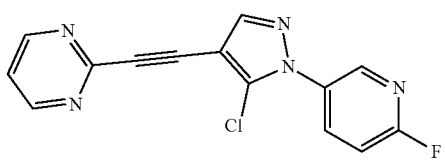

Compound 19

Experimental Section

Procedure for Preparation of 71

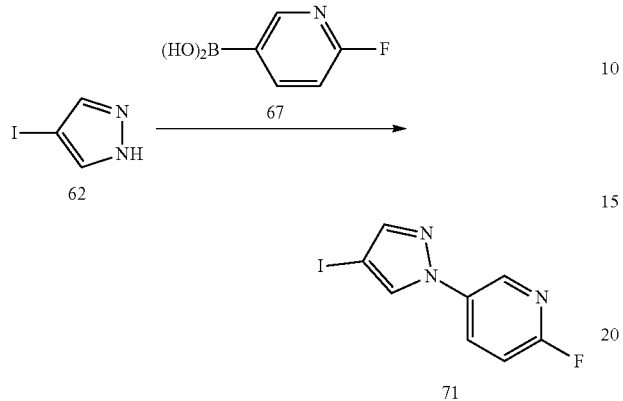

To a solution of 62 (1 g, 5.16 mmol) and 67 (1.09 g, 7.73 mmol) in DCM (20 ml) was added Cu(OAc)$_2$ (1.87 g, 10.3 mmol) and pyridine (1.22 g, 15.5 mmol) at room temperature under 02 atmosphere, the mixture was stirred at room temperature overnight. The suspension was filtered and the filter cake was washed with DCM (20 ml). The combined organic layers were washed with water and dried over Na$_2$SO$_4$. The crude product was purified by silica gel chromatography to give product 71 (0.6 g, 40%).

LCMS: m/z, 290.9 (M+H)$^+$.

Procedure for Preparation of 72

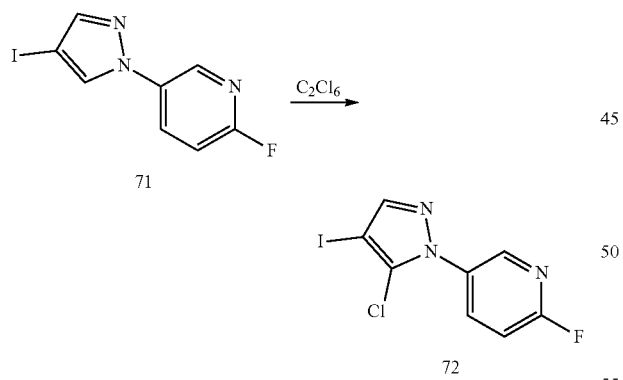

To a solution of 71 (500 mg, 1.75 mmol) in 20 mL of degassed THF was added a solution of LDA (1.05 mL, 2.1 mmol) at −78° C. After stirring 30 minutes, a solution of perchloroethane (500 mg, 2.1 mmol) in THF (2 mL) was added, and stirred at the same condition for another 30 minutes. The reaction mixture was quenched with sat.NH$_4$C$_1$. After solvent was removed, it was extracted with DCM and water, the organic layer was dried and purified by prep-TLC to give the title product 72 (400 mg, 35%).

LCMS: m/z, 323.9 (M+H)$^+$.

Procedure for Preparation of 73

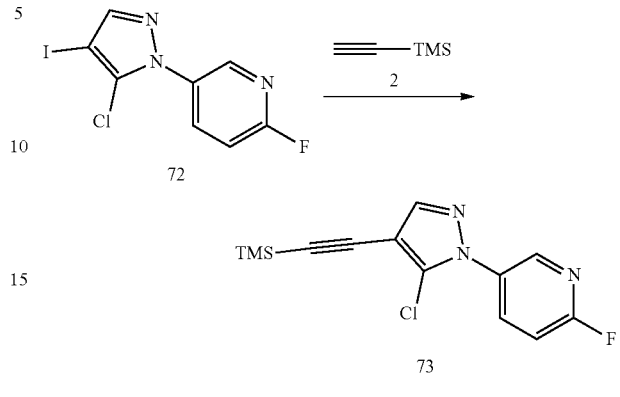

To a solution of 72 (320 mg, 1.0 mmol) in 4 mL of degassed THF was added successively CuI (1 mg, 0.02 mmol), 2 (855 mg, 1.0 mmol), Et$_3$N (120 mg, 1.2 mmol) and Pd(PPh$_3$)$_2$Cl$_2$ (3 mg, 0.005 mmol). The mixture was then degassed for 2 minutes under N$_2$ atmosphere and stirred at 90° C. for 1 h under microwave. Most of the solvent was removed. The residue was dissolved in EtOAc (30 mL). The organic layer was washed with brine (2×20 mL) and dried over anhydrous Na$_2$SO$_4$, filtered and evaporated to dryness on a rotary evaporator, which was purified by TLC plate to give of the product 73 (280 mg, 95.9%).

Procedure for Preparation of 74

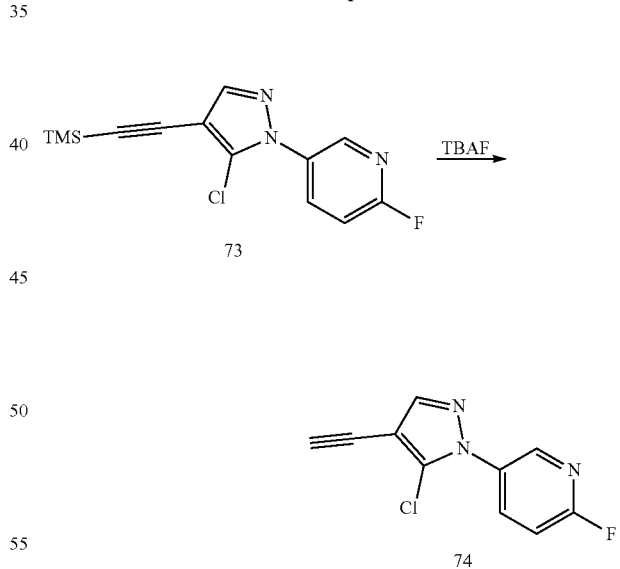

To a solution of 73 (240 mg, 0.82 mmol) in THF (4 mL) was added a solution of TBAF-THF (1.2 mL, 1.2 mmol). The mixture was stirred at rt. for 1 h. TLC showed the reaction was reacted complete, most of the solvent was removed. The residue was dissolved in EtOAc (20 mL). The organic layer was washed with brine (2×10 mL) and dried over anhydrous Na$_2$SO$_4$, filtered and evaporated to give the product 74 (150 mg, 83%), which was directly used for next step.

Procedure for Preparation of Compound 19

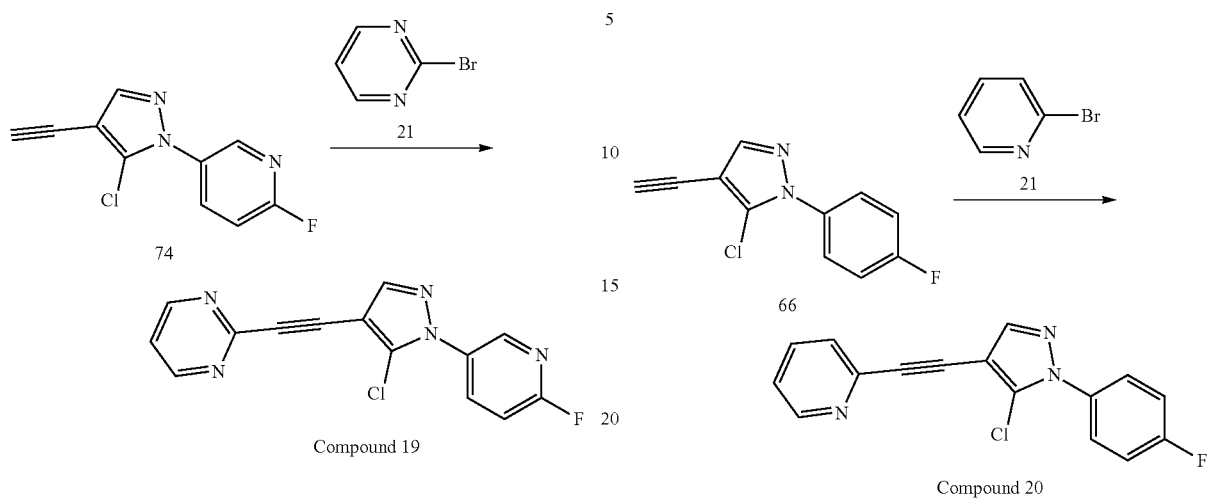

Compound 19

To a solution of 74 (80 mg, 0.36 mmol) in 4 mL of degassed THF was added solid CuI (9.5 mg, 0.05 mmol), 21 (63 mg, 0.4 mmol), Et$_3$N (111 mg, 1.1 mmol) and Pd(PPh$_3$)$_2$Cl$_2$ (14 mg, 0.02 mmol). The mixture was then degassed for 2 minutes under N$_2$ atmosphere and stirred at 90° C. for 1 h under microwave. Most of the solvent was removed. The residue was dissolved in EtOAc (30 mL). The organic layer was washed with brine (2×20 mL) and dried over anhydrous Na$_2$SO$_4$, filtered and evaporated to give the residue which was purified by prep-HPLC to afford the desired product Compound 19 (23 mg, 21.3%).

LCMS: m/z, 300.0 (M+H)$^+$;

$^1$H NMR (400 MHz, CDCl$_3$): δ7.13 (dd, J$_1$=3.30 Hz, J$_2$=8.68 Hz, 1H), 7.27-7.31 (m, 1H), 7.99 (s, 1H), 8.07 (m, 1H), 8.54 (d, J=1.71 Hz, 1H), 8.79 (d, J=4.89 Hz, 2H).

Example Compound 20

Preparation of Preparation of 2-((5-chloro-1-(4-fluorobenzyl)-1H-pyrazol-4-yl) ethynyl) pyridine

Experimental Section

Procedure for Preparation of Compound 20

To a solution of 66 (100 mg, 0.45 mmol), 21 (108 mg, 0.68 mmol), CuI (9 mg, 0.045 mmol), Et$_3$N (136 mg, 1.35 mmol) in THF (5 mL) was added Pd(PPh$_3$)$_2$Cl$_2$ (31 mg, 0.045 mmol). The suspension was degassed under vacuo and purged with N$_2$ several times. The mixture was stirred at 90° C. for 6 hours under N$_2$ atmosphere, then the mixture was filtered and concentrated under vacuo.

The residue was purified by prep-HPLC to give the desired product Compound 20 (40 mg, yield: 30%).

LCMS: n/z, 298.0 (M+H)$^+$;

$^1$H NMR (400 MHz, CHLOROFORM-d): δ 7.17-7.30 (m, 3H), 7.51-7.56 (m, 3H), 7.65-7.74 (m, 1H), 7.88 (s, 1H), 8.55-8.72 (m, 1H).

Example Compound 21

Preparation of 2-(5-chloro-1-(4-(trifluoromethoxy)phenyl)-1H-pyrazol-4-yl) pyridine

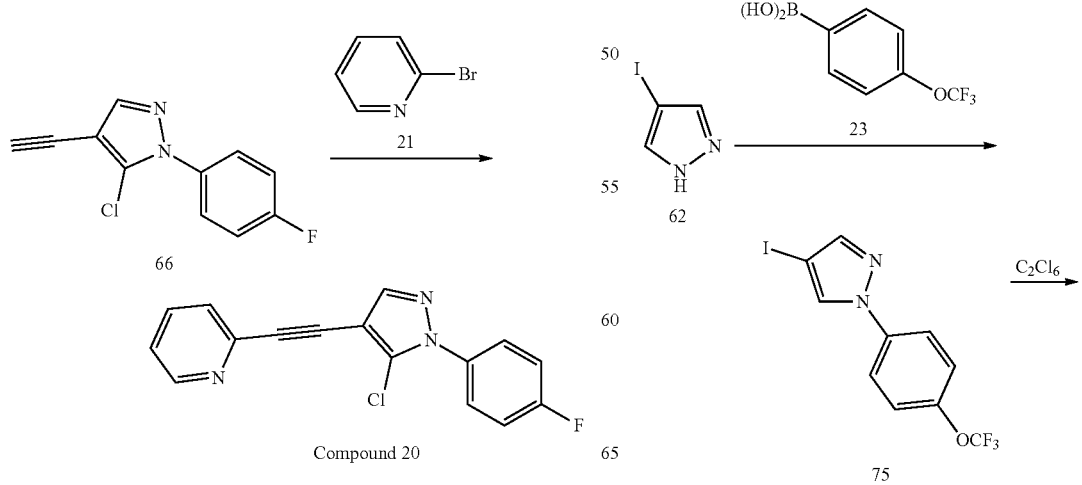

73

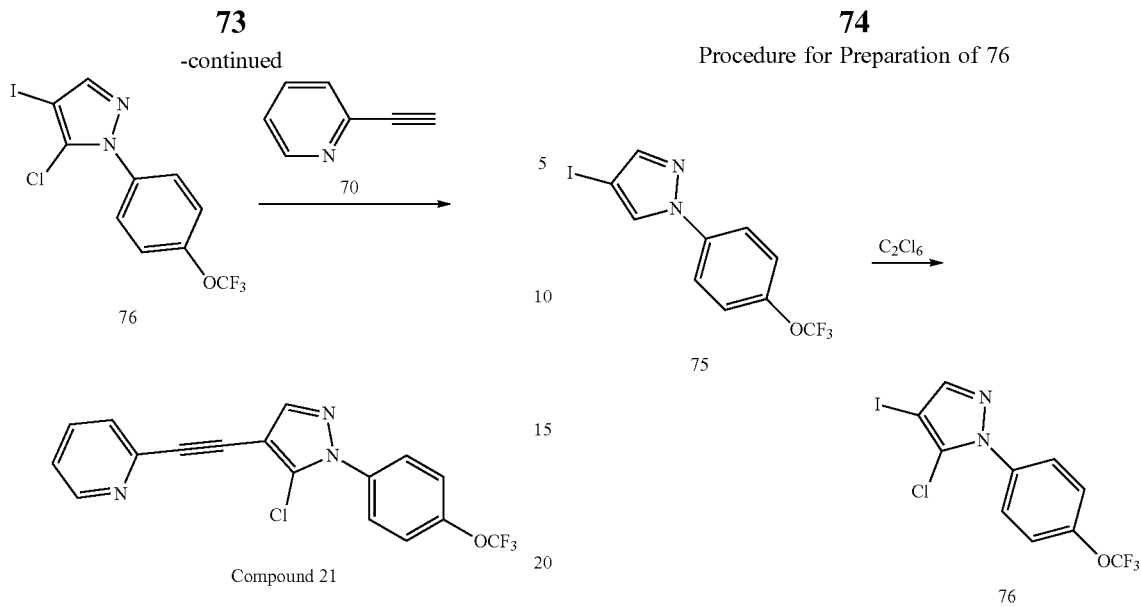

Compound 21

Experimental Section

Procedure for Preparation of 75

To a solution of 62 (5 g, 25.78 mmol), 23 (7.96 g, 38.67 mmol) and Cu(AcO)$_2$ (7.96 g, 38.67 mmol) in 3 mL of degassed DCM was added successively Pyridine (6.12 g, 77.33 mmol) at room temperature. After the reaction mixture was stirred at room temperature for 12 hours, it was filtrated and most of the solvent was removed. The residue was dissolved in EtOAc (60 mL). The organic layer was washed with brine (2×30 mL) and dried over anhydrous Na$_2$SO$_4$, filtered and evaporated to dryness on a rotary evaporator, which was purified by chromatography to give the product 75 (3.7 g, 40.5%).

$^1$H NMR (400 MHz, CDCl$_3$): δ7.24 (d, J=8.4 Hz, 2H), 7.60 (d, J=8.8 Hz, 2H), 7.66 (s, 1H). 7.87 (s, 1H).

74

Procedure for Preparation of 76

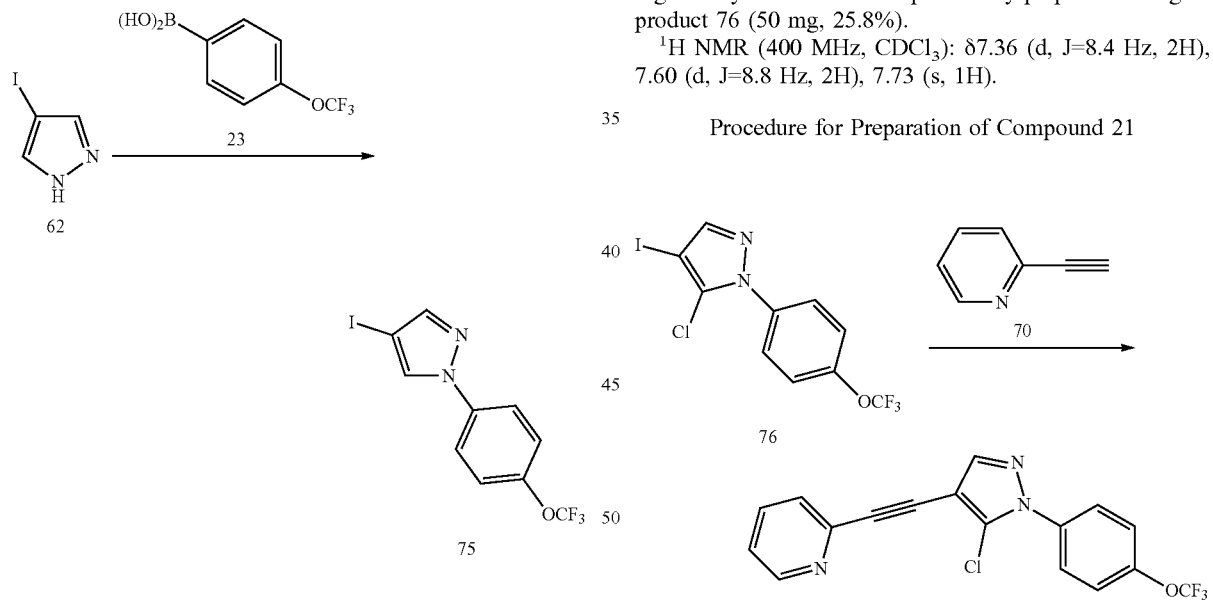

To a solution of 75 (177 mg, 0.5 mmol) in 3 mL of degassed THF, LDA (0.3 mL, 0.6 mmol) was added at −78° C. After stirring 30 minutes, perchloroethane (119 mg, 0.6 mmol) was added, then stirred at the same condition for another 30 minutes. It was quenched with sat.NH$_4$C$_1$. The solvent was removed and extracted with DCM and water, the organic layer was dried and purified by prep-HPLC to give product 76 (50 mg, 25.8%).

$^1$H NMR (400 MHz, CDCl$_3$): δ7.36 (d, J=8.4 Hz, 2H), 7.60 (d, J=8.8 Hz, 2H), 7.73 (s, 1H).

Procedure for Preparation of Compound 21

To a solution of 76 (40 mg, 0.1 mmol) in 3 mL of degassed dioxane was added successively CuI (1 mg, 0.005 mmol), 70 (16 mg, 0.15 mmol), Et$_3$N (21 mg, 0.2 mmol) and Pd(PPh)$_2$Cl$_2$ (15 mg, 0.005 mmol). The mixture was then degassed for 2 minutes under N$_2$ atmosphere and heated to 80° C. overnight. Then most of the solvent was removed, the residue was dissolved in EtOAc (30 mL) and the organic layer was washed with brine (2×20 mL) and dried over anhydrous Na$_2$SO$_4$, filtered and evaporated to give a residue which was purified by prep-HPLC to give of the desired product Compound 21 (25 mg, 66.7%).

LCMS: m/z, 364.0 (M+H)+;
1H NMR (400 MHz, CDCl3): δ7.25 (s, 1H), 7.36 (d, J=8.56 Hz, 2H), 7.53 (d, J=7.83 Hz, 1H), 7.60-7.74 (m, 3H), 7.89 (s, 1H), 8.63 (d, J=4.40 Hz, 1H).

Example Compound 22

Preparation of 2-(5-chloro-1-(4-(trifluoromethoxy)phenyl)-1H-pyrazol-4-yl) pyrimidine

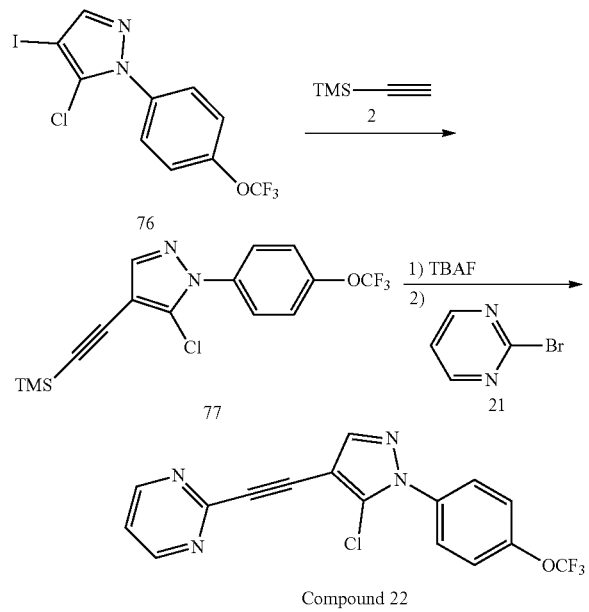

Experimental Section

Procedure for Preparation of 77

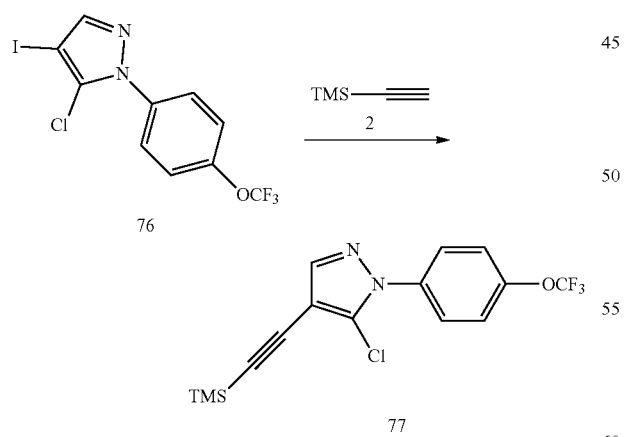

To a solution of 76 (350 mg, 0.87 mmol) in 4 mL of degassed THF was added successively CuI (8 mg, 0.04 mmol), 2 (171 mg, 1.7 mmol), Et3N (263 mg, 2.6 mmol) and Pd(PPh3)2Cl2 (28 mg, 0.04 mmol). The mixture was then degassed for 2 minutes under N2 atmosphere and stirred at 90° C. for 1 h under microwave. Then most of the solvent was removed, and the residue was dissolved in EtOAc (30 mL). The organic layer was washed with brine (2×20 mL) and dried over anhydrous Na2SO4, filtered and evaporated to afford the residue which was purified by flash chromatography to give product 77 (295 mg, 91.3%) LCMS: m/z, 359.0 (M+H)+;

Procedure for Preparation of Compound 22

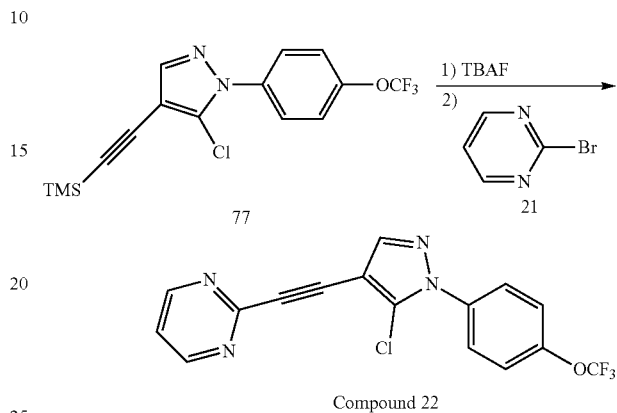

To a solution of 77 (370 mg, 1 mmol) in 4 mL of degassed THF was added a solution of TBAF (1.5 mL, 1.5 mmol). It was stirred at room temperature for h. Then solid CuI (9.5 mg, 0.05 mmol), 21 (240 mg, 1.5 mmol), Et3N (303 mg, 3 mmol) and Pd(PPh3)2Cl2 (35 mg, 0.05 mmol) was added into it. The mixture was then degassed for 2 minutes under N2 atmosphere and stirred at 90° C. for 1 h under microwave. Most of the solvent was removed. The residue was dissolved in EtOAc (30 mL). The organic layer was washed with brine (2×20 mL) and dried over anhydrous Na2SO4, filtered and evaporated to dryness on a rotary evaporator, which was purified by flash chromatography to give the desired product Compound 22 (196 mg, 45.9%).

LCMS: m/z, 365.0 (M+H)+;
1H NMR (400 MHz, CDCl3): δ7.27 (s, 1H), 7.37 (d, J=8.38 Hz, 2H), 7.66 (d, J=8.82 Hz, 2H), 7.97 (s, 1H), 8.78 (d, J=4.85 Hz, 2H).

Example Compound 23

Preparation of 2-fluoro-5-(4-(pyridin-2-yl)-1H-pyrazol-1-yl) pyridine

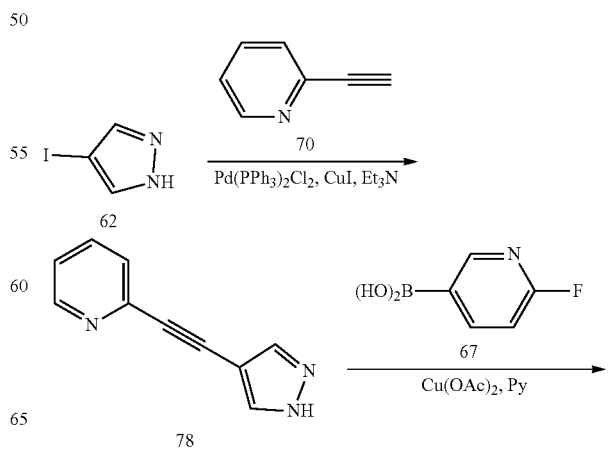

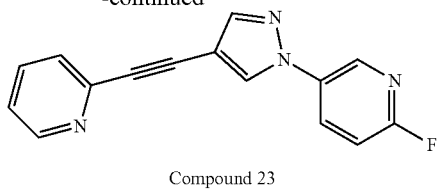

Compound 23

Experimental Section

Procedure for Preparation of 78

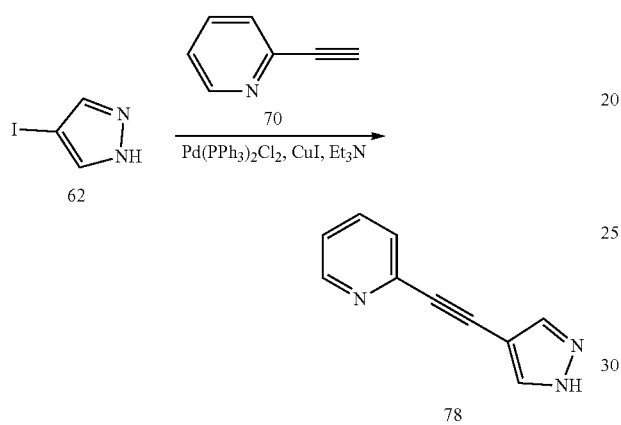

To a solution of compound 62 (1.06 g, 10.31 mmol), 70 (1 g, 5.16 mmol), CuI (98 mg, 0.516 mmol), Et$_3$N (1.57 g, 15.47 mmol) in Toluene (40 mL) was added Pd(PPh$_3$)$_2$Cl$_2$ (181 mg, 0.258 mmol). The mixture was stirred at 100° C. overnight. The mixture was filtered and concentrated under vacuo. The residue was purified by silica gel chromatography (eluting with 0-80% EA in PE) to give product 78 (350 mg, 40%).

LCMS: m/z, 170.1 (M+H)$^+$.

Procedure for Preparation of Compound 23

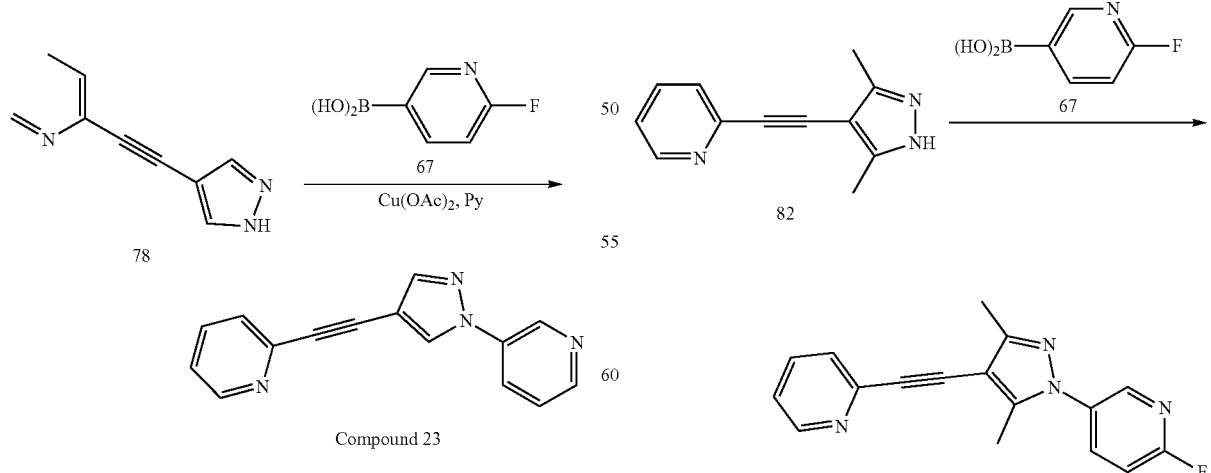

To a solution of 78 (50 mg, 0.296 mmol) in DCM (8 mL) was added 67 (83 mg, 0.591 mmol), Cu(OAc)$_2$ (107 mg, 0.591 mmol), pyridine (70 mg, 0.887 mmol). The mixture was stirred at room temperature overnight under O$_2$ atmosphere, then the mixture was filtered and concentrated under vacuo. The residue was purified by prep-TLC to give the desired product Compound 23 (20 mg, 26%).

LCMS: m/z, 265.1 (M+H)$^+$;

$^1$H NMR (400 MHz, CDCl$_3$): δ 8.63 (s, 1H), 8.57-8.55 (m, 1H), 8.17-8.15 (m, 2H), 7.95 (s, 1H), 7.70 (m, 1H), 7.52-7.50 (m, 1H), 7.26 (m, 1H), 7.10-7.08 (m, 1H).

Example Compound 24

Preparation of 5-(3, 5-dimethyl-4-(pyridin-2-yl)-1H-pyrazol-1-yl)-2-fluoropyridine

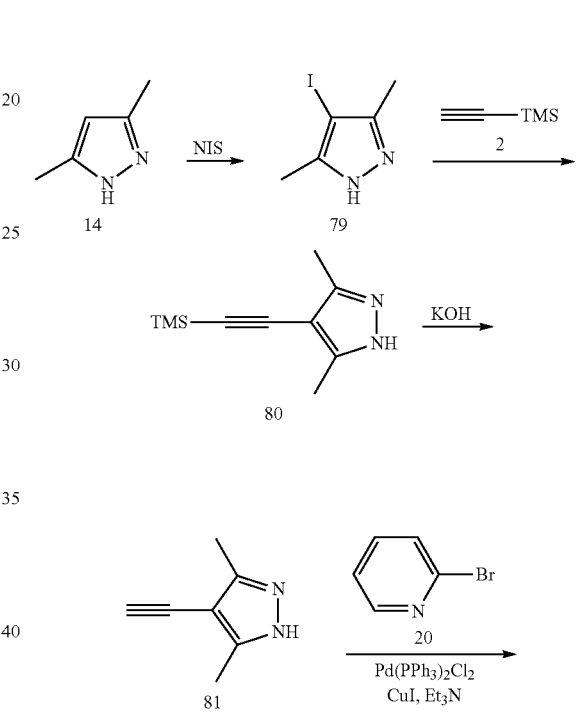

Experimental Section

Procedure for Preparation of 79

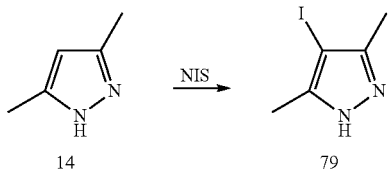

To a solution of 79 (3.00 g, 31.21 mmol) in 50 mL of degassed CHCl₃ was added NIS (7.02 g, 31.21 mmol). The mixture was heated to reflux and stirred for 18 hours. LCMS showed that starting material was consumed, then the reaction mixture was cooled to room temperature and filtered. The filtrate was concentrated to give the product 79 (5.5 g, 79%).

LCMS: m/z 223 (M+H)⁺.

Procedure for Preparation of 80

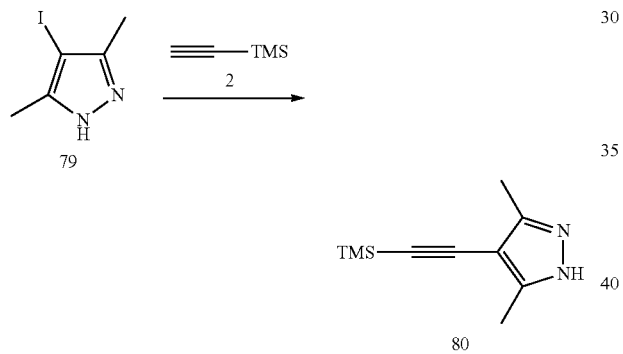

To a solution of 79 (3.00 g, 13.51 mmol) in 100 mL of degassed THF was added successively CuI (257 mg, 1.35 mmol), 2 (2.65 g, 27.02 mmol), Pd(PPh₃)₂Cl₂ (948 mg, 1.35 mmol) and Et₃N (4.10 g, 40.54 mmol). The mixture was stirred at 80° C. for 18 hours. LCMS showed that the reaction was completed. The reaction mixture was filtered and the filtrate was concentrated and purified by chromatograph column to give the product 80 (2.2 g, yield 85%).

LCMS: m/z 193 (M+H)⁺.

Procedure for Preparation of 81

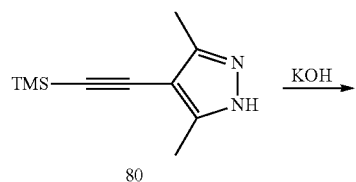

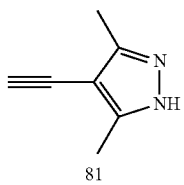

To a solution of 80 (2.20 g, 11.44 mmol) in MeOH (30 mL) was added KOH (1.28 g, 22.88 mmol). Then the reaction mixture was stirred at rt. for 1 h. LCMS showed that the reaction was complete, then the reaction mixture was quenched with 50 mL water, extracted with DCM (3×50 mL). The combined organic layer was washed with brine, dried over Na₂SO₄, concentrated to give the 80 (1.1 g, yield 80%).

Procedure for Preparation of 82

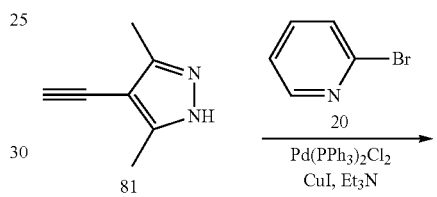

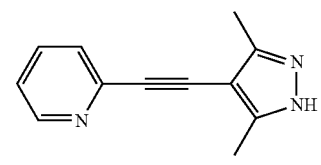

To a solution of 81 (1.00 g, 8.32 mmol) in 50 mL of degassed THF was added successively CuI (159 mg, 0.83 mmol), 20 (2.63 g, 16.65 mmol), Pd(PPh₃)₂Cl₂ (584 mg, 0.83 mmol) and Et₃N (2.53 g, 24.97 mmol). The mixture was stirred at 80° C. for 18 hours. LCMS showed that the reaction was completed, then the reaction mixture was filtered and the filtrate was concentrated and purified by prep-TLC to give the product 82 (1.1 g, yield 67%).

LCMS: n/z 198 (M+H)⁺.

Procedure for Preparation of Compound 24

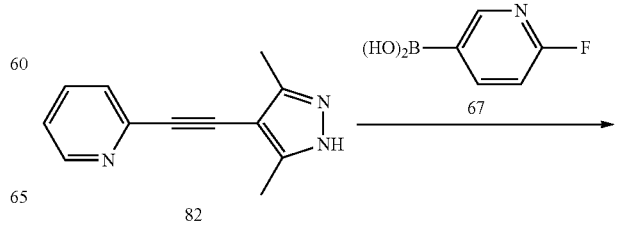

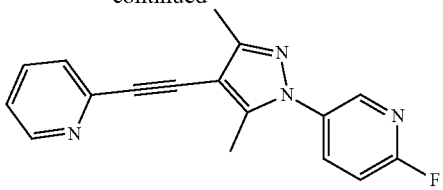

Compound 24

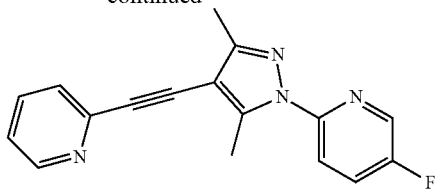

Compound 25

To a solution of 82 (100 mg, 0.51 mmol) in 5 mL of degassed DCM was added successively 67 (142 mg, 1.01 mmol), Cu(OAc)$_2$ (184 mg, 1.01 mmol), and pyridine (120 mg, 1.52 mmol). The reaction mixture was then degassed for 1 minute under O$_2$ atmosphere and stirred at room temperature overnight. The reaction mixture was filtered and the filtrate was concentrated. The obtained residue was purified by prep-TLC give the product Compound 24 (22 mg, yield 15%).

LCMS: m/z 293 (M+H)$^+$;

$^1$H NMR (400 MHz, CDCl3): δ 8.62 (d, J=4.4 Hz, 1H), 8.33 (s, 1H), 7.96-7.93 (m, 1H), 7.68-7.66 (m, 1H), 7.50 (d, J=8.0 Hz, 1H), 7.25-7.23 (m, 1H), 7.08-7.05 (m, 1H), 2.47 (s, 3H), 2.42 (s, 3H).

Example Compound 25

Preparation of 2-(3, 5-dimethyl-4-(pyridin-2-ylethynyl)-H-pyrazol-1-yl)-5-fluoropyridine

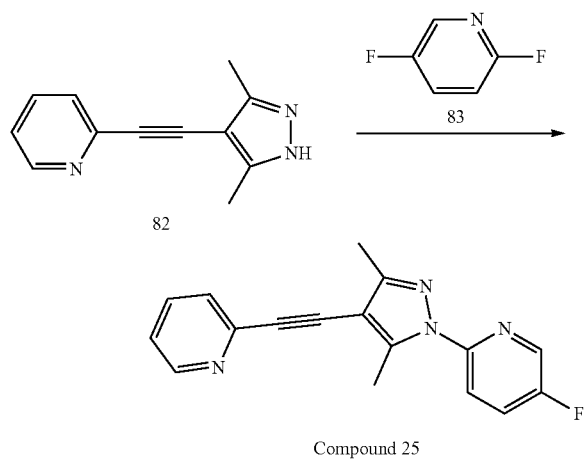

Experimental Section

Procedure for Preparation of Compound 25

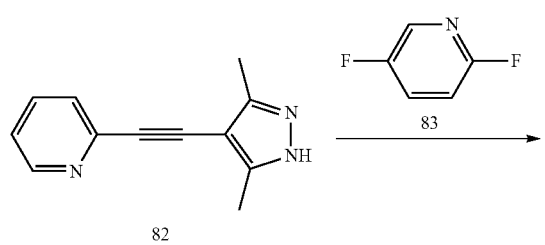

To a solution of 82 (50 mg, 0.25 mmol) in 5 mL of degassed DMF was added successively 83 (44 mg, 0.38 mmol), Cs$_2$CO$_3$ (248 mg, 0.76 mmol). The reaction mixture was stirred at 110° C. for 2 hours, then was filtered and the filtrate was concentrated and purified by prep-TLC to give the desired product Compound 25 (14 mg, yield 19%).

LCMS: m/z 293 (M+H)$^+$;

$^1$H NMR (400 MHz, CDCl$_3$): δ8.61 (d, J=4.4 Hz, 1H), 8.28 (d, J=2.8 Hz, 1H), 7.89-7.85 (m, 1H), 7.67-7.64 (m, 1H), 7.53-7.49 (m, 2H), 7.24-7.22 (m, 1H), 2.76 (s, 3H), 2.42 (s, 3H); Example Compound 26

Preparation of 2-((1-(4-(2-methoxyethoxy) phenyl)-1H-pyrazol-4-yl)ethynyl) pyridine

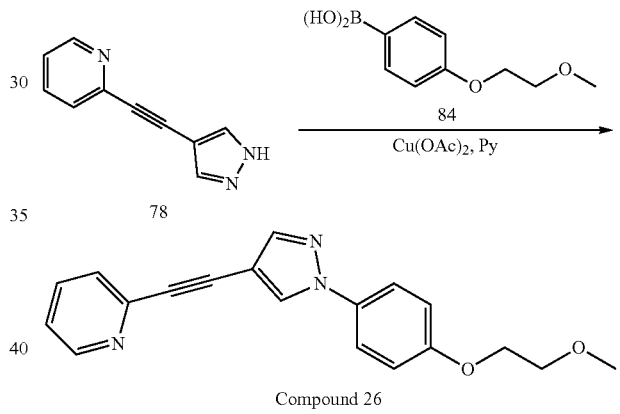

Experimental Section

Procedure for Preparation of Compound 26

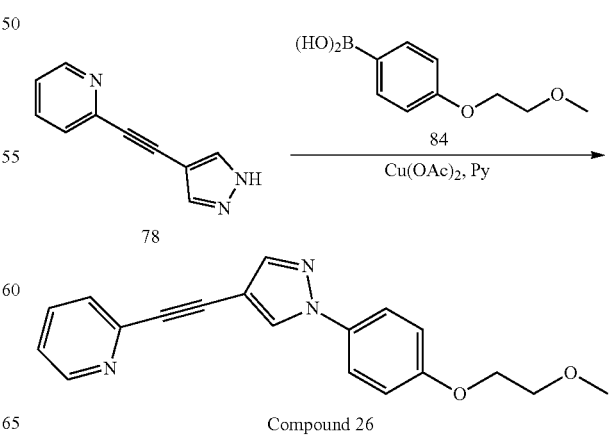

To a solution of 78 (50 mg, 0.296 mmol) in DCM (20 mL) was added 84 (116 mg, 0.591 mmol), Cu(OAc)$_2$ (107 mg, 0.591 mmol), pyridine (70 mg, 0.887 mmol). The mixture was stirred at room temperature overnight under O$_2$ atmosphere. The mixture was filtered and concentrated under vacuo. The residue was purified by prep-TLC to give the desired product Compound 26 (30 mg, 32%).

LCMS: m/z, 320.2 (M+H)$^+$;

$^1$H NMR (400 MHz, CDCl$_3$): δ 8.55 (s, 1H), 8.00 (s, 1H), 7.81 (s, 1H), 7.61 (m, 1H), 7.52-7.49 (m, 2H), 7.43-7.41 (m, 1H), 7.19-7.18 (m, 1H), 6.96-6.94 (m, 2H), 4.11-4.08 (m, 2H), 3.72-3.70 (m, 2H), 3.40 (s, 3H).

Example Compound 27

Preparation of 5-fluoro-2-(4-(pyridin-2-ylethynyl)-1H-pyrazol-1-yl)pyridine

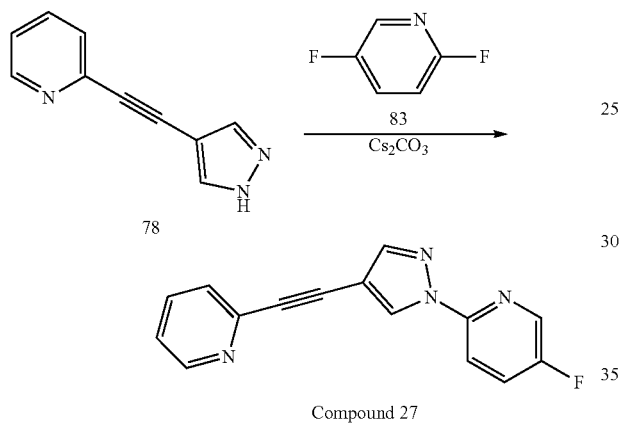

Experimental Section

Procedure for Preparation of Compound 27

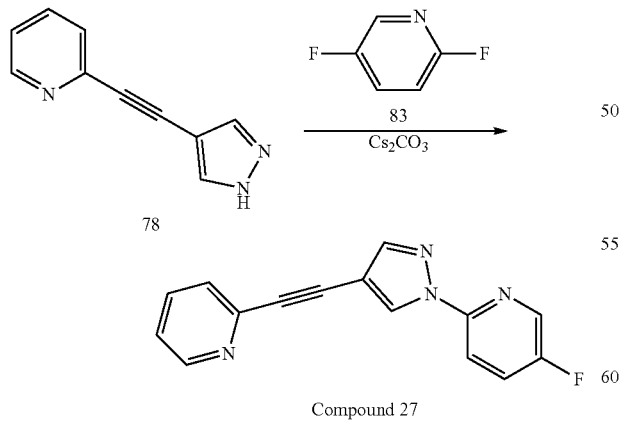

To a solution of 78 (50 mg, 0.296 mmol) in DMF (5 mL) was added 83 (102 mg, 0.887 mmol), Cs$_2$CO$_3$ (289 mg, 0.887 mmol). The reaction mixture was stirred at 100° C. for 2 hours, then it was filtered and concentrated under vacuo. The residue was purified by prep-TLC to give the product Compound 27 (25 mg, 32%).

LCMS: m/z, 265.1 (M+H)$^+$;

$^1$H NMR (400 MHz, CDCl$_3$): δ 8.70 (s, 1H), 8.62-8.61 (s, 1H), 8.27 (s, 1H), 7.99-7.97 (m, 1H), 7.89 (s, 1H), 7.68-7.66 (m, 1H), 7.56-7.54 (m, 1H), 7.51-7.49 (m, 1H), 7.24 (m, 1H)

Example Compound 28

Preparation of 2-(2-methoxyethoxy)-5-(4-(pyridin-2-ylethynyl)-1H-pyrazol-1-yl) pyridine

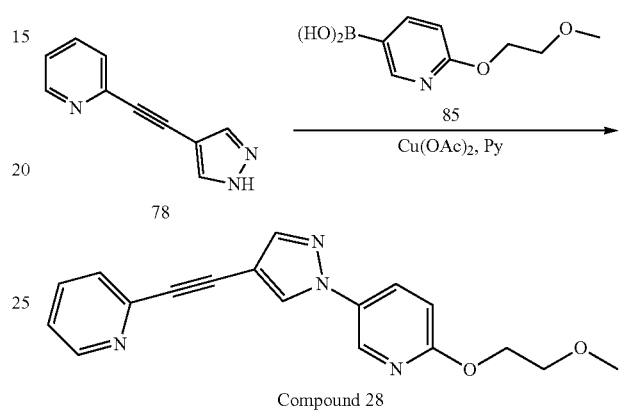

Experimental Section

Procedure for Preparation of Compound 28

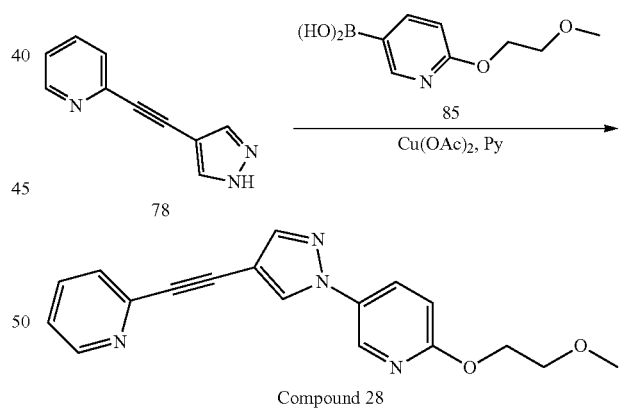

To a solution of 78 (40 mg, 0.236 mmol) in DCM (15 mL) was added 85 (93 mg, 0.473 mmol), Cu(OAc)$_2$ (86 mg, 0.473 mmol), pyridine (56 mg, 0.709 mmol). The reaction mixture was stirred at room temperature overnight under O$_2$ atmosphere, then it was filtered and concentrated under vacuo. The residue was purified by prep-TLC to give the desired product Compound 28 (15 mg, 20%).

LCMS: m/z, 321.1 (M+H)$^+$;

$^1$H NMR (400 MHz, CDCl$_3$): δ 8.62 (s, 1H), 8.36 (s, 1H), 8.01 (s, 1H), 7.86-7.81 (m, 2H), 7.64 (m, 1H), 7.45-7.43 (m, 1H), 7.20-7.18 (m, 1H), 6.87-6.85 (m, 1H), 4.46-4.44 (m, 2H), 3.71-3.69 (m, 2H), 3.39-3.36 (m, 3H).

Example Compound 29

Preparation of 3-fluoro-5-(3-(2-methoxyethoxy)-5-methyl-4-(pyridin-2-ylethynyl)-1H-pyrazol-1-yl)benzonitrile

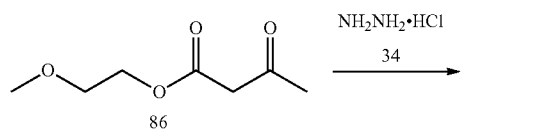

86

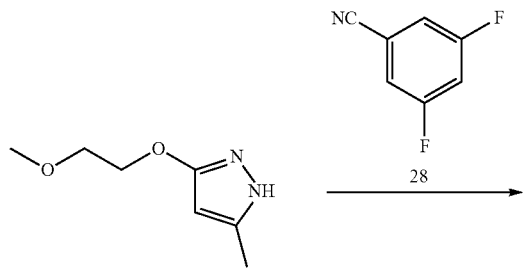

87

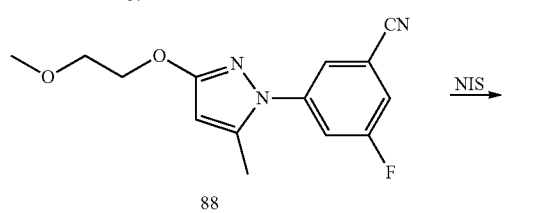

88

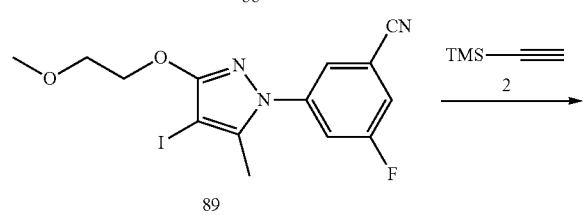

89

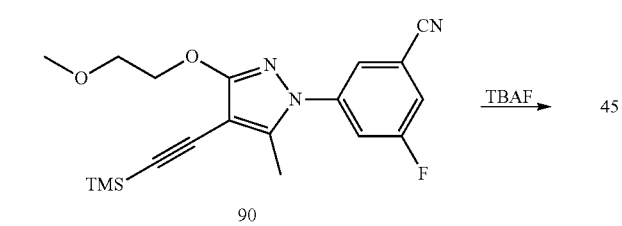

90

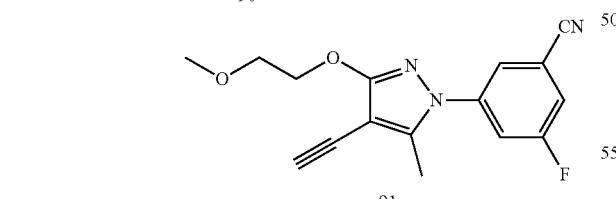

91

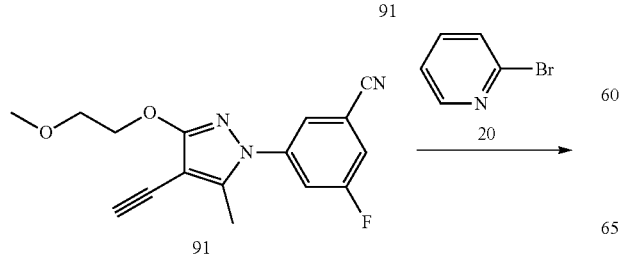

91

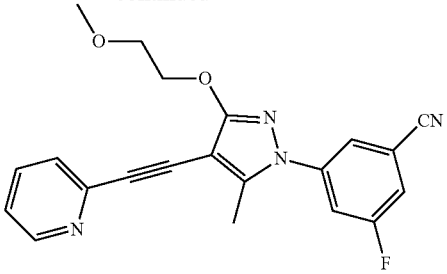

Compound 29

Procedure for Preparation of 87

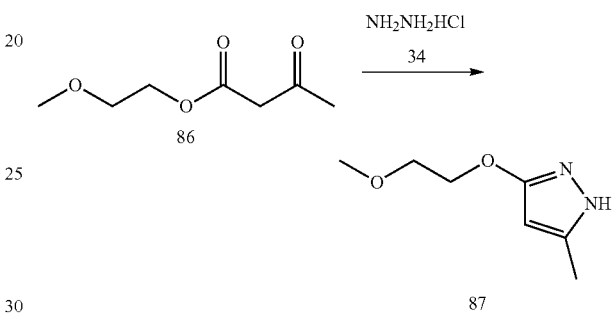

To a solution of 86 (3.2 g, 20 mmol) in EtOH (30 mL) was added a solid of NH$_2$NH$_2$HCl (1.4 g, 20 mmol) at room temperature. It was stirred at 60° C. for 6 hours. The reaction mixture was concentrated and the obtained residue was treated with saturated NaHCO$_3$ solution (200 mL), extracted with DCM (3×150 mL). The combined organic layer was dried over Na$_2$SO$_4$, filtered and concentrated to give the desired product 87 (1 g, 32.3%) LCMS: m/z, 157.1 (M+H)$^+$, $^1$H NMR (400 MHz, DMSO–d$_6$): δ2.13 (s, 3H), 3.26–3.30 (m, 3H), 3.53–3.61 (m, 2H), 4.05-4.14 (m, 2H), 5.37–5.44 (m, 1H).

Procedure for Preparation of 88

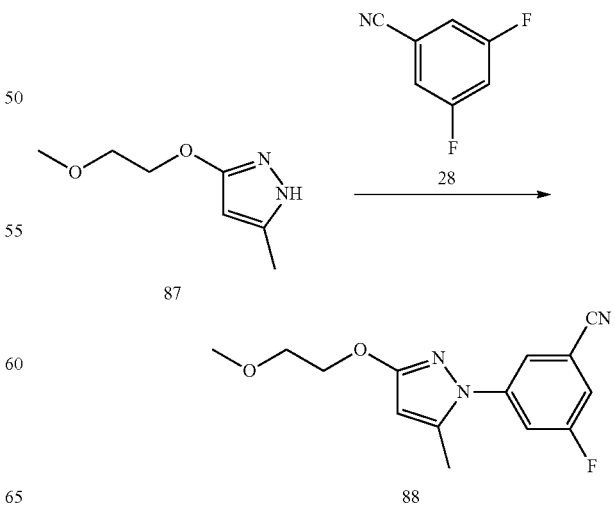

To a solution of 87 (156 mg, 1 mmol), 28 (224 mg, 1.1 mmol) in DMF (3 mL) was added solid $Cs_2CO_3$ (664 mg, 2 mmol) at room temperature. Then it was stirred at 100° C. for 3 hours, after cooling to room temperature, water (6 mL) was added into the mixture with stirring at ice bath slowly. Gradually, solid was formed, it was filtrated. The residue was purified by TLC to afford the product 88 (80 mg, 29%).

$^1$H NMR (400 MHz, $CDCl_3$): δ2.35-2.49 (m, 3H) 3.37-3.50 (m, 3H) 3.67-3.80 (m, 2H) 4.24-4.43 (m, 2H) 5.76 (s, 1H) 7.20-7.24 (m, 1H) 7.48 (dd, $J_1$=2.09 Hz, $J_2$=9.70 Hz, 1H) 7.58 (s, 1H).

Procedure for Preparation of 89

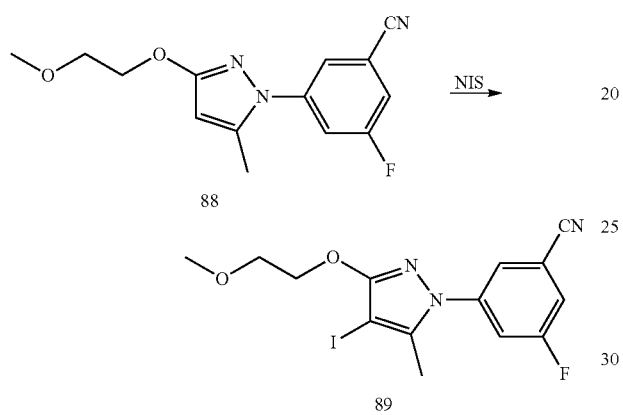

To a solution of 88 (250 mg, 0.91 mmol) in $CHCl_3$ (3 mL) was added NIS (225 mg, 1 mmol). Then the reaction mixture was stirred at reflux for 2 hours. LCMS showed that the reaction was complete. The reaction mixture was concentrated to give the desired product, which was purified by TLC to afford the product 89 (300 mg, 82.4%).

LCMS: m/z, 402.0 (M+H)$^+$.

Procedure for Preparation of 90

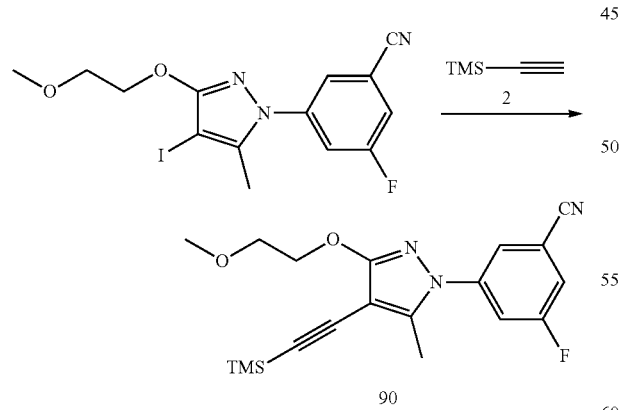

To a solution of 89 (350 mg, 0.87 mmol) in 4 mL of degassed THF was added successively CuI (8 mg, 0.04 mmol), 2 (171 mg, 1.7 mmol), $Et_3N$ (263 mg, 2.6 mmol) and $Pd(PPh_3)_2Cl_2$ (28 mg, 0.04 mmol). The mixture was then degassed for 2 minutes under $N_2$ atmosphere and stirred at 90° C. for 1 hour under microwave. Most of the solvent was removed. The residue was dissolved in EtOAc (30 mL). The organic layer was washed with brine (2×20 mL) and dried over anhydrous $Na_2SO_4$, filtered and evaporated to give a residue which was purified by TLC to give product 90 (300 mg, 92.5%)

LCMS: m/z, 372.1 (M+H)$^+$.

Procedure for Preparation of 91

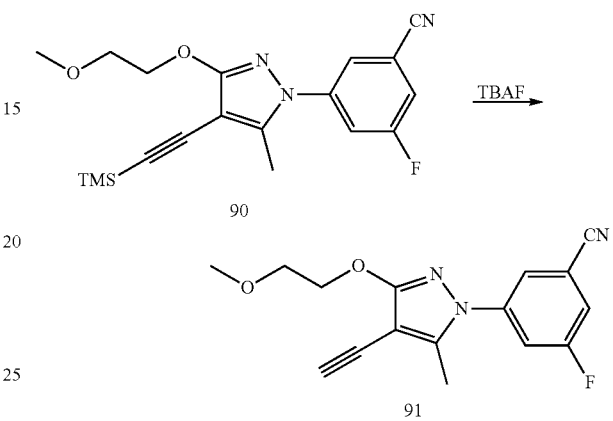

To a solution of 90 (300 mg, 0.81 mmol) in THF (4 mL) was added a solution of TBAF-THF (1.2 mL, 1.2 mmol). The mixture was stirred at room temperature for 1 hour. Most of the solvent was removed. The residue was dissolved in EtOAc (20 mL). The organic layer was washed with brine (2×10 mL) and dried over anhydrous $Na_2SO_4$, filtered and evaporated to dryness on a rotary evaporator, which was purified by TLC to give product 91 (200 mg, 82.6%).

LCMS: m/z, 300.0 (M+H)$^+$;

$^1$H NMR (400 MHz, $CDCl_3$): δ2.40 (s, 3H), 3.21 (s, 1H), 3.38 (s, 3H), 3.66-3.75 (m, 2H), 4.33-4.41 (m, 2H), 7.23 (d, J=7.50 Hz, 1H), 7.37-7.45 (m, 1H), 7.52 (s, 1H).

Procedure for Preparation of Compound 29

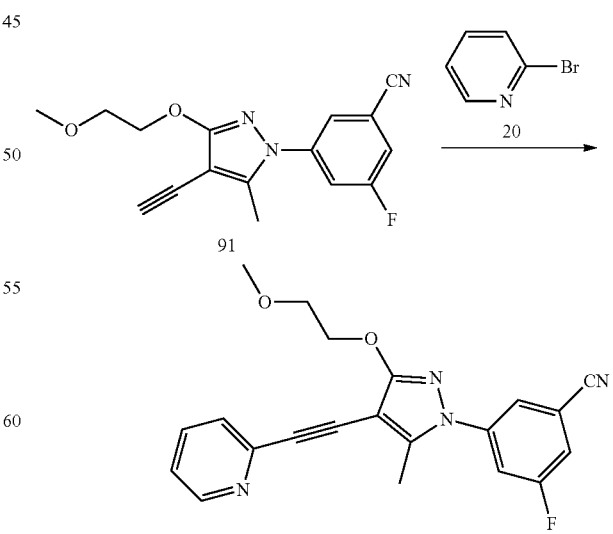

Compound 29

To a solution of 91 (50 mg, 0.17 mmol) in 3 mL of degassed THF was added successively CuI (1.8 mg, 0.009 mmol), 20 (29 mg, 0.18 mmol), Et₃N (34 mg, 0.34 mmol) and Pd(PPh₃)₂Cl₂ (0.7 mg, 0.009 mmol). The mixture was then degassed for 2 minutes under N₂ atmosphere and stirred at 90° C. for 1 h under microwave. Most of the solvent was removed. The residue was dissolved in EtOAc (30 mL). The organic layer was washed with brine (2×20 mL) and dried over anhydrous Na₂SO₄, filtered and evaporated to give the residue which was purified by flash chromatography to give the desired product Compound 29 (25 mg, 33.3%).

LCMS: n/z, 377.1 (M+H)⁺;

¹H NMR (400 MHz, CDCl₃): δ2.55 (s, 3H), 3.45 (s, 3H), 3.79 (t, J=4.80 Hz, 2H), 4.46 (t, J=4.80 Hz, 2H), 7.21 (m, 1H), 7.29 (m, 1H), 7.50 (m, 2H), 7.66 (m, 2H), 8.76 (d, J=4.40 Hz, 1H).

Example Compound 30

Preparation of 3-fluoro-5-(3-(2-methoxyethoxy)-5-methyl-4-(pyrimidin-2-ylethynyl)-1H-pyrazol-1-yl)benzonitrile

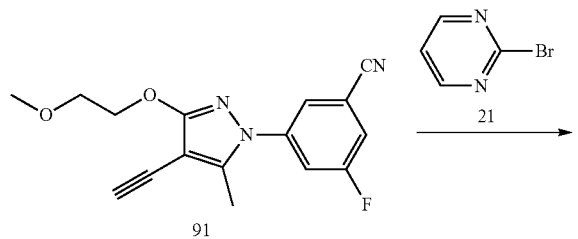

Compound 30

To a solution of 91 (40 mg, 0.2 mmol) in 3 mL of degassed dioxane was added successively CuI (1 mg, 0.01 mmol), 9 (32 mg, 0.3 mmol), Et₃N (42 mg, 0.4 mmol) and Pd(PPh₃)₂Cl₂ (30 mg, 0.01 mmol). The mixture was then degassed for 2 minutes under N₂ atmosphere and heated to 120° C. overnight. Most of the solvent was removed. The residue was dissolved in EtOAc (30 mL). The organic layer was washed with brine (2×20 mL) and dried over anhydrous Na₂SO₄, filtered and evaporated to give a residue which was purified by prep-HPLC to give the desired product Compound 30 (25 mg, 66.7%).

LCMS: m/z, 378.1 (M+H)⁺;

¹H NMR (400 MHz, CDCl₃): δ2.57 (s, 3H), 3.44 (s, 3H), 3.78 (t, J=4.80 Hz, 2H), 4.44 (t, J-=4.80 Hz, 2H), 7.20 (m, 1H), 7.23 (d, J=12.0 Hz, 1H), 7.50 (d, J=9.6 Hz, 1H), 7.61 (s, 1H), 8.73 (d, J=5.20 Hz, 2H).

Example Compound 31

Preparation of 2-((3-(2-methoxyethoxy)-1-(4-(trifluoromethoxy)phenyl)-1H-pyrazol-4-yl)ethynyl)pyridine

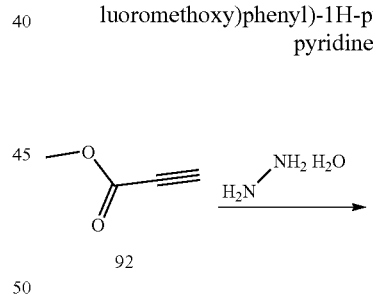

Procedure for Preparation of Compound 30

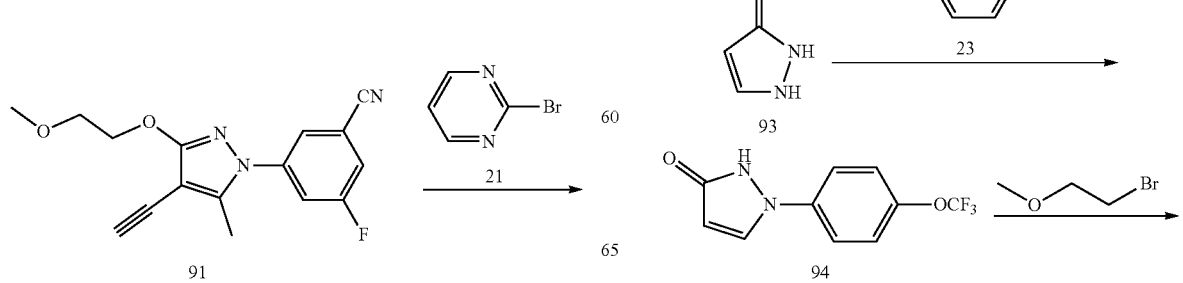

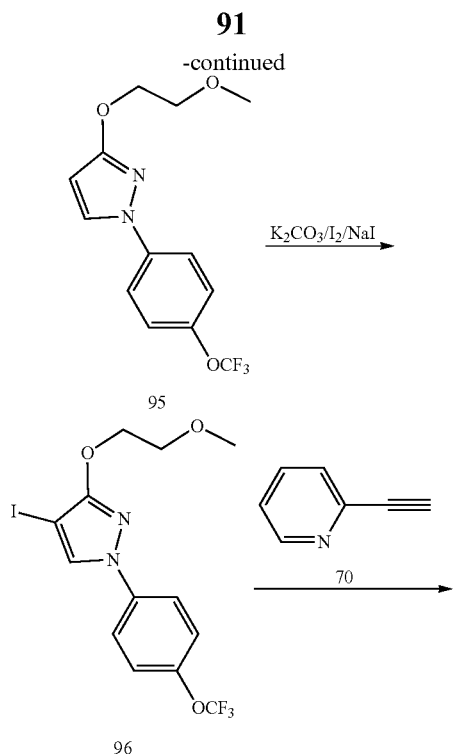

Experimental Section

Procedure for Preparation of 93

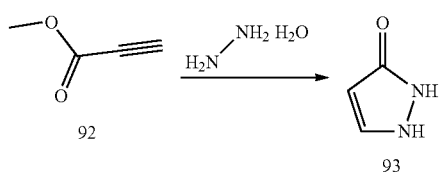

The compound of hydrazine monohydrate (85%, 4.81 g, 95.2 mmol) was added drop-wise to a cooled (ice bath) solution of 92 (8 g, 96.2 mmol) in methanol (50 mL). The reaction was allowed to stir for 30 minutes at room temperature, then, the solvent was removed under vacuo. The remaining aqueous layer was extracted with EtOAc (75 mL*5) and the combined organic layers were dried (MgSO$_4$), filtered and concentrated in vacuo to yield the title product 93 (5 g, yield: 62%)

$^1$HNMR (400 MHz, DMSO-d$_6$): δ5.40 (s, 2H), 7.32 (s, 2H).

Procedure for Preparation of 94

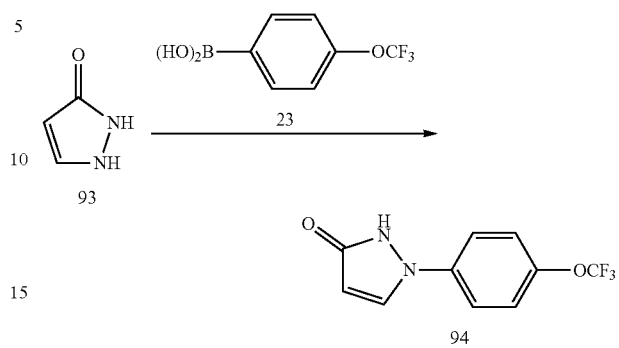

To a solution of 93 (1 g, 11.9 mmol) and 23 (3.67 g, 17.8 mmol) in DCM (20 ml) was added Cu(OAc)$_2$ (4.32 g, 23.8 mmol) and pyridine (2.82 g, 35.7 mmol) at room temperature under O$_2$, The mixture was stirred at room temperature overnight. The suspension was filtered through a pad of Celite and filter cake was washed with DCM (30 ml). The combined organic layers were washed with water and dried over Na$_2$SO$_4$. The crude product was purified by silica gel chromatography to give product 94 (50 mg, yield: 1.7%).

LCMS: m/z, 245.1 (M+H)$^+$

Procedure for Preparation of 95

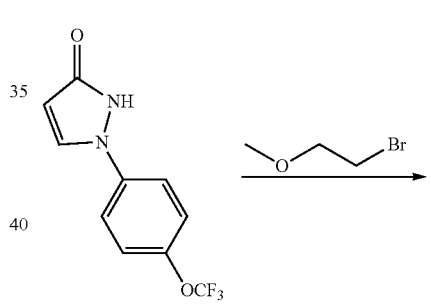

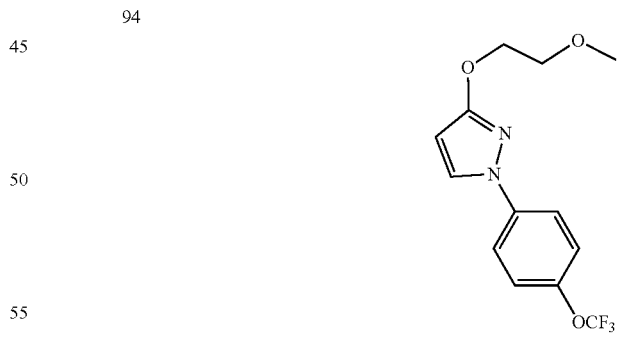

To a solution of 94 (250 mg, 1.02 mmol) and 1-bromo-2-methoxyethane (284 mg, 2.05 mmol) in DMF (15 ml) was added NaI (183 mg, 1.02 mmol) and K$_2$CO$_3$ (424 mg, 3.07 mmol). The mixture was heated at 60° C. overnight. The mixture was extracted with EtOAc (75 mL 2) and the combined organic layers were dried (MgSO$_4$), filtered and concentrated in vacuo, which was purified by silica gel chromatography to give product 95 (200 mg, yield: 64%).

LCMS: m/z, 303.1 (M+H)$^+$.

Procedure for Preparation of 96

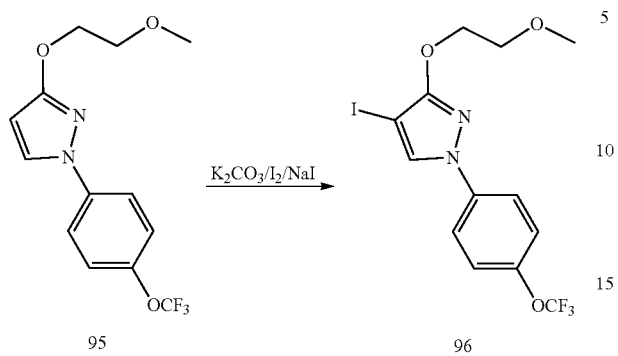

To a solution of 95 (20 mg, 66.2 ummol) in CHCl₃ (5 ml) was added NIS (22 mg, 99.3 umol). the mixture was heated at 60° C. for 1 hour, then, The reaction mixture was concentrated to dryness, which was purified by prep-TLC to afford the title product 96 (20 mg, yield: 70%).

¹HNMR (400 MHz, CDCl₃): δ3.43 (s, 3H), 3.71~7.73 (m, 2H), 4.38~4.41 (m, 2H), 7.17~7.21 (m, 2H), 7.49~7.52 (m, 2H), 7.67 (s, 1H).

Procedure for Preparation of Compound 31

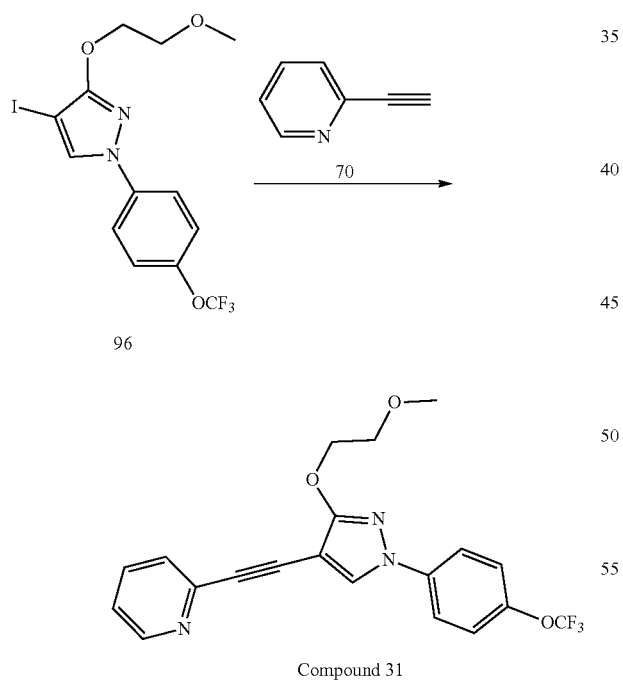

To a solution of 96 (100 mg, 0.23 mmol), 70 (50 mg, 0.47 mol), CuI (5 mg, 0.023 mol), Et₃N (70 mg, 0.39 mol) in THF (5 mL) was added Pd(PPh₃)₂Cl₂ (15 mg, 0.0023 mol). The suspension was degassed under vacuo and purged with N₂ several times. The mixture was stirred at 90° C. for 6 hours under N₂ atmosphere. The mixture was filtered and concentrated under vacuo. The residue was purified by prep-TLC to give desired product Compound 31 (20 mg, yield: 20%).

LCMS: m/z, 404.1 (M+H)⁺;

¹HNMR (400 MHz, CDCl₃): δ 3.46 (s, 3H), 3.61-3.63 (m, 2H), 4.44-4.49 (m, 2H), 7.15-7.26 (m, 3H), 7.45-7.51 (m, 1H), 7.57-7.621 (m, 3H), 7.82 (s, 1H), 8.57 (s, 1H).

Example Compound 32

Preparation of 3-fluoro-5-(3-(2-methoxyethoxy)-4-(pyridin-2-ylethynyl)-1H-pyrazol-1-yl)benzonitrile

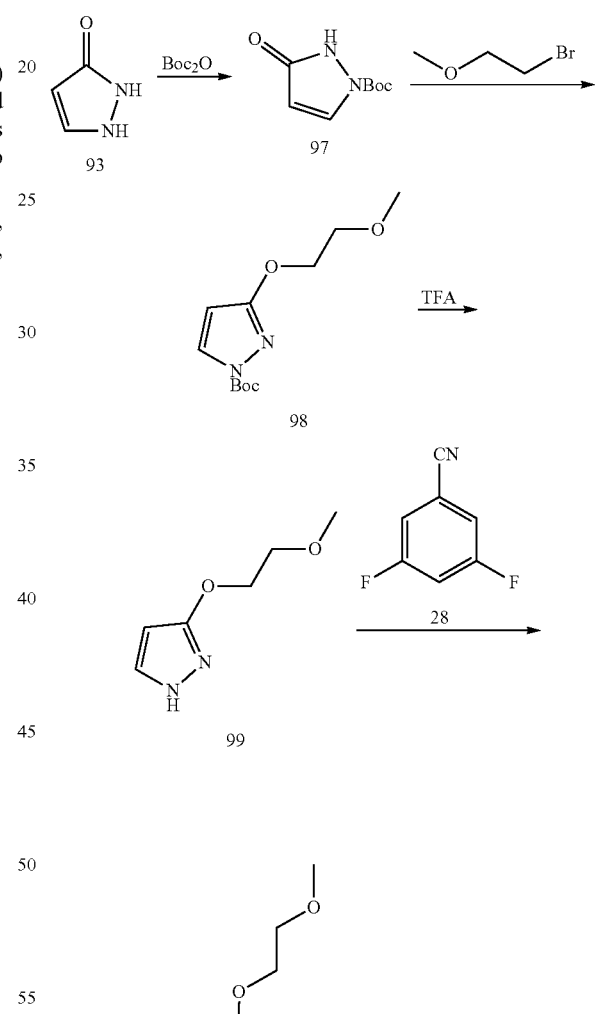

-continued

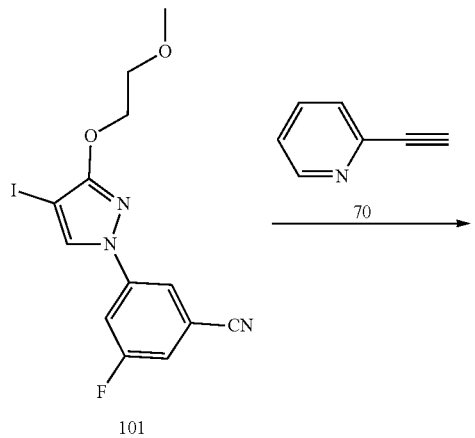

101

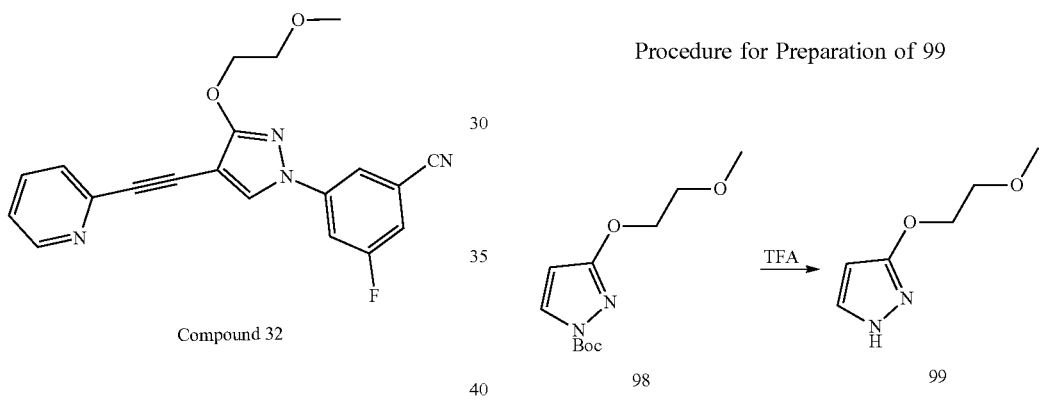

Compound 32

Experimental Section

Procedure for Preparation of 85

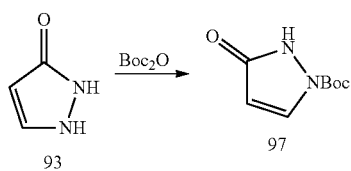 [SMILES: "Boc2O" ; O=c1cc[nH][nH]1 ; CC(C)(C)OC(=O)n1ccc(=O)[nH]1]

To a solution of 93 (2 g, 23.8 mmol) in DCM (20 ml) was added Boc₂O (5.71 g, 26.2 mmol) and Et₃N (2.65 g, 26.2 mmol). The mixture was stirred at room temperature for 6 hours. The mixture was extracted with EtOAc (100 mL×2) and the combined organic layers were dried (MgSO₄), filtered and concentrated in vacuo to yield the title product 97 (4 g, yield: 91%)

¹HNMR (400 MHz, CDCl₃): δ1.54 (s, 9H), 5.71 (s, 2H), 7.46 (s, 1H), 7.73 (s, 1H).

Procedure for Preparation of 98

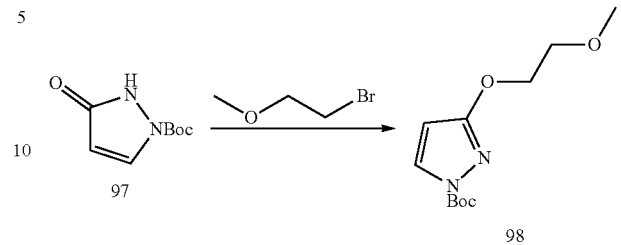

To a solution of 97 (2 g, 11 mmol) and 1-bromo-2-methoxyethane (3 g, 22 mmol) in DMF (25 ml) was added NaI (1.6 g, 11 mmol) and K₂CO₃ (4.5 mg, 32.6 mmol), the mixture was heated at 60° C. overnight, then the mixture was cool to room temperature and extracted with EtOAc (75 mL). The combined organic layers were dried (MgSO₄), filtered and concentrated in vacuo to yield the title product 98 (1.5 g, yield: 57%)

LCMS: m/z, 242.3 (M+H)⁺

Procedure for Preparation of 99

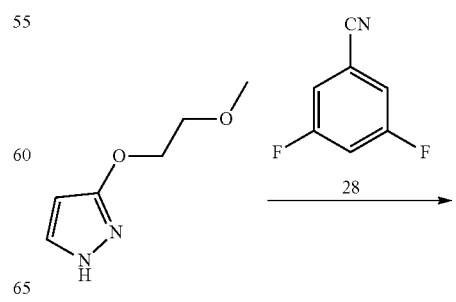

To a solution of 98 (2 g, 11 mmol) in DCM (15 ml) was added TFA (5 ml), the mixture was stirred at room temperature for 3 hours, the solvent was removed under vacuo. The remaining residue was extracted with EtOAc (100 mL×3) and the combined organic layers were dried (MgSO₄), filtered and concentrated in vacuo to yield the title product 99 (1.1 g, yield: 93%)

Procedure for Preparation of 100

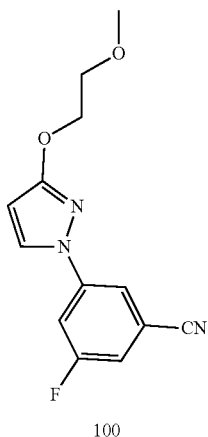

100

To a solution of 99 (170 mg, 1.2 mmol) and 28 (166 mg, 1.2 mmol) in DMF (5 ml) was added Cs₂CO₃ (467 mg, 1.44 mmol). The mixture was heated at 601° C. overnight, the mixture was extracted with EtOAc (50 mL×2) and the combined organic layers were dried (MgSO₄), filtered and concentrated in vacuo to afford the crude product, which was purified by silica gel chromatography to afford the title product 100 (250 mg, yield: 80%).

¹HNMR (400 MHz, CDCl₃): δ 3.45 (s, 3H), 3.72-3.75 (m, 2H), 4.59-4.62 (m, 2H), 6.09 (s, 1H), 7.15-7.24 (m, 1H), 7.59-7.64 (m, 1H), 7.59-7.66 (m, 2H).

Procedure for Preparation of 101

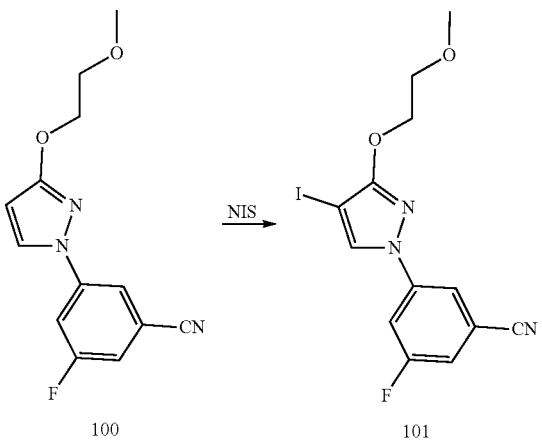 [SMILES: COCCOc1ccn(-c2cc(F)cc(C#N)c2)n1 ; "NIS" ; COCCOc1nn(-c2cc(F)cc(C#N)c2)cc1I]

100    101

To a solution of 100 (250 mg, 0.96 mmol) in CHCl₃ (15 ml) was added NIS (323 mg, 1.44 mmol). The mixture was heated at 60° C. for 3 hours, then was extracted with EtOAc (50 mL) and the combined organic layers were dried (MgSO₄), filtered and concentrated in vacuo, which was purified by silica gel chromatography to give product 101 (300 mg, yield: 81%).

¹HNMR (400 MHz, CDCl₃): δ 3.46 (s, 3H), 3.71-3.78 (m, 2H), 4.47-4.53 (m, 2H), 7.17-7.22 (m, 1H), 7.55-7.63 (m, 1H), 7.64 (s, 1H), 7.77 (s, 2H).

Procedure for Preparation of Compound 32

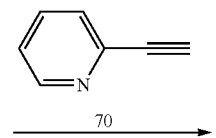

101

Compound 32

To a solution of 101 (300 mg, 0.77 mmol), 70 (160 mg, 1.55 mmol), CuI (15 mg, 0.077 mmol), Et₃N (235 mg, 2.32 mmol) in THF (5 mL) was added Pd(PPh₃)₂Cl₂ (53 mg, 0.077 mmol). The suspension was degassed under vacuum and purged with N₂ several times. The mixture was stirred at 90° C. for 6 hours under N₂ atmosphere. The mixture was filtered and concentrated under vacuo. The residue was purified by prep-TLC to give the product Compound 32 (30 mg, yield: 10%).

LCMS: m/z, 363.1 (M+H)⁺;

¹HNMR (400 MHz, CDCl₃): δ 3.47 (s, 3H), 3.81-3.84 (m, 2H), 4.46-4.54 (m, 2H), 7.15-7.21 (m, 2H), 7.53-7.57 (m, 2H), 7.65-7.71 (m, 2H), 7.98 (s, 1H), 8.65 (s, 1H).

Example Compound 33

Preparation of 3-fluoro-5-(4-(pyridin-2-ylethynyl)-1H-pyrazol-1-yl)pyridine

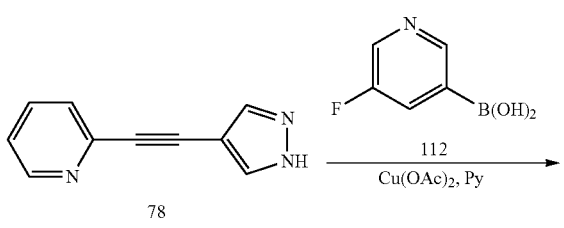

78

-continued

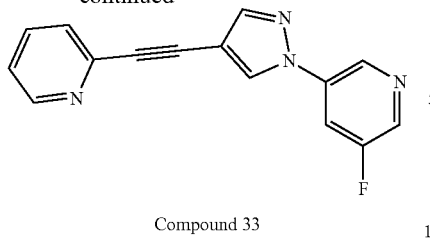

Compound 33

Experimental Section

Procedure for Preparation of Compound 33

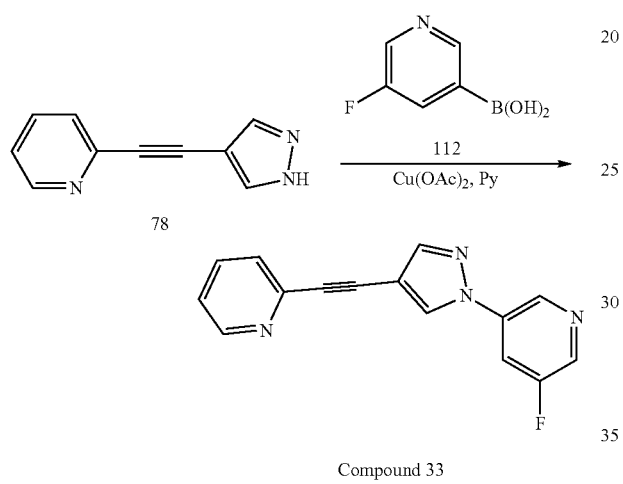

To a solution of 78 (50 mg, 0.296 mmol) in DCM (8 mL) was added 112 (83 mg, 0.591 mmol), Cu(OAc)$_2$ (107 mg, 0.591 mmol), pyridine (70 mg, 0.887 mmol). The mixture was stirred at room temperature overnight under O$_2$ atmosphere. The mixture was filtered and concentrated under vacuo. The residue was purified by prep-TLC to give product Compound 33 (6 mg, 8%).

LCMS: m/z, 265.1 (M+H)$^+$;

$^1$H NMR (400 MHz, CDCl$_3$): δ 8.81 (s, 1H), 8.64-8.62 (m, 1H), 8.46 (s, 1H), 8.22 (s, 1H), 7.97 (s, 1H), 7.89-7.86 (m, 1H), 7.71-7.69 (m, 1H), 7.52-7.50 (m, 1H), 7.27-7.26 (m, 1H).

Example Compound 34

Preparation of 2-((1-(6-fluoropyridin-3-yl)-1H-pyrazol-4-yl)ethynyl)pyrimidine

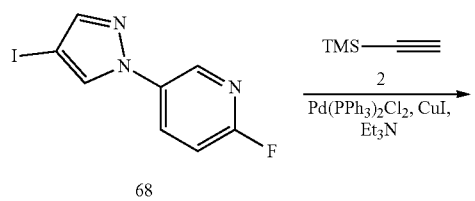

-continued

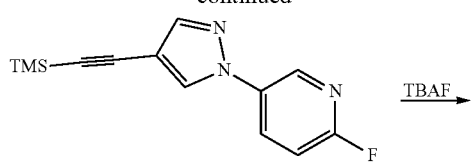

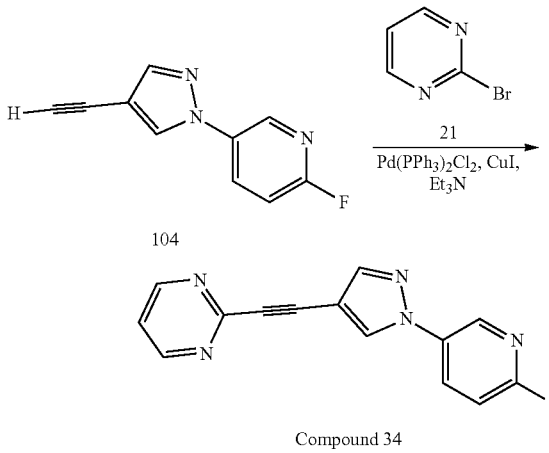

Compound 34

Experimental Section

Procedure for Preparation of 103

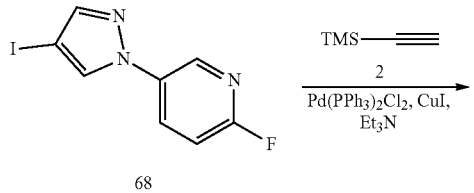

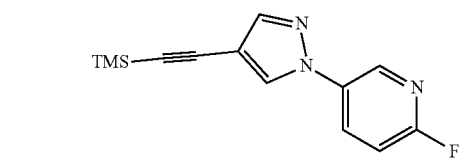

To a solution of 68 (400 mg, 1.38 mmol) in CH$_3$CN (20 mL) was added successively CuI (26 mg, 0.138 mmol), 2 (272 mg, 2.77 mmol), Et$_3$N (420 mg, 4.15 mmol) and Pd(PPh$_3$)$_2$Cl$_2$ (49 mg, 0.069 mmol). The mixture was then degassed for 1 minute under N$_2$ atmosphere and stirred at 80° C. overnight. The reaction mixture was filtered and concentrated to give the crude product which was purified by silica gel chromatography to give product 103 (300 mg, 84%).

LCMS: m/z, 260.1 (M+H)$^+$.

Procedure for Preparation of 104

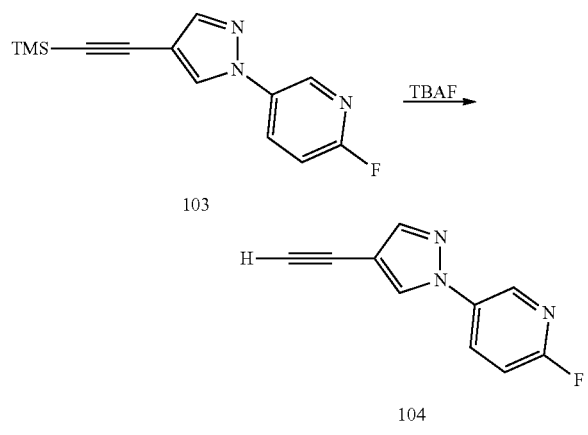

To a solution of compound 103 (300 mg, 1.16 mmol) in THF (20 mL) was added TBAF (1.74 mL, 1.74 mmol) dropwise. The mixture was stirred at room temperature for 2 hours. The reaction mixture was quenched with water and extracted with EtOAc (3×20 mL). The combined organics was concentrated by vacuo to give product 104 (200 mg, crude).

LCMS: m/z, 188.2 (M+H)$^+$.

Procedure for Preparation of Compound 34

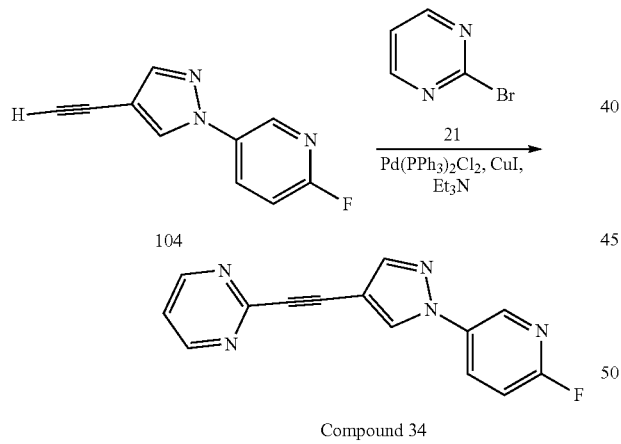

To a solution of 104 (80 mg, 0.427 mmol) in THF (3 mL) was added successively CuI (8 mg, 0.043 mmol), 21 (136 mg, 0.854 mmol), Et$_3$N (130 mg, 1.28 mmol) and Pd(PPh$_3$)$_2$Cl$_2$ (15 mg, 0.021 mmol). The mixture was then degassed for 1 minute under N$_2$ atmosphere and stirred at 90° C. for 1 h under microwave. The reaction mixture was filtered and concentrated to give the crude product which was purified by prep-TLC to give product Compound 34 (20 mg, 18%).

LCMS: m/z, 266.0 (M+H)$^+$;

$^1$H NMR (400 MHz, CDCl$_3$): δ 8.77 (s, 1H), 8.56 (s, 1H), 8.21-8.15 (m, 2H), 8.01 (s, 1H), 7.26-7.24 (m, 1H), 7.11-7.08 (m, 1H).

Example Compound 35

Preparation of 2-((5-chloro-1-(4-(trifluoromethyl)phenyl)-1H-pyrazol-4-yl) ethynyl)pyridine

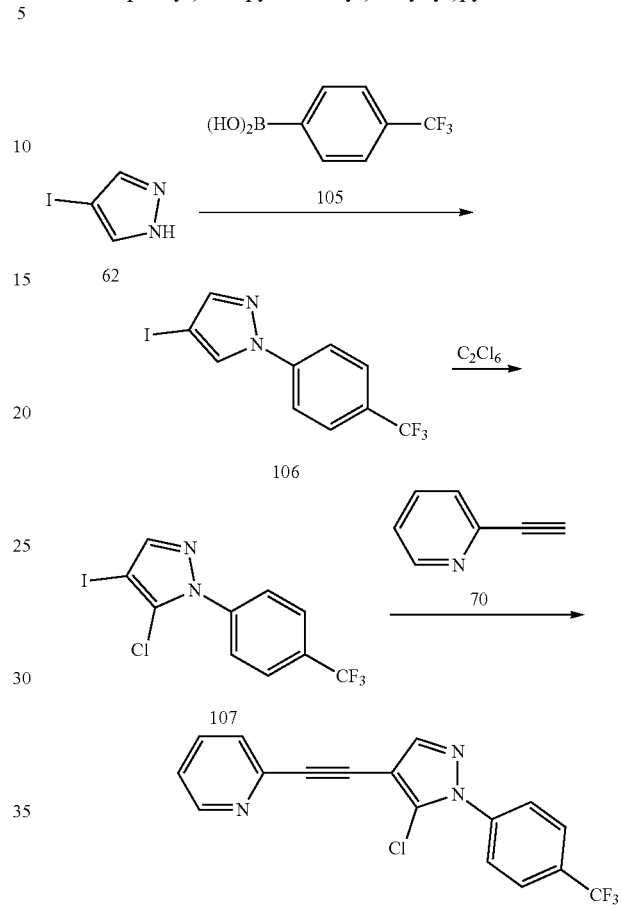

Compound 35

Experimental Section

Procedure for Preparation of 106

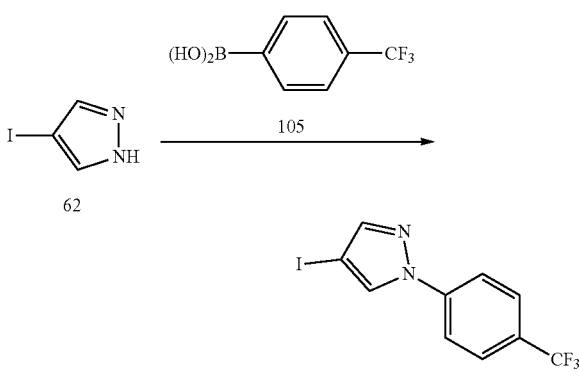

To a solution of 62 (1.3 g, 6.5 mmol), 105 (1.5 g, 7.8 mmol) and Cu(AcO)$_2$ (2.4 g, 13 mmol) in 50 mL of degassed DCM was added successively Pyridine (1.5 g, 19.4 mmol) at room temperature. The mixture was stirred at room temperature for 12 hours. It was filtrated and most of the solvent was removed. The residue was dissolved in EtOAc (60 mL). The organic layer was washed with brine (2×30 mL) and dried over anhydrous Na$_2$SO$_4$, filtered and evaporated to dryness on a rotary evaporator, which was purified by chromatography to give of the desired product 106 (g, 43.5%).

$^1$H NMR (400 MHz, CDCl$_3$): δ7.77-7.80 (m, 5H), 8.03 (s, 1H)

Procedure for Preparation of 107

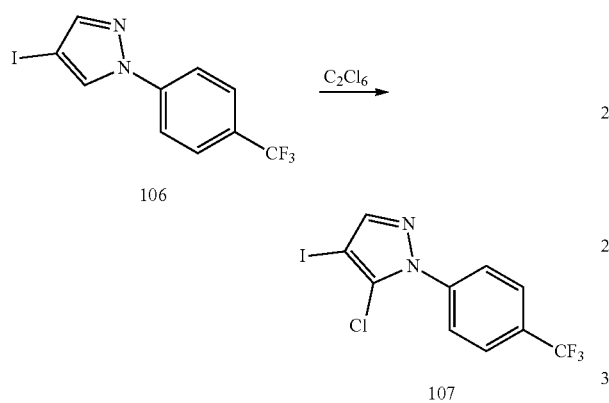

To a solution of 106 (100 mg, 0.3 mmol) in 10 mL of degassed THF was added LDA (0.21 mL, 0.42 mmol) at −78° C. After stirring 30 minutes, perchloroethane (98 mg, 0.42 mmol) was added. It was stirred at the same condition for another 30 minutes. Then the reaction mixture was quenched with sat.NH$_4$Cl. The solvent was removed, the residue was extracted with DCM and water, the organic layer was dried and purified by prep-TLC to give title product 107 (50 mg, 45%).

$^1$H NMR (400 MHz, CDCl$_3$): 7.64-7.77 (m, 5H).

Procedure for Preparation of Compound 35

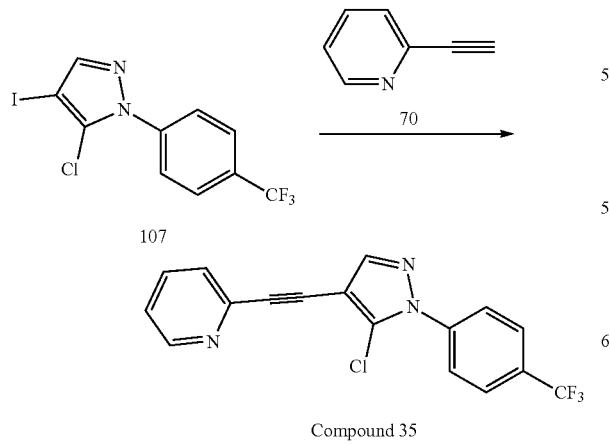

To a solution of 107 (50 mg, 0.131 mmol) in 4 mL of degassed THF was added solid CuI (1.3 mg, 0.007 mmol), 70 (21 mg, 0.20 mmol), Et$_3$N (39 mg, 0.39 mmol) and Pd(PPh$_3$)$_2$Cl$_2$ (5 mg, 0.007 mmol). The mixture was then degassed for 2 minutes under N$_2$ atmosphere and stirred at 90° C. for 1 h under microwave. Most of the solvent was removed. The residue was dissolved in EtOAc (30 mL). The organic layer was washed with brine (2×20 mL) and dried over anhydrous Na$_2$SO$_4$, filtered and evaporated to give the residue which was purified by prep-HPLC to afford the product Compound 35 (5 mg, 11%).

LCMS: m/z, 348.0 (M+H)$^+$;

$^1$H NMR (400 MHz, CDCl$_3$): δ7.30 (m, 1H), 7.56 (m, 1H), 7.70 (m, 1H), 7.79 (s, 4H), 7.94 (s, 1H), 8.65 (s, 1H).

Example Compound 36

Preparation of 2-((5-chloro-1-(4-(trifluoromethyl)phenyl)-1H-pyrazol-4-yl)ethynyl) pyrimidine

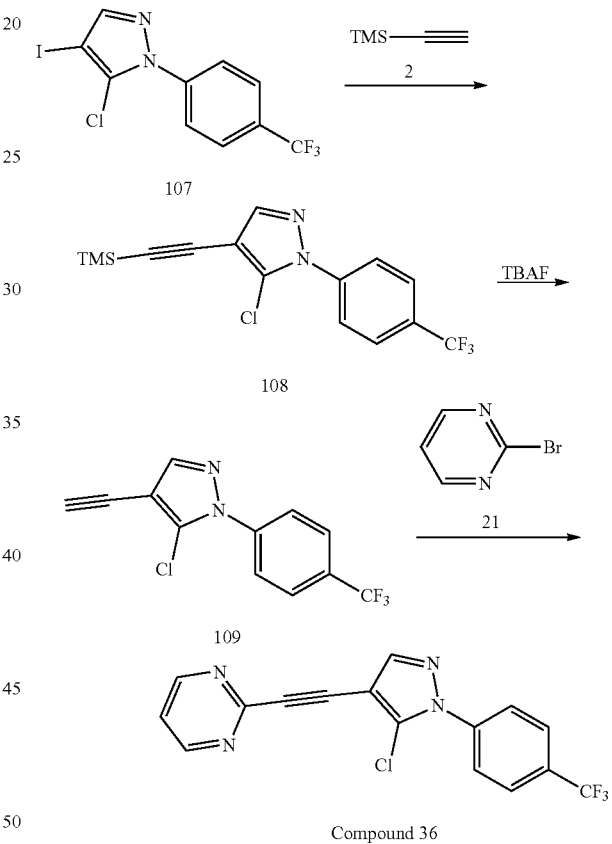

Experimental Section

Procedure for Preparation of 108

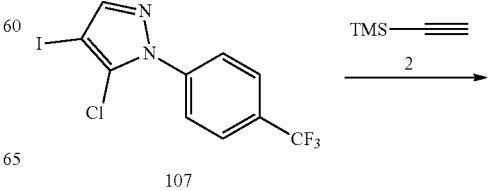

-continued

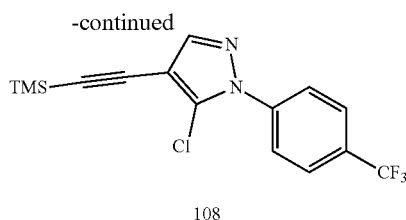

108

To a solution of 107 (80 mg, 0.2 mmol) in 4 mL of degassed THF was added successively CuI (1 mg, 0.005 mmol), 2 (171 mg, 0.2 mmol), Et$_3$N (30 mg, 0.3 mmol) and Pd(PPh$_3$)$_2$Cl$_2$ (3 mg, 0.005 mmol). The mixture was then degassed for 2 minutes under N$_2$ atmosphere and stirred at 90° C. for 1 hour under microwave. Then most of the solvent was removed. The residue was dissolved in EtOAc (30 mL). The organic layer was washed with brine (2×20 mL) and dried over anhydrous Na$_2$SO$_4$, filtered and evaporated to dryness on a rotary evaporator, which was purified by TLC plate to give the product 108 (70 mg, 95.9%)

LCMS: m/z, 343.1 (M+H)$^+$.

Procedure for Preparation of 109

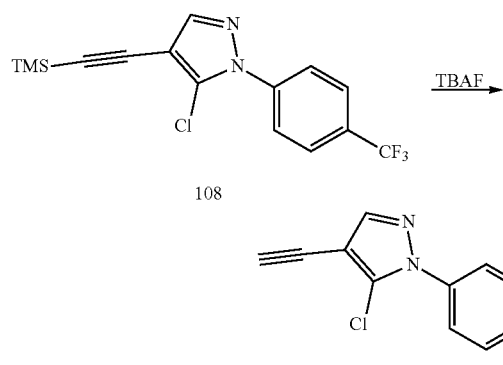

To a solution of 108 (70 mg, 0.2 mmol) in THF (4 mL) was added a solution of TBAF-THF (10.2 mL, 0.3 mmol). The mixture was stirred at room temperature for 1 hour. TLC showed the reaction was complete, then most of the solvent was removed. The residue was dissolved in EtOAc (20 mL). The organic layer was washed with brine (2×10 mL) and dried over anhydrous Na$_2$SO$_4$, filtered and evaporated to give the product 109 (50 mg, 90.4%), which was directly used for next step LCMS: m/z, 271.3 (M+H)$^+$.

Procedure for Preparation of Compound 36

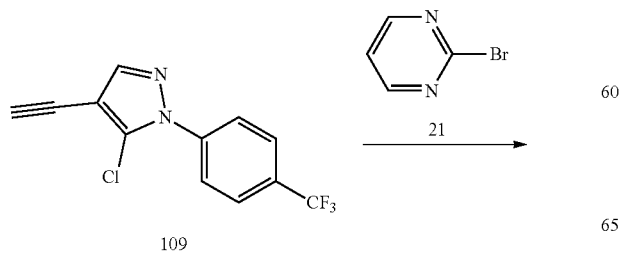

-continued

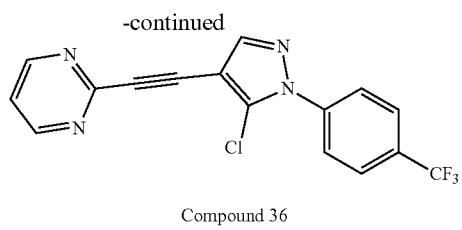

Compound 36

To a solution of 109 (50 mg, 0.19 mmol) in 4 mL of degassed THF was added solid CuI (2 mg, 0.01 mmol), 21 (35 mg, 0.22 mmol), Et$_3$N (58 mg, 0.57 mmol) and Pd(PPh$_3$)$_2$Cl$_2$ (7 mg, 0.01 mmol). The mixture was then degassed for 2 minutes under N$_2$ atmosphere and stirred at 90° C. for 1 hour under microwave. Then most of the solvent was removed. The residue was dissolved in EtOAc (30 mL). The organic layer was washed with brine (2×20 mL) and dried over anhydrous Na$_2$SO$_4$, filtered and evaporated to give a residue which was purified by prep-HPLC to give of the product Compound 36 (17 mg, 26.6%).

LCMS: m/z, 349.0 (M+H)$^+$;

$^1$H NMR (400 MHz, CDCl$_3$): δ7.27 (m, 1H), 7.79 (s, 4H), 7.98 (s, 1H), 8.78 (d, J=4.8 Hz, 2H).

Example Compound 37

Preparation of 3-(3-(difluoromethoxy)-5-methyl-4-(pyridin-2-ylethynyl)-1H-pyrazol-1-yl)-5-fluorobenzonitrile

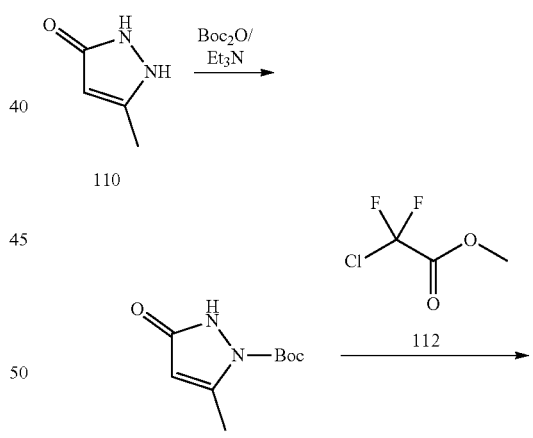

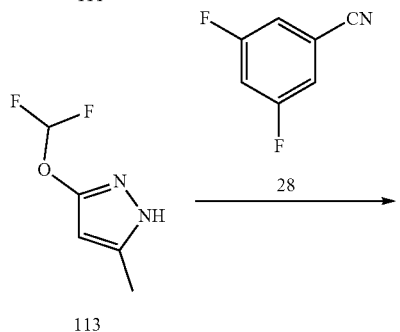

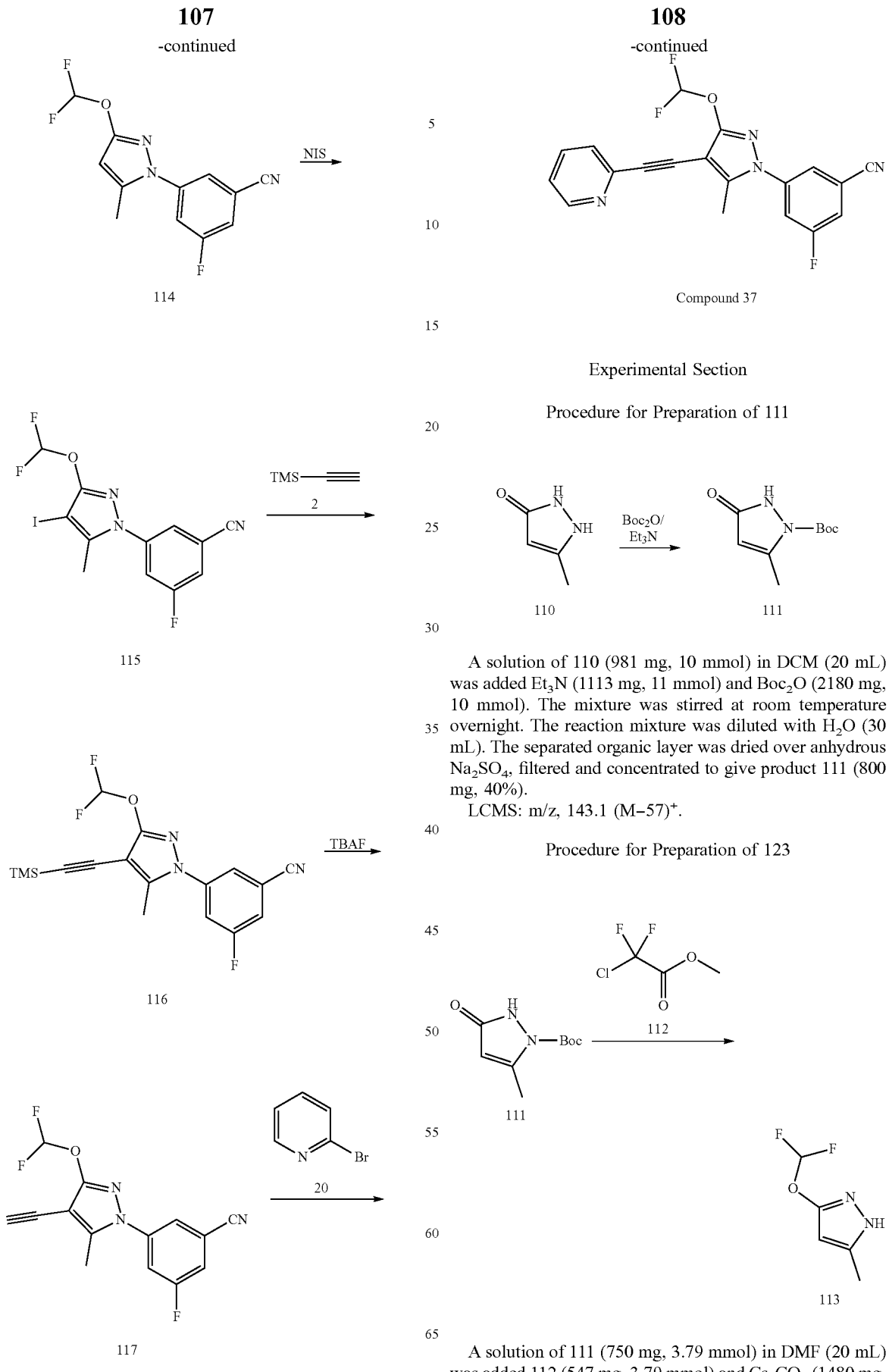

Experimental Section

Procedure for Preparation of 111

A solution of 110 (981 mg, 10 mmol) in DCM (20 mL) was added Et₃N (1113 mg, 11 mmol) and Boc₂O (2180 mg, 10 mmol). The mixture was stirred at room temperature overnight. The reaction mixture was diluted with H₂O (30 mL). The separated organic layer was dried over anhydrous Na₂SO₄, filtered and concentrated to give product 111 (800 mg, 40%).

LCMS: m/z, 143.1 (M−57)⁺.

Procedure for Preparation of 123

A solution of 111 (750 mg, 3.79 mmol) in DMF (20 mL) was added 112 (547 mg, 3.79 mmol) and Cs₂CO₃ (1480 mg, 4.54 mmol). The mixture was stirred at 100° C. for 6 hours. After cooling, the mixture was diluted with H₂O (60 mL), and extracted with EtOAc (15 mL). The organic layer was dried over anhydrous Na₂SO₄, filtered and concentrated to give product 113 (350 mg, 60%).

LCMS: m/z, 149.1 (M+H)⁺.

Procedure for Preparation of 114

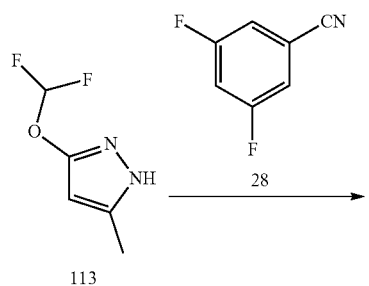

A solution of 113 (320 mg, 2.16 mmol) in DMF (15 mL) was added 28 (300 mg, 2.16 mmol) and Cs₂CO₃ (845 mg, 2.59 mmol). The mixture was stirred at 100° C. for 4 hours. After cooling, the reaction mixture was diluted with H₂O (30 mL) and extracted with EtOAc (15 mL). The separated organic layer was dried over anhydrous Na₂SO₄, filtered and concentrated to residue which was purified by prep-TLC to give product 114.

Procedure for Preparation of 115

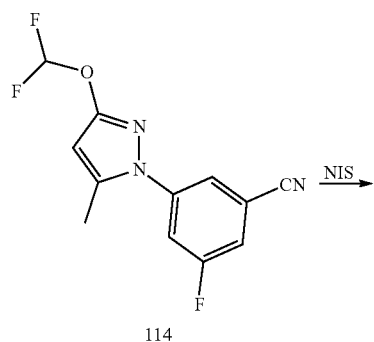

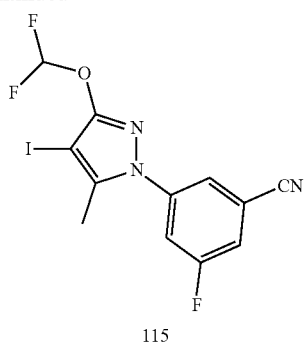

To a solution of 114 (120 mg, 0.449 mmol) in CHCl₃ (15 mL) was added NIS (123 mg, 0.539 mmol). The mixture was stirred at 60° C. for 6 hours. The mixture was quenched with water and extracted with DCM (2×10 mL). The combined organics was concentrated under vacuo and the residue was purified by prep-TLC to give product 115 (120 mg, 68%).

Procedure for Preparation of 116

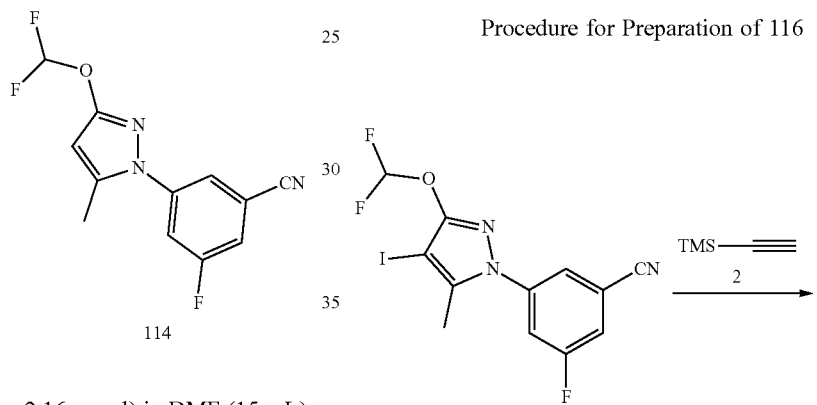

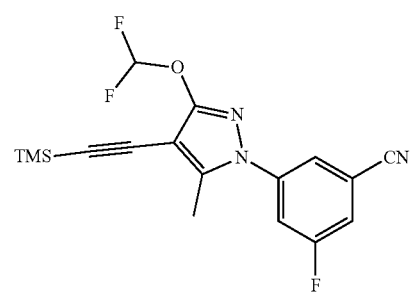

To a solution of 115 (120 mg, 0.305 mmol) in CH₃CN (3 mL) was added successively CuI (6 mg, 0.031 mmol), 2 (60 mg, 0.611 mmol), Et₃N (93 mg, 0.916 mmol) and Pd(PPh₃)₂Cl₂ (11 mg, 0.015 mmol). The mixture was then degassed for 1 minute under N₂ atmosphere and was heated at 90° C. under microwave for 1 hour. The reaction mixture was filtered and evaporated to give crude product, which was purified by prep-TLC to give product 116 (100 mg, 90%).

LCMS: m/z, 364.1 (M+H)⁺.

Procedure for Preparation of 117

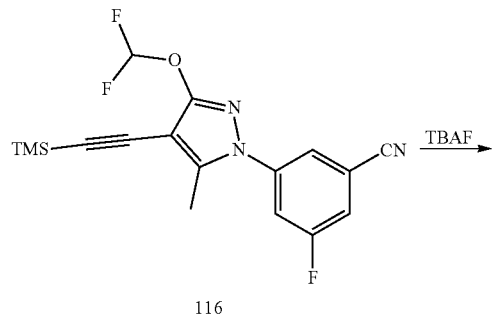

116

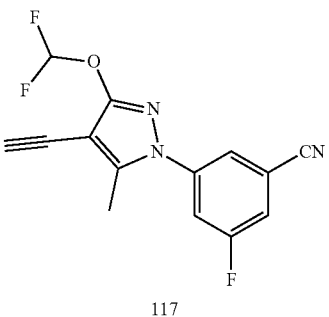

117

A solution of 116 (100 mg, 0.275 mmol) in THF (5 mL). The solution was cooled to 0° C. and TBAF (0.413 mL, 0.413 mmol) was added. The reaction mixture stirred at room temperature for 2 hours. The mixture was quenched with water and extracted with EA (3×10 mL). The combined organics was concentrated by vacuo to give the crude product 117 (80 mg, crude).

Procedure for Preparation of Compound 37

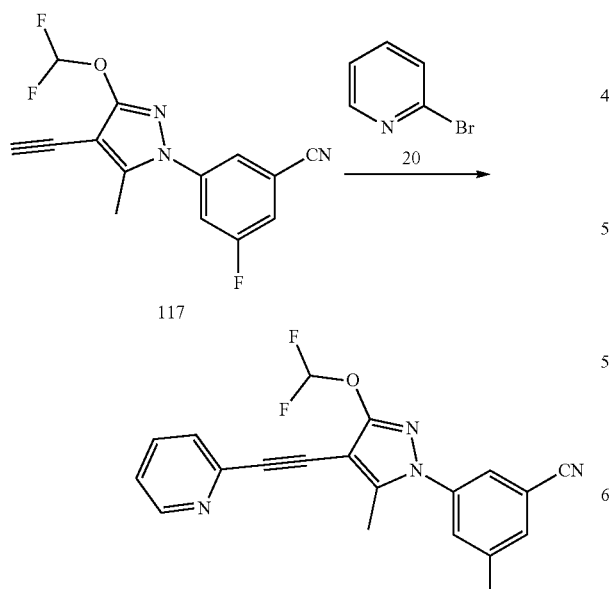

Compound 37

To a solution of 117 (80 mg, 0.275 mmol) in THF (3 mL) was added successively CuI (5 mg, 0.027 mmol), 20 (87 mg, 0.549 mmol), Et$_3$N (83 mg, 0.824 mmol) and Pd(PPh$_3$)$_2$Cl$_2$ (10 mg, 0.014 mmol). The mixture was then degassed for 1 minute under N$_2$ atmosphere and stirred at 90° C. for 1 hour under microwave. The reaction mixture was filtered and concentrated to give the crude product which was purified by prep-HPLC to give product Compound 37 (20 mg, 18%).

LCMS: m/z, 369.1 (M+H)$^+$;

$^1$H NMR (400 MHz, CDCl$_3$): δ 8.63-8.62 (m, 1H), 7.71-7.69 (m, 1H), 7.61 (s, 1H), 7.55-7.50 (m, 2H), 7.48-7.46 (m, 1H), 7.27-7.25 (m, 1H), 7.08-6.90 (m, 1H), 2.57 (s, 3H).

Example Compound 38

Preparation of 3-(3-chloro-4-(pyridin-2-ylethynyl)-1H-pyrazol-1-yl)-5-fluorobenzonitrile

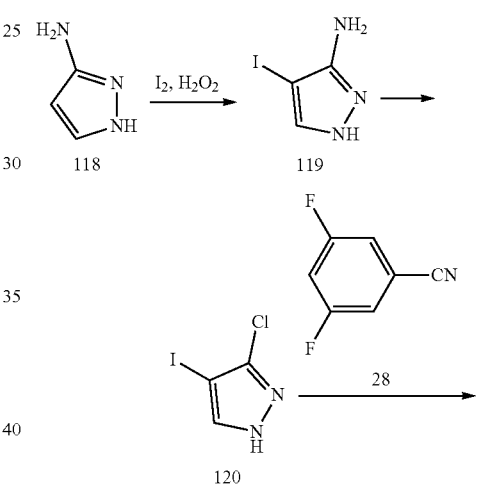

118         119

120

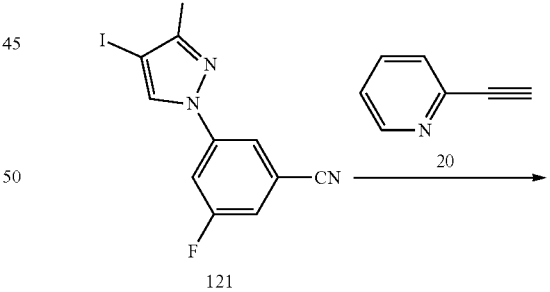

121

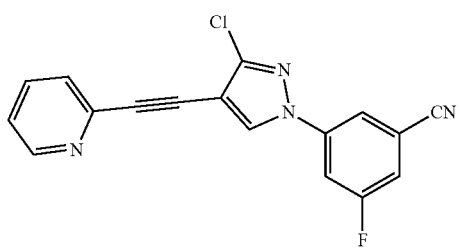

Compound 38

Experimental Section

Procedure for Preparation of 119

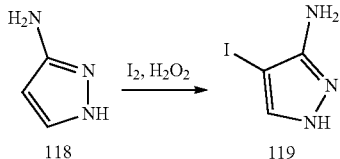 [SMILES: Nc1cc[nH]n1 ; Nc1n[nH]cc1I]

To a solution of 118 (1.0 g, 12.0 mmol) in 10 mL of H$_2$O was added 30% of H$_2$O$_2$ (0.82 g, 7.2 mmol) and 2 (1.5 g, 6.0 mmol), the mixture was stirred at room temperature for 1 hour. The mixture was treated with 20 mL of saturated Na$_2$S$_2$O$_3$ solution and filtered. The filter cake was washed by water and dried in air overnight to afford crude product 119 which was used for the next step directly (2.0 g, 79.5% yield).

$^1$HNMR (400 MHz, DMSO): δ4.55 (br, 2H), 7.38 (s, 1H), 12.0 (br, 1H).

Procedure for Preparation of 120

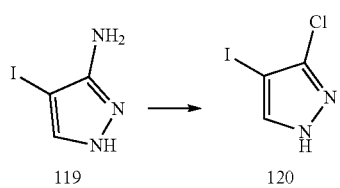 [SMILES: Nc1n[nH]cc1I ; Clc1n[nH]cc1I]

A solution of 119 (20.0 g, 100.0 mmol) in 60.0 mL of water, was added 100.0 mL of concentrated HCl and 30.0 mL of 85% H$_3$PO$_4$, the mixture was cooled to −5° C. A solution of NaNO$_2$ (7.0 g, 100.0 mmol) in 30.0 mL of H$_2$O was added over 30 minutes, the temperature was kept at −2° C. After stirred for 1 hour, the above mixture was added to a solution of CuCl (15 g, 150.0 mmol) in 100.0 mL of concentrated HCl. The mixture was heated to 60° C. until the mixture was no gas goes off, then extracted with chloroform. The organic phase was washed with water, brine, dried over Na$_2$SO$_4$, filtered and concentrated to dryness. The residue was purified by flash chromatography column on silicone gel to afford product 120 (1.6 g, yield: 6.9%).

LCMS: m/z, 228.9 (M+H)$^+$.

Procedure for Preparation of 121

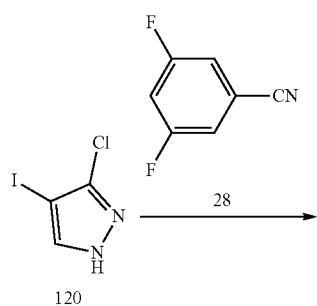

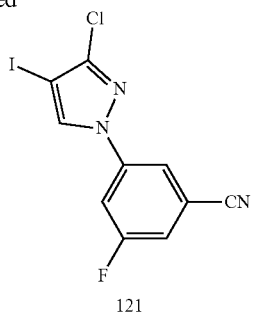

To a solution of 120 (73.0 mg, 0.5 mmol) and 28 (100.0 mg, 0.4 mmol) in DMF (2.0 mL) was added Cs$_2$CO$_3$ (260.6 mg, 0.8 mmol at room temperature, the mixture was stirred at 80° C. for 30 minutes. TLC showed the reaction was completed. The reaction mixture was treated with water, extracted with 15 mL of EA. The organic phase was separated, washed by water, brine, dried over Na$_2$SO$_4$, filtered and concentrated to dryness. The residue was purified by pre-TLC to afford product 121 (100.0 mg, yield: 66.7%).

$^1$HNMR (400 MHz, CDCl$_3$): δ7.31 (d, J=2 Hz, 1H), 7.65-7.68 (m, 1H), 7.74 (s, 1H), 7.95 (s, 1H).

Procedure for Preparation of Compound 38

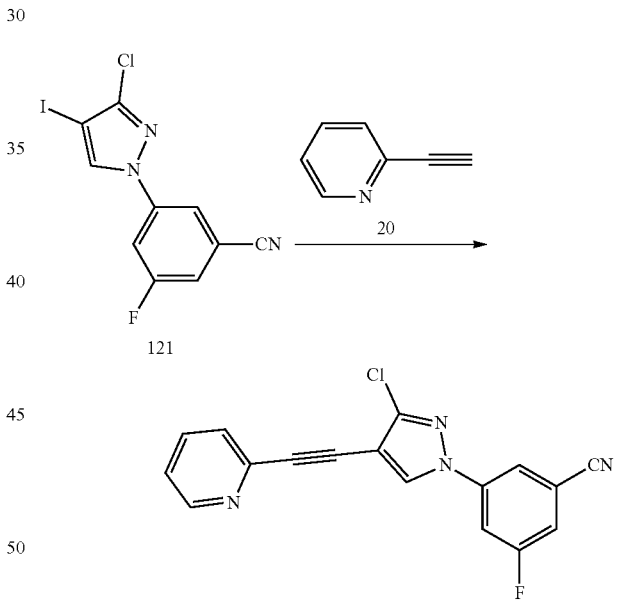

Compound 38

To a solution of 121 (60.0 mg, 0.17 mmol) and 20 (26.7 mg, 0.26 mmol) in THF (3.0 mL) was added Pd(PPh$_3$)$_2$Cl$_2$ (1.4 mg, 0.002 mmol), CuI (0.7 mg, 0.005 mmol) and Et$_3$N (34.4 mg, 0.34 mmol) at room temperature, the mixture was heated at 90° C. by microwave for 1 hour under N$_2$ atmosphere. The reaction mixture was concentrated to dryness and the residue was purified by prep-HPLC to afford product Compound 38 (9.0 mg, yield: 16.7%).

LCMS: m/z, 323.0 (M+H)$^+$;

$^1$HNMR (400 MHz, CDCl$_3$): δ7.28-7.31 (m, 2H), 7.55 (d, H=8.0 Hz, 1H), 7.67-7.76 (m, 3H), 8.11 (s, 1H), 8.64 (d, J=4.4 Hz, 1H).

Example Compound 39

Preparation of 3-(3-chloro-4-(pyrimidin-2-ylethynyl)-1H-pyrazol-1-yl)-5-fluorobenzonitrile

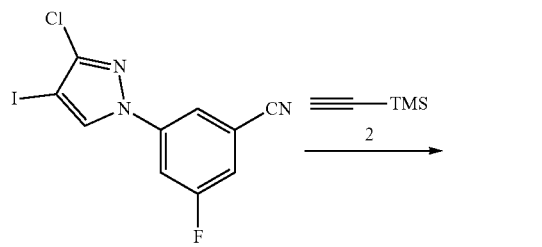

121

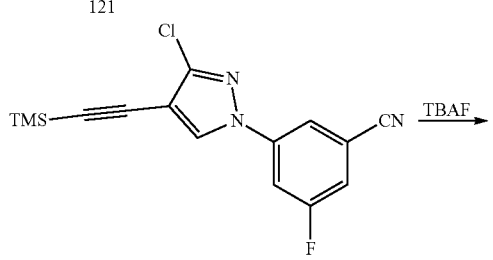

122

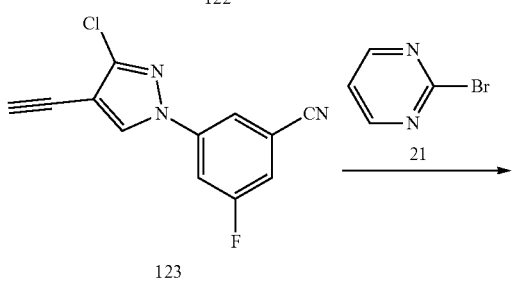

123

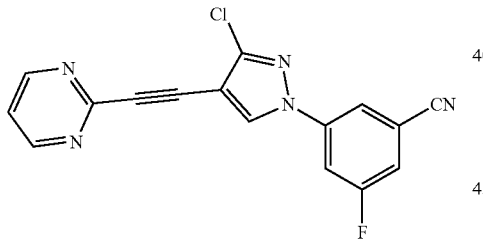

Compound 39

Experimental Section

Procedure for Preparation of 122

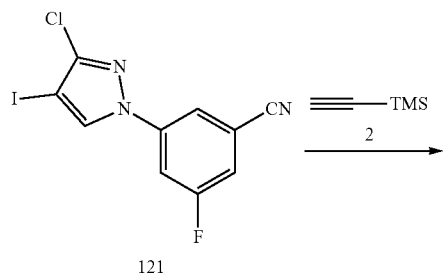

121

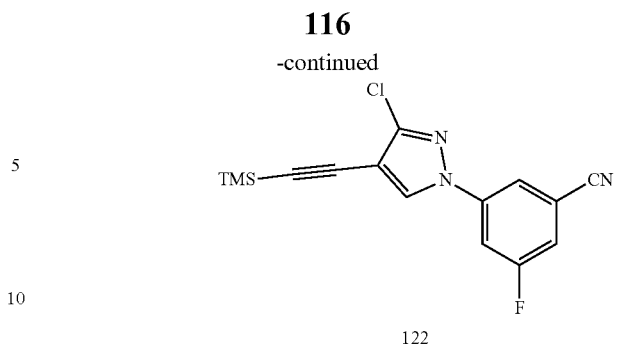

122

To a solution of 121 (100.0 mg, 0.3 mmol) and 2 (57.0 mg, 0.6 mmol) in THF (3.0 mL) was added Pd(PPh$_3$)$_2$Cl$_2$ (2.1 mg, 0.003 mmol), CuI (1.1 mg, 0.006 mmol) and Et$_3$N (60.0 mg, 0.6 mmol) at room temperature, the mixture was heated at 90° C. by microwave for 1 hour under N$_2$ atmosphere. The reaction mixture was concentrated to dryness, and the crude product was purified by prep-TLC to afford title product 122 (50.0 mg, 55.0% yield).

Procedure for Preparation of 123

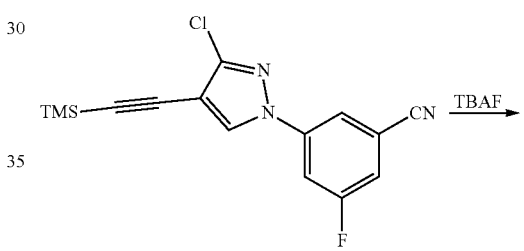

122

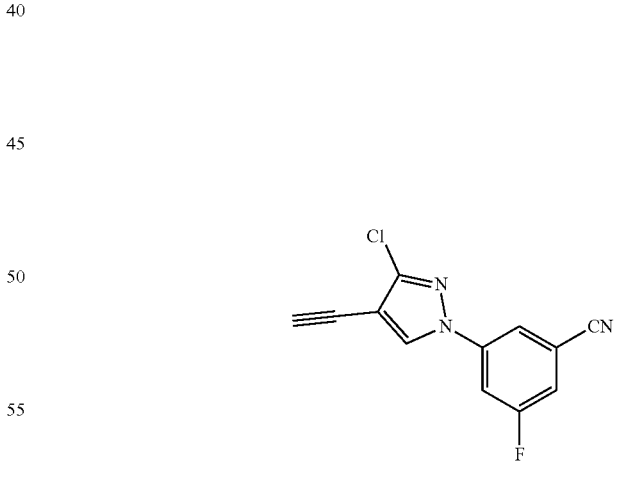

123

To a solution of 122 (50.0 mg, 0.16 mmol) in THF (3.0 mL) was added 0.2 mL of TBAF in THF solution (0.2 mmol, 1M), the reaction mixture was stirred at room temperature for 1 hour and then concentrated to dryness. The crude product 123 was used for the next step directly (38.6 mg, 100% yield).

Procedure for Preparation of Compound 39

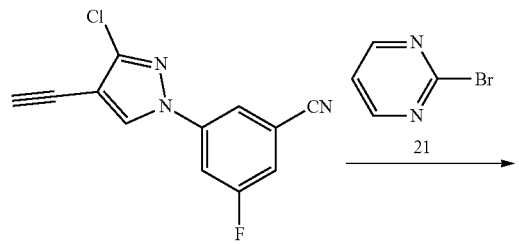

123

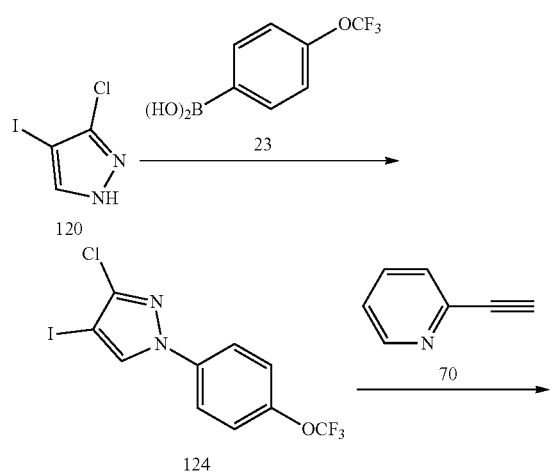

Compound 39

To a solution of 123 (38.6 mg, 0.16 mmol) and 21 (37.5 mg, 0.24 mmol) in THF (3.0 mL) was added Pd(PPh$_3$)$_2$Cl$_2$ (1.4 mg, 0.002 mmol), CuI (0.7 mg, 0.004 mmol) and Et$_3$N (60.0 mg, 0.6 mmol) at room temperature, the mixture was heated at 90° C. by microwave for 1 hour under N$_2$ atmosphere. The reaction mixture was concentrated to dryness, and the crude product was purified by prep-HPLC to afford product Compound 39 (9.0 mg, yield: 17.7%).

LCMS: m/z, 323.9 (M+H)$^+$;

$^1$HNMR (400 MHz, CDCl$_3$): δ7.27-7.31 (m, 1H), 7.34 (d, J=8.0 Hz, 1H), 7.72 (d, J=8.0 Hz, 1H), 7.75 (s, 1H), 8.17 (s, 1H), 8.78 (d, J=4.4 Hz, 2H).

Example Compound 40

Preparation of 2-((3-chloro-1-(4-(trifluoromethoxy)phenyl)-1H-pyrazol-4-yl) ethynyl)pyridine

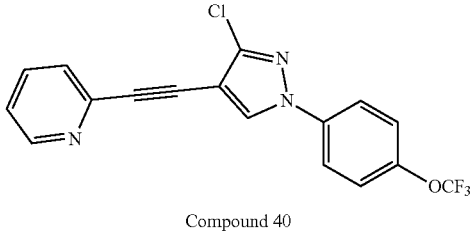

Compound 40

Experimental Section

Procedure for Preparation of 124

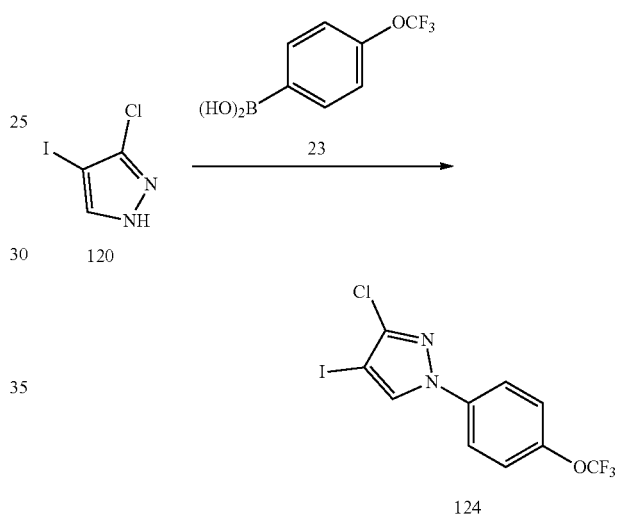

To a solution of 120 (100.0 mg, 0.4 mmol) and 23 (135.2 mg, 0.6 mmol) in DCM (10.0 mL) was added pyridine (95 mg, 1.2 mmol) and Cu(OAc)$_2$ (218 mg, 1.2 mmol), the mixture was stirred at room temperature under O2 balloon overnight. The reaction mixture was filtered and the filtrate was concentrated to dryness. The residue was purified by pre-TLC to afford product 124 (70.0 mg, yield: 41.1%).

LCMS: m/z, 388.8 (M+H)$^+$.

Procedure for Preparation of Compound 40

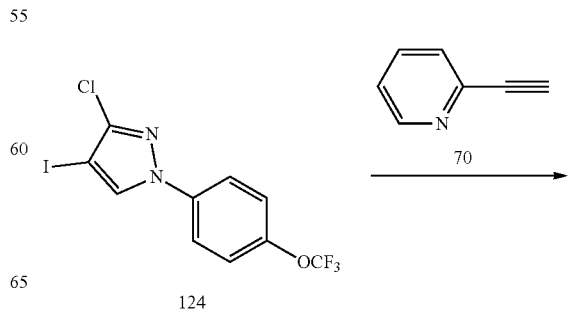

124

-continued

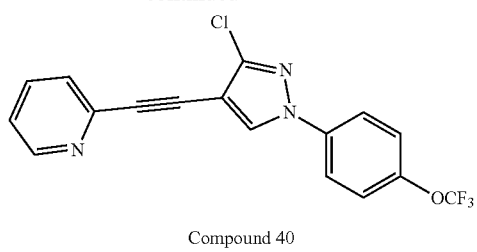

Compound 40

To a solution of 124 (70.0 mg, 0.18 mmol) and 70 (27.8 mg, 0.27 mmol) in THF (3.0 mL) was added Pd(PPh$_3$)$_2$Cl$_2$ (1.4 mg, 0.002 mmol), CuI (0.7 mg, 0.005 mmol) and Et$_3$N (36.4 mg, 0.36 mmol) at room temperature, the mixture was heated at 90° C. by microwave for 1 hour under N$_2$ atmosphere.

The reaction mixture was concentrated to dryness, and the crude product was purified by prep-HPLC to afford Compound 40 (7.0 mg, yield: 10.8%).

LCMS: m/z, 363.9 (M+H)$^+$.

$^1$HNMR (400 MHz, CDCl$_3$): δ7.27-7.29 (m, 1H), 7.34 (d, J=8.0 Hz, 2H), 7.55 (d, J=8.0 Hz, 1H), 7.67-7.71 (m, 3H), 8.08 (s, 1H), 8.63 (d, J=4.0 Hz, 1H).

Example Compound 41

Preparation of 2-((3-chloro-1-(4-(trifluoromethoxy) phenyl)-1H-pyrazol-4-yl) ethynyl)pyrimidine

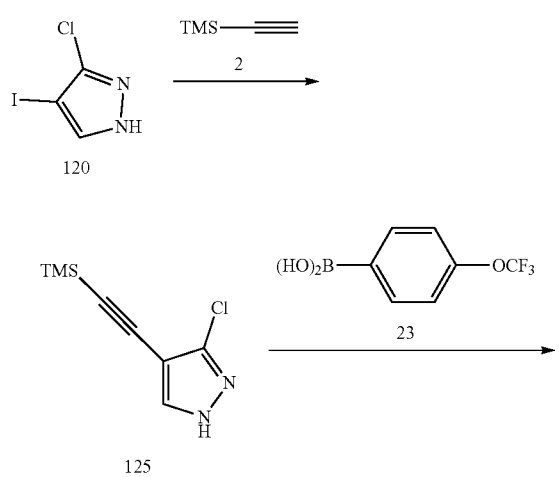

-continued

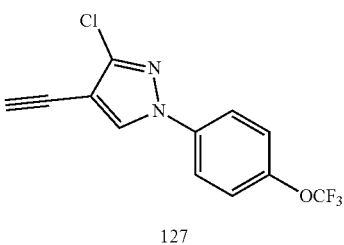

127

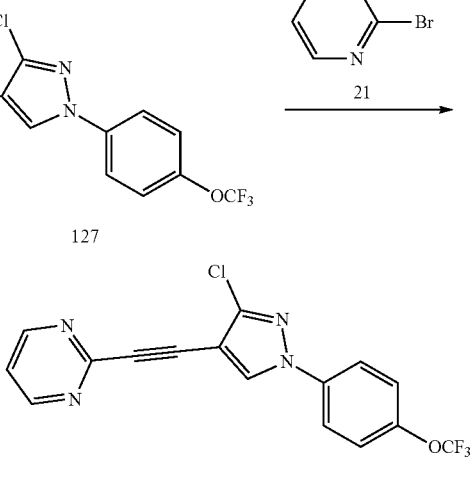

Compound 41

Experimental Section

Procedure for Preparation of 125

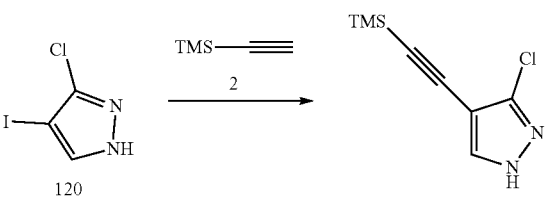

To a solution of 120 (228.0 mg, 1.0 mmol) and 2 (147.0 mg, 1.5 mmol) in THF (3.0 mL) was added Pd(PPh$_3$)$_2$Cl$_2$ (7.0 mg, 0.01 mmol), CuI (3.8 mg, 0.02 mmol) and Et$_3$N (202.4 mg, 2.0 mmol) at room temperature, the mixture was heated at 90° C. by microwave for 1 hour under N$_2$ atmosphere. The reaction mixture was purified by prep-TLC to afford product 125 (150.0 mg, yield: 75.4%/).

LCMS: m/z, 199.1 (M+H)$^+$.

Procedure for Preparation of 26

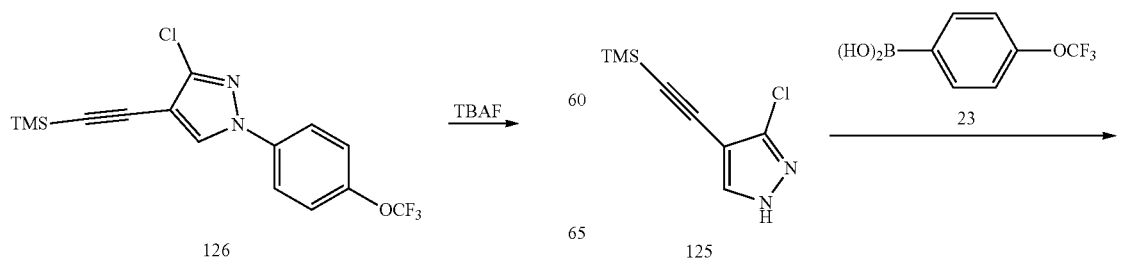

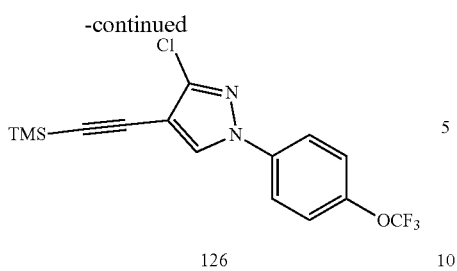

126

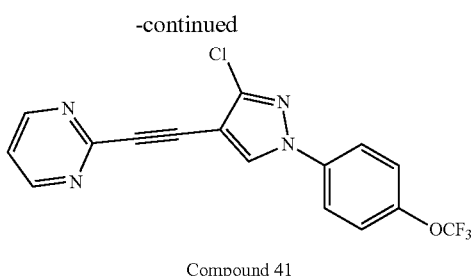

Compound 41

To a solution of 125 (75.0 mg, 0.38 mmol) and 23 (155.4 mg, 0.75 mmol) in DCM (10.0 mL) was added pyridine (90.1 mg, 1.14 mmol) and Cu(OAc)$_2$ (207.0 mg, 1.14 mmol), the mixture was stirred at room temperature under O2 balloon overnight. The reaction mixture was filtered and the filtrate was concentrated to dryness. The residue was purified by pre-TLC to afford product 126 (80.0 mg, yield: 59.1%).

LCMS: m/z, 359.0 (M+H)$^+$.

Procedure for Preparation of 127

To a solution of 127 (63.9 mg, 0.22 mmol) and 21 (53.2 mg, 0.33 mmol) in THF (3.0 mL) was added Pd(PPh$_3$)$_2$Cl$_2$ (1.4 mg, 0.002 mmol), CuI (0.7 mg, 0.004 mmol) and Et$_3$N (44.5 mg, 0.44 mmol) at room temperature, the mixture was heated at 90° C. by microwave for 1 hour under N$_2$ atmosphere. The reaction mixture was concentrated to dryness and the residue was purified by prep-HPLC to afford product Compound 41 (15.0 mg, yield: 18.7%).

LCMS: m/z, 365.0 (M+H)$^+$;

$^1$HNMR (400 MHz, CDCl$_3$): δ7.27 (d, J=4.0 Hz, 1H), 7.34 (d, J=8.0 Hz, 2H), 7.69 (d, J=8.0 Hz, 2H), 8.15 (s, 1H), 8.77 (d, J=4.0 Hz, 2H).

Example Compound 42

Preparation of 2-((3-chloro-1-(4-fluorophenyl)-1H-pyrazol-4-yl)ethynyl)pyridine

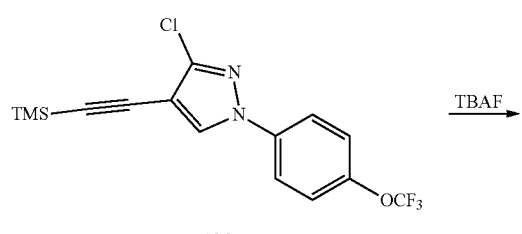

To a solution of 126 (80.0 mg, 0.22 mmol) in THF (3.0 mL) was added 0.22 mL of TBAF in THF solution (0.22 mmol, 1M), the reaction mixture was stirred at room temperature for 1 hour and then concentrated to dryness. The crude product 127 was used for the next step directly (63.9 mg, yield: 100%).

Procedure for Preparation of Compound 41

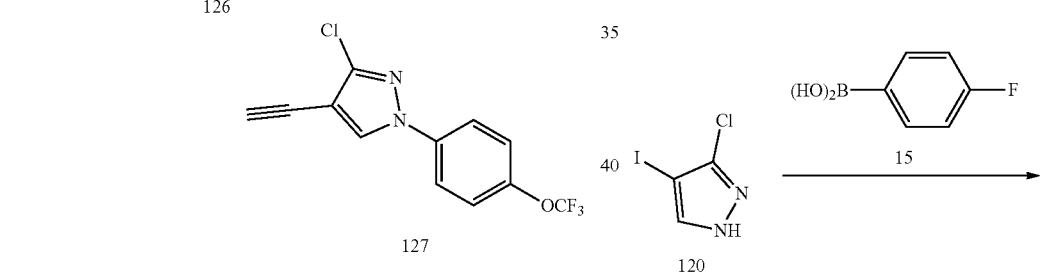

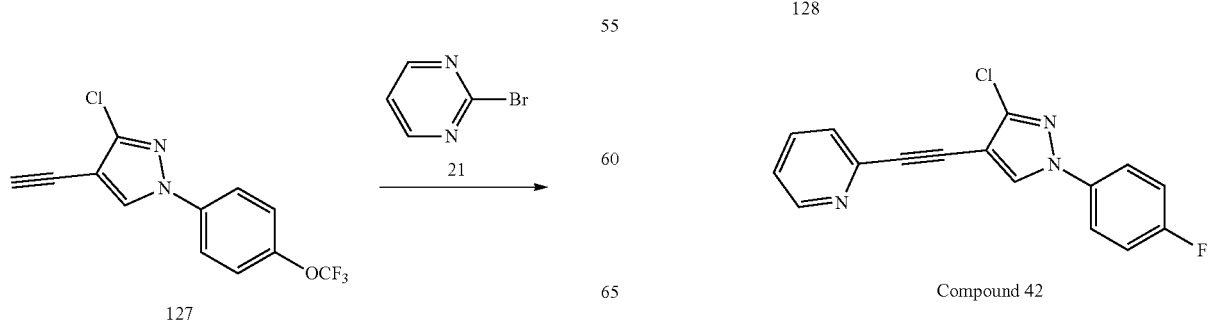

Compound 42

Experimental Section

Procedure for Preparation of 128

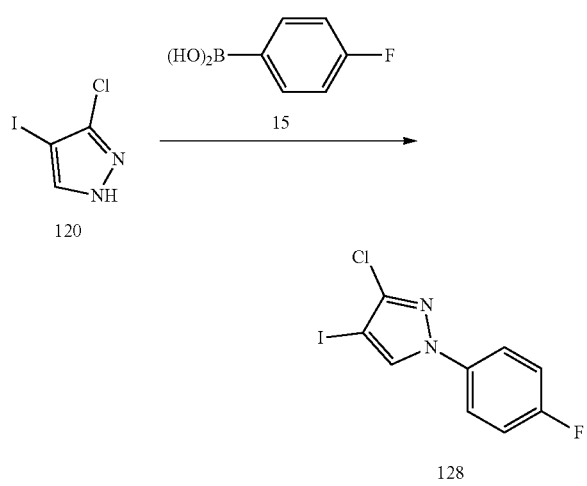

To a solution of 120 (100.0 mg, 0.4 mmol) and 15 (92.0 mg, 0.6 mmol) in DCM (10.0 mL) was added pyridine (95 mg, 1.2 mmol) and Cu(OAc)$_2$ (218 mg, 1.2 mmol), the mixture was stirred at room temperature under 02 balloon overnight. The reaction mixture was filtered and the filtrate was concentrated to dryness. The residue was purified by prep-TLC to afford product 128 (120.0 mg, yield: 85.0%).

LCMS: m/z, 322.9 (M+H)$^+$.

Procedure for Preparation of Compound 42

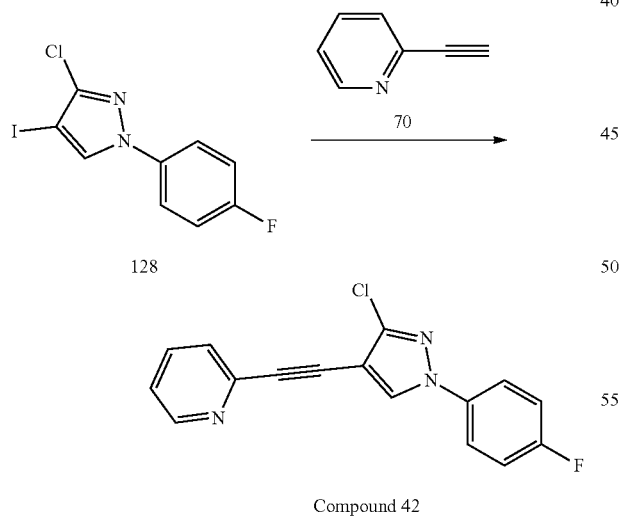

To a solution of 128 (60.0 mg, 0.18 mmol) and 70 (28.7 mg, 0.28 mmol) in THF (3.0 mL) was added Pd(PPh$_3$)$_2$Cl$_2$ (1.4 mg, 0.002 mmol), CuI (0.7 mg, 0.005 mmol) and Et$_3$N (36.4 mg, 0.36 mmol) at room temperature, the mixture was heated at 90° C. by microwave for 1 hour under N$_2$ atmosphere. The reaction mixture was concentrated to dryness and the crude product was purified by prep-HPLC to afford Compound 42 (8.0 mg, 14.4% yield).

LCMS: m/z, 298.0 (M+H)$^+$;
$^1$HNMR (400 MHz, CDCl$_3$): δ7.13-7.18 (m, 2H), 7.27-7.29 (m, 1H), 7.51-7.64 (m, 3H), 7.66-7.69 (m, 1H), 8.03 (s, 1H), 8.61 (d, J=4.4 Hz, 1H).

Example Compound 43

Preparation of 2-((3-chloro-1-(4-fluorophenyl)-1H-pyrazol-4-yl)ethynyl)pyrimidine

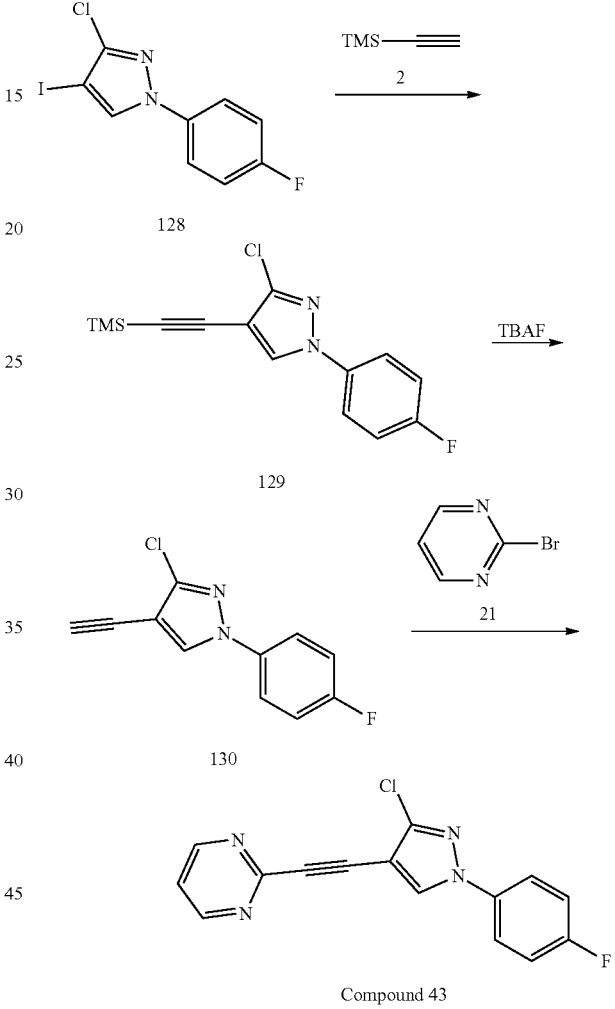

Experimental Section

Procedure for Preparation of 129

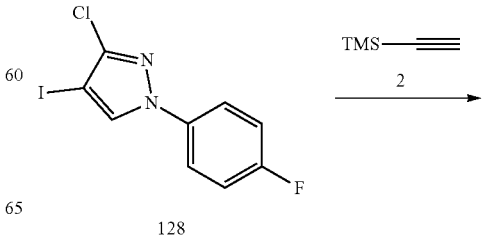

125

-continued

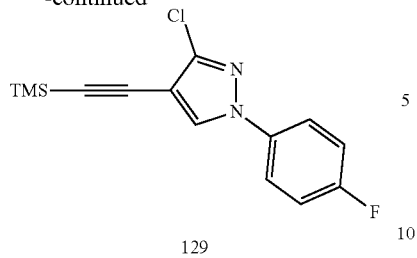

129

To a solution of 128 (50.0 mg, 0.15 mmol) and 2 (30.5 mg, 0.3 mmol) in THF (3.0 mL) was added Pd(PPh₃)₂Cl₂ (1.4 mg, 0.002 mmol), CuI (0.7 mg, 0.004 mmol) and Et₃N (30.0 mg, 0.30 mmol) at room temperature, the mixture was heated at 90° C. by microwave for 1 hour under N₂ atmosphere. The reaction mixture was concentrated to dryness and the crude product 129 was used for the next step directly without purification (45.4 mg, yield: 100.0%).

Procedure for Preparation of 130

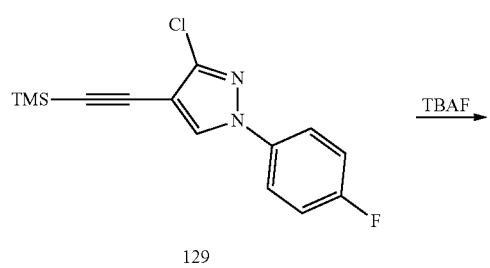

To a solution of 129 (45.4 mg, 0.15 mmol) in THF (3.0 mL) was added 0.15 mL of TBAF (0.15 mmol, 1M in THF), the reaction mixture was stirred at room temperature for 1 hour and then concentrated to dryness. The crude product 130 was used for the next step directly (34.2 mg, yield: 1000).

Procedure for Preparation of Compound 43

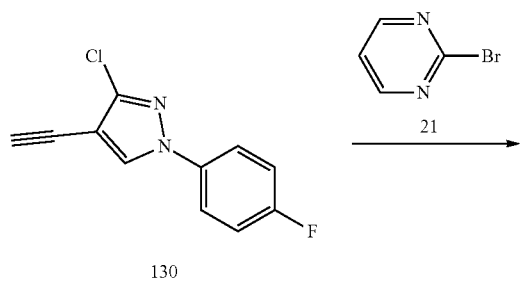

126

-continued

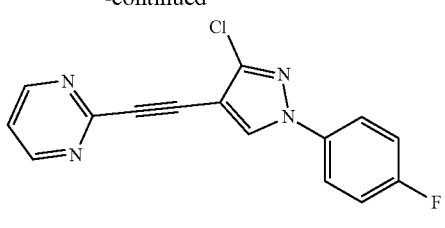

Compound 43

To a solution of 130 (34.2 mg, 0.15 mmol) and 21 (49.3 mg, 0.3 mmol) in THF (3.0 mL) was added Pd(PPh₃)₂Cl₂ (1.4 mg, 0.002 mmol), CuI (0.7 mg, 0.004 mmol) and Et₃N (30.0 mg, 0.3 mmol) at room temperature, the mixture was heated at 900° C. by microwave for 1 hour under N₂ atmosphere. The reaction mixture was concentrated to dryness and the residue was purified by prep-HPLC to afford product Compound 43 (2.5 mg, yield: 5.4%).

LCMS: m/z, 299.0 (M+H)⁺;

¹HNMR (400 MHz, CDCl₃): δ7.18 (t, J=8.0 Hz, 2H), 7.27 (d, J=4.0 Hz, 1H), 7.60-7.63 (m, 2H), 8.10 (s, 1H), 8.77 (d, J=4.0 Hz, 2H).

Example Compound 44

Preparation of 3-(3-chloro-4-(pyridin-2-ylethynyl)-1H-pyrazol-1-yl)-5-fluoropyridine

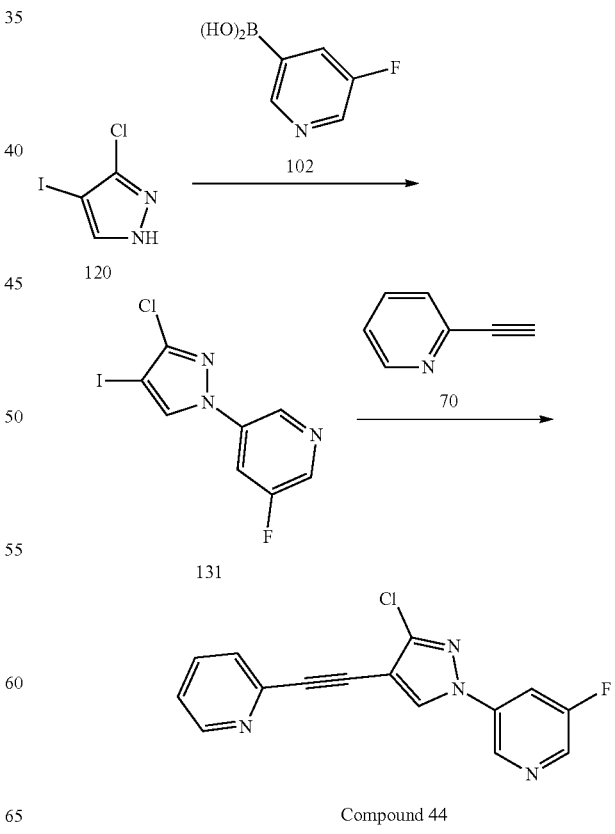

Experimental Section

Procedure for Preparation of 131

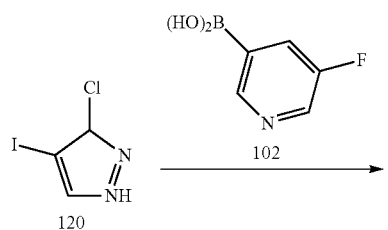

To a solution of 120 (100.0 mg, 0.4 mmol) and 102 (123.4 mg, 0.8 mmol) in DCM (10.0 mL) was added pyridine (95 mg, 1.2 mmol) and Cu(OAc)$_2$ (218 mg, 1.2 mmol), the mixture was stirred at room temperature under 02 balloon overnight. The reaction mixture was filtered and the filtrate was concentrated to dryness. The residue was purified by flashing chromatography column on silicon gel to afford product 131 (70.0 mg, yield: 50%).

$^1$HNMR (400 MHz, CDCl$_3$): δ7.76-7.84 (m, 1H), 7.98 (s, 1H), 8.46 (s, 1H), 8.73 (s, 1H).

Procedure for Preparation of Compound 44

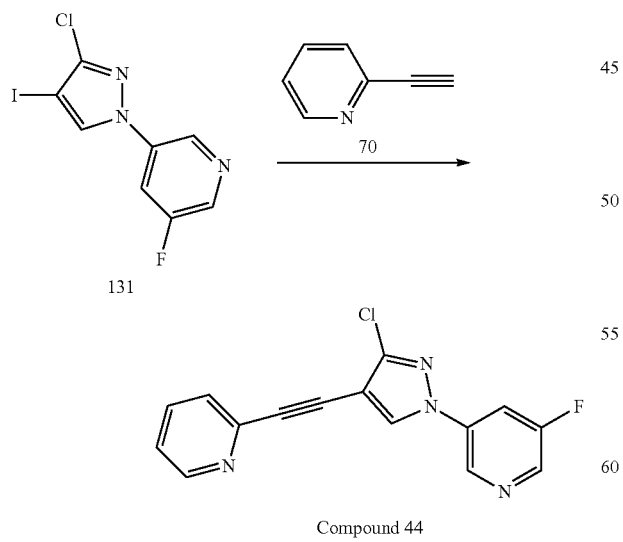

To a solution of 131 (70.0 mg, 0.21 mmol) and 70 (33.5 mg, 0.32 mmol) in THF (3.0 mL) was added Pd(PPh$_3$)$_2$Cl$_2$ (1.4 mg, 0.002 mmol), CuI (0.7 mg, 0.005 mmol) and Et$_3$N (34.4 mg, 0.34 mmol) at room temperature, the mixture was heated at 90° C. by microwave for 1 hour under N$_2$ atmosphere. The reaction mixture was concentrated to dryness, and the crude product was purified by prep-HPLC to give product Compound 44 (7.0 mg, yield: 10.8%).

LCMS: m/z, 299.0 (M+H)$^+$;

$^1$HNMR (400 MHz, CDCl$_3$): δ7.30 (d, J=5.6 Hz, 1H), 7.56 (d, J=7.6 Hz, 1H), 7.72 (t, J=7.6 Hz, 1H), 7.84 (d, J=8.8 Hz, 1H), 8.17 (s, 1H), 8.48 (s, 1H), 8.64 (d, J=3.6 Hz, 1H), 8.76 (s, 1H).

Example Compound 45

Preparation of 2-((3-chloro-1-(5-fluoropyridin-3-yl)-1H-pyrazol-4-yl)ethynyl) pyrimidine

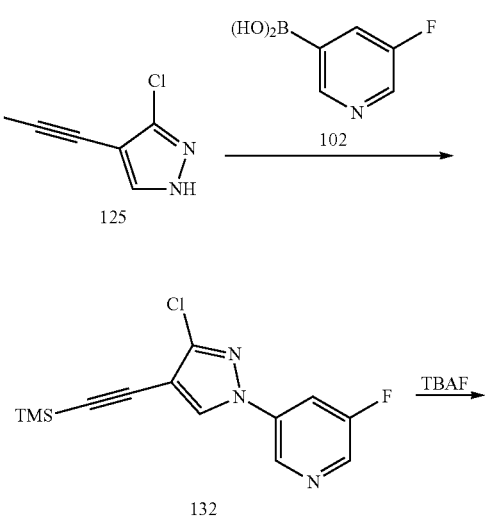

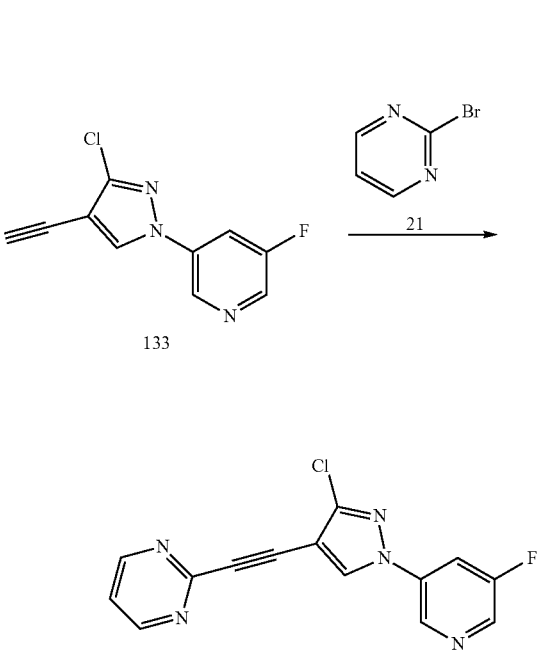

Experimental Section

Procedure for Preparation of 132

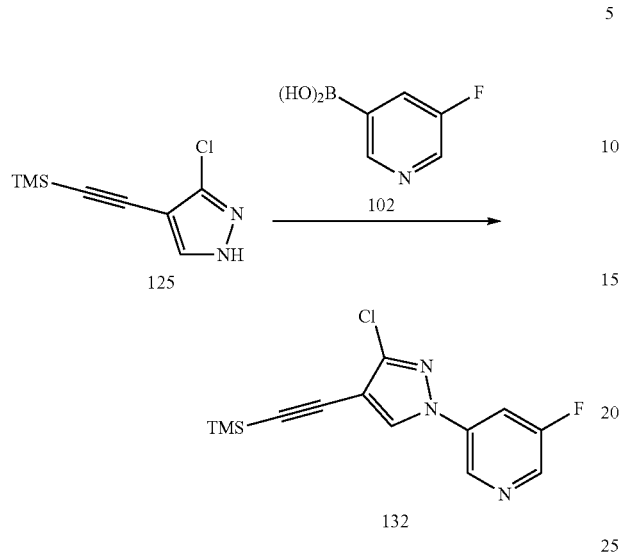

To a solution of 125 (75.0 mg, 0.38 mmol) and 102 (106.4 mg, 0.75 mmol) in DCM (10.0 mL) was added pyridine (90.1 mg, 1.14 mmol) and Cu(OAc)$_2$ (207.0 mg, 1.14 mmol), the mixture was stirred at room temperature under O2 balloon overnight. The reaction mixture was filtered and the filtrate was concentrated to dryness. The residue was purified by prep-TLC to afford product 132 (70.0 mg, yield: 63.1%).

LCMS: m/z, 294.0 (M+H)$^+$.

Procedure for Preparation of 133

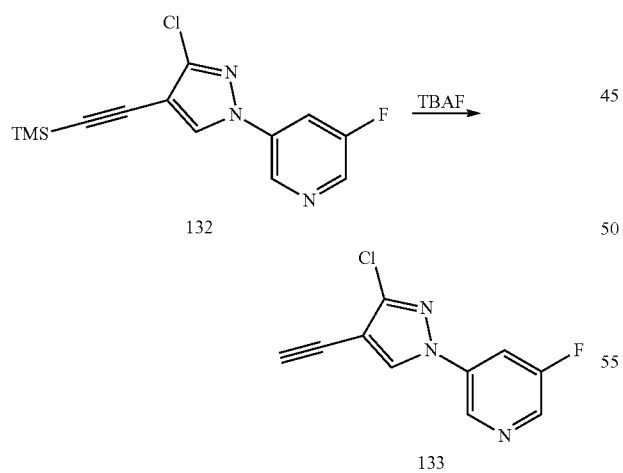

To a solution of 132 (70.0 mg, 0.24 mmol) in THF (3.0 mL) was added 0.24 mL of TBAF (0.24 mmol, 1M in THF), the reaction mixture was stirred at room temperature for 1 hour and is then concentrated to dryness. The crude product 133 was used for the next step directly (52.8 mg, yield: 100%).

Procedure for Preparation of Compound 45

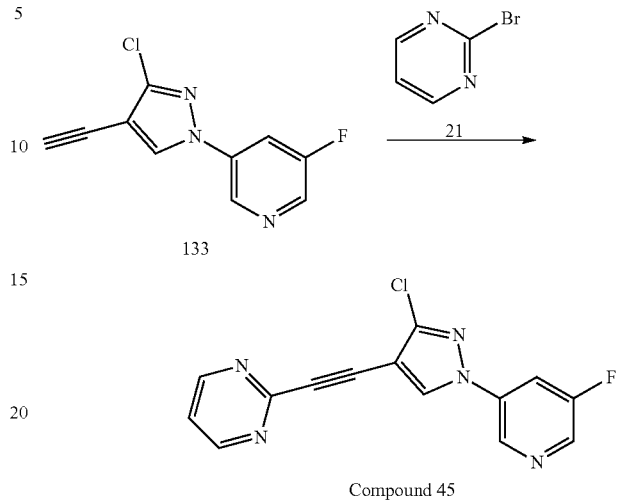

To a solution of 133 (52.8 mg, 0.24 mmol) and 21 (56.8 mg, 0.36 mmol) in THF (3.0 mL) was added Pd(PPh)$_2$Cl$_2$ (1.4 mg, 0.002 mmol), CuI (0.7 mg, 0.004 mmol) and Et$_3$N (48.6 mg, 0.48 mmol) at room temperature, the mixture was heated at 90° C. by microwave for 1 hour under N$_2$ atmosphere. The reaction mixture was concentrated to dryness and the residue was purified by prep-HPLC to afford product Compound 45 (5.0 mg, yield: 7.0%).

LCMS: m/z, 300.0 (M+H)$^+$;

$^1$HNMR (400 MHz, CDCl$_3$): δ7.29 (t, J=4.0 Hz, 1H), 7.84 (dt, J=8.0, 4.0 Hz, 1H), 8.23 (s, 1H), 8.49 (d, J=2.0 Hz, 1H), 8.76 (d, J=2.0 Hz, 1H), 7.78 (d, J=4.0 Hz, 2H).

Example Compound 46

Preparation of 2-((1-(4-(methylsulfonyl)phenyl)-1H-pyrazol-4-yl)ethynyl)pyridine

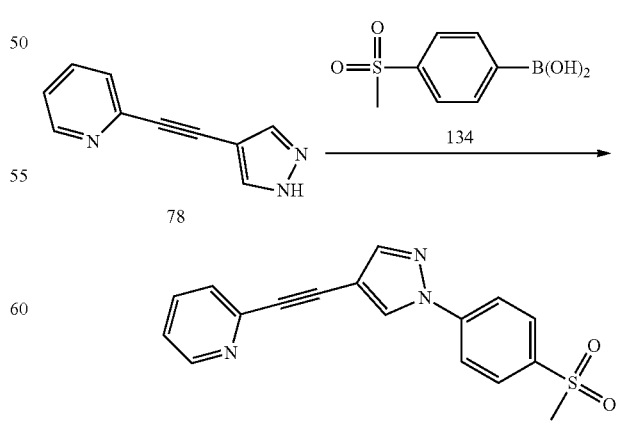

Experimental Section

Procedure for Preparation of Compound 46

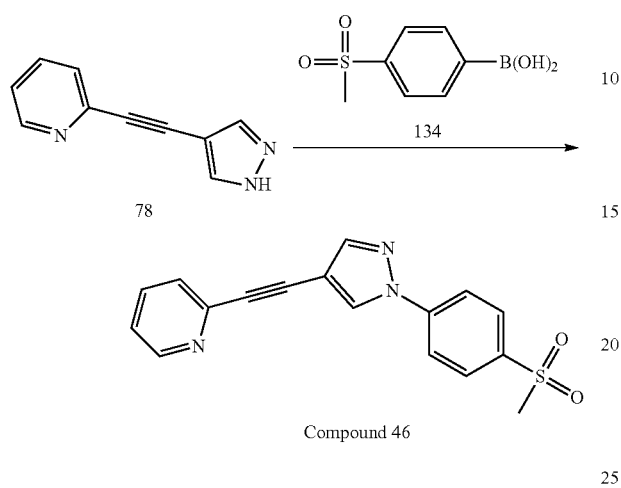

To a solution of 78 (70 mg, 0.414 mmol) in DCM (20 mL) was added compound 134 (166 mg, 0.828 mmol), Cu(OAc)$_2$ (150 mg, 0.828 mmol), pyridine (98 mg, 1.24 mmol). The mixture was stirred at room temperature overnight under O$_2$ atmosphere. The mixture was filtered and concentrated under vacuo. The residue was purified by prep-HPLC to give product Compound 46 (6 mg, yield: 4%).

LCMS: n/z, 324.0 (M+H)$^+$;

$^1$H NMR (400 MHz, CDCl$_3$) δ 8.63 (s, 1H), 8.26 (s, 1H), 8.09-8.06 (m, 2H), 7.97 (s, 1H), 7.93-7.91 (m, 2H), 7.71 (m, 1H), 7.52 (m, 1H), 7.28 (m, 1H), 3.10 (s, 3H).

Example Compound 47

Preparation of 3-(3-(difluoromethoxy)-4-(pyridin-2-ylethynyl)-1H-pyrazol-1-yl)-5-fluorobenzonitrile

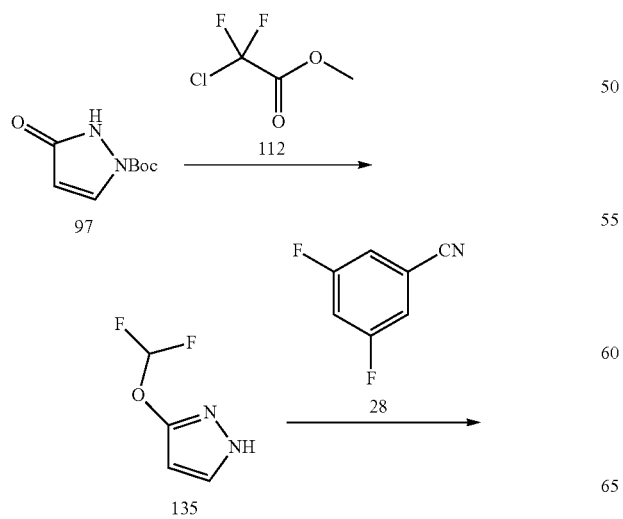

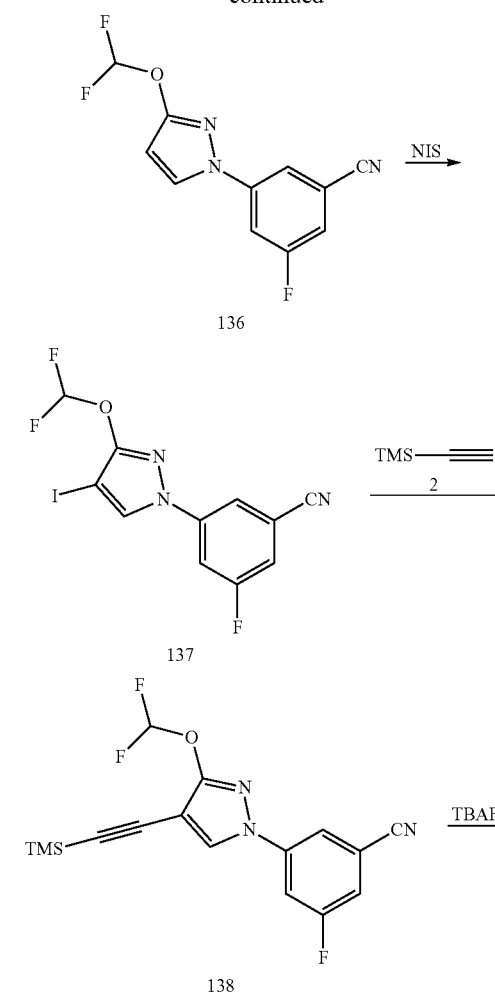

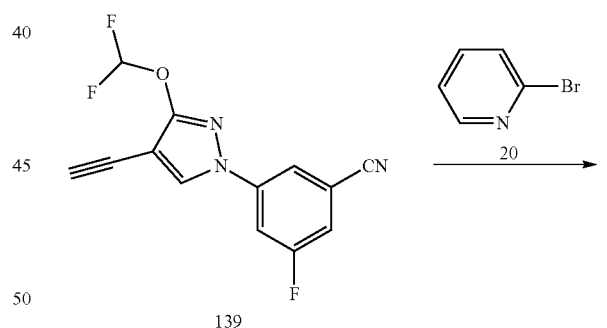

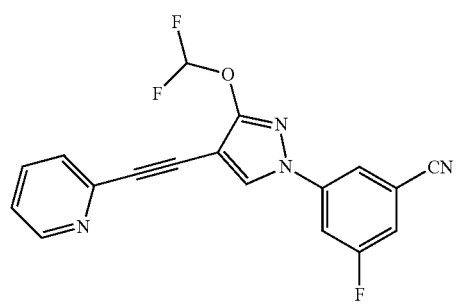

Compound 47

Experimental Section

Procedure for Preparation of 135

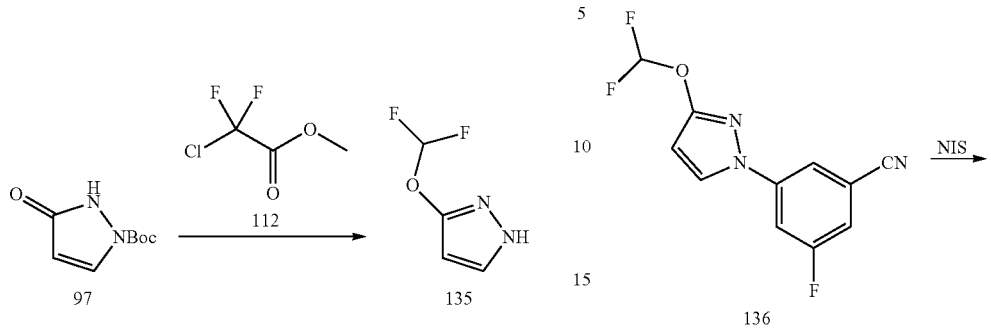

To a solution of 97 (280 mg, 1.52 mmol) in DMF (20 mL) was added 112 (145 mg, 1.82 mmol) and $Cs_2CO_3$ (991 mg, 3.04 mmol). The mixture was stirred at 60° C. for 4 hours. The mixture was filtered and concentrated by vacuo to give product 135 (200 mg, crude).

Procedure for Preparation of 136

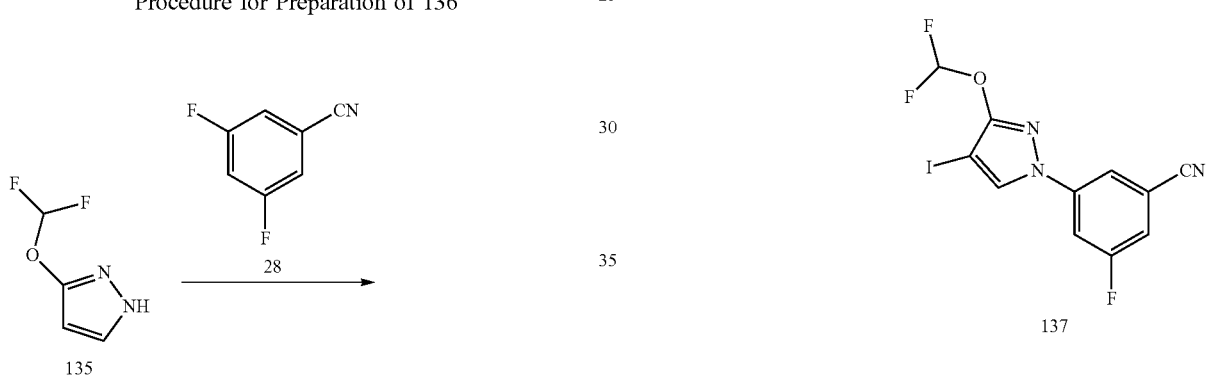

To a solution of 135 (100 mg, 0.746 mmol) in $CH_3CN$ (10 mL) was added 28 (124 mg, 0.895 mmol) and $Cs_2CO_3$ (486 mg, 1.49 mmol). The mixture was stirred at 70° C. for 2 hours. The mixture was filtered and concentrated by vacuo to give the crude product which was purified by prep-TLC to give product 136 (70 mg, 37%).

LCMS: m/z, 254.0 (M+H)$^+$.

Procedure for Preparation of 137

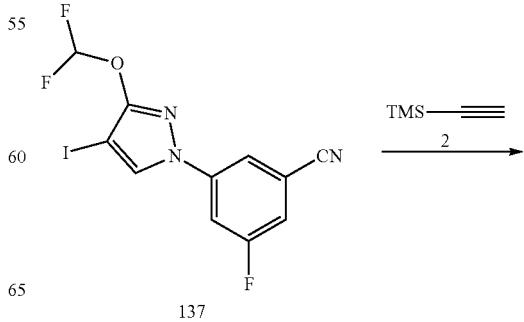

To a solution of compound 136 (130 mg, 0.513 mmol) in $CHCl_3$ (15 mL) was added NIS (139 mg, 0.616 mmol). The mixture was stirred at 60° C. for 6 hours. The mixture was quenched with water and extracted with DCM (2×10 mL). The combined organics was concentrated under vacuo and the residue was purified by prep-TLC to give product 137 (170 mg, 87%).

LCMS: m/z, 379.9 (M+H)$^+$.

Procedure for Preparation of 138

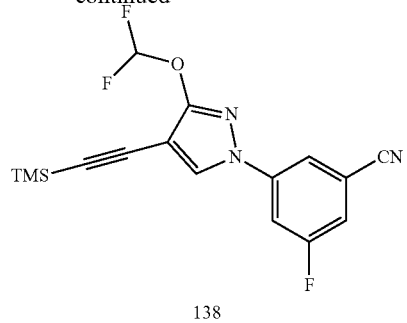

138

To a solution of 137 (170 mg, 0.448 mmol) in CH₃CN (3 mL) was added successively CuI (9 mg, 0.045 mmol), 2 (88 mg, 0.897 mmol), Et₃N (136 mg, 1.35 mmol) and Pd(PPh₃)₂Cl₂ (16 mg, 0.022 mmol). The mixture was then degassed for 1 minute under N₂ atmosphere and was heated at 90° C. under microwave for 1 hour. The reaction mixture was filtered and evaporated to give crude product, which was purified by prep-TLC to give product 138 (130 mg, yield: 83%). LCMS: m/z, 350.1 (M+H)⁺.

Procedure for Preparation of 139

A solution of 126 (130 mg, 0.372 mmol) in THF (5 mL) was cooled to 0° C. and TBAF (0.558 mL, 0.558 mmol) was added. The reaction mixture stirred at room temperature for 1 hour. The mixture was quenched with water and extracted with EtOAc (3×10 mL). The combined organics was concentrated by vacuo to give the crude product 139 (90 mg, yield: 87%).

Procedure for Preparation of Compound 47

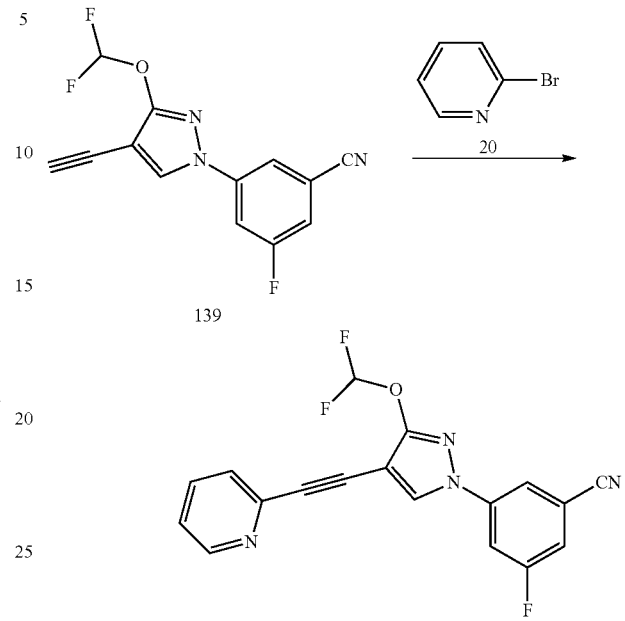

Compound 47

To a solution of 139 (90 mg, 0.325 mmol) in THF (3 mL) was added successively CuI (6 mg, 0.032 mmol), 20 (103 mg, 0.649 mmol), Et₃N (99 mg, 0.974 mmol) and Pd(PPh₃)₂Cl₂ (11 mg, 0.016 mmol). The mixture was then degassed for 1 minute under N₂ atmosphere and stirred at 90° C. for 1 hour under microwave. The reaction mixture was filtered and concentrated to give the crude product which was purified by prep-HPLC to give Compound 47 (30 mg, yield: 26%).

LCMS: m/z, 355.1 (M+H)⁺;
¹H NMR (400 MHz, CDCl₃): δ 8.64 (s, 1H), 8.06 (s, 1H), 7.73-7.72 (m, 2H), 7.72-7.71 (m, 1H), 7.61-7.56 (m, 1H), 7.32-7.26 (m, 2H), 7.14-6.96 (m, 1H).

Example Compound 48

Preparation of 3-fluoro-5-(3-(2-hydroxyethoxy)-4-(pyridin-2-ylethynyl)-1H-pyrazol-1-yl)benzonitrile

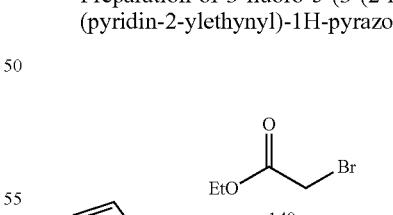

-continued

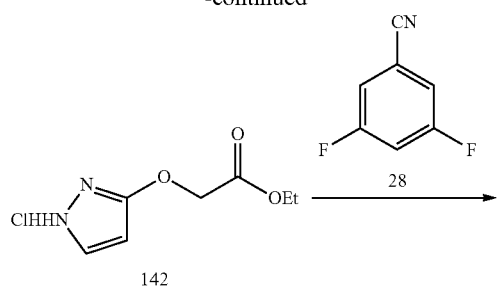
142

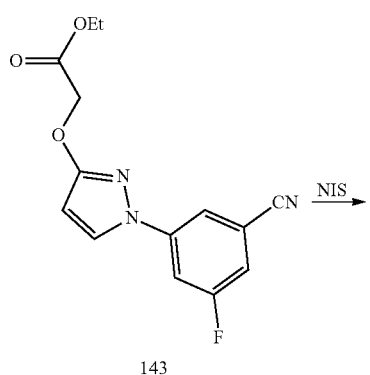
143

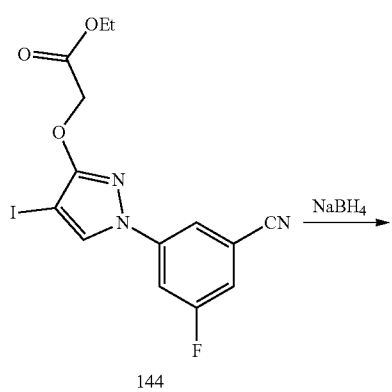
144

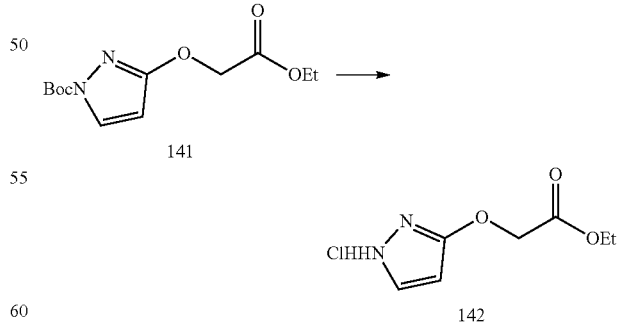
145

-continued

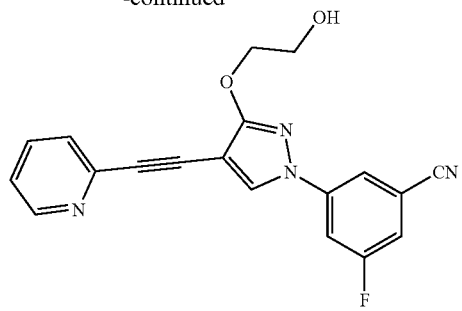
Compound 48

Experimental Section

Procedure for Preparation of 141

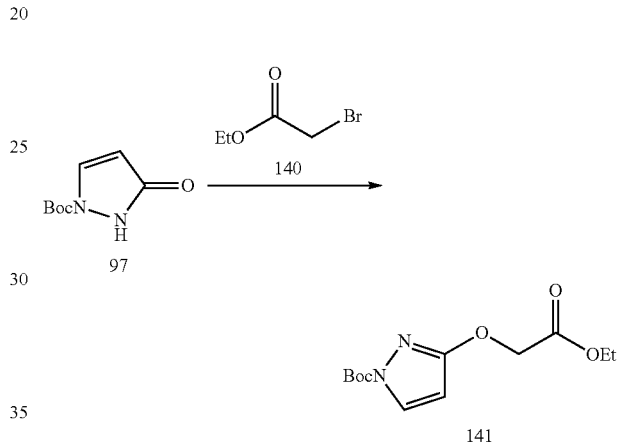
141

To a solution of 97 (500 mg, 2.71 mmol) in 30 mL of dioxane was added successively compound 140 (680 mg, 4.07 mmol) and $Cs_2CO_3$ (2.65 g, 8.14 mmol). The reaction vessel was sealed and stirred at room temperature for 18 hours. LCMS showed that the reaction was complete. The reaction mixture was filtered and the filtrate was concentrated to give the product 141 (650 mg, crude).
LCMS: m/z 215 (M+H)$^+$.

Procedure for Preparation of 142

A solution of 141 (650 mg, 1.21 mmol) in HCl/EA (20 mL) was stirred at room temperature for 1 hour. LCMS showed that starting material was consumed. The reaction mixture was concentrated to give the product 142 as HCl salt (480 mg, crude).
LCMS: m/z 171 (M+H)$^+$.

Procedure for Preparation of 143

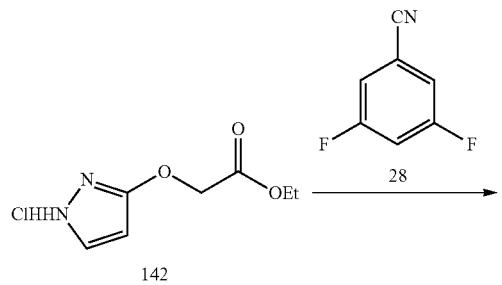

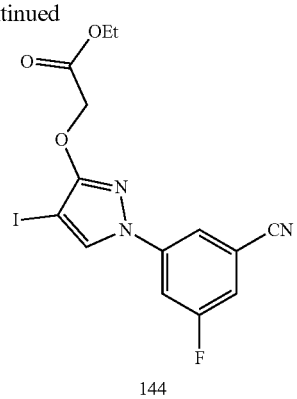

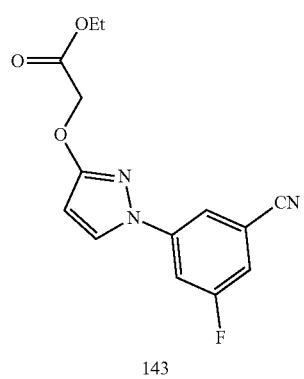

To a solution of compound 142 (400 mg, 1.94 mmol) in 20 mL of degassed DMF was added successively compound 28 (539 mg, 3.87 mmol) and Cs$_2$CO$_3$ (1.89 g, 5.87 mmol). The mixture was heated to 110° C. and stirred for 1 hour. The reaction mixture was treated with water (50 ml), extracted with DCM (2×50 ml). The combined organic layer was dried over Na$_2$SO$_4$, concentrated and purified by prep-TLC to give the product 143 (130 mg, yield: 23%).

LCMS: m/z 290 (M+H)$^+$.

Procedure for Preparation of 144

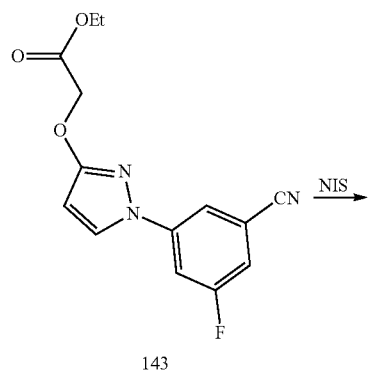

To a solution of compound 143 (130 mg, 0.45 mmol) in 30 mL of degassed CHCl$_3$ was added NIS (152 mg, 0.67 mmol). The mixture was heated to reflux and stirred for 18 hours. LCMS showed that compound 143 was consumed. The reaction mixture was cooled to room temperature and filtered. The filtrate was concentrated and purified by prep-TLC to give the product 144 (150 mg, yield: 80%).

LCMS: m/z 416 (M+H)$^+$.

Procedure for Preparation of 145

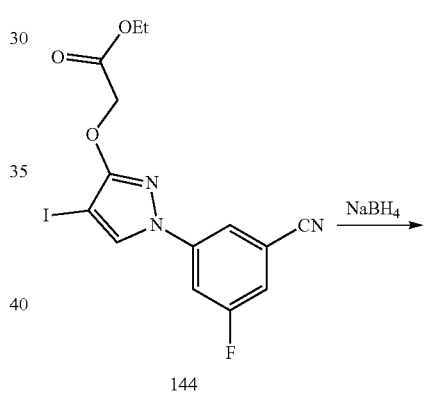

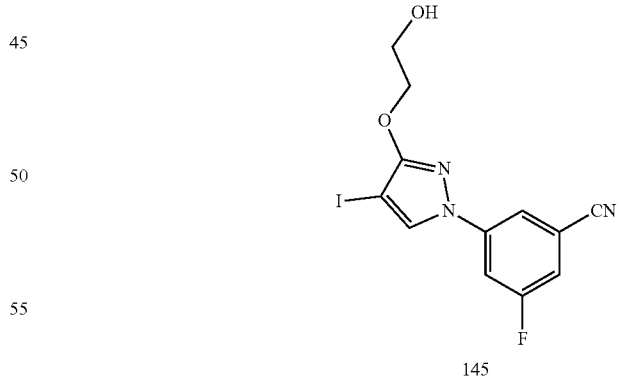

To a solution of compound 144 (150 mg, 0.36 mmol) in 20 mL of CH$_3$OH was added NaBH$_4$ (68 mg, 1.81 mmol). The mixture was stirred at room temperature for 2 hours. LCMS showed that compound 144 was consumed. The reaction mixture was quenched with water (20 ml), extracted with DCM (3×20 ml). The combined organic layer was dried over Na$_2$SO$_4$, concentrated to give the product 145 (110 mg, yield: 82%).

LCMS: m/z 374 (M+H)$^+$.

Procedure for Preparation of Compound 48

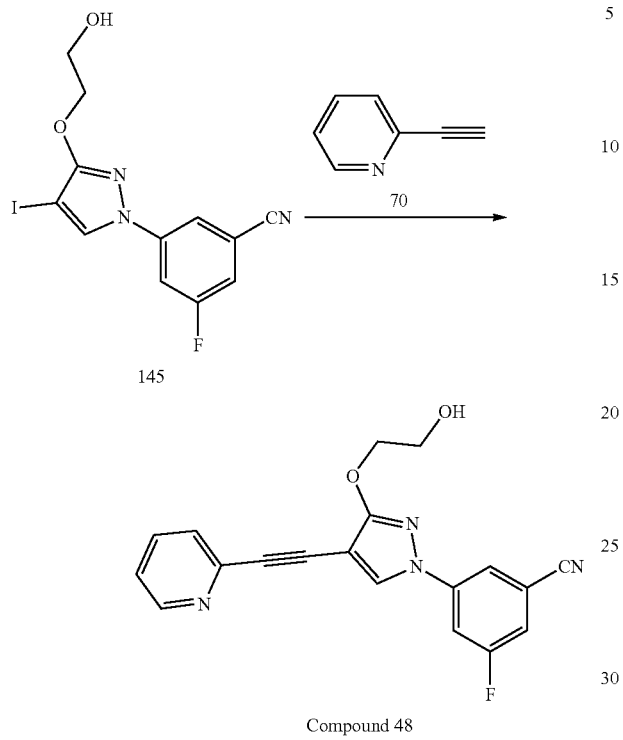

Compound 48

To a solution of compound 145 (90 mg, 0.24 mmol) in 10 mL of degassed THF was added successively CuI (5 mg, 0.024 mmol), compound 70 (50 mg, 0.48 mmol), and Pd(PPh$_3$)$_2$Cl$_2$ (17 mg, 0.024 mmol) and Et$_3$N (73 mg, 0.72 mmol). The mixture was stirred at 80° C. for 18 hours. The reaction mixture was filtered and the filtrate was concentrated to give the crude product, which was purified by prep-HPLC to give the product Compound 48 (22 mg, yield: 26%).

LCMS: m/z 349 (M+H)$^+$;

$^1$H NMR (400 MHz, CDCl$_3$): δ 8.61 (d, J=4.8 Hz, 1H), 7.99 (s, 1H), 7.71-7.67 (m, 2H), 7.26-7.21 (m, 2H), 4.52-4.50 (m, 2H), 4.04-4.03 (m, 2H), 2.67-2.65 (m, 1H).

Example Compound 49

Preparation of 2-(3-chloro-4-(pyridin-2-ylethynyl)-1H-pyrazol-1-yl)-5-fluoropyridine

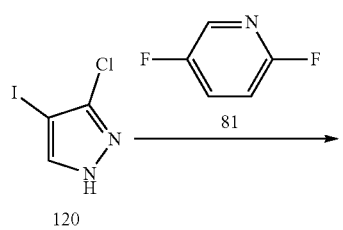

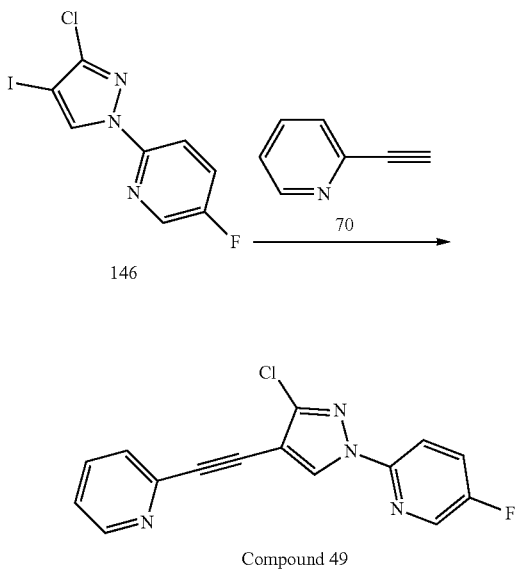

Compound 49

Experimental Section

Procedure for Preparation of 146

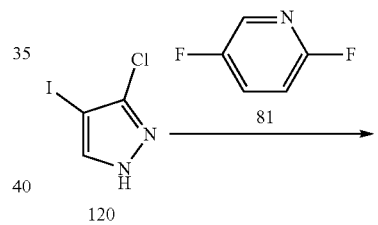

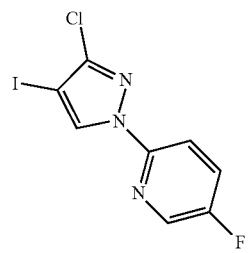

146

To a solution of 120 (150.0 mg, 0.66 mmol) and 81 (113.4 mg, 0.96 mmol) in DMF (5.0 mL) was added Cs$_2$CO$_3$ (430.0 mg, 1.32 mmol) at room temperature, the mixture was stirred at 80° C. for 30 minutes. TLC showed the reaction was completed. The reaction was treated with water, extracted with 15 mL of EA. The organic phase was separated, washed by water, brine, dried over Na$_2$SO$_4$ and concentrated to dryness. The residue was purified by prep-TLC to afford product 146 (80.0 mg, yield: 37.6%).

LCMS: m/z, 323.9 (M+H)$^+$.

143

Procedure for Preparation of Compound 49

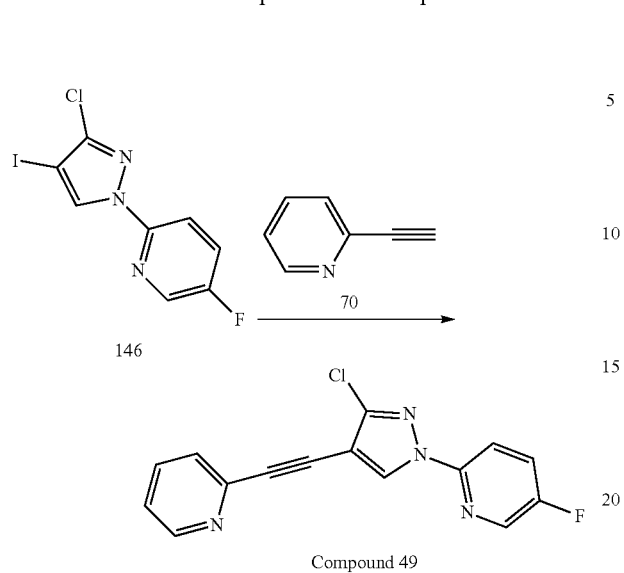

Compound 49

To a solution of 146 (80.0 mg, 0.25 mmol) and 70 (38.2 mg, 0.37 mmol) in THF (3.0 mL) was added Pd(PPh$_3$)$_2$Cl$_2$ (1.4 mg, 0.002 mmol), CuI (0.7 mg, 0.005 mmol) and Et$_3$N (36.4 mg, 0.36 mmol) at room temperature, the mixture was heated at 90° C. by microwave for 1 hour under N$_2$ atmosphere. The reaction mixture was concentrated to dryness, and the crude product was purified by prep-HPLC to afford title product Compound 49 (13.0 mg, yield: 17.6%).

LCMS: m/z, 299.0 (M+H)$^+$;

$^1$HNMR (400 MHz, CDCl$_3$): δ7.21-7.22 (m, 1H), 7.48-7.53 (m, 2H), 7.64 (dt, J=8.0, 4.0 Hz, 1H), 7.88 (dd, J=8.0, 4.0 Hz, 1H), 8.21 (d, J=4.0 Hz, 1H), 8.57 (d, J=8.0 Hz, 1H), 8.59 (s, 1H).

Example Compound 50

Preparation of 3-fluoro-5-(5-methyl-4-(pyridin-2-ylethynyl)-1H-pyrazol-1-yl) benzonitrile

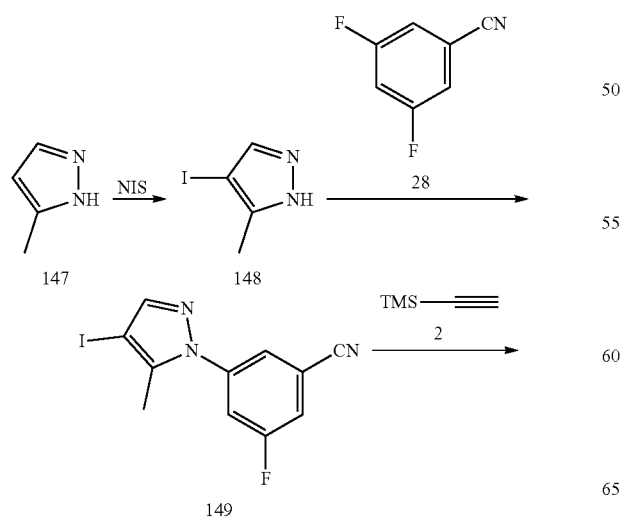

144

-continued

Compound 50

Experimental Section

Procedure for Preparation of 148

To a solution of 147 (300 mg, 3.65 mmmol) in CHCl$_3$ (20 ml) was added NIS (1.07 g, 4.75 mmol). The mixture was stirred at 70° C. for 2 hours, cooled to room temperature. The mixture was diluted with EtOAc (70 mL), washed with brine (20 mL) and the organic layers was dried (MgSO$_4$), filtered and concentrated in vacuum, which was purified by silica gel chromatography to give title product 148 (600 mg, yield: 79%).

LCMS: m/z, 208.9 (M+H)$^+$.

Procedure for Preparation of 149

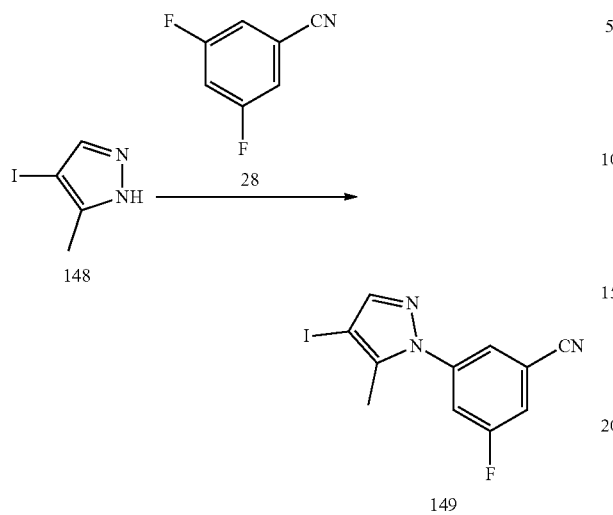

To a solution of 148 (300 mg, 1.44 mmol) and 28 (241 mg, 1.73 mmol) in DMF (10 ml) was added $Cs_2CO_3$ (940 mg, 2.88 mmol). The mixture was heated at 60° C. for 2 hours, then, the reaction mixture was concentrated to dryness, which was purified by prep-TLC to afford the title product 149 (300 mg, yield: 64%).

$^1$H NMR (400 MHz, $CDCl_3$): δ7.91-7.89 (m, 1H), 7.83-7.81 (m, 1H), 7.73 (s, 1H), 7.61-7.57 (m, 1H), 7.25-4.23 (m, 1H), 2.33 (s, 3H).

Procedure for Preparation of 150

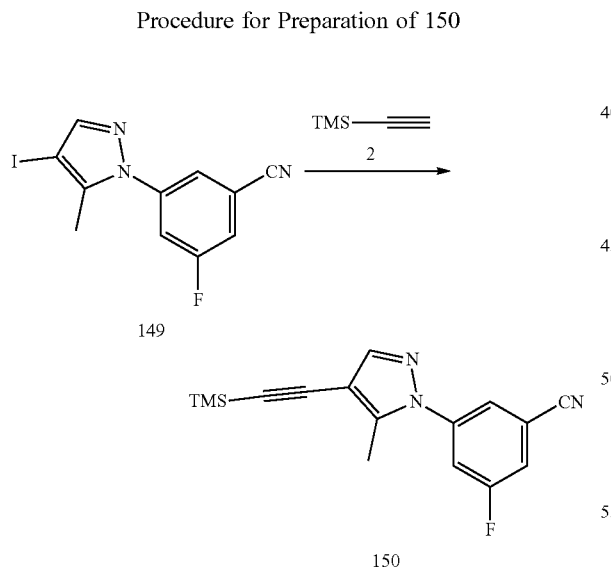

To a solution of 149 (200 mg, 0.6 mmol) and 2 (120 mg, 1.2 mmol), CuI (12 mg, 0.06 mmol), $Et_3N$ (186 mg, 1.8 mmol) in THF (5 mL) was added $Pd(PPh_3)_2Cl_2$ (21 mg, 0.03 mmol). The mixture was stirred at 90° C. for 6 hours under $N_2$ atmosphere. The mixture was filtered and concentrated under vacuo. The residue was purified by prep-TLC to give the product 150 (120 mg, yield: 67%).

LCMS: m/z, 298.1 $(M+H)^+$.

Procedure for Preparation of 151

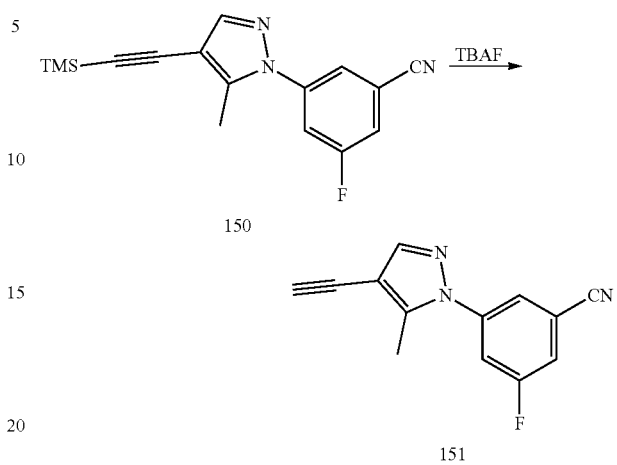

To a solution of 150 (160 mg, 0.54 mmol) in THF (4 mL) was added TBAF (0.81 mL, 0.81 mmol, 1.0M in THF). The mixture was stirred at 20° C. for 2 hours. The mixture was diluted with EtOAc (30 mL) and washed with brine (20 mL), dried over $Na_2SO_4$, concentrated under vacuum. The residue was purified by prep-TLC to give the product 151 (100 mg, yield: 82%).

LCMS: m/z, 226.1 $(M+H)^+$.

Procedure for Preparation of Compound 50

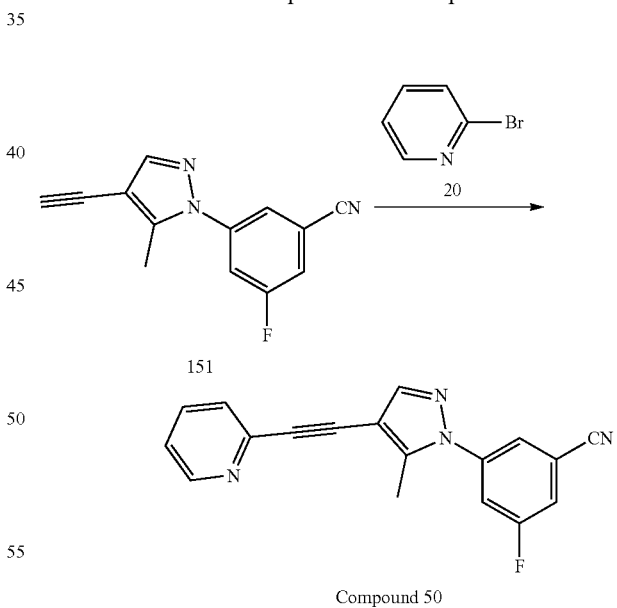

To a solution of compound 152 (90 mg, 0.4 mmol) and 20 (81 mg, 0.82 mmol), CuI (9 mg, 0.04 mmol), $Et_3N$ (117 mg, 1.2 mmol) in THF (5 mL) was added $Pd(PPh_3)_2Cl_2$ (27 mg, 0.04 mmol). The mixture was stirred at 90° C. for 6 hours under $N_2$ atmosphere. The mixture was filtered and concentrated under vacuum. The residue was purified by prep-TLC to give the product Compound 50 (20 mg, yield: 16%).

LCMS: m/z, 303.1 $(M+H)^+$;

¹H NMR (400 MHz, CDCl₃): δ 8.59-8.68 (m, 1H), 8.07 (s, 1H), 7.78 (s, 1H), 7.69 (s, 2H), 7.52 (s, 1H), 7.26-7.29 (m, 2H), 2.48 (s, 3H).
Example Compound 51
Preparation of 2-((1-(4-fluorophenyl)-5-methoxy-1H-pyrazol-4-yl)ethynyl)pyridine
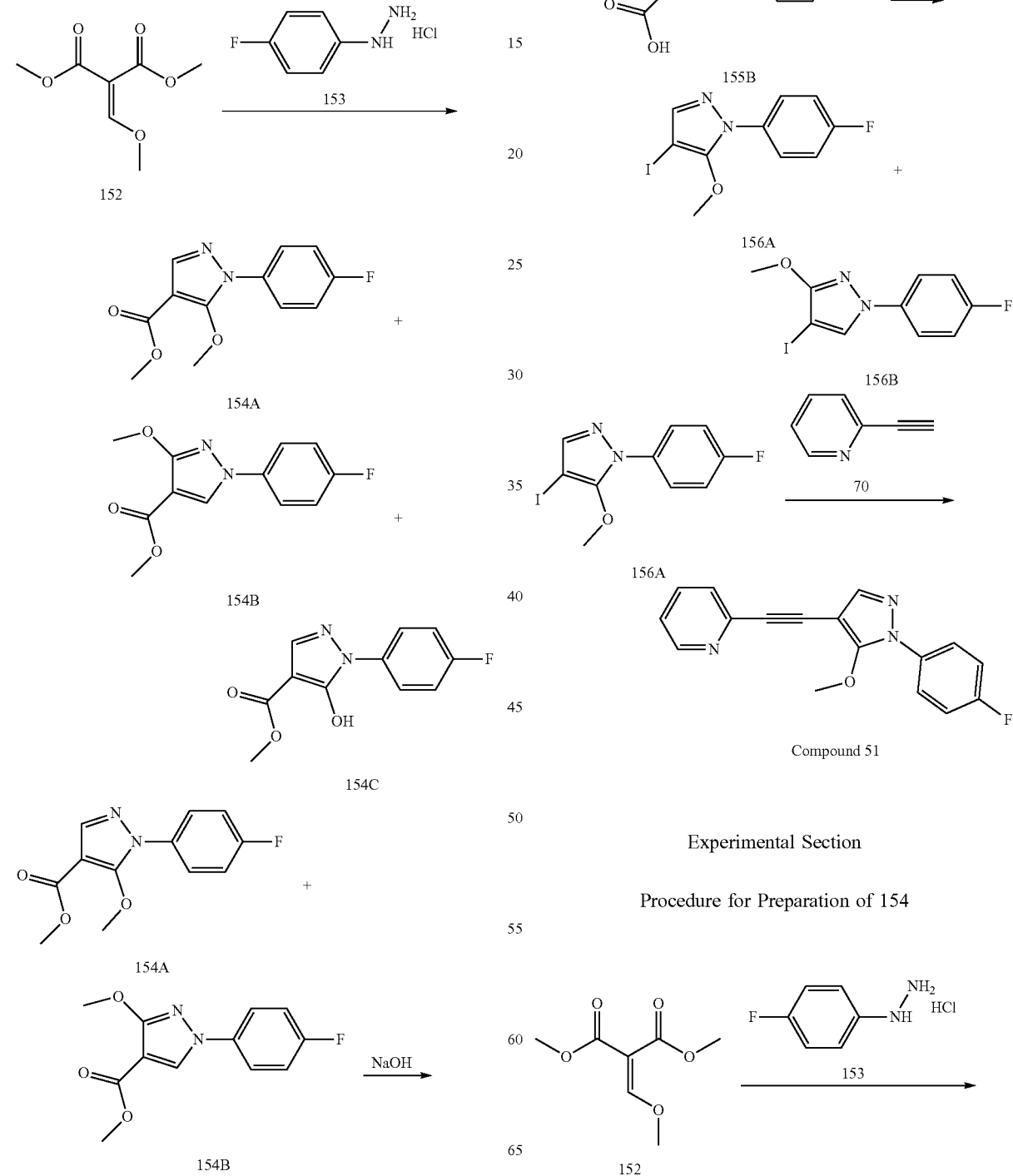
Compound 51
Experimental Section
Procedure for Preparation of 154

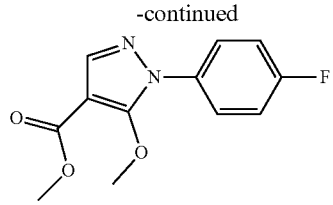

154A

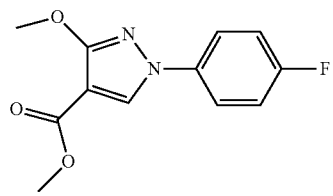

154B

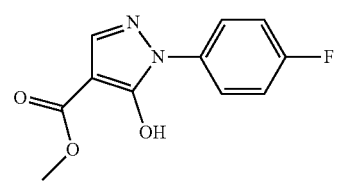

154C

To a solution of 152 (5.00 g, 28.71 mmol) in 250 mL of MeOH was added compound 141 (4.90 g, 30.15 mmol). The mixture was stirred at 70° C. for 18 hours. The reaction mixture was concentrated and the obtained residue was treated with saturated NaHCO₃ solution, extracted with DCM (2×300 mL). The combined organic layer was dried over Na₂SO₄, concentrated and purified by chromatograph column to give a mixture of compound 154A and compound 154B (1.1 g, yield 15%) and 1.6 g of compound 154° C.

$^1$H NMR (400 MHz, CDCl₃): δ 8.19 (s, 1H), 7.91 (s, 1H), 7.63-7.58 (m, 3H), 7.17-7.12 (m, 3H), 4.14 (s, 3H), 4.08 (s, 1.4H), 3.86 (s, 4H), 3.77 (s, 1.3H).

Procedure for Preparation of 155A and 155B

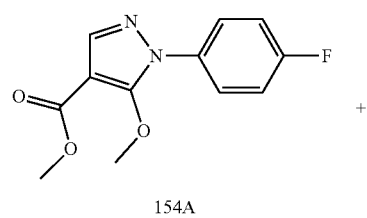

154A

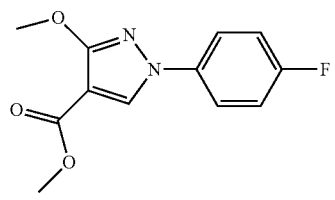

154B

→ NaOH

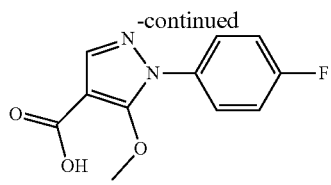

155A

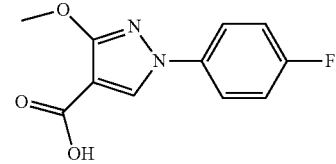

155B

To a solution of compound 154A and compound 154B (900 mg, 3.60 mmol) in 30 mL/30 mL of EtOH/H₂O was added NaOH (432 mg, 10.79 mmol). The mixture was stirred at 80° C. for 2 hours. The reaction mixture was concentrated and the obtained residue was acidified with 1 N HCl solution to pH=5-6, extracted with DCM (2×30 mL). The combined organic layer was dried over Na₂SO₄, concentrated to give a mixture of compound 155A and compound 155B (700 mg, yield 82%).

LCMS: m/z 237 (M+H)⁺;

$^1$H NMR (400 MHz, CDCl₃): δ 8.28 (s, 0.45H), 8.00 (s, 1H), 7.64-7.61 (m, 3H), 7.19-7.15 (m, 3H), 4.17 (s, 3H), 4.12 (s, 1.3H).

Procedure for Preparation of 156A and 156B

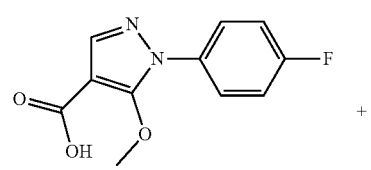

155A

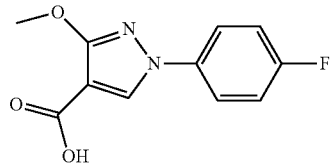

155B

→ NIS

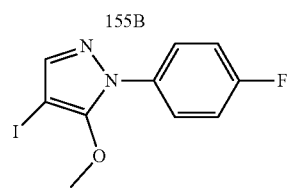

156A

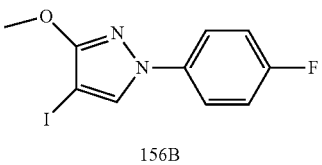

156B

To a solution of a mixture of compound 155A and compound 155B (700 mg, 2.96 mmol) in 30 mL of DMF was added NIS (1.00 g, 4.45 mmol) and NaHCO₃ (996 mg, 11.85 mmol). The mixture was stirred at 60° C. for 48 hours. LCMS showed that the reaction was complete. The reaction mixture was concentrated and purified by prep-TLC to give the products compound 154A (260 mg, yield 27%) and compound 156B (110 mg, yield 11%).

¹H NMR (400 MHz, CDCl₃): δ 7.62-7.58 (m, 2H), 7.51 (s, 1H), 7.16-7.12 (m, 2H), 3.97 (s, 3H).

Procedure for Preparation of Compound 51

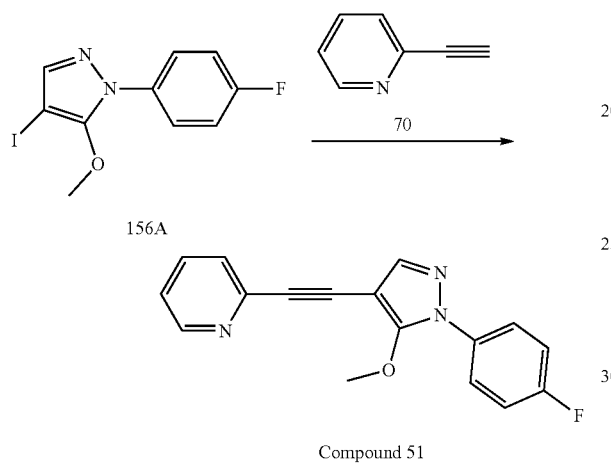

Compound 51

To a solution of compound 156A (120 mg, 0.38 mmol) in 10 mL of degassed THF was added successively CuI (8 mg, 0.038 mmol), compound 70 (79 mg, 0.75 mmol), and Pd(PPh₃)₂Cl₂ (26 mg, 0.038 mmol) and Et₃N (115 mg, 1.13 mmol). The mixture was stirred at 80° C. for 18 hours. The reaction mixture was filtered and the filtrate was concentrated to give the crude product, which was purified by prep-HPLC to give the product Compound 51 (15 mg, yield 14%).

LCMS: m/z 294 (M+H)⁺:

¹H NMR (400 MHz, CDCl₃): δ 8.60 (s, 1H), 7.68-7.61 (m, 4H), 7.44 (d, J=7.6 Hz, 1H), 7.25-7.23 (m, 1H), 7.15-7.11 (m, 2H), 4.41 (s, 3H).

Example Compound 52

Preparation of 2-((1-(4-fluorophenyl)-3-methoxy-1H-pyrazol-4-yl)ethynyl)pyridine

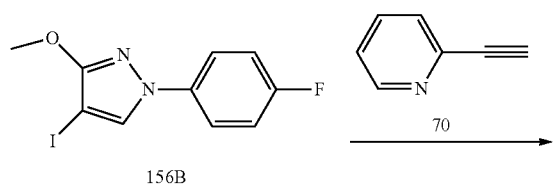

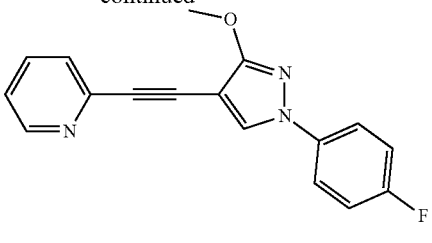

Compound 52

Experimental Section

Procedure for Preparation of Compound 52

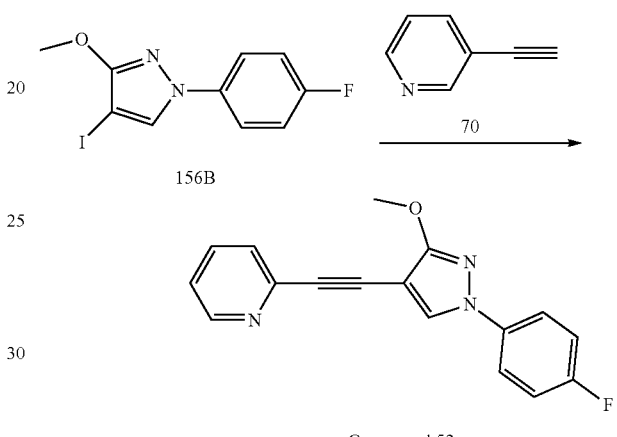

Compound 52

To a solution of 156B (110 mg, 0.35 mmol) in 5 mL of degassed THF was added successively CuI (7 mg, 0.035 mmol), 70 (71 mg, 0.71 mmol), and Pd(PPh₃)₂Cl₂ (24 mg, 0.035 mmol) and Et₃N (105 mg, 1.04 mmol). The mixture was stirred at 80° C. for 18 hours. The reaction mixture was filtered and the filtrate was concentrated to give the crude product, which was purified by prep-HPLC to give the product Compound 52 (10 mg, yield 10%).

LCMS: m/z 294 (M+H)⁺;

¹H NMR (400 MHz, CDCl₃): δ 8.59 (s, 1H), 7.90 (s, 1H), 7.65-7.54 (m, 4H), 7.19-7.10 (m, 3H), 4.06 (s, 3H).

Example Compound 53

Preparation of 3-(3-(2-(dimethylamino)ethoxy)-4-(pyridin-2-ylethynyl)-1H-pyrazol-1-yl)-5-fluorobenzonitrile

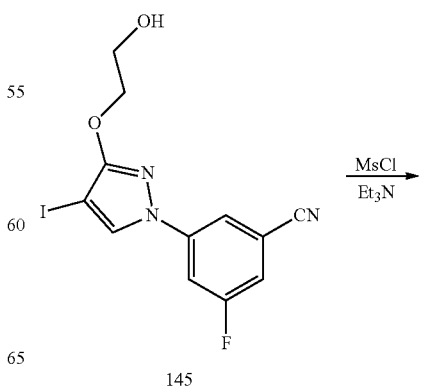

145

153

-continued

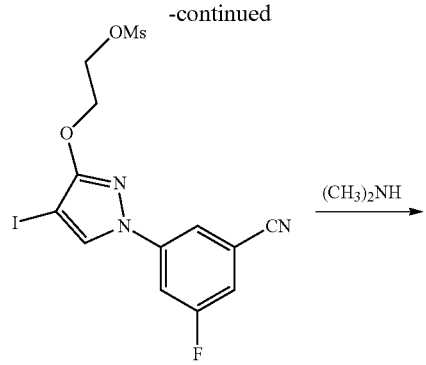
157

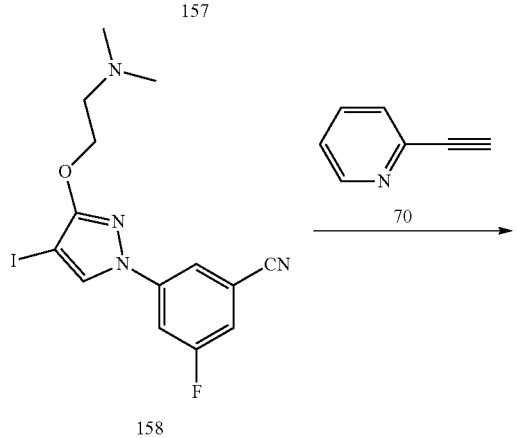
158

Experimental Section

Procedure for Preparation of 157

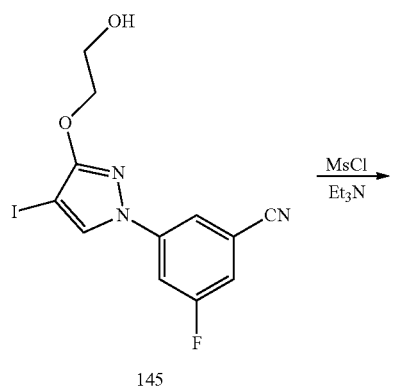
145

154

-continued

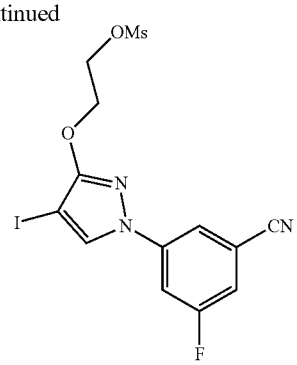
157

To a solution of 145 (150 mg, 0.402 mmol) in DCM (20 mL) was added TEA (69 mg, 0.683 mmol). The mixture was cooled to 0° C. and added MsCl (69 mg, 0.603 mmol) dropwise. The mixture was allowed to warm to room temperature and stirred for 1 hour. The mixture was quenched with water and extracted with EA (2×20 mL). The combined organics was concentrated by vacuo to give the crude product 145 (180 mg, crude).

LCMS: m/z, 451.8 (M+H)+.

Procedure for Preparation of 158

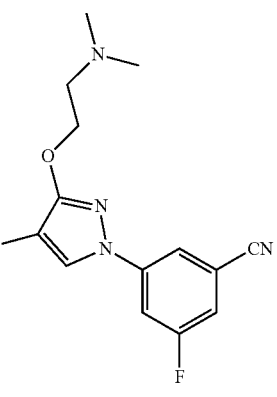
158

To a solution of 157 (100 mg, 0.222 mmol) in THF (5 mL) was added compound dimethyl amine (in MeOH) (1.11 mL, 1.11 mmol) dropwise. The mixture was stirred at 60° C. for 5 hours. The mixture was quenched with water and extracted with EA (2×20 mL). The combined organics was concentrated by vacuo to give the crude product which was purified by prep-TLC to give product 158 (80 mg, 90%).

LCMS: m/z, 401.0 (M+H)+.

Procedure for Preparation of Compound 53

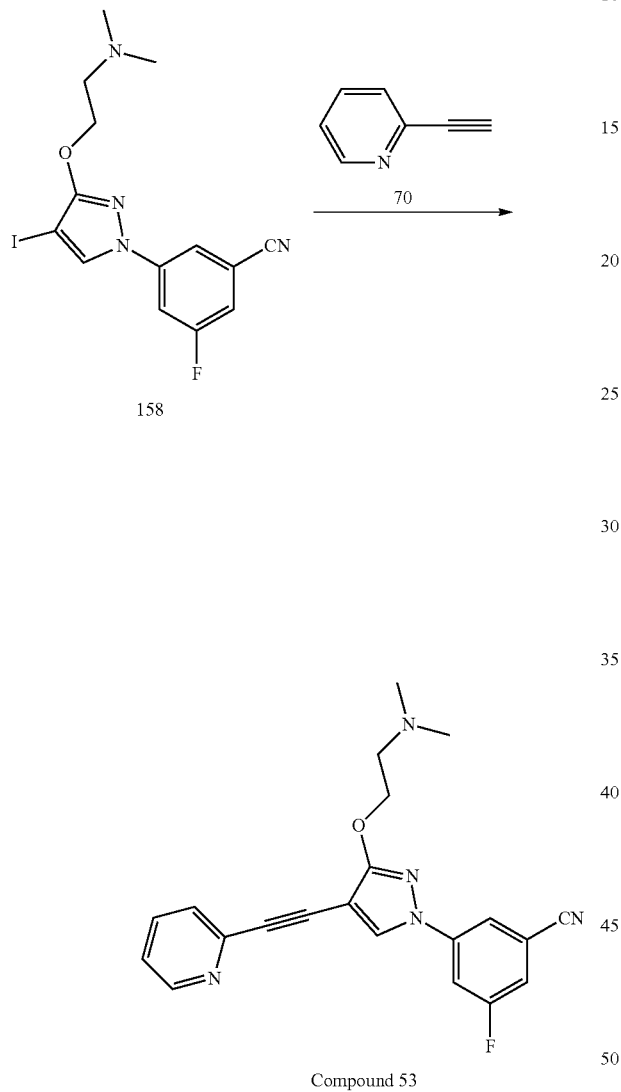

158

Compound 53

To a solution of 158 (65 mg, 0.162 mmol) in THF (3 mL) was added successively CuI (3 mg, 0.016 mmol), 70 (34 mg, 0.325 mmol), Et₃N (49 mg, 0.487 mmol) and Pd(PPh₃)₂Cl₂ (6 mg, 0.008 mmol). The mixture was then degassed for 1 minute under N₂ atmosphere and stirred at 90° C. for 1 hour under microwave. The reaction mixture was filtered and concentrated to give the crude product which was purified by prep-HPLC to give product Compound 53 (4 mg, 7%).

LCMS: m/z, 376.1 (M+H)+;

$^1$H NMR (400 MHz, CDCl₃): δ 8.61 (s, 1H), 7.98 (s, 1H), 7.70-7.66 (m, 2H), 7.58-7.56 (m, 1H), 7.50-7.48 (m, 1H), 7.22-7.20 (m, 2H), 4.51-4.48 (m, 2H), 2.86-2.83 (m, 2H), 2.40 (s, 6H).

Example Compound 54

Preparation of 3-(3-cyclopropyl-4-(pyridin-2-ylethynyl)-1H-pyrazol-1-yl)-5-fluorobenzonitrile

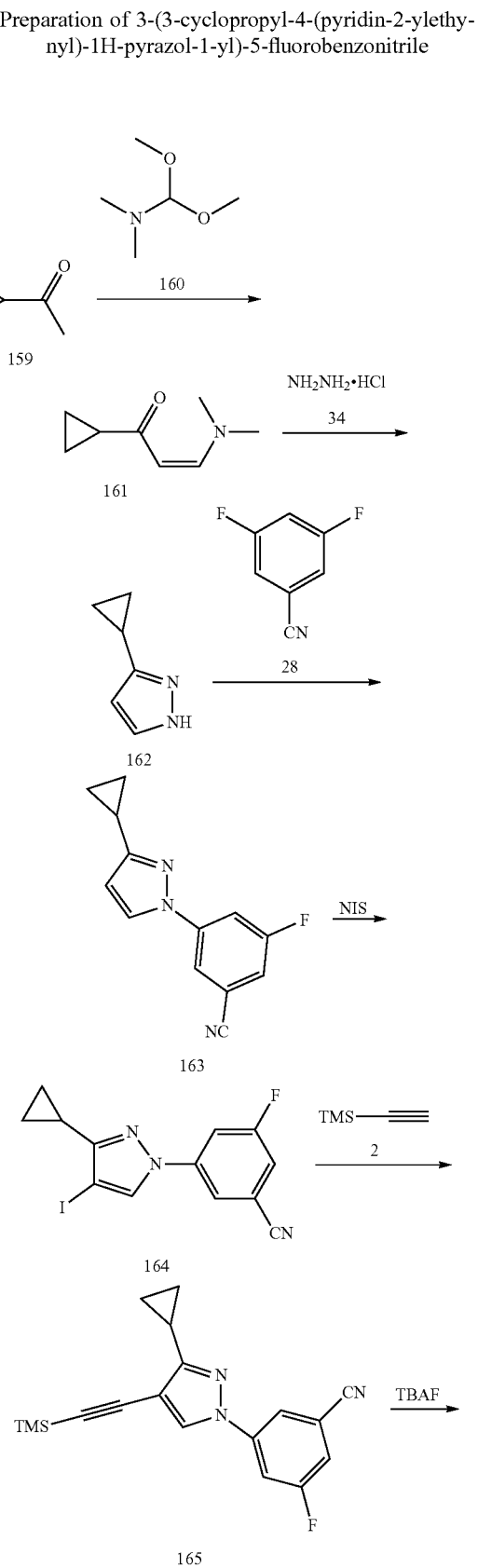

-continued

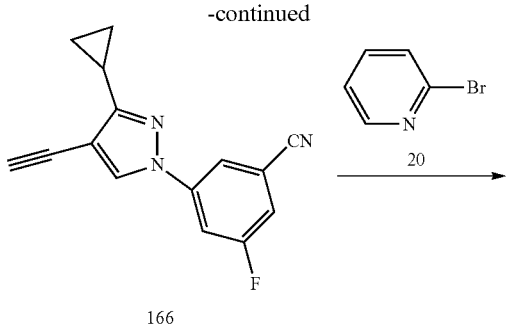

166

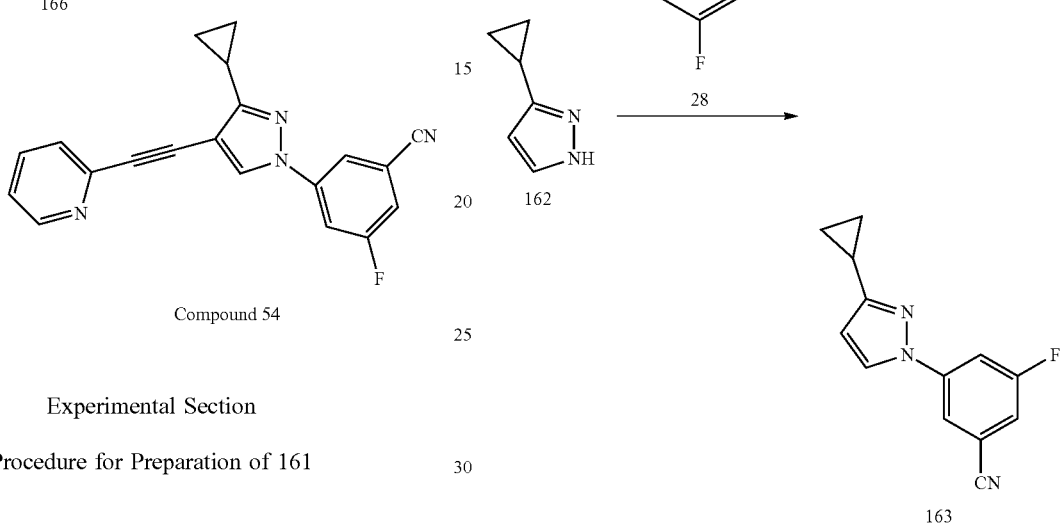

Compound 54

Experimental Section

Procedure for Preparation of 161

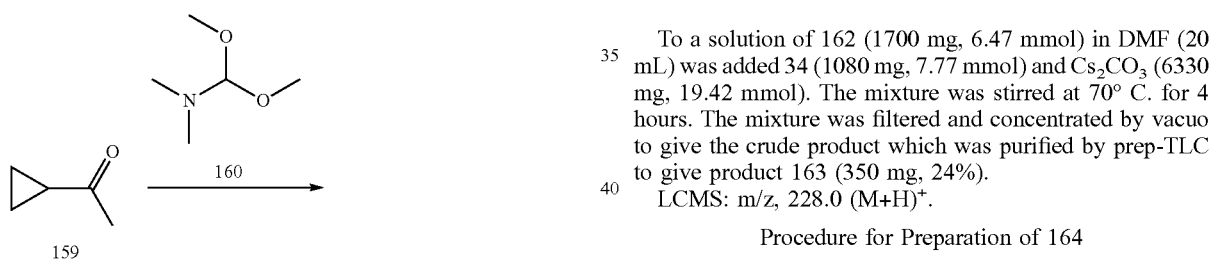

159 → 161

To a solution of 159 (700 mg, 8.32 mmol) in DMF (10 mL) was added 160 (4.96 g, 41.61 mmol) dropwise. The mixture was stirred at 110° C. for 12 hours. The mixture was concentrated by vacuo to give product 161 (1.1 g, crude).

Procedure for Preparation of 162

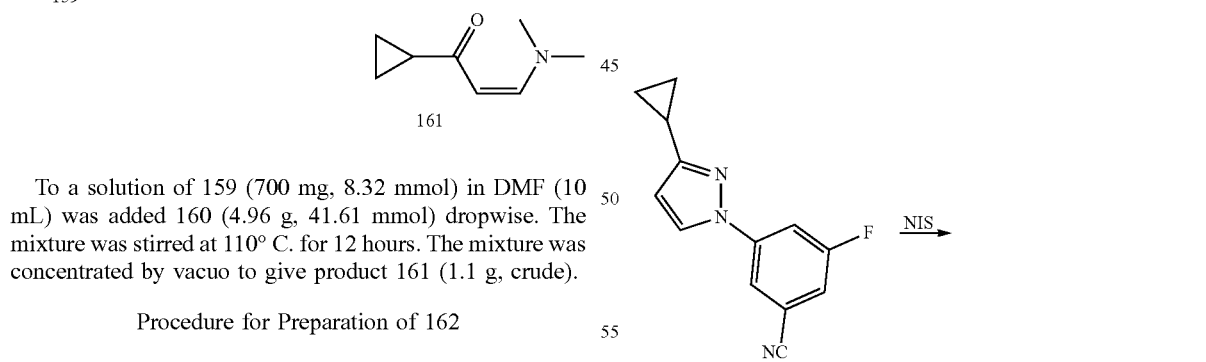

161 → 162

To a solution of 161 (600 mg, 4.31 mmol) in EtOH (30 mL) was added 34 (2360 mg, 34.48 mmol). The mixture was stirred at refluxing temperature for 12 hours. The mixture was filtered and residue was concentrated by vacuo to give crude product 162 (700 mg, crude).

Procedure for Preparation of 163

162 → 163

To a solution of 162 (1700 mg, 6.47 mmol) in DMF (20 mL) was added 34 (1080 mg, 7.77 mmol) and $Cs_2CO_3$ (6330 mg, 19.42 mmol). The mixture was stirred at 70° C. for 4 hours. The mixture was filtered and concentrated by vacuo to give the crude product which was purified by prep-TLC to give product 163 (350 mg, 24%).

LCMS: m/z, 228.0 $(M+H)^+$.

Procedure for Preparation of 164

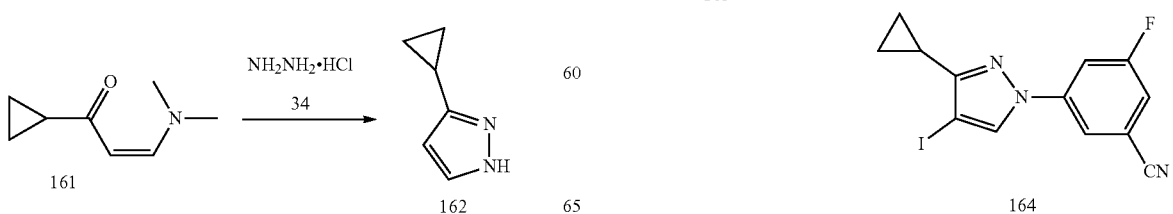

163 → 164

To a solution of 163 (350 mg, 1.54 mmol) in CHCl₃ (25 mL) was added NIS (520 mg, 2.31 mmol). The mixture was stirred at 60° C. for 5 hours. The mixture was quenched with water and extracted with DCM (2×10 mL). The combined organic phase was concentrated under vacuo and the residue was purified by prep-TLC to give product 164 (400 mg, 74%).

Procedure for Preparation of 165

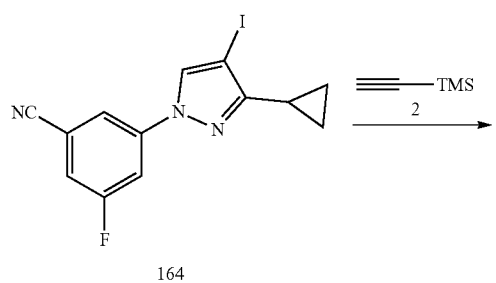

164

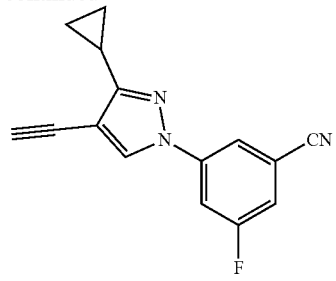

166

To a solution of 164 (450 mg, 1.27 mmol) in CH₃CN (10 mL) was added successively CuI (24 mg, 0.127 mmol), 2 (250 mg, 2.55 mmol), Et₃N (387 mg, 3.82 mmol) and Pd(PPh₃)₂Cl₂ (45 mg, 0.064 mmol). The mixture was then degassed for 1 minute under N₂ atmosphere and stirred at 90° C. for 1 hour under microwave. The reaction mixture was filtered and concentrated to give the crude product which was purified by prep-TLC to give 165 (400 mg, 97%).

LCMS: m/z, 324.0 (M+H)⁺.

Procedure for Preparation of 166

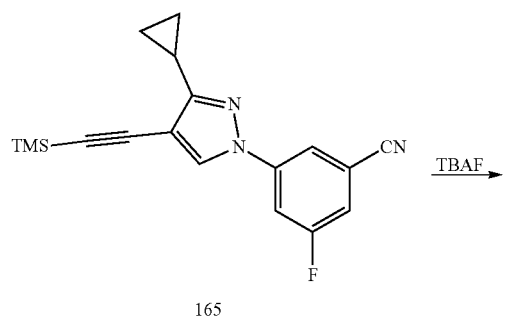

165

A solution of 165 (400 mg, 1.24 mmol) in THF (10 mL). The solution was cooled to 0° C. and TBAF (1.86 mL, 1.86 mmol) was added. The reaction mixture stirred at room temperature for 1 hour. The mixture was quenched with water and extracted with EA (3×10 mL). The combined organic phase was concentrated by vacuo to give the crude product 166 (210 mg, 68%).

Procedure for Preparation of Compound 54

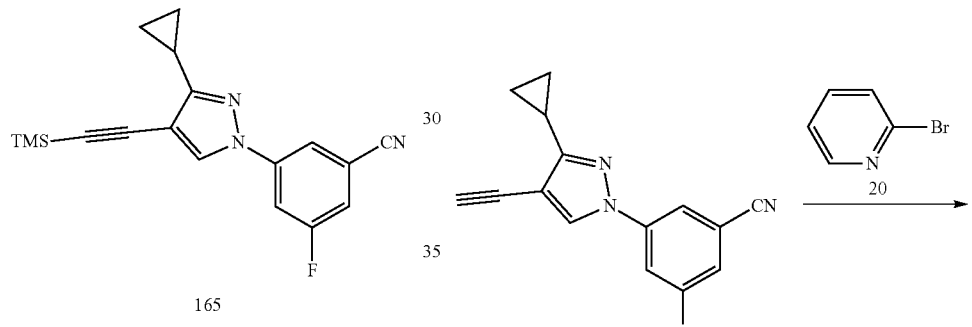

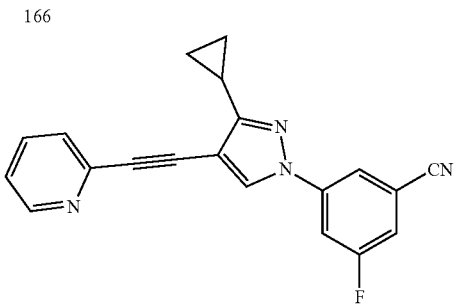

Compound 54

To a solution of compound 166 (70 mg, 0.279 mmol) in THF (3 mL) was added successively CuI (5 mg, 0.028 mmol), 20 (88 mg, 0.557 mmol), Et₃N (85 mg, 0.836 mmol) and Pd(PPh₃)₂Cl₂ (10 mg, 0.014 mmol). The mixture was then degassed for 1 minute under N₂ atmosphere and stirred at 90° C. for 1 hour under microwave. The reaction mixture was filtered and concentrated to give the crude product which was purified by prep-HPLC to give the product Compound 54 (6 mg, 7%).

LCMS: m/z, 329.1 (M+H)⁺;

¹H NMR (400 MHz, CDCl₃): δ 8.62 (s, 1H), 8.03 (s, 1H), 7.73-7.61 (m, 3H), 7.51-7.49 (m, 1H), 7.25-7.24 (m, 2H), 2.19-2.16 (m, 1H), 1.08-1.05 (m, 4H).

Example Compound 55

Preparation of 3-(3-cyclopropyl-4-(pyrimidin-2-ylethynyl)-1H-pyrazol-1-yl)-5-fluorobenzonitrile

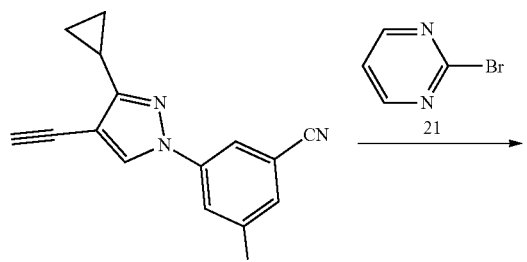

166

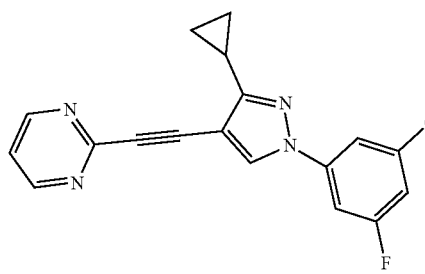

Compound 55

Experimental Section

Procedure for Preparation of Compound 55

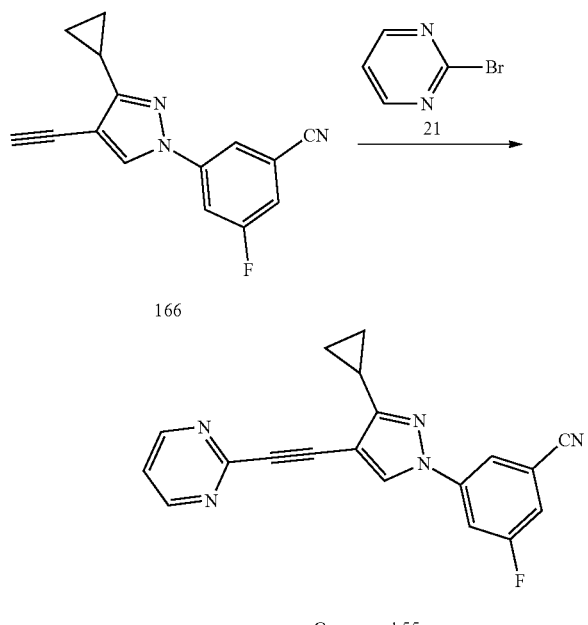

To a solution of 166 (70 mg, 0.279 mmol) in THF (3 mL) was added successively CuI (5 mg, 0.028 mmol), 21 (89 mg, 0.557 mmol), Et₃N (85 mg, 0.836 mmol) and Pd(PPh₃)₂Cl₂ (10 mg, 0.014 mmol). The mixture was then degassed for 1 minute under N₂ atmosphere and stirred at 90° C. for 1 hour under microwave. The reaction mixture was filtered and concentrated to give the crude product which was purified by prep-HPLC to give product Compound 55 (3 mg, 3%).

LCMS: m/z, 330.1 (M+H)⁺;

¹H NMR (400 MHz, CDCl₃): δ 8.76 (s, 1H), 8.75 (s, 1H), 8.09 (s, 1H), 7.73 (s, 1H), 7.63-7.61 (m, 1H), 7.25-7.23 (m, 2H), 2.21 (m, 1H), 1.14-1.13 (m, 2H), 1.09-1.07 (m, 2H).

Example Compound 56

Preparation of 2-((1-(4-fluorophenyl)-5-(2-methoxy-ethoxy)-1H-pyrazol-4-yl ethynyl)pyridine

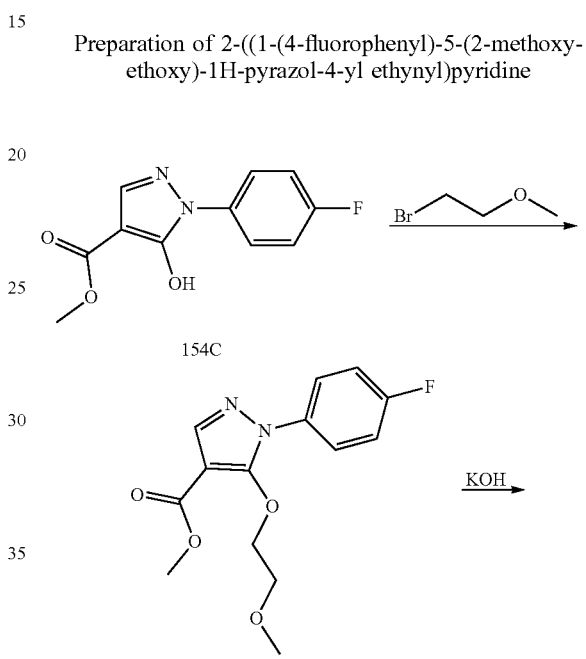

-continued

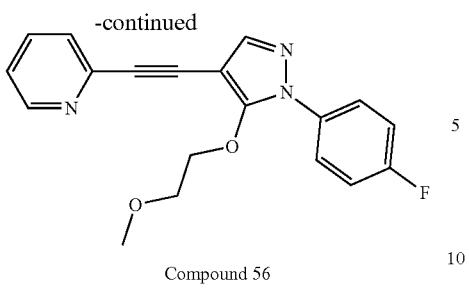

Compound 56

Experimental Section

Procedure for Preparation of 167

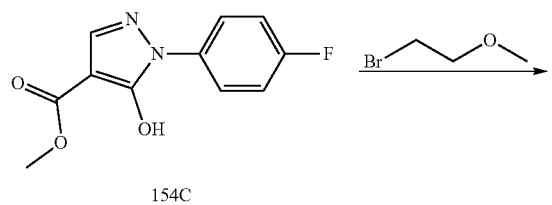

154C

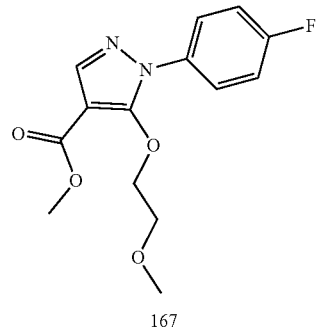

167

To a solution of 154C (800 mg, 3.4 mmol) and 1-bromo-2-methoxy-ethane (942 mg, 6.8 mmol) in DMF (15 ml) was added NaI (508 mg, 3.4 mmol) and $K_2CO_3$ (1400 mg, 10.2 mmol), the mixture was heated at 60° C. for 3 hours. After cooling to room temperature, water (30 ml) was added into above mixture with stirring at ice bath. Gradually, white solid was formed. It was filtrated and the residue was the product 167 (900 mg, 90.3%).

LCMS: m/z, 295.0 (M+H)$^+$.

Procedure for Preparation of 168

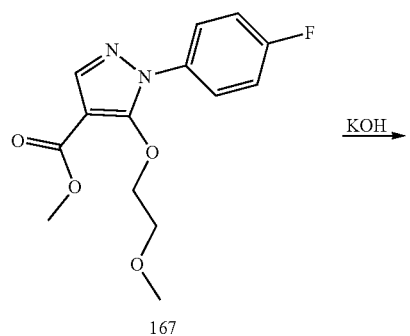

167

-continued

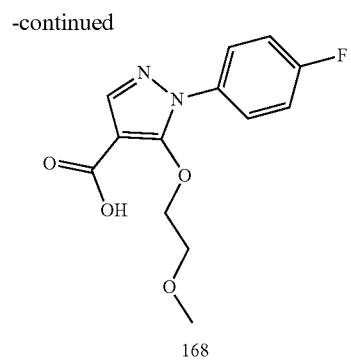

168

To a solution of 167 (0.9 g, 3.1 mmol) in MeOH (10 mL) was added a solution of 35% KOH (5 mL). Then it was heated to reflux for 2 hours. Most of the solvent was removed. It was adjust pH to 2 by a solution of HCl (6 mol/L) with stirring at ice bath. Then white solid was gradually formed. It was filtrated, the residue was washed with water and evaporated to give the product 168 (750 mg, 87.5%).

LCMS: m/z, 343.1 (M+H)$^+$.

Procedure for Preparation of 169

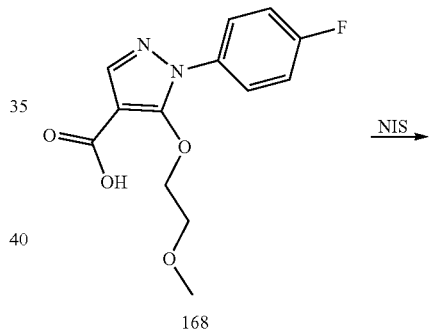

168

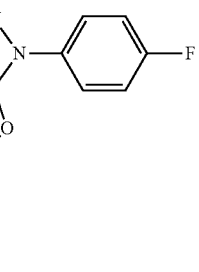

169

To a solution of 168 (350 mg, 1.25 mmol) in dry DMF (6 mL) was added solid NIS (422 mg, 1.87 mmol) and $NaHCO_3$ (525 mg, 6.24 mmol). Then it was heated to 80° C. for 24 hours. After cooling to room temperature, water (20 mL) as added into it. It was extracted with EtOAc (20 mL×3). The organics was collected, washed with brine (20 mL), evaporated to give the crude product which was purified by chromatography to give the product 169 (200 mg, 44.2%).

LCMS: m/z, 362.9 (M+H)$^+$;

$^1$H NMR (400 MHz, CDCl$_3$): δ3.48 (s, 3H), 3.79-3.82 (m, 2H), 7.46-7.48 (m, 2H), 7.09-7.14 (m, 3H), 7.50-7.54 (m, 2H), 7.72 (s, 1H).

Procedure for Preparation of Compound 56

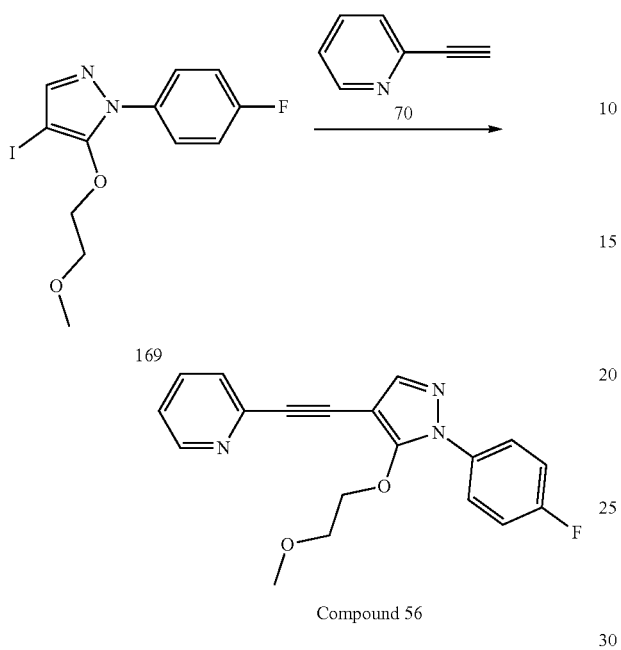

Compound 56

To a solution of 169 (60 mg, 0.16 mmol) in 4 mL of degassed THF was added solid CuI (0.2 mg, 0.008 mmol), 70 (20 mg, 020 mmol), Et$_3$N (48 mg, 0.48 mmol) and Pd(PPh$_3$)$_2$Cl$_2$ (1.4 mg, 0.008 mmol) was added into it. The mixture was then degassed for 2 minutes under N$_2$ atmosphere and stirred at 90° C. for 1 hour under microwave. Most of the solvent was removed. The residue was dissolved in EtOAc (30 mL). The organic layer was washed with brine (2×20 mL) and dried over anhydrous Na$_2$SO$_4$, filtered and evaporated to dryness on a rotary evaporator, which was purified by pre-HPLC to give the product Compound 56 (15 mg, 26.8%).

LCMS: m/z, 338.1 (M+H)$^+$;

$^1$H NMR (400 MHz, CDCl$_3$): δ3.47 (s, 3H), 3.82 (t, J=4.8 Hz, 2H), 4.52 (t, J=4.8 Hz, 2H), 7.11-7.13 (m, 2H), 7.13-7.15 (m, 1H), 7.49-7.57 (m, 3H), 7.65-7.67 (m, 1H), 7.92 (s, 1H), 8.60 (s, 1H).

Example Compound 57

Preparation of 2-((1-(4-fluorophenyl)-5-(2-methoxyethoxy)-1H-pyrazol-4-yl) ethynyl)pyrimidine

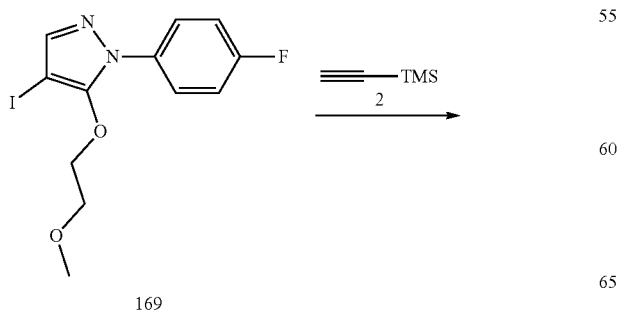

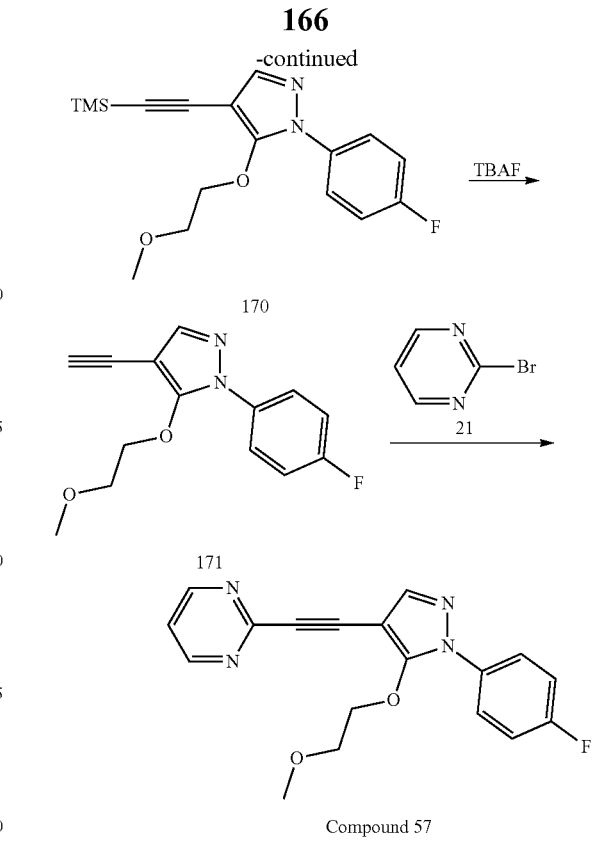

Compound 57

Experimental Section

Procedure for Preparation of 170

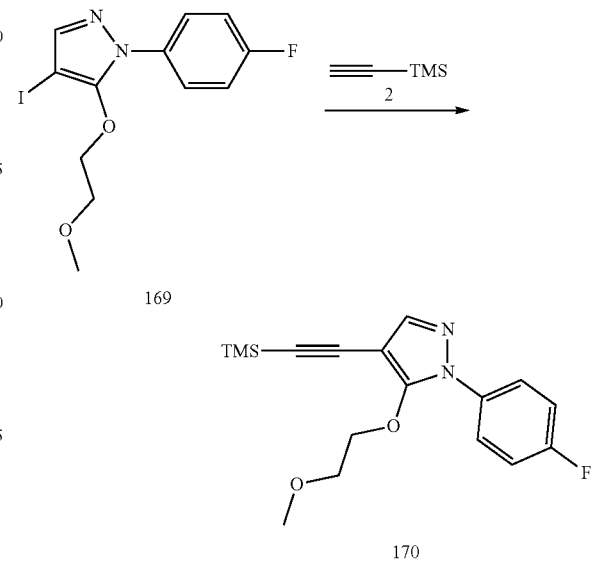

To a solution of compound 169 (108 mg, 0.3 mmol) in 4 mL of degassed THF was added successively CuI (3 mg, 0.015 mmol), 2 (58.9 mg, 0.6 mmol), Et$_3$N (90 mg, 0.9 mmol) and Pd(PPh$_3$)$_2$Cl$_2$ (9 mg, 0.015 mmol). The mixture was then degassed for 2 minutes under N$_2$ atmosphere and stirred at 90° C. for 1 hour under microwave. Most of the solvent was removed. The residue was dissolved in EtOAc (30 mL). The organic layer was washed with brine (2×20 mL) and dried over anhydrous Na₂SO₄, filtered and evaporated to dryness on a rotary evaporator, which was purified by flash chromatography to give product 170 (80 mg, 80.2%).

LCMS: m/z, 333.0 (M+H)⁺.

Procedure for Preparation of 171

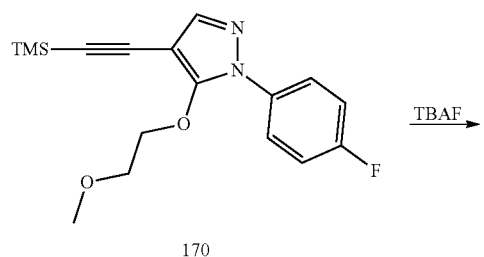

To a solution of 170 (80 mg, 0.24 mmol) in THF (4 mL) was added a solution of TBAF-THF (0.36 mL, 0.36 mmol). The mixture was stirred at room temperature for 1 hour. TLC showed the reaction was complete. Most of the solvent was removed. The residue was dissolved in EtOAc (20 mL). The organic layer was washed with brine (2×10 mL) and dried over anhydrous Na₂SO₄, filtered and evaporated to give a crude product 171 (60 mg, crude), which was directly used for next step.

Procedure for Preparation of Compound 57

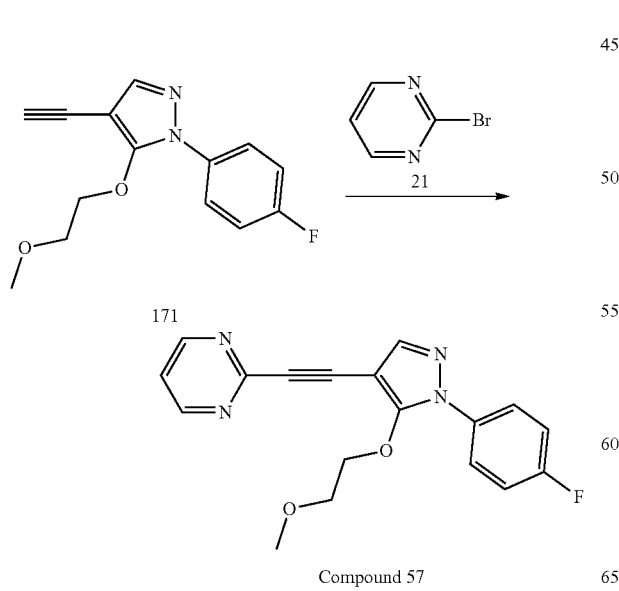

To a solution of 171 (60 mg, 0.23 mmol) in 4 mL of degassed THF was added solid CuI (2 mg, 0.01 mmol), 21 (43.2 mg, 0.27 mmol), Et₃N (70 mg, 0.69 mmol) and Pd(PPh₃)₂Cl₂ (7 mg, 0.01 mmol). The mixture was then degassed for 2 minutes under N₂ atmosphere and stirred at 90° C. for 1 hour under microwave. Most of the solvent was removed. The residue was dissolved in EtOAc (30 mL). The organic layer was washed with brine (2×20 mL) and dried over anhydrous Na₂SO₄, filtered and evaporated to dryness on a rotary evaporator, which was purified by pre-HPLC to give the product Compound 57 (15 mg, 19.2%).

LCMS: m/z, 339.0 (M+H)⁺;

¹H NMR (400 MHz, CDCl₃): δ3.48 (s, 3H), 3.82-3.84 (m, 2H), 4.52-4.54 (m, 2H), 7.12-7.23 (m, 3H), 7.55-7.58 (m, 2H), 7.99-7.57 (s, 1H), 8.74 (d, J=5.2 Hz, 2H).

Example Compound 58

Preparation of 2-((3-chloro-1-(4-(methylsulfonyl) phenyl)-1H-pyrazol-4-yl) ethynyl)pyridine

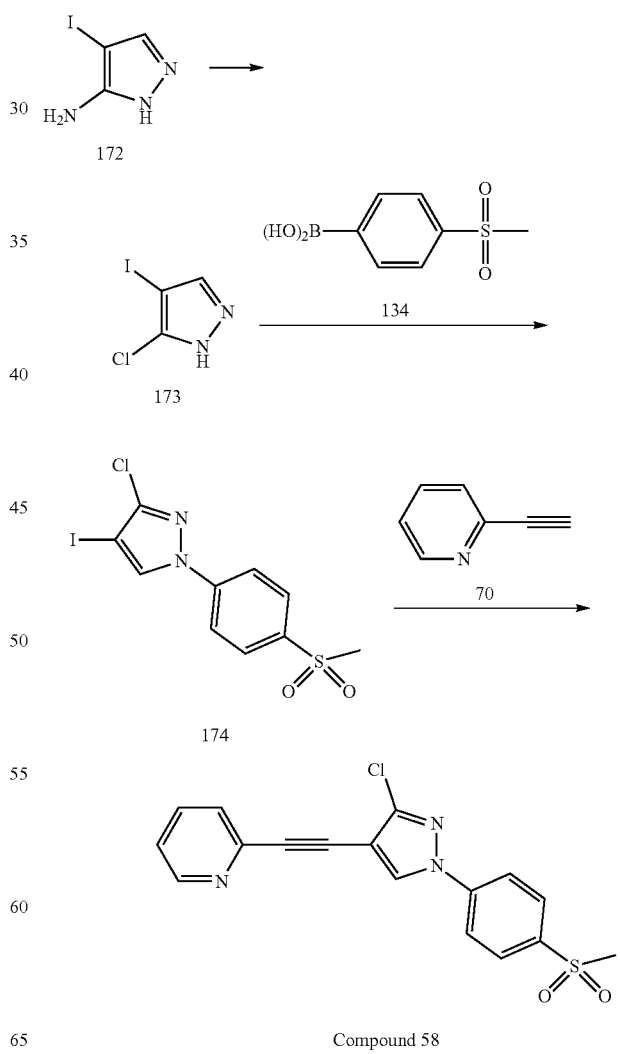

Experimental Section

Procedure for Preparation of 173

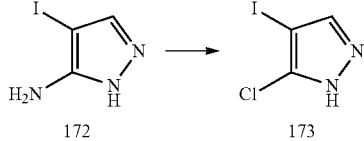 [SMILES: Nc1[nH]ncc1I ; Clc1[nH]ncc1I]

To a solution of 172 (2.0 g, 10.0 mmol) in 6.0 mL of water, 10.0 mL of concentrated HCl and 3.0 mL of 85% $H_3PO_4$ were added, the mixture was cooled to −5° C. A solution of $NaNO_2$ (0.7 g, 10.0 mmol) in 3.0 mL of $H_2O$ was added over 30 minutes, the temperature was kept at −2° C. After stirred for 1 hour, the above mixture was added to a solution of CuCl (1.5 g, 15.0 mmol) in 10.0 mL of concentrated HCl. The resultant mixture was heated to 60° C. until the mixture was no gas goes off, extracted with chloroform. The organic phase was washed by water, brine, dried over sodium sulfate and concentrated to dryness. The residue was purified by flash chromatography column on silica gel to afford product 173 (160 mg, 6.9%)

Procedure for Preparation of 174

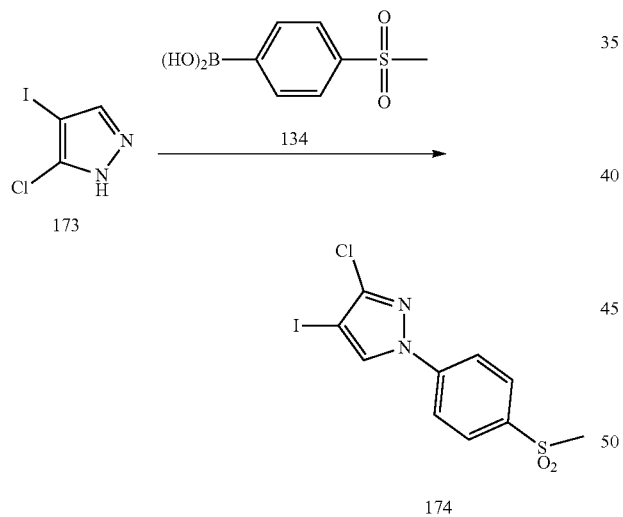

To a solution of 173 (500 mg, 2.2 mmol), 134 (525 mg, 2.6 mmol) and $Cu(AcO)_2$ (795 mg, 4.4 mmol) in dry DCM (5 mL) was added pyridine (520 mg, 6.6 mmol) and pyridine 1-oxide (625 mg, 6.6 mmol) at room temperature. After adding, it was stirred at room temperature under O2 protected for 60 hours. It was filtrated and most of the solvent was removed. The residue was dissolved in EtOAc (60 mL). The organic layer was washed with brine (2×30 mL) and dried over anhydrous $Na_2SO_4$, filtered and evaporated to give a residue, which was purified by chromatography column to give the desired product 174 (120 mg, 14.3%).

LCMS: m/z, 474.8 (M+H)+.

Procedure for Preparation of Compound 58

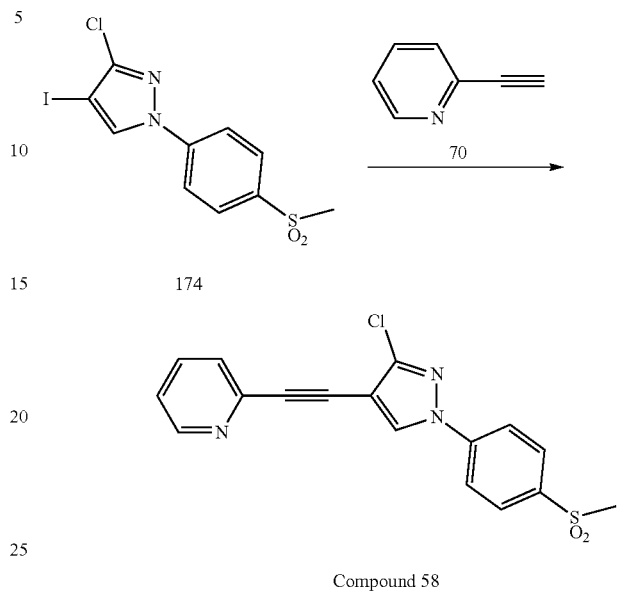

To a solution of 174 (60 mg, 0.15 mmol) in 4 mL of degassed THF was added solid CuI (1.6 mg, 0.008 mmol), 70 (20 mg, 0.2 mmol), $Et_3N$ (50 mg, 0.18 mmol) and $Pd(PPh_3)_2Cl_2$ (5.6 mg, 0.008 mmol) was added into it. The mixture was then degassed for 2 minutes under $N_2$ atmosphere and stirred at 90° C. for 1 hour under microwave. Most of the solvent was removed. The residue was dissolved in EtOAc (30 mL). The organic layer was washed with brine (2×20 mL) and dried over anhydrous $Na_2SO_4$, filtered and evaporated to dryness on a rotary evaporator, which was purified by HPLC to give of the product Compound 58 (10 mg, 17.9%).

LCMS: m/z, 357.9 (M+H)+;

$^1$H NMR (400 MHz, $CDCl_3$): δ3.09 (s, 3H), 7.27-7.29 (m, 1H), 7.55-7.56 (m, 1H), 7.69-7.71 (m, 1H), 7.86-7.88 (m, 1H), 8.05 (m, 1H), 8.07 (m, 1H), 8.20 (s, 2H), 8.63 (d, J=4.8 Hz, 2H).

Example Compound 59

Preparation of 3-fluoro-5-(4-methyl-3-(pyridin-2-ylethynyl)-1H-pyrazol-1-yl) benzonitrile

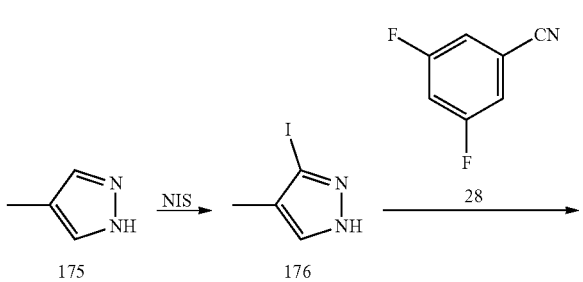

171
-continued

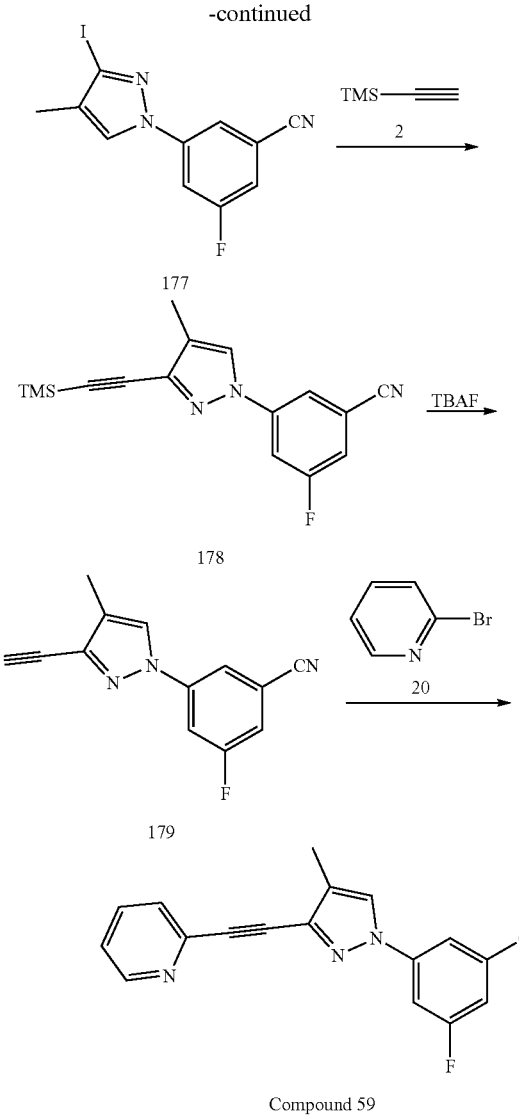

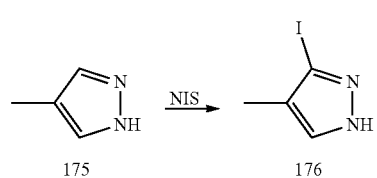

Compound 59

Experimental Section

Procedure for Preparation of 176

To a solution of 175 (0.5 g, 6.1 mmmol) in CHCl$_3$ (20 ml) was added NIS (1.64 g, 7.31 mmol). The mixture was stirred at 70° C. for 2 hours, cooled to room temperature. The remaining aqueous layer was extracted with EtOAc (75 mL) and the combined organic layers were dried (MgSO$_4$), filtered and concentrated in vacuum to yield the title product 176 (0.6 g, yield: 47%).

LCMS: m/z, 208.9 (M+H)$^+$.

172

Procedure for Preparation of 177

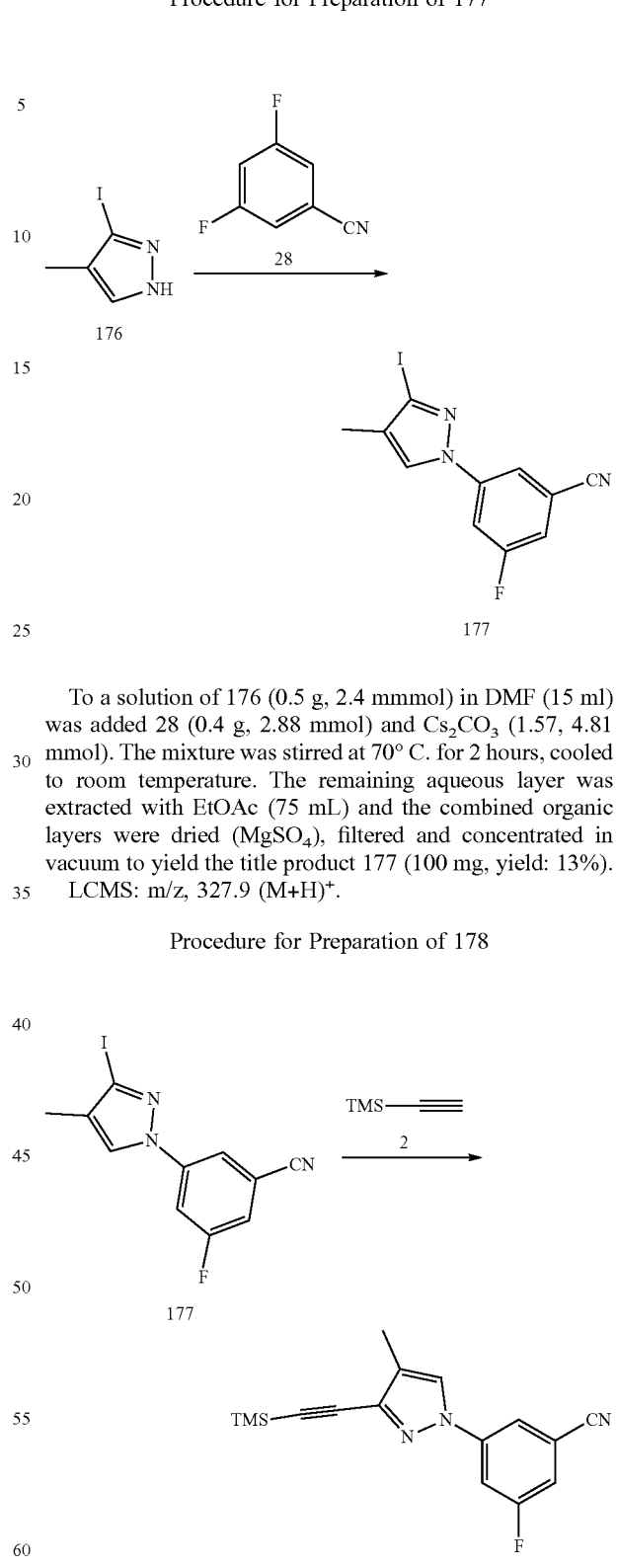

To a solution of 176 (0.5 g, 2.4 mmmol) in DMF (15 ml) was added 28 (0.4 g, 2.88 mmol) and Cs$_2$CO$_3$ (1.57, 4.81 mmol). The mixture was stirred at 70° C. for 2 hours, cooled to room temperature. The remaining aqueous layer was extracted with EtOAc (75 mL) and the combined organic layers were dried (MgSO$_4$), filtered and concentrated in vacuum to yield the title product 177 (100 mg, yield: 13%).

LCMS: m/z, 327.9 (M+H)$^+$.

Procedure for Preparation of 178

To a solution of 177 (250 mg, 0.76 mmol), 2 (150 mg, 1.52 mmol), CuI (15 mg, 0.076 mmol), Et$_3$N (230 mg, 2.28 mmol) in THF (15 mL) was added Pd(PPh$_3$)$_2$Cl$_2$ (53 mg, 0.076 mmol). The suspension was degassed under vacuum and purged with N₂ several times. The mixture was stirred at 90° C. for 6 hours under N₂ atmosphere. The mixture was filtered and concentrated under vacuo. The residue was purified by prep-TLC to give the product 178 (180 mg, yield: 79%).

1H NMR (400 MHz, CDCl₃): δ7.49-7.43 (m, 3H), 6.87-6.84 (m, 1H), 1.89 (s, 3H).

Procedure for Preparation of 179

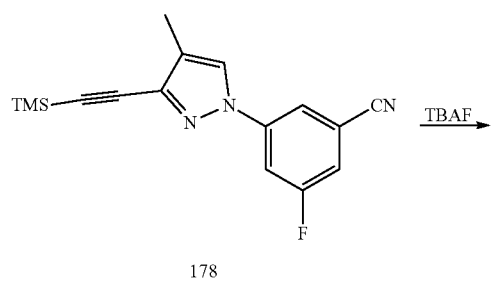

178

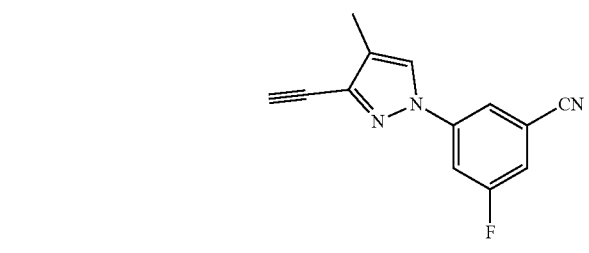

179

To a solution of 178 (180 mg, 0.605 mmol) in 5 mL of degassed THF was added TBAF (0.91 mL, 0.907 mmol) at room temperature. After stirring 2 hours, the solvent was removed. It was extracted with DCM (20 mL) and washed with brine (10 mL). The organic layer was dried over Na₂SO₄ and purified by Prep-TLC to give title product 179 (136 mg, yield: 100%).

LCMS: m/z, 226.1 (M+H)⁺.

Procedure for Preparation of Compound 59

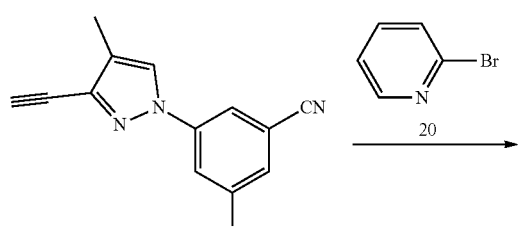

179

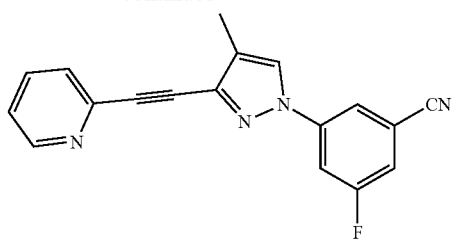

Compound 59

To a solution of 179 (70 mg, 0.31 mmol) and 20 (74 mg, 0.47 mmol), CuI (6 mg, 0.031 mmol), Et₃N (94 mg, 0.93 mmol) in degassed THF (5 mL) was added Pd(PPh₃)₂Cl₂ (22 mg, 0.03 mmol). The suspension was degassed under vacuum and purged with N₂ several times. The mixture was stirred at 90° C. for 6 hours under N₂ atmosphere. The mixture was filtered and concentrated under vacuum to afford crude product, which was purified by Prep-HPLC to give the product Compound 59 (7 mg, yield: 16%).

LCMS: m/z, 303.1 (M+H)⁺;

1H NMR (400 MHz, CDCl₃): δ8.53-8.61 (m, 1H), 8.28 (s, 1H), 8.05 (s, 1H), 7.86-7.99 (m, 2H), 7.65-7.74 (m, 1H) 7.41-7.54 (m, 2H), 2.28 (s, 3H).

Example Compound 60

Preparation of 3-fluoro-5-(4-methyl-3-(pyrimidin-2-ylethynyl)-1H-pyrazol-1-yl) benzonitrile

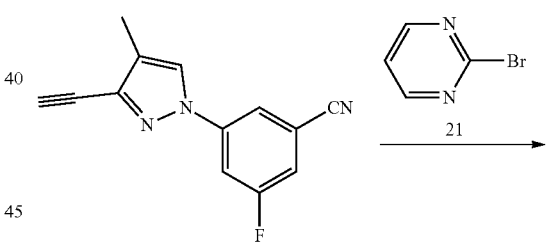

179

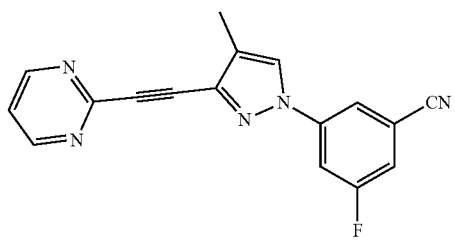

Compound 60

Experimental Section

Procedure for Preparation of Compound 60

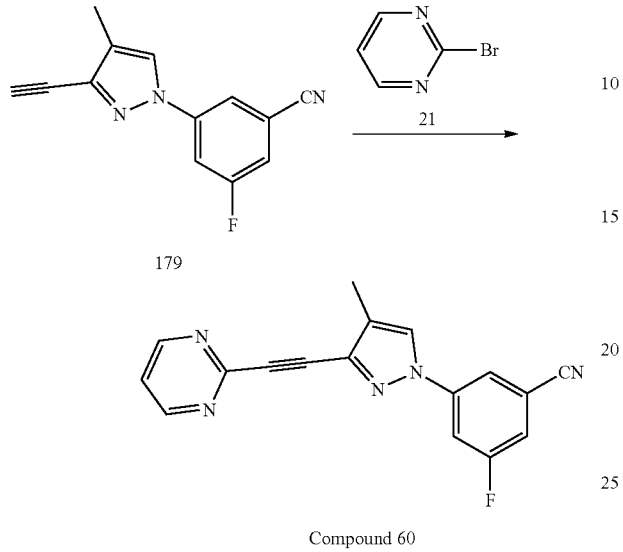

Compound 60

To a solution of 179 (70 mg, 0.31 mmol) and 21 (74 mg, 0.47 mmol), CuI (6 mg, 0.031 mmol), Et$_3$N (94 mg, 0.93 mmol) in degassed THF (5 mL) was added Pd(PPh$_3$)$_2$Cl$_2$ (22 mg, 0.03 mmol). The suspension was degassed under vacuum and purged with N$_2$ several times. The mixture was stirred at 90° C. for 6 hours under N$_2$ atmosphere. The mixture was filtered and concentrated under vacuum to afford crude product, which was purified by Prep-HPLC to give the product Compound 60 (8 mg, yield: 21%).

LCMS: m/z, 304.1 (M+H)$^+$;

$^1$H NMR (400 MHz, CDCl$_3$): δ8.79-8.78 (m, 1H), 7.76-7.73 (m, 3H), 7.28-7.2 (m, 2H), 2.29 (s, 3H).

Example Compound 61

Preparation of 3-(4-chloro-3-(pyridin-2-ylethynyl)-1H-pyrazol-1-yl)-5-fluorobenzonitrile

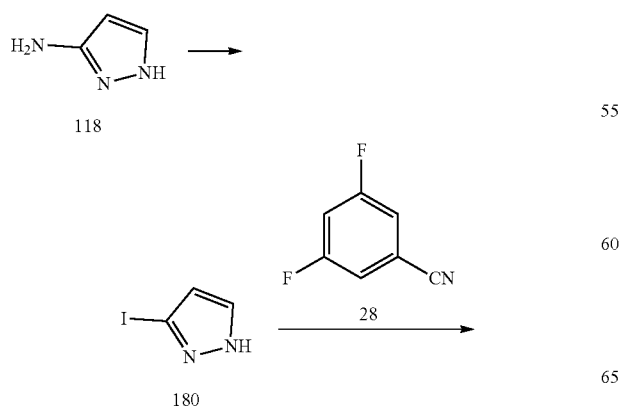

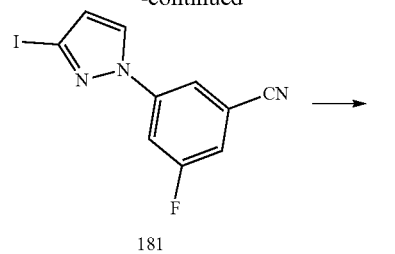

181

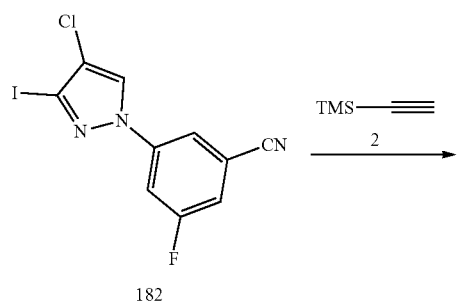

182

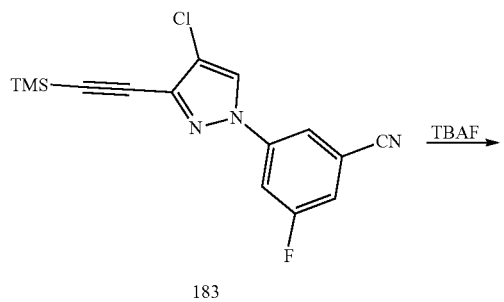

183

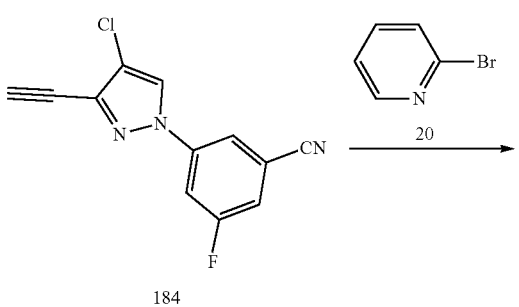

184

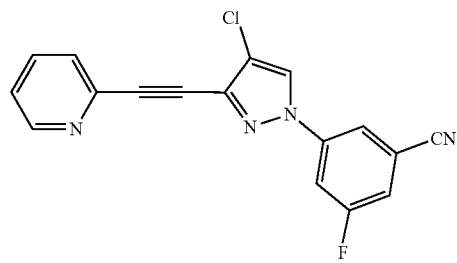

Compound 61

Experimental Section

Procedure for Preparation of 180

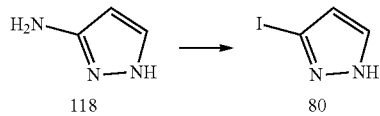

To a stirred suspension of 118 (2.00 g, 24.07 mmol) in concentrated HCl (32 mL) was added a solution of NaNO$_2$ (3.32 g, 48.14 mmol) in water (5 mL) over 5 minutes at 0° C. To the resulting orange reaction mixture was added a solution of KI (9.99 g, 60.18 mmol) in water (10 mL) over 10 minutes. The reaction mixture was stirred at 0° C. for 30 minutes and then kept at 28° C. for another 2 hours. TLC showed the reaction was complete, then, solvent THF (30 mL) was added, followed by water (30 mL). The aqueous mixture was extracted with EtOAc (3×80 mL) and the combined organic extracts were washed with Na$_2$S$_2$O$_3$ (2×40 mL), dried over Na$_2$SO$_4$, filtered and concentrated in vacuum to afford product 180 (2.00 g, crude), the crude product was used directly for the next step without purification.

LCMS: m/z, 194.9 (M+H)$^+$.

Procedure for Preparation of 181

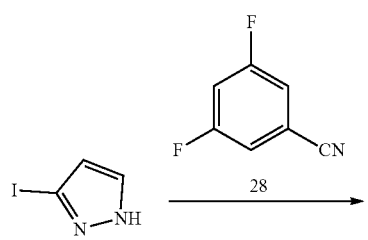

To a mixture of compound 168 (2.00 g, 10.31 mmol) and 16 (1.72 g, 12.37 mmol) in DMF (20 mL), was added Cs$_2$CO$_3$ (6.72 g, 20.62 mmol) in one portion at 29° C. The mixture was heated to 70° C. and stirred for 2 hours. LCMS showed the reaction was completed. The mixture was cooled to 29° C. and concentrated in reduced pressure at 40° C. The residue was poured into water (40 mL) and stirred for 5 minutes. The aqueous phase was extracted with EtOAc (80 mL×2). The combined organic phase was washed with saturated brine (20 mL), dried with anhydrous Na$_2$SO$_4$, filtered and concentrated in vacuum. The residue was purified by silica gel chromatography to afford product 169 (1.50 g, yield: 46.47%).

$^1$H NMR (400 MHz, CDCl$_3$): δ7.62-7.84 (m, 3H), 7.28-7.26 (m, 1H), 6.68-6.67 (m, 1H).

Procedure for Preparation of 182

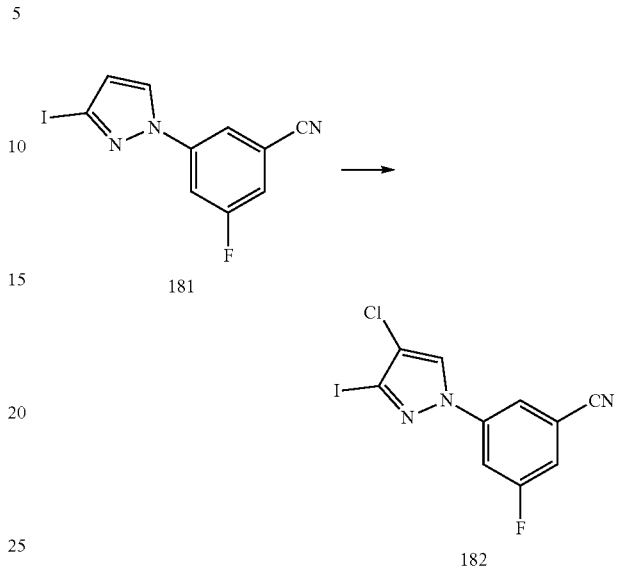

The mixture of 181 (500.00 mg, 1.60 mmol) and NCS (319.89 mg, 2.40 mmol) in a 5 mL single-necked round bottom flask, was stirred at 120° C. for 1 hour. Then cooled down to 29° C. LCMS showed the starting material was consumed completely and the desired compound was detected. The residue was partitioned between ethyl acetate (100 mL) and H$_2$O (50 mL). The organic phase was washed with saturated brine (20 mL), dried with anhydrous Na$_2$SO$_4$, filtered and concentrated in vacuum to afford product 182 (200.00 mg, crude), which was used directly for the next step without purification LCMS: m/z, 347.9 (M+H)$^+$.

Procedure for Preparation of 183

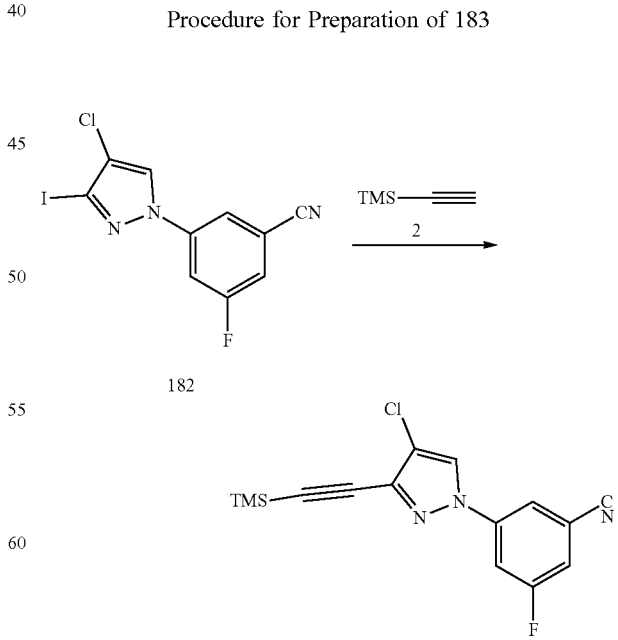

Mixture of 182 (600.00 mg, 1.73 mmol), 2 (254.38 mg, 2.59 mmol), CuI (16.47 mg, 86.50 umol) and Et₃N (524.13 mg, 5.18 mmol) and Pd(PPh₃)₂Cl₂ (60.71 mg, 86.50 umol, 0.05 Eq) were taken up into a microwave tube. The sealed tube was heated at 95° C. for 1 hour under microwave. LCMS showed the starting material was consumed completely and the desired compound was detected. Ethyl acetate (100 mL) and H₂O (20 mL) were added into the mixture, the separated organic layer was washed with brine (30 mL), dried over Na₂SO₄ and evaporated to dryness, which was purified by silica gel chromatography to afford product 183 (300.00 mg, yield: 54.67%).

LCMS: m/z, 318.0 (M+H)⁺.

Procedure for Preparation of 184

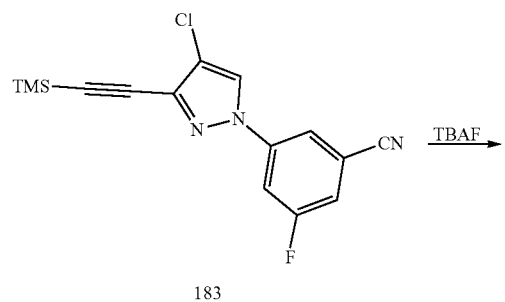

183

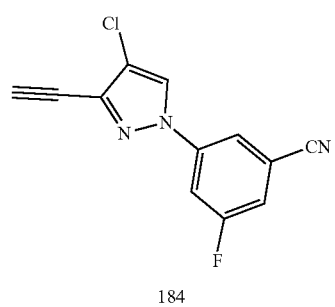

184

To a solution of 183 (300.00 mg, 943.93 umol) in THF (5 mL) was added TBAF (1 M, 1.42 mL) at 0° C. The reaction mixture was stirred at 0° C. for 0.5 hour and then kept at room temperature (28° C.) for another 1 hour. LCMS showed the starting material was consumed completely and the title compound was detected. The reaction mixture was concentrated to dryness, which was partitioned between ethyl acetate (100 mL) and H₂O (50 mL). The separated organic layer was washed with saturated brine (20 mL), dried over Na₂SO₄ and evaporated in vacuo to afford 184 (200.00 mg, crude), which was used directly for the next step without purification.

LCMS: m/z, 245.9 (M+H)⁺.

Procedure for Preparation of Compound 61

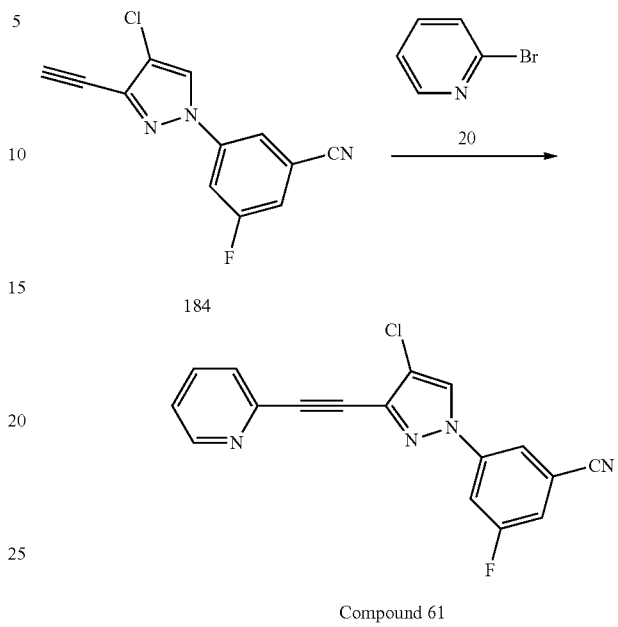

184

Compound 61

A mixture of 184 (200.00 mg, 732.78 umol), 20 (150.51 mg, 952.61 umol), CuI (6.98 mg, 36.64 umol), Et₃N (222.45 mg, 2.20 mmol) and Pd(PPh₃)₂Cl₂ (25.72 mg, 36.64 umol) were taken up into a microwave tube in THF (8 mL). The sealed tube was heated at 95° C. for 1 hour under microwave. LCMS showed the starting material was consumed completely and the title compound was detected. After cooling to 28° C., ethyl acetate (80 mL) and saturated aqueous of Na₂CO₃ (20 mL) were added. The aqueous layer was extracted with ethyl acetate (40 mL×2). The combined organic layers were washed with brine (30 mL), dried over Na₂SO₄, concentrated in vacuum to give the crude product, which was pre-purified by column chromatography followed by prep-HPLC purification to afford product Compound 61 (50.00 mg, yield: 21.14%).

LCMS: m/z, 322.9 (M+H)⁺;

¹H NMR (400 MHz, CDCl₃): δ8.65-8.72 (m, 1H), 7.99 (s, 1H), 7.79-7.82 (m, 1H), 7.70-7.77 (m, 2H), 7.61-7.66 (m, 1H), 7.29-7.36 (m, 2H).

Example Compound 62

Preparation of 5-fluoro-2-(5-methoxy-4-(pyridin-2-ylethynyl)-1H-pyrazol-1-yl)

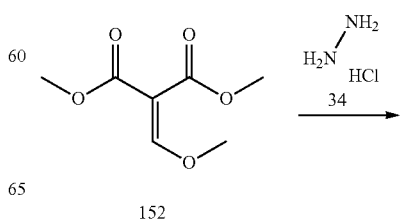

152

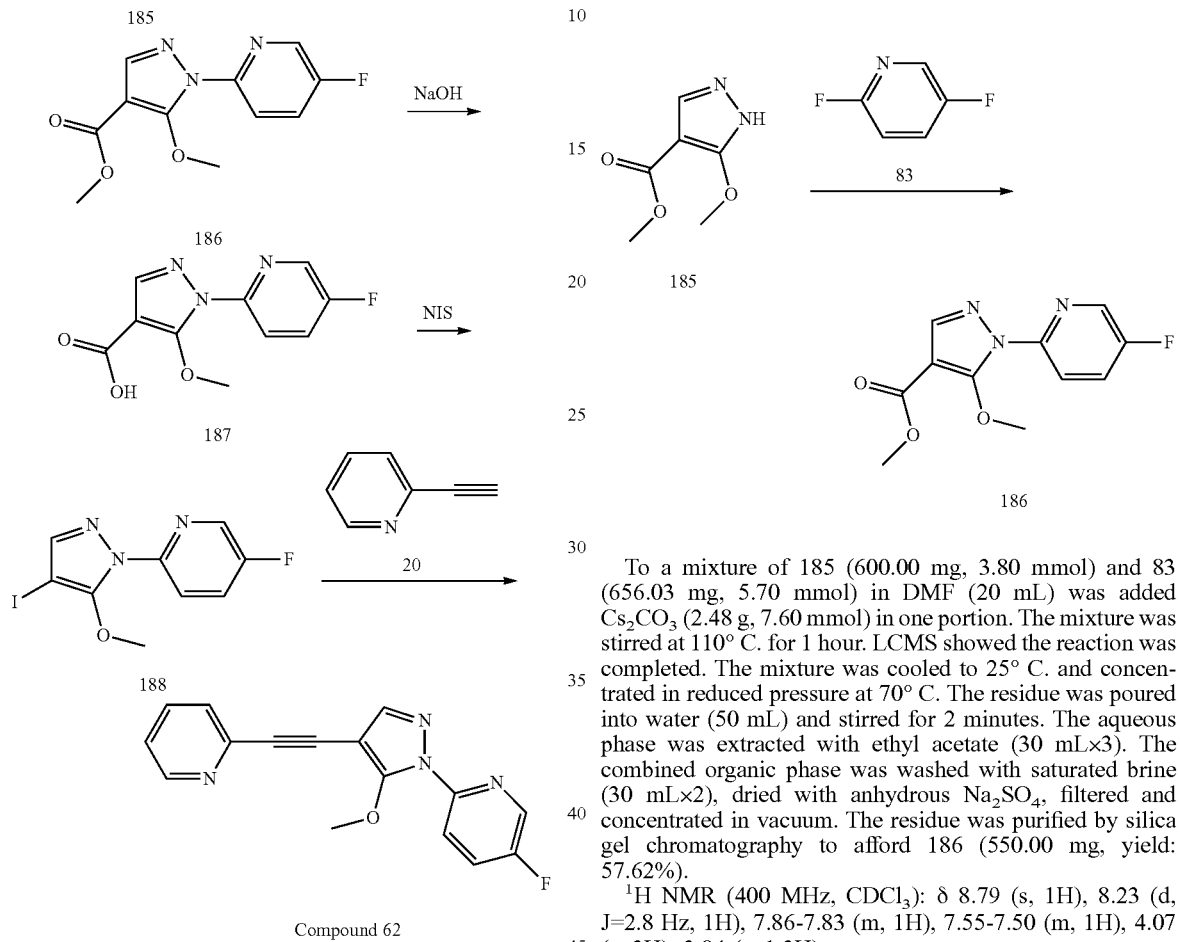

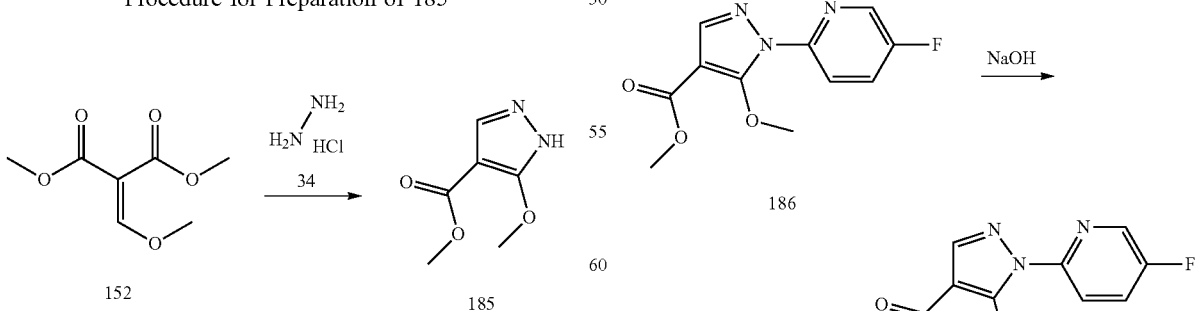

saturated NaHCO₃ solution (100 ml), extracted with DCM (3×50 ml). The combined organic layer was dried over Na₂SO₄, concentrated to give the product 185 (2.0 g, yield: 44%).

LCMS: m/z 157 (M+H)⁺;

¹H NMR (400 MHz, CDCl₃): δ 1.02-9.68 (br, 1H), 7.89 (s, 1H), 4.00 (s, 3H), 3.83 (s, 3H).

Procedure for Preparation of 186

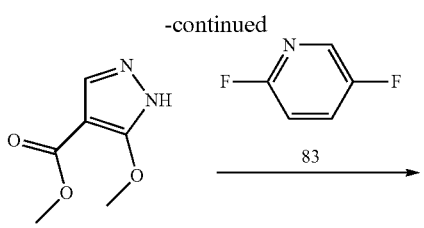

To a mixture of 185 (600.00 mg, 3.80 mmol) and 83 (656.03 mg, 5.70 mmol) in DMF (20 mL) was added Cs₂CO₃ (2.48 g, 7.60 mmol) in one portion. The mixture was stirred at 110° C. for 1 hour. LCMS showed the reaction was completed. The mixture was cooled to 25° C. and concentrated in reduced pressure at 70° C. The residue was poured into water (50 mL) and stirred for 2 minutes. The aqueous phase was extracted with ethyl acetate (30 mL×3). The combined organic phase was washed with saturated brine (30 mL×2), dried with anhydrous Na₂SO₄, filtered and concentrated in vacuum. The residue was purified by silica gel chromatography to afford 186 (550.00 mg, yield: 57.62%).

¹H NMR (400 MHz, CDCl₃): δ 8.79 (s, 1H), 8.23 (d, J=2.8 Hz, 1H), 7.86-7.83 (m, 1H), 7.55-7.50 (m, 1H), 4.07 (s, 3H), 3.84 (s, 1.3H).

Procedure for Preparation of 187

Experimental Section

Procedure for Preparation of 185

To a solution of 152 (5.00 g, 28.71 mmol) in MeOH (50 mL) was added 34 (1.97 g, 28.71 mmol). The mixture was stirred at 70° C. for 18 hours. Then the reaction mixture was concentrated and the obtained residue was treated with To a solution of 186 (300.00 mg, 1.19 mmol) in MeOH (20 mL) was added NaOH (238.00 mg, 5.95 mmol) and H₂O (5 mL). The mixture was stirred at 28° C. for 18 hours. LCMS showed the reaction was completed. The mixture was concentrated in reduced pressure at 50° C. The residue was poured into water (10 mL) and adjusted to pH=5-6 with 1 N HCl solution. The aqueous phase was extracted with ethyl acetate (20 mL×3). The combined organic phase was washed with saturated brine (20 mL×2), dried with anhydrous Na₂SO₄, filtered and concentrated in vacuum to afford 187 (240.00 mg, 85.03% yield).

LCMS: m/z 238 (M+H)⁺.

Procedure for Preparation of 188

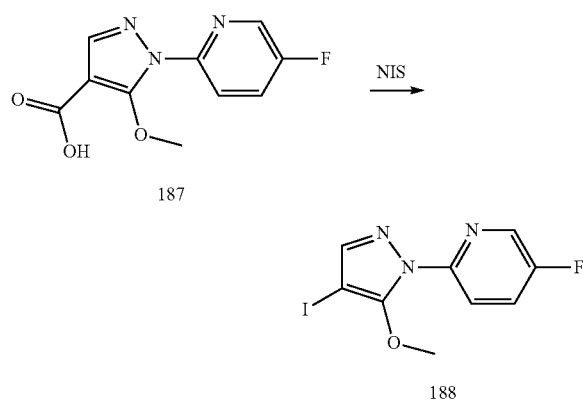

187

188

To a mixture of 187 (300.00 mg, 1.26 mmol) and NIS (569.11 mg, 2.53 mmol) in DMF (10 mL) was added NaHCO₃ (850.05 mg, 10.12 mmol) in one portion at 25° C. under N₂ atmosphere. The mixture was stirred at 80° C. for 24 hours. LCMS showed the reaction was completed. The mixture was cooled to 25° C. and concentrated in reduced pressure at 60° C. The residue was poured into water (30 mL) and stirred for 10 minutes. The aqueous phase was extracted with ethyl acetate (30 mL×3). The combined organic phase was washed with saturated brine (20 mL×2), dried with anhydrous Na₂SO₄, filtered and concentrated in vacuo. The residue was purified by silica prep-TLC to afford product 188 (80.00 mg, 19.90% yield).

LCMS: m/z 320 (M+H)⁺.

Procedure for Preparation of Compound 62

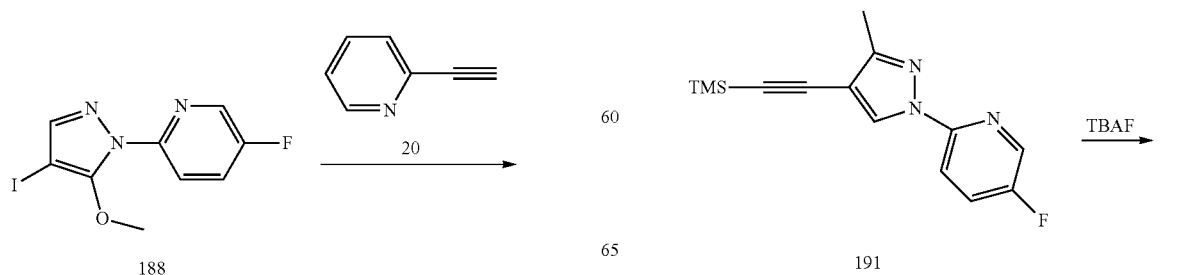

188

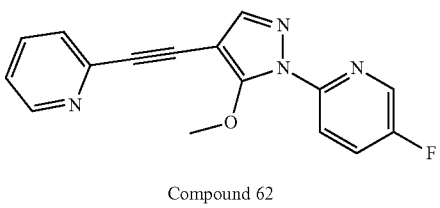

Compound 62

A mixture of 188 (80.00 mg, 250.73 umol), 20 (51.71 mg, 501.46 umol), CuI (4.78 mg, 25.07 umol), TEA (50.74 mg, 501.46 umol) and Pd(PPh₃)₂Cl₂ (17.60 mg, 25.07 umol) were taken up into a microwave tube in THF (5 mL). The sealed tube was heated at 90° C. for 1 hour under microwave. LCMS showed the starting material was consumed. After cooling to 25° C., ethyl acetate (20 mL) and water (20 mL) were added. The aqueous layer was extracted with ethyl acetate (20 mL×2). The combined organic layers were washed with brine (20 mL), dried over Na₂SO₄, concentrated in vacuo to give the crude product, which was purified by prep-HPLC to give product Compound 62 (22.00 mg, 29.82% yield).

LCMS: m/z 295 (M+H)⁺;

¹H NMR: (400 MHz, CDCl₃); δ 8.60 (s, 1H), 8.51 (s, 1H), 8.21 (d, J=2.8 Hz, 1H), 7.83-7.80 (m, 1H), 7.68-7.65 (m, 1H), 7.53-7.48 (m, 2H), 7.25-7.24 (m, 1H), 4.06 (s, 3H);

Example Compound 63

Preparation of 5-fluoro-2-(3-methyl-4-(pyridin-2-ylethynyl)-1H-pyrazol-1-yl)

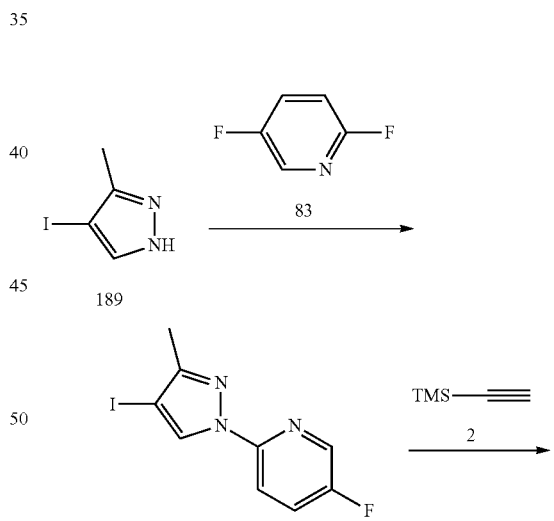

189

190

191

Procedure for Preparation of 191

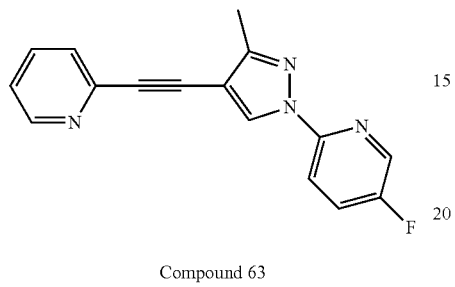

190

191

To a solution of 190 (50.00 mg, 141.88 umol) and 2 (30.81 mg, 313.64 umol) in 4 mL of degassed THF was added a solution of Et₃N (47.61 mg, 470.46 umol), solid CuI (1.35 mg, 7.09 umol) and Pd(PPh₃)₂Cl₂ (4.98 mg, 7.09 umol) at 25° C. The mixture was then degassed for 2 minutes under N₂ atmosphere and stirred at 90° C. for 1 hour under microwave. Most of the solvent was removed. The residue was dissolved in EtOAc (30 mL) and filtrated. The organic layer was washed with brine (2×20 mL), dried over anhydrous Na₂SO₄, filtered and evaporated to give the product 191 (43.00 mg, crude).

LCMS: m/z, 274.0 (M+H)⁺.

Procedure for Preparation of 180

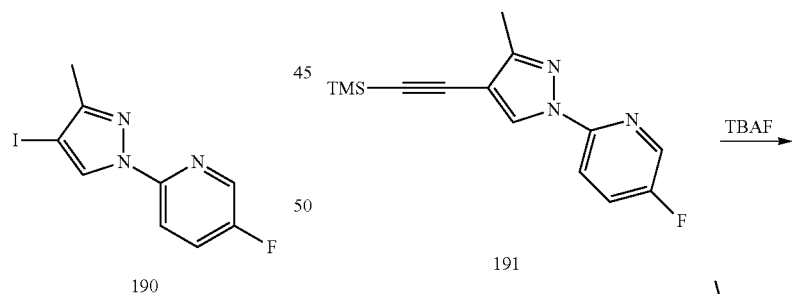

191

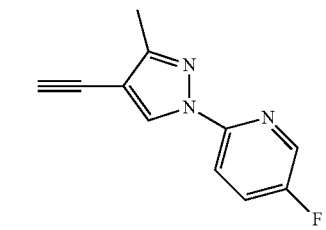

192

To a solution of 191 (43.00 mg, 157.29 umol) in THF (2 mL) was added a solution of TBAF (1M in THF) in one portion at 20° C. It was stirred for 1 hour at the same

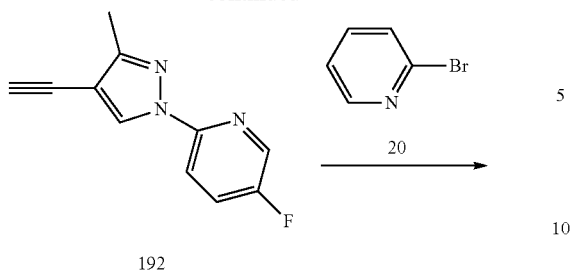

192

Compound 63

Experimental Section

Procedure for Preparation of 190

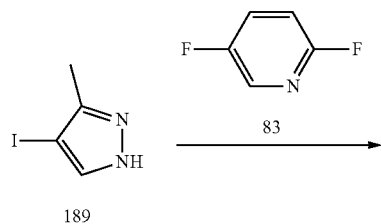

189

190

To a solution of 189 (100.00 mg, 384.62 umol) and 71 (44.26 mg, 384.62 umol) in DMF (3 mL) was added solid Cs₂CO₃ (125.32 mg, 384.6 umol) at 25° C. It was stirred at 80-90° C. for 6 hours. After cooling, water (6 mL) was added into the mixture with stirring at ice bath slowly. Gradually, white solid was formed. It was filtrated and the residue was purified by TLC to afford the product 190 (50.00 mg, yield: 42.89%).

LCMS: m/z, 304.0 (M+H)⁺;

¹H NMR (400 MHz, CDCl₃): δ2.35 (s, 3H), 7.52-7.53 (m, 1H), 7.87-7.90 (m, 2H), 8.21 (d, J=2.8 Hz, 1H), 8.47 (s, 2H).

condition. TLC showed the reaction was complete. Most of the solvent was removed. The residue was dissolved in EtOAc (20 mL). The organic layer was washed with brine (2×10 mL) and dried over anhydrous Na₂SO₄, filtered and evaporated to give the crude product 192 (30.00 mg, crude) which was directly used for next step.

Procedure for Preparation of Compound 63

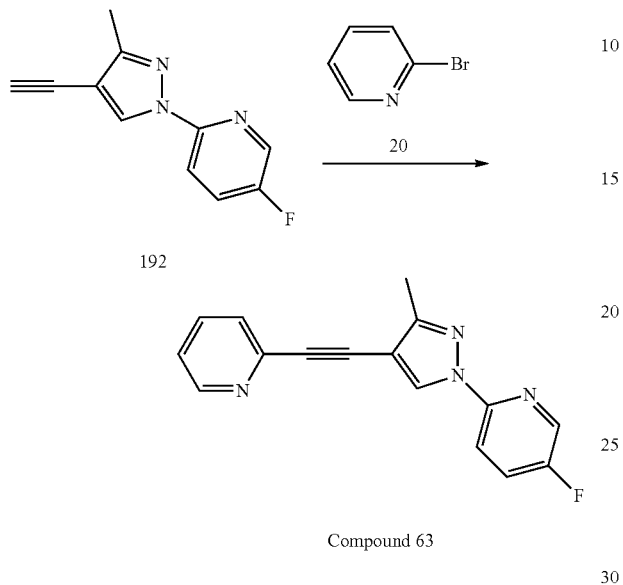

192

Compound 63

To a solution 192 (30.00 mg, 149.11 umol) and 20 (28.27 mg, 178.93 umol) in 4 mL of degassed THF was added solid CuI (1.42 mg, 7.46 umol), Pd(PPh₃)₂Cl₂ (5.23 mg, 7.46 umol) and Et₃N (45.26 mg, 447.32 umol) into it at 25° C. The mixture was then degassed for 2 minutes under N₂ atmosphere and stirred at 90° C. for 1 hour under microwave. LCMS showed the reaction was complete. Most of the solvent was removed. The residue was dissolved in EtOAc (30 mL). The organic layer was washed with brine (2×20 mL) and dried over anhydrous Na₂SO₄, filtered and evaporated to give a residue, which was purified by prep-HPLC to give product Compound 63 (10.00 mg, yield: 23.93%).

LCMS: m/z, 279.0 (M+H)⁺;

¹H NMR (400 MHz, CDCl₃): δ2.48 (S, 3H), 7.21-7.27 (m, 1H), 7.48-7.59 (m, 2H), 7.69 (m, 1H) 7.93 (dd, $J_1$=3.79 Hz, $J_2$=8.93 Hz, 1H), 8.26 (d, J=2.93 Hz, 1H), 8.57-8.67 (m, 2H).

Example Compound 64

Preparation of S-fluoro-2-(3-(2-methoxyethoxy)-4-(pyridin-2-ylethynyl)-1H-pyrazol-1-yl)pyridine

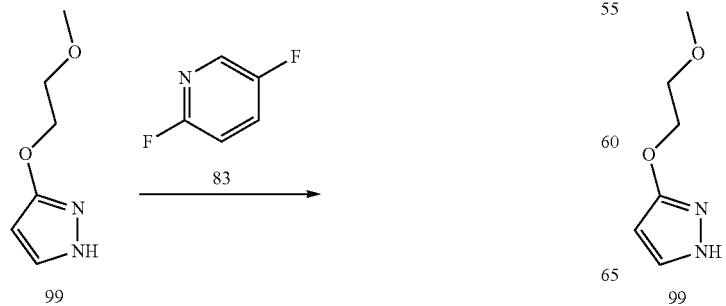

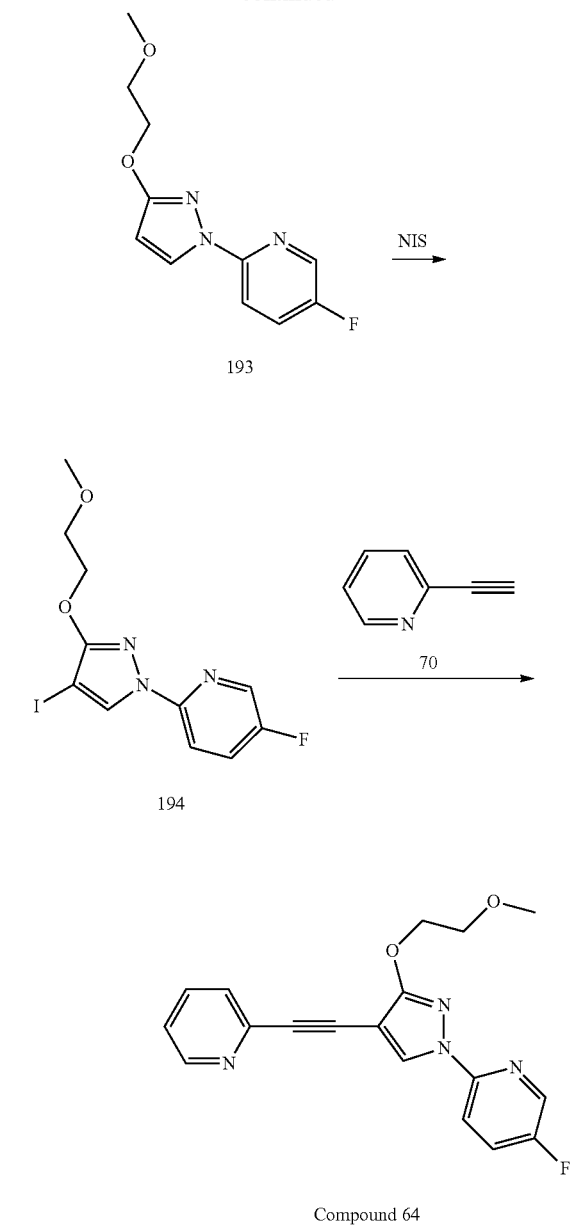

193

194

Compound 64

Experimental Section

Procedure for Preparation of 193

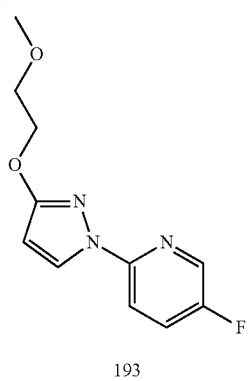

193

To a mixture of 99 (500.00 mg, 3.52 mmol) and 83 (486.10 mg, 4.22 mmol) in DMF (10 mL) was added Cs₂CO₃ (3.44 g, 10.56 mmol) in one portion at room temperature under N₂ atmosphere. The mixture was heated to 70° C. and stirred for 2 hours. LCMS showed the starting material was consumed completely and the title compound was detected. The mixture was cooled to room temperature and concentrated in reduced pressure at 40° C. The residue was poured into water (15 mL) and stirred for 5 minutes. The aqueous phase was extracted with ethyl acetate (30 mL×2). The combined organic phase was washed with saturated brine (20 mL), dried with anhydrous Na₂SO₄, filtered and concentrated in vacuum. The residue was purified by silica gel chromatography to afford product 193 (400.00 mg, yield: 47.90%).

$^1$H NMR (400 MHz, CDCl₃): δ8.16-8.24 (m, 1H), 8.02-8.14 (m, 1H), 7.64-7.76 (m, 1H), 7.34-7.48 (m, 1H), 5.88 (d, J=2.65 Hz, 1H), 4.30-4.43 (m, 2H), 3.65-3.76 (m, 2H), 3.39 (s, 3H).

Procedure for Preparation of 194

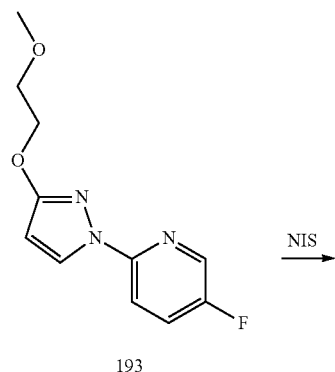

193

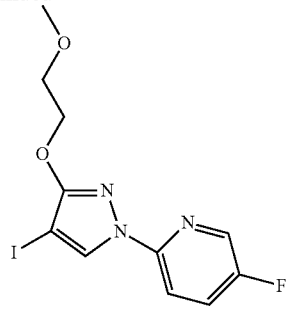

194

To a solution of 193 (400.00 mg, 1.69 mmol) in CHCl₃ (20 mL) was added NIS (493.15 mg, 2.19 mmol) in one portion at room temperature. The mixture was heated to 70° C. and stirred for 5 hours. TLC showed the starting material was consumed completely. The mixture was cooled to room temperature and concentrated in reduced pressure to afford dryness, which was partitioned between ethyl acetate (100 mL) and H₂O (50 mL). The separated organic layer was washed with saturated brine (20 mL), dried over Na₂SO₄ and evaporated in vacuum to afford the crude product, which was purified by silica gel chromatography to afford product 194 (400.00 mg, yield: 65.18%).

$^1$H NMR (400 MHz, CDCl₃): δ8.36 (s, 1H), 8.14-8.21 (m, 1H), 7.69-7.80 (m, 1H), 7.44-7.55 (m, 1H), 4.42-4.53 (m, 2H), 3.75-3.88 (m, 2H), 3.48 (s, 3H).

Procedure for Preparation of Compound 64

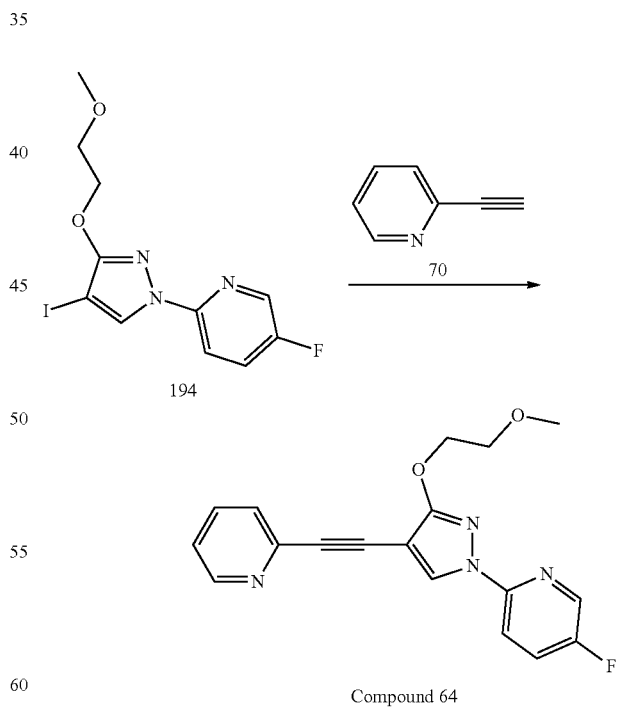

Compound 64

A mixture of 194 (200.00 mg, 550.77 umol), 70 (85.19 mg, 826.16 umol), Pd(PPh₃)₂Cl₂ (19.33 mg, 27.54 umol), CuI (5.24 mg, 27.54 umol) and Et₃N (167.20 mg, 1.65 mmol) in THF (8 mL) was de-gassed and were taken up into a microwave tube. The sealed tube was heated at 95° C. for 1 hour under microwave. LCMS showed the starting material was consumed completely and the desired compound was detected. The mixture was partitioned between ethyl acetate (100 mL) and H₂O (20 mL), the separated organic layer was washed with brine (30 mL), dried over Na₂SO₄ and evaporated to dryness, which was purified by prep-HPLC to afford product Compound 64 (20.00 mg, yield: 10.61%).

LCMS: m/z, 339.1 (M+H)⁺;

¹H NMR (400 MHz, CDCl₃): δ8.53-0.67 (m, 1H), 8.43-0.53 (m, 1H), 8.15-0.24 (m, 1H), 7.74-0.83 (m, 1H), 7.59-0.70 (m, 1H), 7.43-7.54 (m, 2H), 7.16-0.23 (m, 1H), 4.47-0.54 (m, 2H), 3.82 (d, J=4.89 Hz, 2H), 3.46 (s, 3H).

Example Compound 65

Preparation of 2-((1-(4-(trifluoromethoxy)phenyl)-1H-pyrazol-4-yl)ethynyl)pyrazine

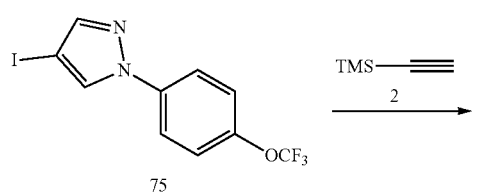

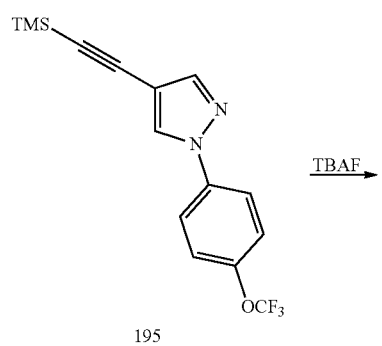

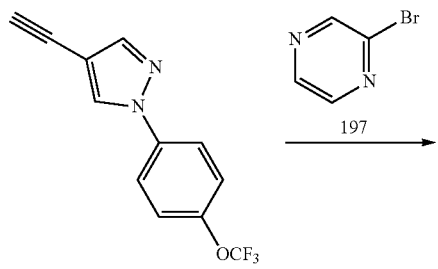

Experimental Section

Procedure for Preparation of 195

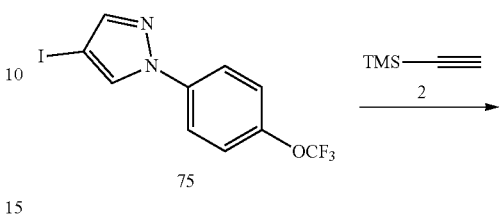

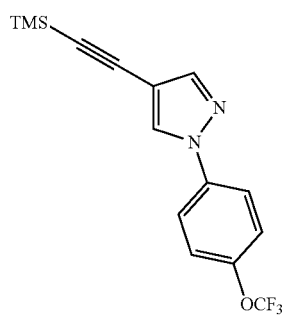

To a mixture of 75 (600.00 mg, 1.75 mmol) and 2 (344.46 mg, 3.51 mmol) in THF (10 mL), was added solid CuI (16.70 mg, 87.68 umol), Et₃N (532.31 mg, 5.26 mmol) and Pd(PPh₃)₂Cl₂ (61.54 mg, 87.68 umol) in one portion at room temperature under N₂ atmosphere. The mixture was stirred at 90° C. for 1 hour in microwave. LCMS showed the reaction was completed. The mixture was cooled to room temperature and concentrated in reduced pressure. The residue was dissolved in ethyl acetate (40 mL), and washed with saturated brine (20 mL×2), dried with anhydrous Na₂SO₄, filtered and concentrated in vacuo to afford product 195 (500.00 mg, crude).

LCMS: m/z, 325.0 (M+H)⁺.

Procedure for Preparation of 196

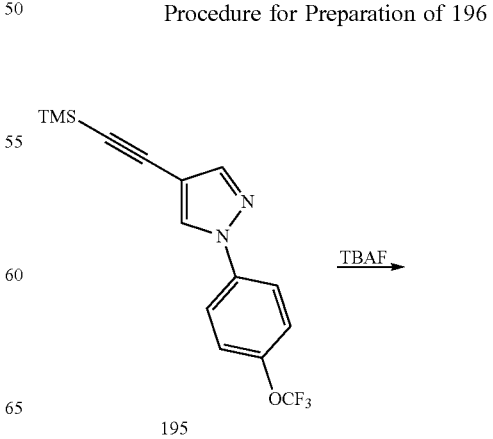

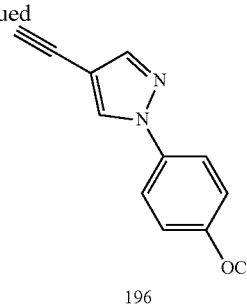

196

To a solution of 195 (500.00 mg, 1.54 mmol) in THF (10 mL), was added TBAF (THF) (1M, 2.31 mL) dropwise at room temperature under N₂ atmosphere. The mixture was stirred at room temperature for 1 hour. TLC showed the reaction was completed. The mixture was concentrated in reduced pressure. The residue was dissolved in ethyl acetate (40 mL). It was washed with saturated brine (20 mL×2), dried with anhydrous Na₂SO₄, filtered and concentrated in vacuum. The residue was purified by silica gel chromatography to afford product 196 (350.00 mg, yield: 90.12%).

¹H NMR (400 MHz, CDCl₃): δ3.12 (s, 1H), 7.33 (d, J=8.8 Hz, 2H), 7.70 (d, J=8.8 Hz, 2H), 7.83 (s, 1H) 8.06 (s, 1H).

Procedure for Preparation of Compound 65

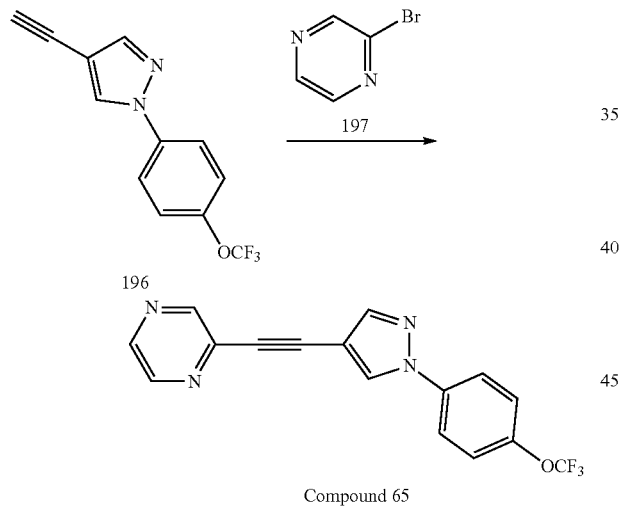

Compound 65

A mixture of 196 (70.00 mg, 277.57 umol), 197 (44.13 mg, 277.57 umol), CuI (2.64 mg, 13.88 umol), Et₃N (84.26 mg, 832.71 umol) and Pd(PPh₃)₂Cl₂ (9.74 mg, 13.88 umol) were taken up into a microwave tube in THF (4 mL). The sealed tube was heated at 90° C. for 1 hour under microwave. TLC showed the starting material was consumed. After cooling to room temperature, H₂O (10 mL) were added. The aqueous layer was extracted with ethyl acetate (15 mL×3). The combined organic layers were washed with brine (15 mL), dried over Na₂SO₄, concentrated in vacuo to give the crude product which was purified by prep-HPLC to afford product Compound 65 (18.00 mg, yield: 19.48%).

LCMS: m/z, 330.9 (M+H)⁺;

¹H NMR (400 MHz, CDCl₃): δ7.36 (d, J=8.4 Hz, 2H), 7.74 (d, J=9.2 Hz, 2H), 7.96 (s, 1H), 8.20 (s, 1H), 8.50 (d, J=2.8 Hz, 1H), 8.59 (s, 1H), 8.75 (s, 1H).

Example Compound 66

Preparation of 3-fluoro-5-(4-(pyridin-2-ylethynl)-1H-pyrazol-1-yl) benzonitrile

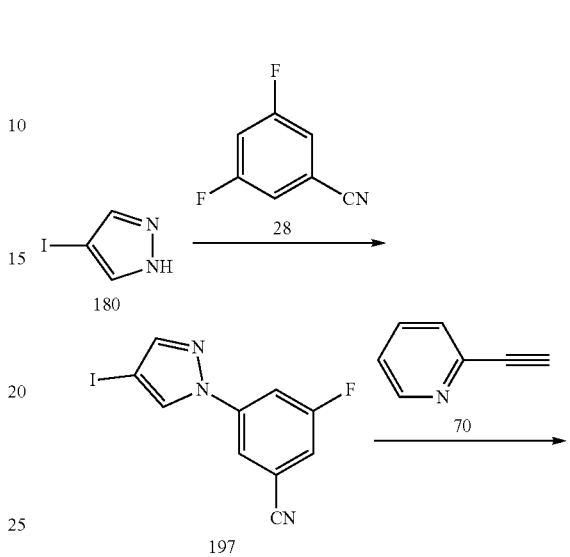

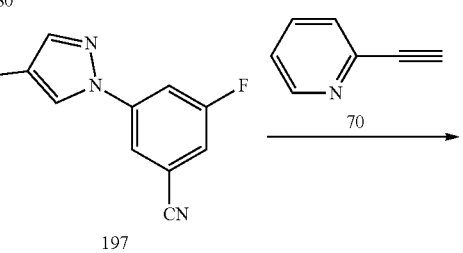

Compound 66

Experimental Section

Procedure for Preparation of 197

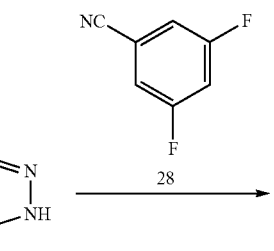

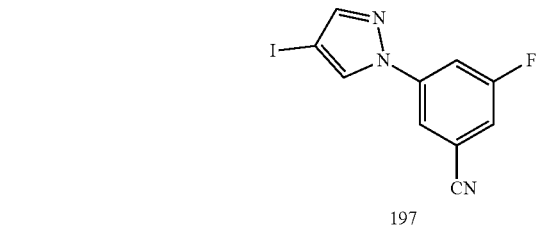

197

To a mixture of 180 (193.97 mg, 1.00 mmol) and 28 (139.10 mg, 1.00 mmol) in DMF (5 mL), was added Cs₂CO₃ (325.82 mg, 1.00 mmol) in one portion at room temperature. The mixture was then heated to 80° C. for 1.5 hours under N₂ atmosphere. TLC showed the reaction was completed. The mixture was cooled to room temperature and was then poured into water (15 mL) slowly. A white solid precipitated out from the mixture, filtered off. The solid was dried to afford product 197 (300.00 mg, yield: 67.08%).

LCMS: m/z, 313.9 (M+H)⁺.

Procedure for Preparation of Compound 66

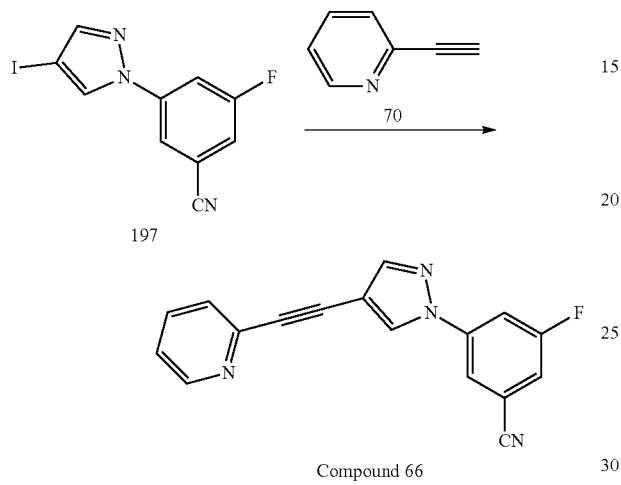

Compound 66

Mixture of 197 (100.00 mg, 319.42 umol), 70 (32.94 mg, 319.42 umol), CuI (3.04 mg, 15.97 umol), Et₃N (96.97 mg, 958.26 umol) and Pd(PPh₃)₂Cl₂ (11.21 mg, 15.97 umol) were taken up into a microwave tube in THF (3 mL). The sealed tube was heated at 90° C. for 1 hour under microwave. LCMS showed only the desired product. After cooling to room temperature, H₂O (10 mL) were added. The aqueous layer was extracted with ethyl acetate (15 mL×3). The combined organic layers were washed with brine (15 mL), dried over Na₂SO₄, concentrated in vacuo to give the crude product which was purified by prep-HPLC to afford product Compound 66 (34.00 mg, yield: 35.700%).

LCMS: m/z, 289.0 (M+H)⁺;

¹H NMR (400 MHz, CDCl₃): δ7.30-7.49 (m, 2H), 7.51-7.68 (m, 1H), 7.70-7.74 (m, 1H), 7.81 (s, 1H), 7.91 (s, 1H), 8.16 (s, 1H), 8.61 (d, J=4.4 Hz, 1H).

Example Compound 67

Preparation of 5-fluoro-2-(3-(pyridin-2-ylethynyl)-1H-pyrazol-1-yl)pyridine

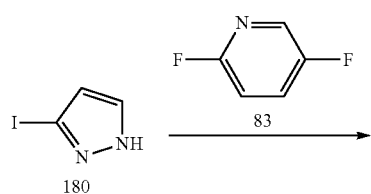

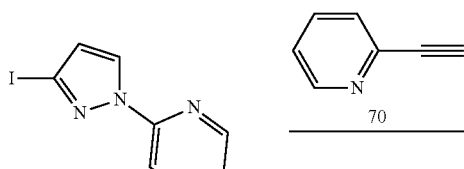

198

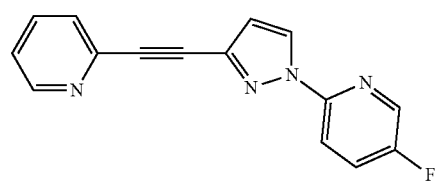

Compound 67

Experimental Section

Procedure for Preparation of 198

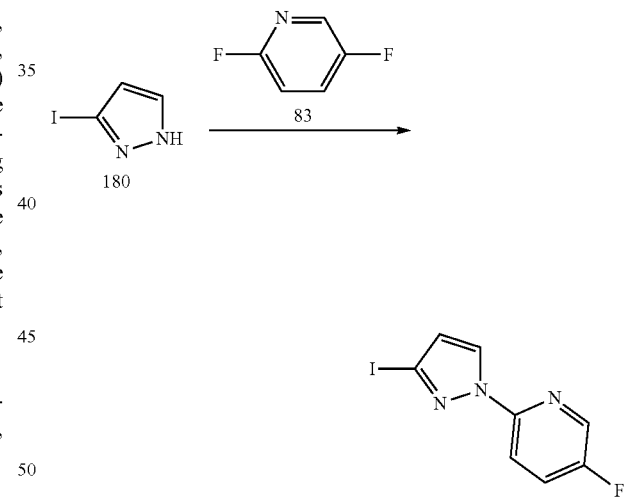

198

To a solution of 180 (100.00 mg, 515.54 umol) and 83 (71.19 mg, 618.65 umol) in DMF (3 mL) was added solid Cs₂CO₃ (251.96 mg, 773.31 umol) in one charge at room temperature. It was stirred at 80-90° C. for 6 hours. After cooling, water (10 mL) was added into the mixture with stirring at ice bath slowly. Gradually, solid was formed. It was filtrated. The residue was the product 198 (70.00 mg, crude) which was used for next step directly.

LCMS: m/z, 290.0 (M+H)⁺;

¹HNMR (400 MHz, CDCl₃): δ6.62 (d, J=2.8 Hz, 1H), 7.53-7.58 (m, 1H), 7.97-8.00 (m, 1H), 8.24 (d, J=2.4 Hz, 1H), 8.31 (d, J=2.4 Hz, 1H).

Procedure for Preparation of Compound 67

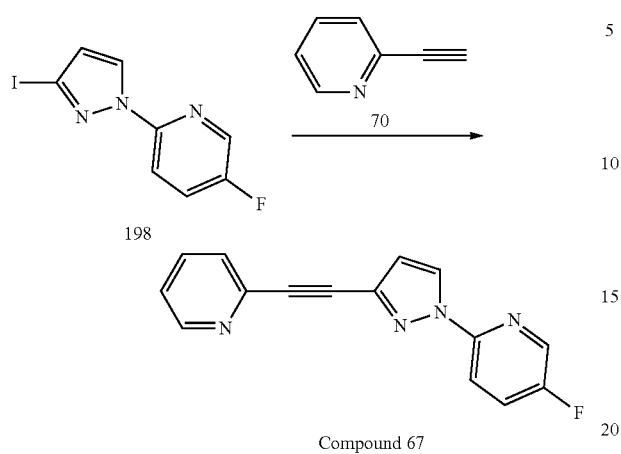

Compound 67

Mixture of 198 (60.00 mg, 207.58 umol), 70 (32.1 mg, 311.36 umol), CuI (3.95 mg, 20.76 umol), TEA (63.01 mg, 622.73 umol), and Pd(PPh$_3$)$_2$Cl$_2$ (7.28 mg, 10.38 umol) were taken up into a microwave tube in THF (3 mL). The sealed tube was heated at 90° C. for 1 hour under microwave. LCMS showed the starting material was consumed. After cooling to room temperature, ethyl acetate (5 mL) and H$_2$O (3 mL) were added. The aqueous layer was extracted with ethyl acetate (5 mL×2). The combined organic layers were washed with brine (5 mL), dried over Na$_2$SO$_4$, concentrated in vacuo to give the crude product, which was purified by prep-HPLC to afford product Compound 67 (16.00 mg, yield: 28.91%).

LCMS: m/z, 265.0 (M+H)$^+$;

$^1$HNMR (400 MHz, CDCl$_3$): δ6.71 (d, J=2.4 Hz, 1H), 7.25-7.27 (m, 1H), 7.56-7.60 (m, 2H), 7.67-7.72 (m, 1H), 8.03 (dd, J=4.0, 8.8 Hz, 1H), 8.26 (d, J=2.8 Hz, 1H), 8.4 (d, J=2.8 Hz, 1H), 8.63 (d, J=4.4 Hz, 1H).

Example Compound 68

Preparation of 2-(3-(difluoromethoxy)-4-(pyridin-2-ylethynyl)-1H-pyrazol-1-yl)-5-fluoropyridine

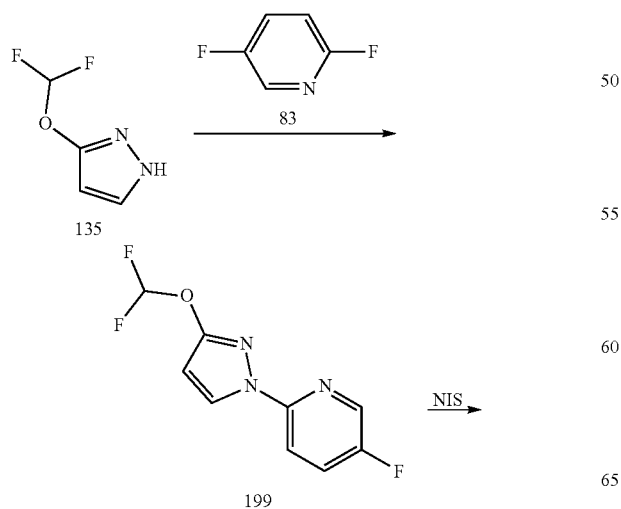

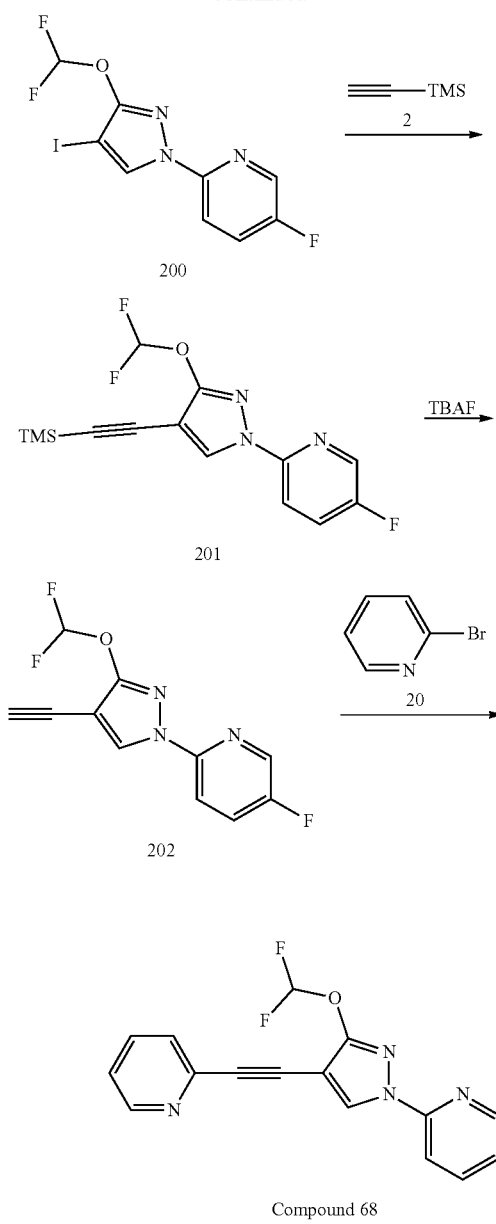

Compound 68

Experimental Section

Procedure for Preparation of 199

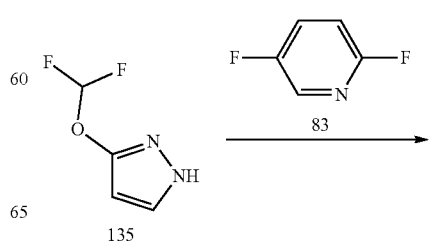

199
-continued

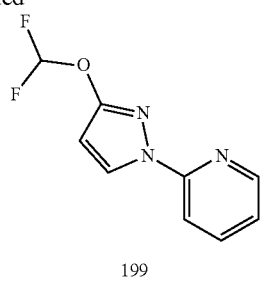

199

To a mixture of compound 135 (370.00 mg, 2.76 mmol) and 199 (635.24 mg, 5.52 mmol) in DMF (10 mL), was added $Cs_2CO_3$ (2.70 g, 8.28 mmol) in one portion at room temperature. The mixture was heated at 70° C. for 4 hours. LCMS showed the reaction was completed. The mixture was cooled to room temperature and filtered. The filtrate concentrated in reduced pressure. The residue was purified by silica gel chromatography to afford product 199 (200.00 mg, yield: 31.62%).

$^1$H NMR (400 MHz, $CDCl_3$): δ 8.36 (s, 1H), 8.21 (s, 1H), 7.83-7.80 (m, 1H), 7.54-7.51 (m, 1H), 7.15-6.78 (m, 1H), 6.09 (s, 1H).

Procedure for Preparation of 200

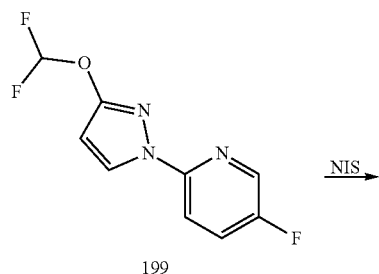

To a mixture of compound 199 (200.00 mg, 872.75 umol) in $CHCl_3$ (10 mL), was added NIS (294.53 mg, 1.31 mmol) in one portion at room temperature. Then the mixture was heated at 60° C. for 5 hours. LCMS showed the reaction was completed. The mixture was cooled to room temperature and concentrated in reduced pressure. The residue was poured into water (10 mL). The aqueous phase was extracted with DCM (20 mL×2). The combined organic phase was dried with anhydrous $Na_2SO_4$, filtered and concentrated in vacuum. The residue was purified by silica gel chromatography to afford product 200 (260.00 mg, yield: 83.91%).

LCMS: m/z, 355.8 (M+H)$^+$.

200
Procedure for Preparation of 201

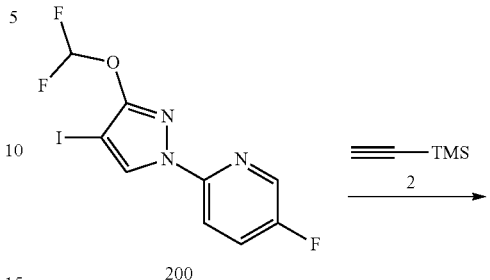

Mixture of 200 (260.00 mg, 732.29 umol), 2 (215.78 mg, 2.20 mmol), CuI (13.95 mg, 73.23 umol), TEA (222.30 mg, 2.20 mmol) and $Pd(PPh_3)_2Cl_2$ (25.70 mg, 36.61 umol) were taken up into a microwave tube in THF (5 mL). The sealed tube was heated at 90° C. for 1 hour under microwave. LCMS showed the starting material was consumed and only the desired product. After cooling to room temperature, the mixture was concentrated in reduced pressure. The residue was purified by silica gel chromatography to afford product 201 (200.00 mg, yield: 83.94%).

LCMS: m/z, 325.9 (M+H)$^+$.

Procedure for Preparation of 202

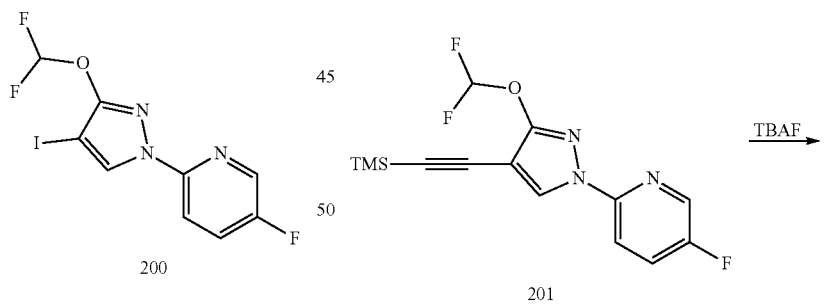

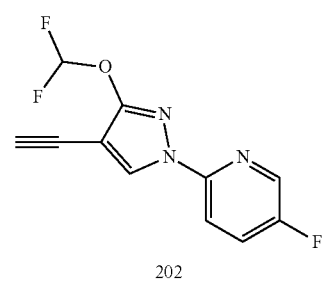

To a mixture of 201 (200.00 mg, 614.70 umol) in THF (15 mL), was added TBAF (in THF) (1 M, 922.05 uL) dropwise at room temperature. The mixture was stirred at room temperature for 3 hours. LCMS showed the reaction was completed. The mixture was poured into water (10 mL). The aqueous phase was extracted with ethyl acetate (20 mL×2). The combined organic phase was washed with saturated brine (10 mL), dried with anhydrous $Na_2SO_4$, filtered and concentrated in vacuum to afford product 202 (150.00 mg, crude) which was used directly for next step.

LCMS: m/z, 254.0 $(M+H)^+$.

Procedure for Preparation of Compound 68

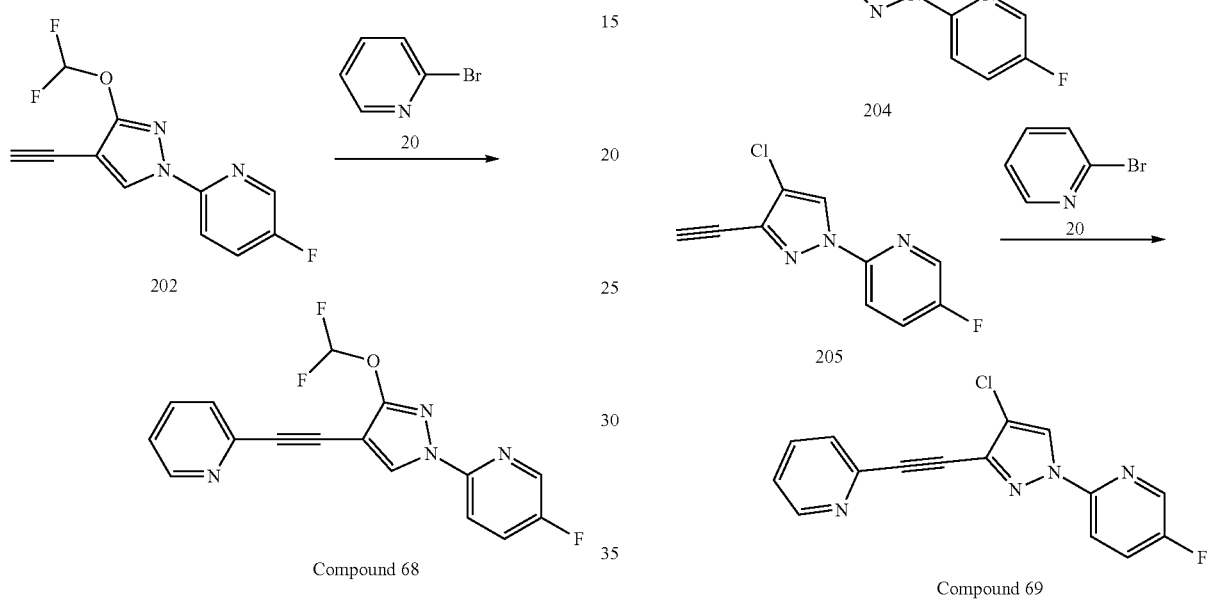

Compound 68

Mixture of 202 (200.00 mg, 789.95 umol), 20 (249.62 mg, 1.58 mmol), CuI (15.04 mg, 79.00 umol), TEA (239.81 mg, 2.37 mmol) and $Pd(PPh_3)_2Cl_2$ (27.72 mg, 39.50 umol) were taken up into a microwave tube in THF (4 mL). The sealed tube was heated at 90° C. for 1 hour under microwave. TLC showed the starting material was consumed. After cooling to room temperature, the mixture was concentrated in reduced pressure. The residue was purified by prep-HPLC to afford product Compound 68 (15.00 mg, yield: 5.73%).

LCMS: m/z, 331.0 $(M+H)^+$;
$^1$H NMR (400 MHz, $CDCl_3$): δ 8.62-8.59 (m, 2H), 8.25 (s, 1H), 7.84-7.81 (m, 1H), 7.70-7.69 (m, 1H), 7.54-7.53 (m, 2H), 7.31-7.95 (m, 2H).

Example Compound 69

Preparation of 2-(4-chloro-3-(pyridin-2-ylethynyl)-1H-pyrazol-1-yl)-5-fluoropyridine

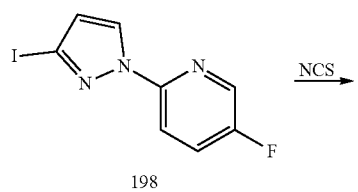

198

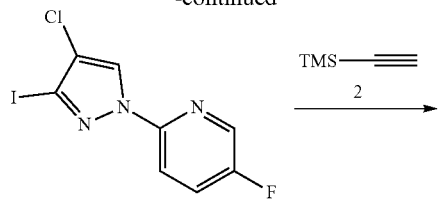

203

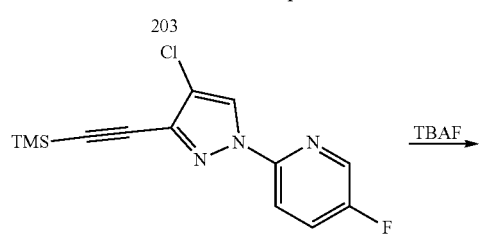

204

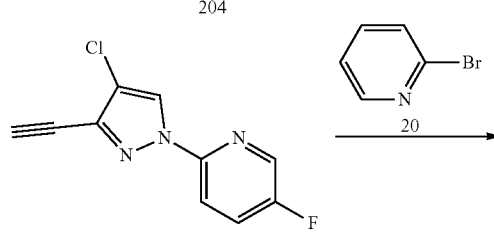

205

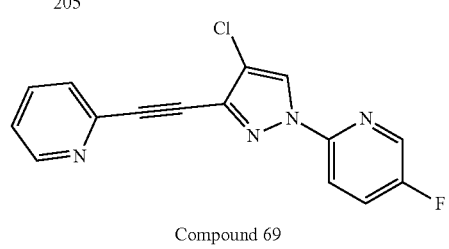

Compound 69

Experimental Section

Procedure for Preparation of 203

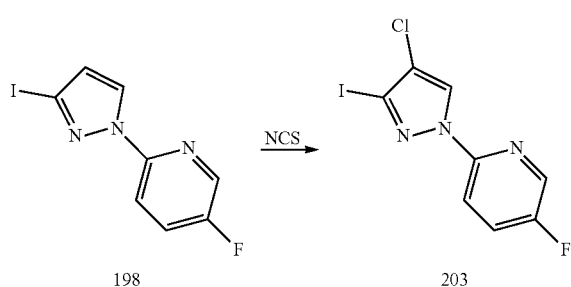 [SMILES: Fc1ccc(-n2ccc(I)n2)nc1 ; "NCS" ; Fc1ccc(-n2cc(Cl)c(I)n2)nc1]

The mixture of compound 198 (200.00 mg, 691.92 umol) and NCS (138.59 mg, 1.04 mmol) in a 5 mL single-necked round bottom flask. The mixture was stirred at 120° C. for 1 hour. Then cooled down to room temperature. LCMS showed the starting material was consumed completely and the desired compound was detected. The residue was partitioned between ethyl acetate (100 mL) and $H_2O$ (50 mL). The organic phase was washed with saturated brine (20 mL), dried with anhydrous $Na_2SO_4$, filtered and concentrated in vacuum to afford product 203 (220.00 mg, crude), which was used directly for the next step without purification.

LCMS: m/z, 323.9 (M+H)⁺.

Procedure for Preparation of 204

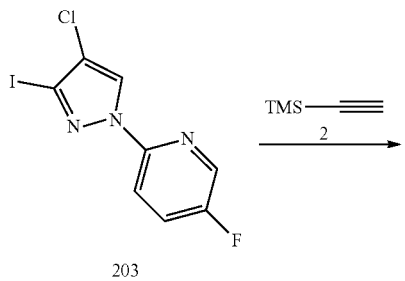
203

TMS—≡
2

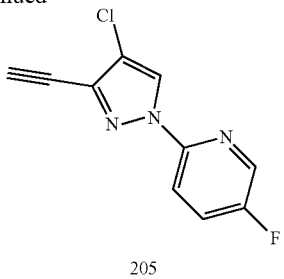
204

Mixture of compound 203 (220.00 mg, 536.59 umol), 2 (79.06 mg, 804.89 umol), Et₃N (162.89 mg, 1.61 mmol) and CuI (5.11 mg, 26.83 umol) and Pd(PPh₃)₂Cl₂ (18.83 mg, 26.83 umol) in THF (8 mL) was de-gassed and were taken up into a microwave tube. The sealed tube was heated at 95° C. for 1 hour under microwave. LCMS showed the starting material was consumed completely and the desired compound was detected. The mixture was partitioned between ethyl acetate (100 mL) and H₂O (20 mL), the separated organic layer was washed with brine (30 mL), dried over Na₂SO₄ and evaporated to dryness, which was purified by silica gel chromatography to afford product 204 (120.00 mg, yield: 76.12%).

LCMS: m/z, 294.0 (M+H)⁺.

Procedure for Preparation of 205

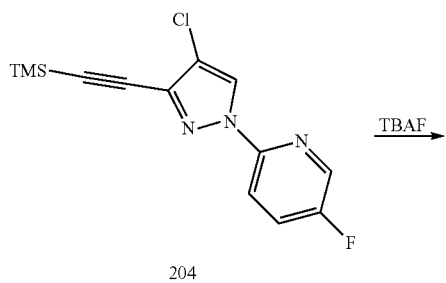
204

TBAF

205

To a solution of compound 204 (170.00 mg, 578.62 umol) in THF (5 mL) was added TBAF (1M, 867.94 uL) at 0° C. The reaction mixture was stirred at 0° C. for 0.5 hour and then kept at room temperature for 1 hour. LCMS showed the starting material was consumed completely and the title compound was detected. The reaction mixture was concentrated to dryness, which was partitioned between ethyl acetate (100 mL) and H₂O (50 mL). The separated organic layer was washed saturated brine (20 mL), dried over Na₂SO₄ and evaporated in vacuo to afford product 205 (120.00 mg, crude), which was used directly for the next step without purification.

LCMS: n/z, 222.0 (M+H)⁺.

Procedure for Preparation of Compound 69

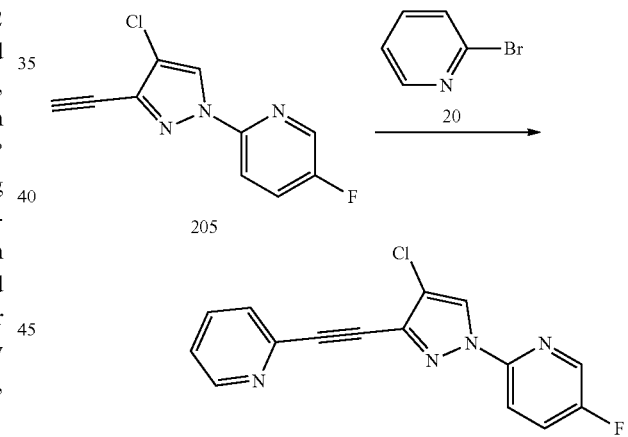

Compound 69

Mixture of compound 205 (150.00 mg, 676.83 umol), 20 (160.41 mg, 1.02 mmol), CuI (6.45 mg, 33.84 umol), Et₃N (205.47 mg, 2.03 mmol) and Pd(PPh₃)₂Cl₂ (23.75 mg, 33.84 umol) were taken up into a microwave tube in THF (8 mL). The sealed tube was heated at 95° C. for 1 hour under microwave. LCMS showed the starting material was consumed completely and the title compound was detected. After cooling to room temperature, ethyl acetate (80 mL) and saturated aqueous of Na₂CO₃ (20 mL) were added. The aqueous layer was extracted with ethyl acetate (40 mL×2). The combined organic layers were washed with brine (30 mL), dried over Na₂SO₄, concentrated in vacuum to give the crude product, which was purified prep-HPLC to afford product Compound 69 (15.00 mg, yield: 7.32%).

LCMS: m/z, 299.0 (M+H)⁺;

¹H NMR (400 MHz, CDCl₃): δ8.66 (d, J=4.85 Hz, 1H), 8.51 (s, 1H), 8.25 (d, J=2.65 Hz, 1H), 8.00 (dd, J=8.93, 3.86 Hz, 1H), 7.68-7.75 (m, 1H), 7.54-7.65 (m, 2H), 7.26-7.34 (m, 1H).

Example Compound 70

Preparation of 3-fluoro-5-(3-(pyridin-2-ylethnyl)-1H-pyrazol-1-yl)pyridine

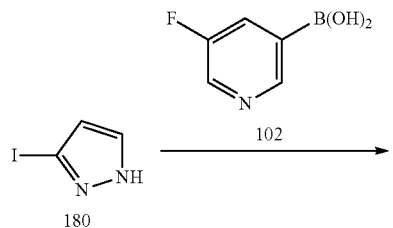

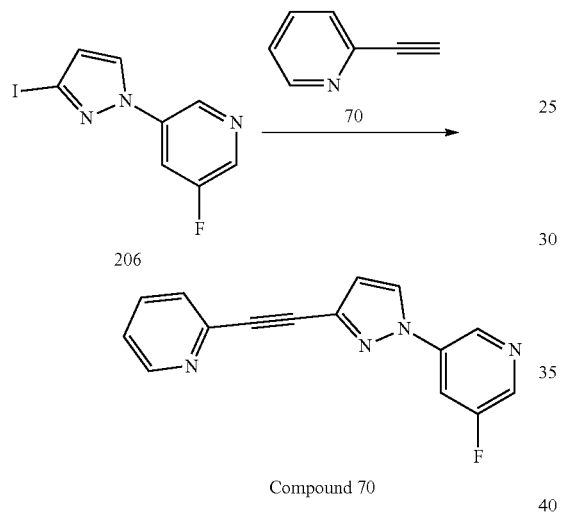

Compound 70

Experimental Section

Procedure for Preparation of 206

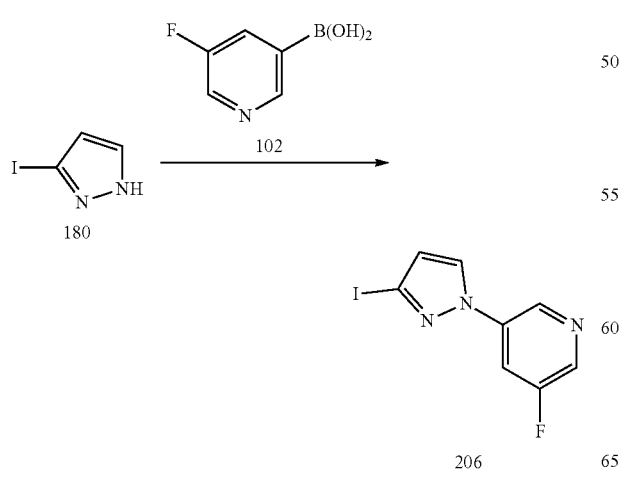

To a mixture of compound 180 (300.00 mg, 1.55 mmol) and 102 (327.62 mg, 2.32 mmol) in DCM (20 mL), was added pyridine (367.02 mg, 4.64 mmol), Cu(OAc)₂ (561.83 mg, 3.09 mmol) and 1-oxidopyridin-1-ium (442.21 mg, 4.65 mmol, 3.00 Eq) in one portion at room temperature. The mixture was stirred at room temperature for 48 hours under O2 protected. LCMS showed the reaction was completed. The mixture was filtrated and the filtrate was concentrated in reduced pressure. The residue was dissolved in ethyl acetate (40 mL). The organic phase was washed with water (30 mL×2), saturated brine (30 mL×1), dried over anhydrous Na₂SO₄, filtered and concentrated in vacuum. The residue was purified by silica gel chromatography to afford product 206 (380.00 mg, yield: 84.82%).

LCMS: m/z, 289.9 (M+H)⁺.

Procedure for Preparation of Compound 70

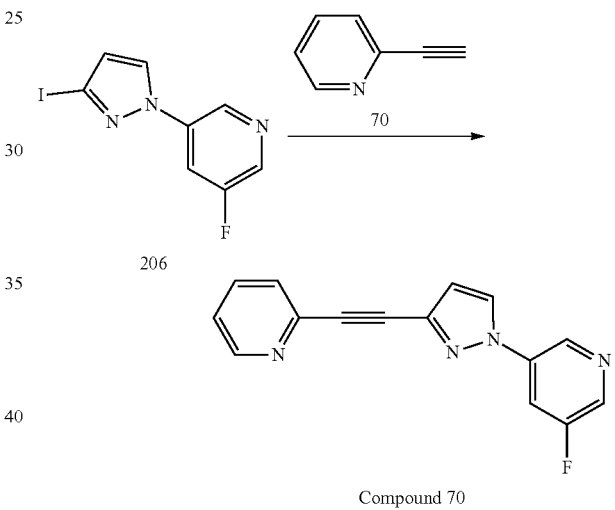

Compound 70

A mixture of 206 (190.00 mg, 657.33 umol), 70 (101.68 mg, 985.99 umol), CuI (6.26 mg, 32.87 umol), Et₃N (199.54 mg, 1.97 mmol) and Pd(PPh₃)₂Cl₂ (23.07 mg, 32.87 umol) were taken up into a microwave tube in THF (3 mL). The sealed tube was heated at 90° C. for 1 hour under microwave. TLC showed the starting material was consumed completely. After cooling to room temperature, H₂O (10 mL) were added. The aqueous layer was extracted with ethyl acetate (15 mL×3). The combined organic layers were washed with brine (15 mL), dried over Na₂SO₄, concentrated in vacuo to give the crude product which was purified by prep-HPLC to afford product Compound 70 (20.00 mg, yield: 11.40%).

LCMS: m/z, 265.1 (M+H)⁺;

¹H NMR (400 MHz, CDCl₃): δ6.79 (d, J=2.4 Hz, 1H), 7.25-7.29 (m, 1H), 7.59-7.61 (m, 1H), 7.69-7.72 (m, 1H), 7.91-7.93 (m, 1H), 7.98-7.99 (m, 1H), 8.44 (d, J=2.4 Hz, 1H), 8.65 (m, 1H), 8.82 (s, 1H).

Example Compound 71

Preparation of 2-((1-(pyridin-2-yl)-1H-pyrazol-3-yl)ethynyl)pyridine

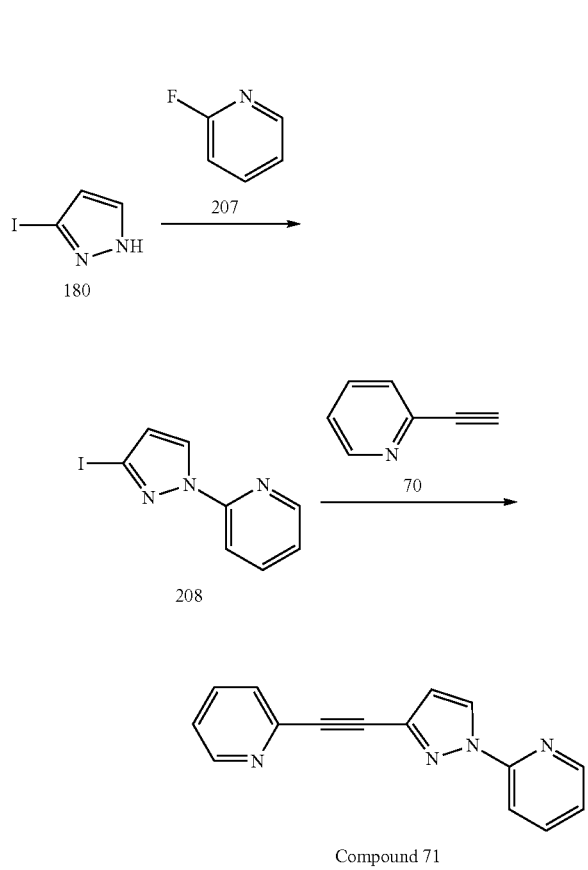

Experimental Section

Procedure for Preparation of 208

To a solution of 180 (100.00 mg, 515.54 umol) and 207 (60.06 mg, 618.65 umol) in DMF (3 mL) was added solid $Cs_2CO_3$ (251.96 mg, 773.31 umol) in one portion at room temperature. It was stirred at 90° C. for 4 hours. After cooling, water (20 mL) was added into the mixture with stirring at ice bath slowly. Gradually, solid was formed. It was filtrated to afford the product 208 (80.00 mg, crude), which was used for next step directly.

LCMS: m/z, 272.0 (M+H)⁺.

Procedure for Preparation of Compound 71

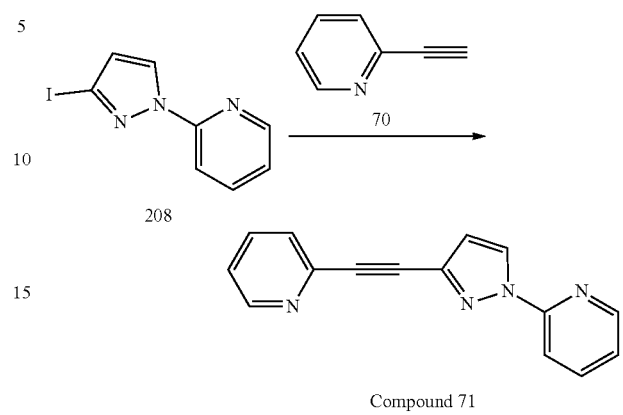

Mixture of compound 208 (50.00 mg, 184.46 umol), 70 (22.83 mg, 221.35 umol), CuI (3.51 mg, 18.45 umol), TEA (56.00 mg, 553.38 umol), and $Pd(PPh_3)_2Cl_2$ (6.47 mg, 9.22 umol) were taken up into a microwave tube in THF (3 mL). The sealed tube was heated at 90° C. for 1 hour under microwave. LCMS showed the starting material was consumed. After cooling to room temperature, ethyl acetate (5 mL) and $H_2O$ (3 mL) were added. The aqueous layer was extracted with ethyl acetate (5 mL×2). The combined organic layers were washed with brine (5 mL), dried over $Na_2SO_4$, concentrated in vacuo to give the crude product, which was purified by pre-HPLC (neutral) to afford product Compound 71 (10.20 mg, yield: 22.30%).

LCMS: m/z, 247.0 (M+H)⁺;

¹HNMR (400 MHz, CDCl₃): δ6.66 (d. J=2.4 Hz, 1H), 7.15-7.18 (m, 1H), 7.21-7.23 (m, 1H), 7.54 (d, J=8.0 Hz, 1H), 7.64 (t, J=8.0 Hz, 1H), 7.77 (d, J=8.0 Hz, 1H), 7.97 (d, J=8.0 Hz, 1H), 8.36 (d, J=8.0 Hz, 1H), 8.51 (d, J=4.0 Hz, 1H), 8.57 (d, J=4.0 Hz, 1H).

Example Compound 72

Preparation of 5-fluoro-2-(4-methyl-3-(pyridin-2-ylethynyl)-1H-pyrazol-1-yl) pyridine

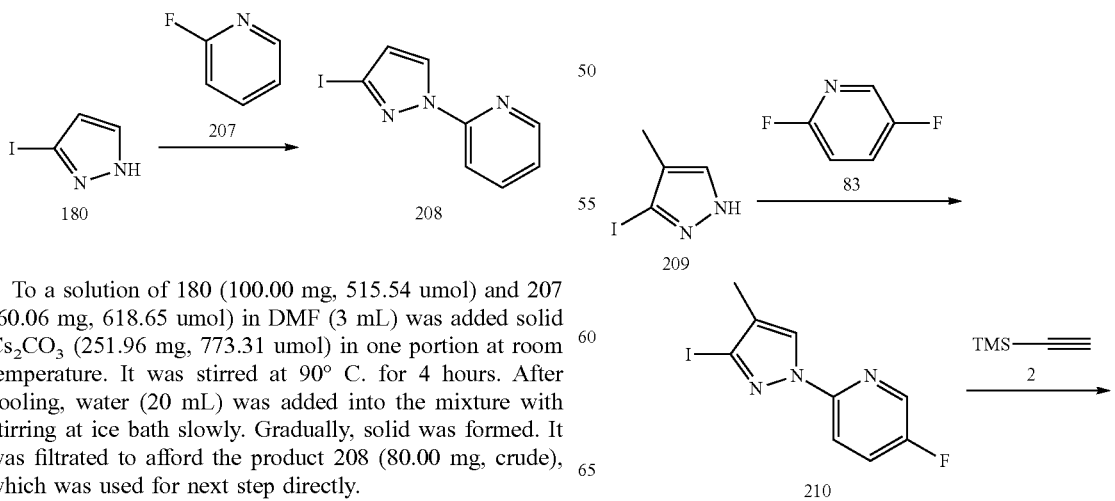

210

Procedure for Preparation of Intermediate 211

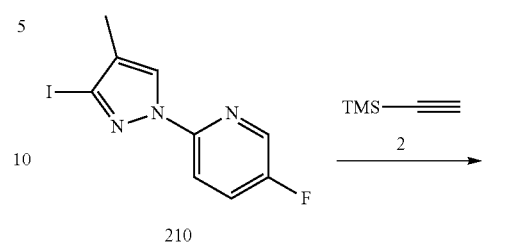

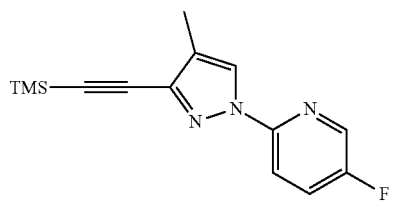

Mixture of compound 210 (260.00 mg, 857.89 umol), 2 (252.79 mg, 2.57 mmol), CuI (16.34 mg, 85.79 umol), TEA (260.43 mg, 2.57 mmol) and Pd(PPh$_3$)$_2$Cl$_2$ (30.11 mg, 42.89 umol) were taken up into a microwave tube in THF (4 mL). The sealed tube was heated at 90° C. for 1 hour under microwave. LCMS showed the starting material was consumed and only the desired product. After cooling to room temperature, the mixture was filtered and concentrated in vacuo. The residue was purified by prep-TLC to give the crude product 211 (200.00 mg, yield: 85.28%).

LCMS: m/z, 274.1 (M+H)$^+$.

Procedure for Preparation of 212

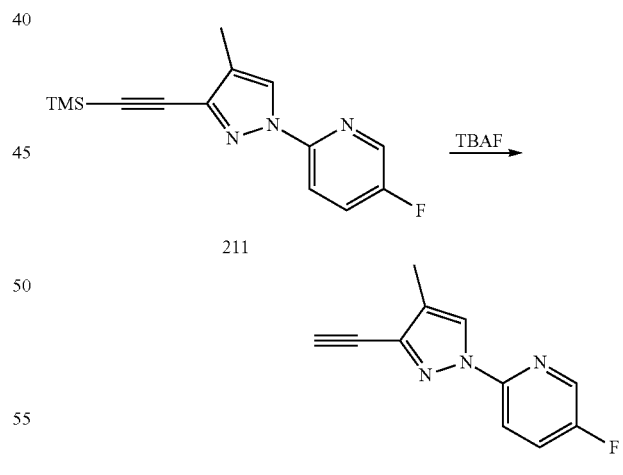

To a mixture of 211 (200.00 mg, 731.58 umol) in THF (15 mL), was added TBAF (in THF) (1M, 1.10 mL) dropwise at room temperature. The mixture was stirred at room temperature for 3 hours. LCMS showed the reaction was completed. The mixture was poured into water (10 mL). The aqueous phase was extracted with ethyl acetate (20 mL×2). The combined organic phase was washed with saturated brine (10 mL), dried with anhydrous Na$_2$SO$_4$, filtered and

209

-continued

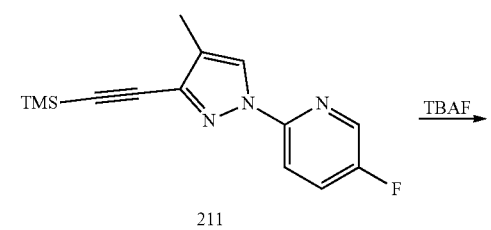

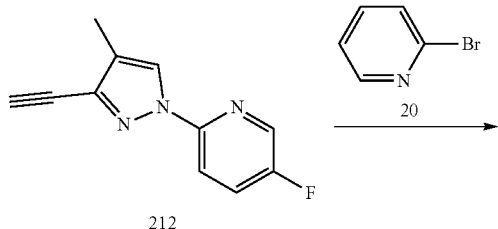

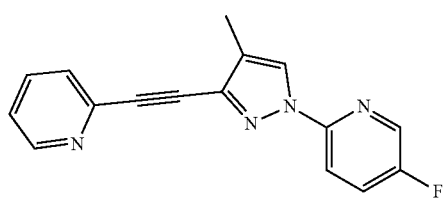

Compound 72

Experimental Section

Procedure for Preparation of 210

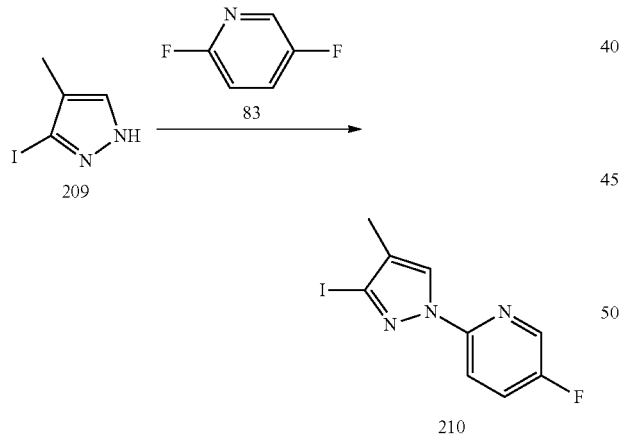

To a mixture of 209 (300.00 mg, 1.44 mmol) and 83 (331.43 mg, 2.88 mmol) in DMF (10 mL), was added Cs$_2$CO$_3$ (1.41 g, 4.33 mmol) in one portion at room temperature. The mixture was heated at 70° C. for 4 hours. LCMS showed the reaction was completed. The mixture was cooled to room temperature and filtered. The filtrate was poured into water (25 mL), filtered and the filter cake was washed with 5 mL of water, dried in vacuum to afford product 210 (260.00 mg, yield: 59.58%).

LCMS: m/z, 303.9 (M+H)$^+$.

concentrated in vacuo to afford product 212 (140.00 mg, crude) which was used directly for next step.

LCMS: m/z, 202.0 (M+H)$^+$.

Procedure for Preparation of Compound 72

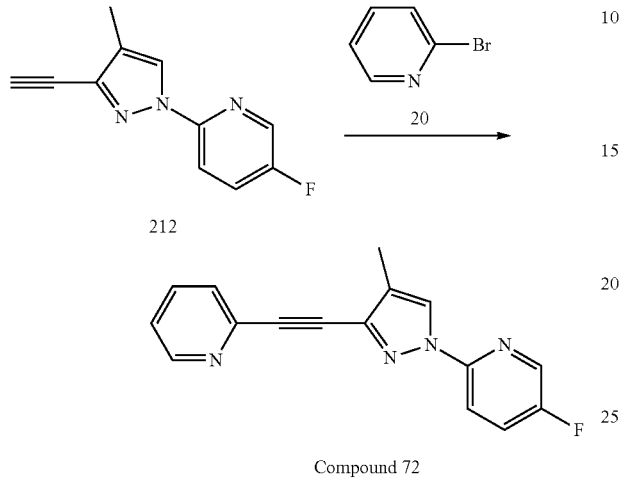

Compound 72

Mixture of 212 (140.00 mg, 695.83 umol), 20 (219.88 mg, 1.39 mmol), CuI (13.25 mg, 69.58 umol), TEA (211.23 mg, 2.09 mmol) and Pd(PPh$_3$)$_2$Cl$_2$ (24.42 mg, 34.79 umol) were taken up into a microwave tube in THF (4 mL). The sealed tube was heated at 90° C. for 1 hour under microwave. TLC showed the starting material was consumed. After cooling to room temperature, the mixture was concentrated in reduced pressure. The residue was purified by prep-HPLC to afford product Compound 72 (20.00 mg, yield: 10.18%).

LCMS: m/z, 279.1 (M+H)$^+$;

$^1$H NMR (400 MHz, CDCl$_3$): δ 8.64-8.63 (m, 1H), 8.29 (s, 1H), 8.23 (s, 1H), 8.01-7.97 (m, 1H), 7.98-7.97 (m, 1H), 7.69-7.68 (m, 1H), 7.60-7.58 (m, 1H), 7.26-7.25 (m, 1H), 2.27 (s, 3H).

Example Compound 73

Preparation of 5-fluoro-2-(5-methyl-3-(pyridin-2-ylethynyl)-1H-pyrazol-1-yl)

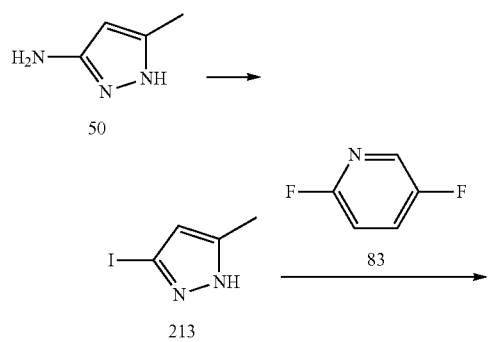

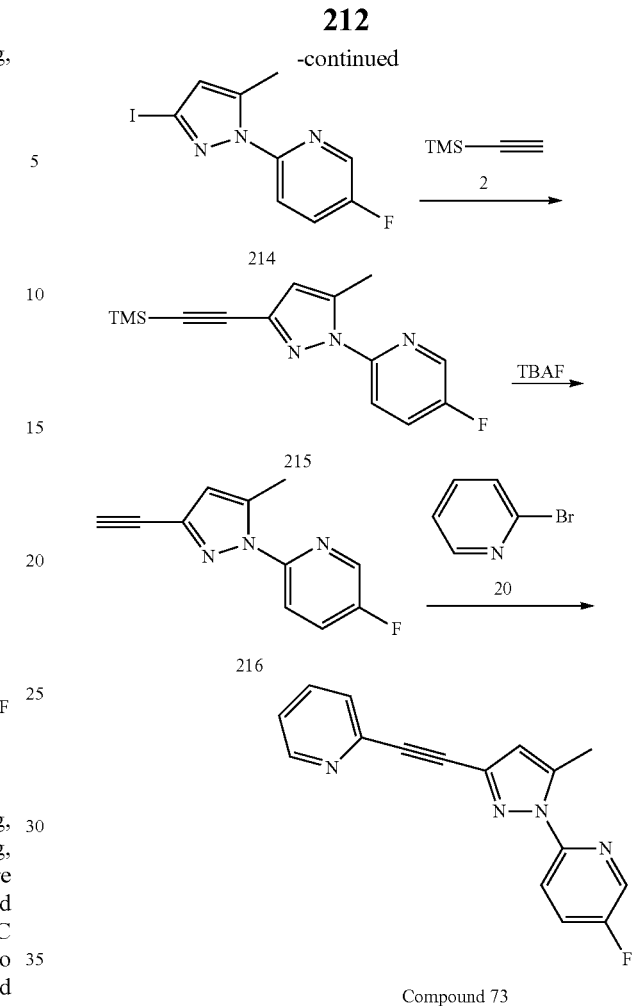

Compound 73

Experimental Section

Procedure for Preparation of 213

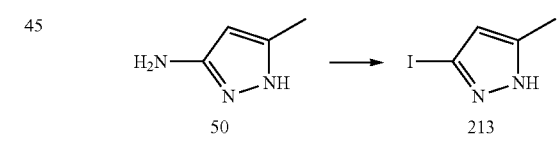

To a mixture of 50 (1.00 g, 10.30 mmol) in concentrated HCl (20 mL) was added NaNO$_2$ (888.08 mg, 12.87 mmol) in water (2 mL) over 4 minutes at 0° C. To the resulting yellow reaction mixture was added a solution of KI (2.56 g, 15.44 mmol) in water (4 mL) over 5 minutes at 0° C., resulting in nitrogen evolution. The reaction mixture was stirred for 3 hours at 0° C. and warmed to room temperature, upon which nitrogen evolution ceased. LCMS showed the reaction was completed. EtOAc (20 mL) was added, followed by adding water (10 mL). The aqueous phase was neutralized with Na$_2$CO$_3$ and the pH of aqueous phase was 8-9, then extracted with EtOAc (30 mL×3). The combined organic phase was washed with Na$_2$S$_2$O$_3$ (10 mL×2), dried over anhydrous Na$_2$SO$_4$, filtered and concentrated in vacuum. The residue was purified by silica gel chromatography to afford product 213 (200.00 mg, yield: 8.40%).

LCMS: m/z, 208.9 (M+H)$^+$.

Procedure for Preparation of 214

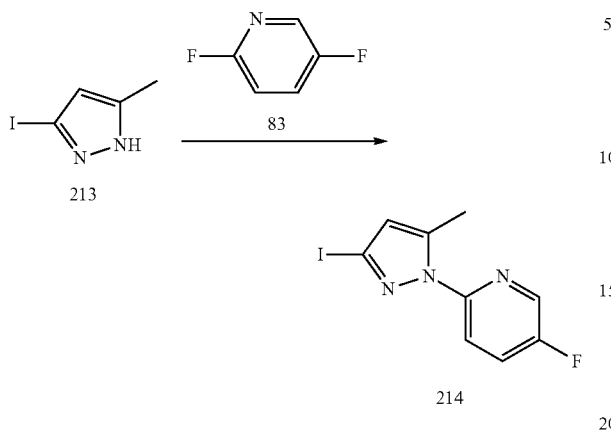

To a mixture of 213 (100.00 mg, 480.77 umol) and 83 (82.99 mg, 721.15 umol) in DMF (5 mL), was added Cs$_2$CO$_3$ (469.93 mg, 1.44 mmol) in one portion at 25° C. The mixture was heated to 100° C. and stirred for 6 hours. LCMS showed about 28% of desired product was detected. The mixture was cooled to 25° C. and filtered. The filtrate was poured into water (25 mL), and extracted with EtOAc (10 mL×3). The combined organic phase was washed with saturated brine (5 mL×2), dried over anhydrous Na$_2$SO$_4$, filtered and concentrated in vacuo to afford product 214 (80.00 mg, crude).

LCMS: m/z, 304.0 (M+H)$^+$.

Procedure for Preparation of 215

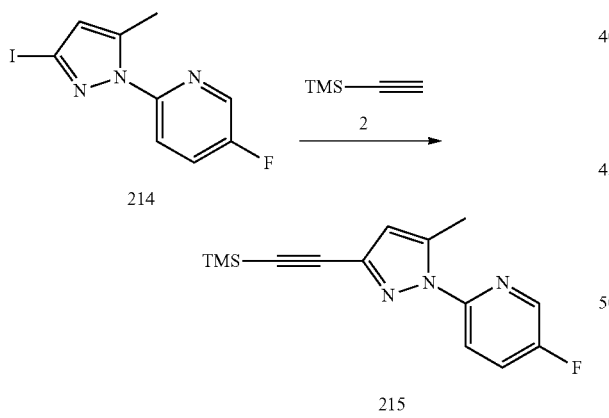

A mixture of 214 (80.00 mg, 263.97 umol), 2 (77.278 mg, 791.90 umol), CuI (5.03 mg, 26.40 umol), TEA (80.13 mg, 791.90 umol) and Pd(PPh$_3$)$_2$Cl$_2$ (9.26 mg, 13.20 umol) in THF (4 mL) was taken up into a microwave tube. The sealed tube was heated at 90° C. for 1 hour under microwave. LCMS showed the starting material was consumed and only the desired product. After cooling to 25° C., the mixture was filtered and concentrated in vacuo. The residue was purified by prep-TLC to give the crude product 215 (40.00 mg, yield: 55.43%).

LCMS: m/z, 274.1 (M+H)$^+$.

Procedure for Preparation of 216

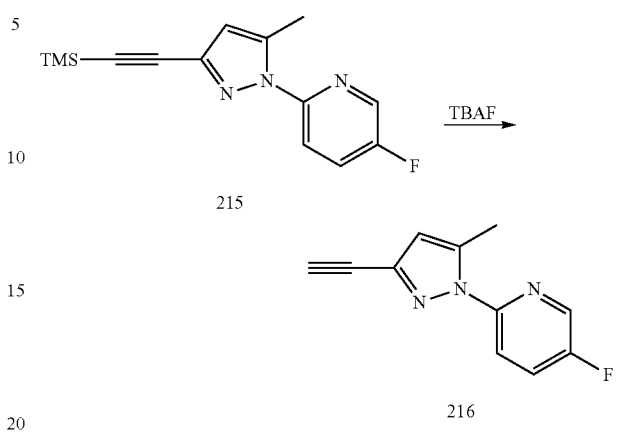

To a mixture of 215 (140.00 mg, 512.11 umol) in THF (15 mL), was added TBAF (in THF) (1 M, 768.16 uL) dropwise at 25° C. The mixture was stirred at 25° C. for 3 hours. TLC showed the reaction was completed. The mixture was poured into water (10 mL). The aqueous phase was extracted with ethyl acetate (20 mL×2). The combined organic phase was washed with saturated brine (10 mL), dried over anhydrous Na$_2$SO$_4$, filtered and concentrated in vacuum to afford product 216 (90.00 mg, crude) and used directly for next step.

LCMS: m/z, 202.1 (M+H)$^+$.

Procedure for Preparation of Compound 73

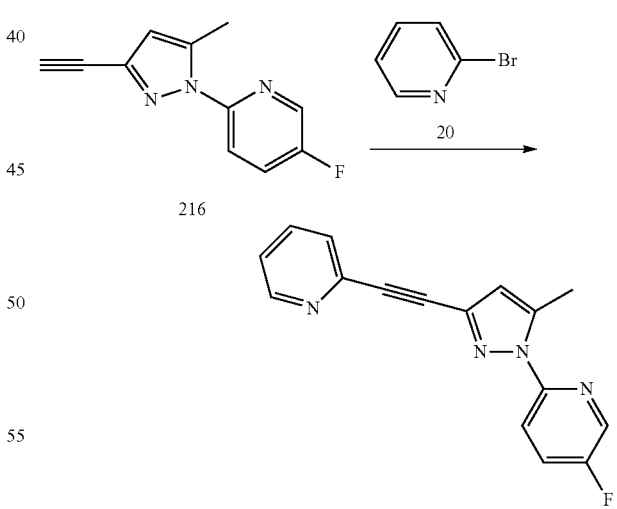

A mixture of 216 (90.00 mg, 447.32 umol), 20 (141.35 mg, 894.63 umol), CuI (8.52 mg, 44.73 umol), TEA (135.79 mg, 1.34 mmol) and Pd(PPh$_3$)$_2$Cl$_2$ (15.70 mg, 22.37 umol) in THF (4 mL) were taken up into a microwave tube. The sealed tube was heated at 90° C. for 1 hour under microwave. TLC showed the starting material was consumed.

After cooling to 25° C., the mixture was concentrated in reduced pressure. The residue was purified by prep-HPLC purification to afford desired product Compound 73 (20.00 mg, yield: 16.07%0).

LCMS: m/z, 279.1 (M+H)$^+$;

$^1$H NMR (400 MHz, CDCl$_3$): δ 8.63-8.62 (m, 1H), 8.28 (s, 1H), 7.96-7.93 (m, 1H), 7.68-7.67 (m, 1H), 7.58-7.55 (m, 2H), 7.25-7.24 (m, 1H), 6.44 (s, 1H), 2.65 (s, 3H).

Example Compound 74

Preparation of 3-fluoro-5-(4-(phenylethynyl)-H-pyrazol-1-yl)benzonitrile

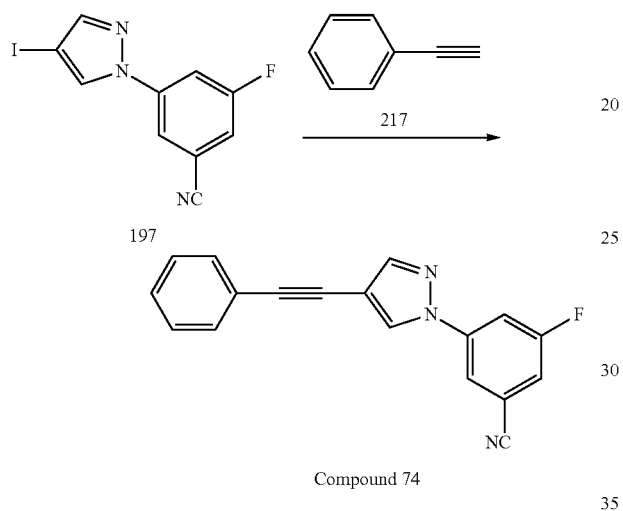

Experimental Section

Procedure for Preparation of Compound 74

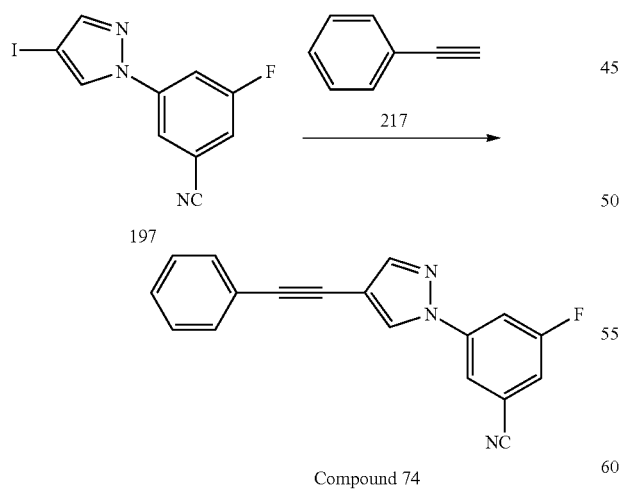

To a solution of 197 (100 mg, 0.319 mmol) and 217 (0.039 ml, 0.351 mmol) in 20 mL of Et$_3$N was added Pd(PPh$_3$)$_2$Cl$_2$ (11.21 mg, 0.016 mmol) and CuI (6.08 mg, 0.032 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by prep-HPLC to yield product Compound 74 (28 mg, yield: 30.5%).

LCMS: m/z 288 (M+H)$^+$;

$^1$H NMR (400 MHz, CDCl$_3$): δ 8.11 (s, 1H), 7.89 (s, 1H), 7.83-7.80 (m, 1H), 7.73 (dt, J=9.5, 2.2 Hz, 1H), 7.53-7.49 (m, 2H), 7.38-7.33 (m, 3H), 7.32-7.28 (m, 1H).

Example Compound 75

Preparation of 3-fluoro-5-(4-(pyridin-2-ylethynyl)-1H-pyrazol-1-yl)benzonitrile

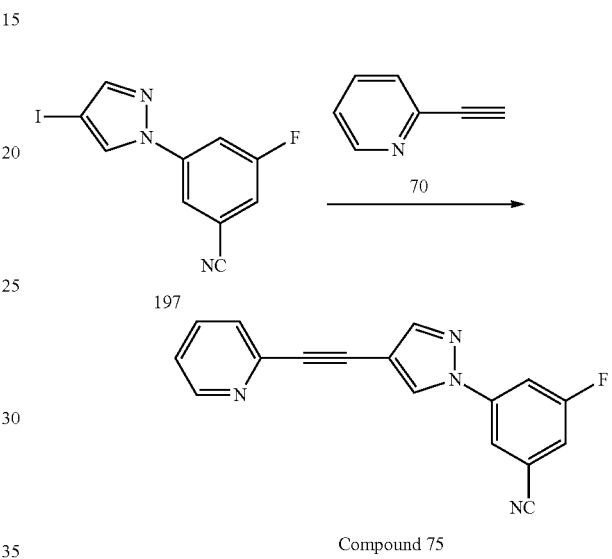

Experimental Section

Procedure for Preparation of Compound 75

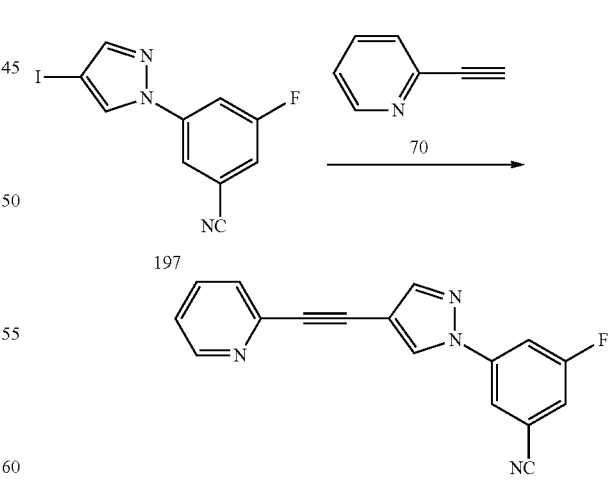

To a solution of 196 (100 mg, 0.319 mmol) and 70 (0.036 mL, 0.351 mmol) in 20 mL of Et$_3$N was added Pd(PPh$_3$)$_2$Cl$_2$ (11.21 mg, 0.016 mmol) and CuI (6.08 mg, 0.032 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by prep-HPLC to give the target product Compound 75 (22 mg, yield: 23.89%).

LCMS: m/z 289 (M+H)$^+$;

$^1$H NMR (400 MHz, CDCl$_3$): δ 8.65-8.61 (m, 1H), 8.17 (s, 1H), 7.94 (s, 1H), 7.81 (s, 1H), 7.75-7.68 (m, 2H), 7.54-7.49 (m, 1H), 7.34-7.27 (m, 2H).

Example Compound 76

Preparation of 3-fluoro-5-(4-(pyridin-3-ylethynyl)-1H-pyrazol-1-yl)benzonitrile

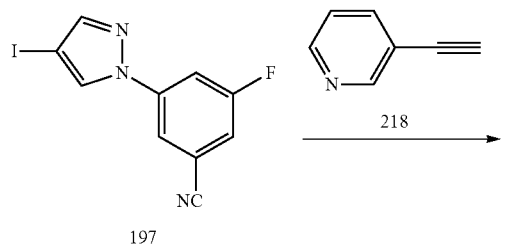

Experimental Section

Procedure for Preparation of Compound 76

To a solution of 197 (100 mg, 0.319 mmol) and 218 (36.2 mg, 0.351 mmol) in 20 mL of Et$_3$N was added Pd(PPh$_3$)$_2$Cl$_2$ (11.21 mg, 0.016 mmol) and CuI (6.08 mg, 0.032 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 76 (20 mg, yield: 21.72%).

LCMS: m/z 289 (M+H)$^+$;

$^1$H NMR (400 MHz, CDCl$_3$): δ 8.75 (d, J=2.1, 1.0 Hz, 1H), 8.57 (dd, J=5.0, 1.7 Hz, 1H), 8.15 (s, 1H), 7.91 (s, 1H), 7.85-7.78 (m, 2H), 7.77-7.72 (m, 1H), 7.35-7.28 (m, 2H).

Example Compound 77

Preparation of 3-fluoro-5-(4-(3-chloro-phenylethynyl)-1H-pyrazol-1-yl) benzonitrile Experimental Section Procedure for Preparation of Compound 77

To a solution of 197 (100 mg, 0.319 mmol) and 219 (0.044 mL, 0.351 mmol) in 20 mL of Et$_3$N was added Pd(PPh$_3$)$_2$Cl$_2$ (11.21 mg, 0.016 mmol) and CuI (6.08 mg, 0.032 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by pep-HPLC to give the target product Compound 77 (23 mg, yield: 22.38%).

LCMS: m/z 322 (M+H)$^+$;

$^1$H NMR (400 MHz, CDCl$_3$): δ 8.12 (s, 1H), 7.89 (s, 1H), 7.81 (s, 1H), 7.73 (dt, J=9.4, 2.2 Hz, 1H), 7.50 (t, J=2.3, 1.5, 0.7 Hz, 1H), 7.39 (dt, J=7.2, 1.6 Hz, 1H), 7.36-7.27 (m, 3H).

Example Compound 78

Preparation of 3-fluoro-5-(4-(pyrimidin-2-ylethynyl)-1H-pyrazol-1-yl) benzonitrile

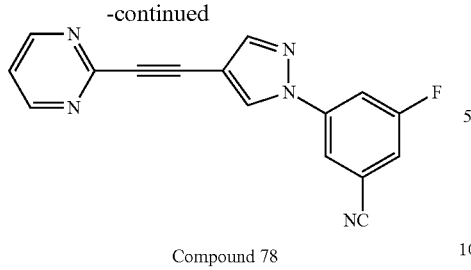

Compound 78

To a solution of 197 (100 mg, 0.319 mmol) and 4 (36.6 mg, 0.351 mmol) in 20 mL of Et₃N was added Pd(PPh₃)₂Cl₂ (11.21 mg, 0.016 mmol) and CuI (6.08 mg, 0.032 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 78 (45 mg, yield: 48.7%).

LCMS: m/z 290 (M+H)⁺;

¹H NMR (400 MHz, CDCL₃): δ 8.77 (d, J=4.8 Hz, 2H), 8.23 (s, 1H), 7.99 (s, 1H), 7.82 (s, 1H), 7.73 (d, J=9.2 Hz, 1H), 7.34-7.27 (m, 2H).

Example Compound 79

Preparation of 3-fluoro-5-(4-(pyridin-4-ylethynyl)-1H-pyrazol-1-yl)benzonitrile

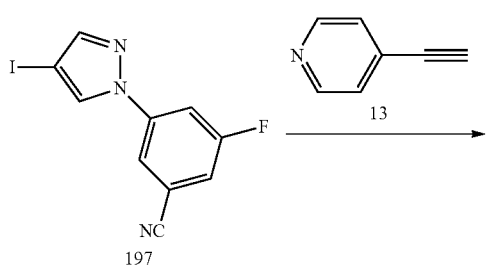

Compound 79

To a solution of 197 (100 mg, 0.319 mmol)) and 13 (32.9 mg, 0.319 mmol) in 20 mL of Et₃N was added Pd(PPh₃)₂Cl₂ (11.21 mg, 0.016 mmol) and CuI (6.08 mg, 0.032 mmol)). The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 79 (25 mg, yield: 27.1%).

LCMS: m/z 289 (M+H)⁺;

¹H NMR (400 MHz, CDCl₃): δ 8.67 (br, 2H), 8.17 (s, 1H), 7.92 (s, 1H), 7.82 (s, 1H), 7.76-7.73 (m, 1H), 7.40 (br, 2H), 7.34-7.32 (m, 1H).

Example Compound 80

Preparation of 3-fluoro-5-(4-(pyrazin-2-ylethynyl)-1H-pyrazol-1-yl)benzonitrile

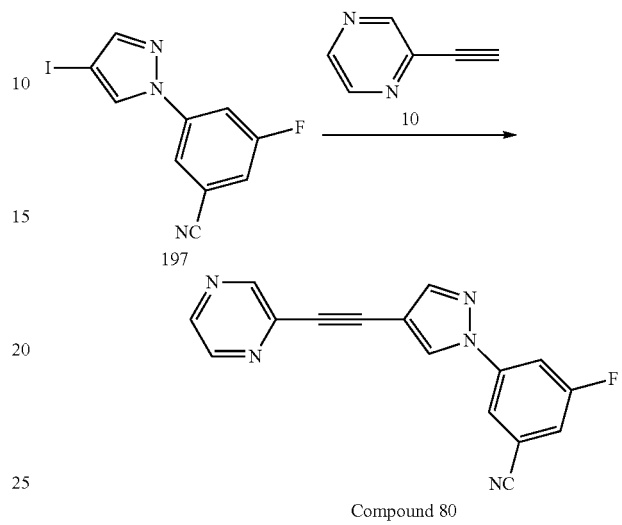

Compound 80

To a solution of 197 (100 mg, 0.319 mmol)) and 10 (36.6 mg, 0.351 mmol) in 20 mL of Et₃N was added Pd(PPh₃)₂Cl₂ (11.21 mg, 0.016 mmol) and CuI (6.08 mg, 0.032 mmol)). The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 80 (25 mg, yield: 27.1%).

LCMS: m/z 290 (M+H)⁺;

¹H NMR (400 MHz, CDCl₃): δ 8.78 (br, 1H), 8.62-8.55 (m, 2H), 8.21 (s, 1H), 7.97 (s, 1H), 7.83 (s, 1H), 7.76-7.73 (m, 1H), 7.35-7.32 (m, 1H).

Example Compound 81

Preparation of 1-(4-fluorophenyl)-4-(phenylethynyl)-1H-pyrazole

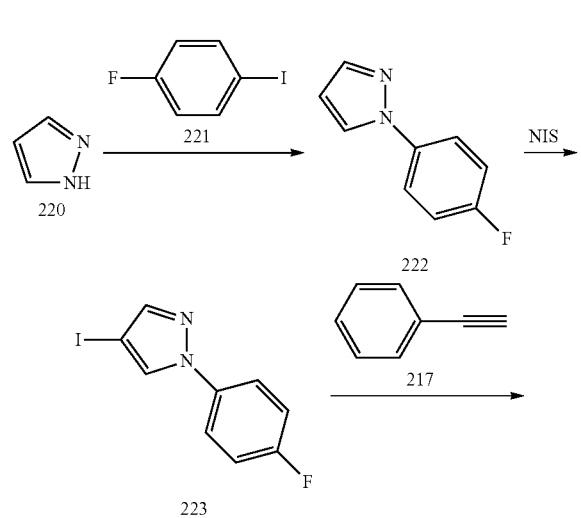

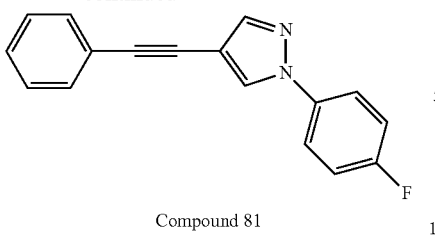

Compound 81

Experimental Section

Procedure for Preparation of 222

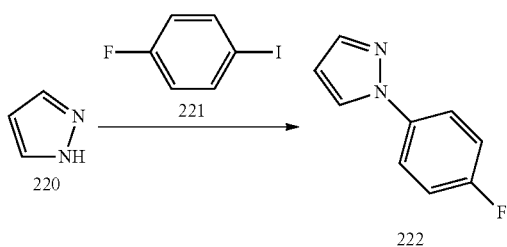

A mixture of 220 (0.613 g, 9.01 mmol), Cs₂CO₃ (4.40 g, 13.51 mmol), 221 (2.0 g, 9.01 mmol) and Cu(OAc)₂ (0.16 g) in 20 mL DMF, was heated at 120° C. for the appropriate time and subsequent cooling, the reaction mixture was diluted with saturated aqueous ammonium chloride. Products were isolated by extraction with ethyl acetate. The organic layer was dried over anhydrous Na₂SO₄, filtered, and concentrated. Product 222 was purified by silica gel column chromatography (1.0 g, yield: 68%).

Procedure for Preparation of 223

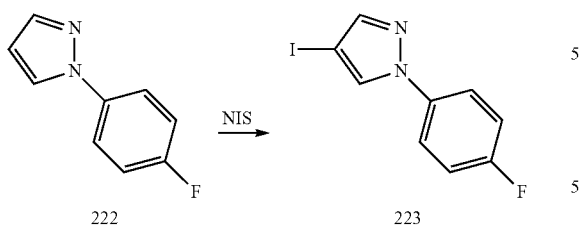

A mixture of 222 (1.0 g) and NIS (1.66 g) in 10 ml AcOH, was heated at 120° C. via MW for 30 minutes. The reaction mixture was diluted with EA, washed with brine, then dried over Na₂SO₄, filtered, and concentrated. The residue was purified by column chromatography on silica gel to afford product 223 (0.8 g, yield: 45%).

LCMS: m/z 289 (M+H)⁺.

Procedure for Preparation of Compound 81

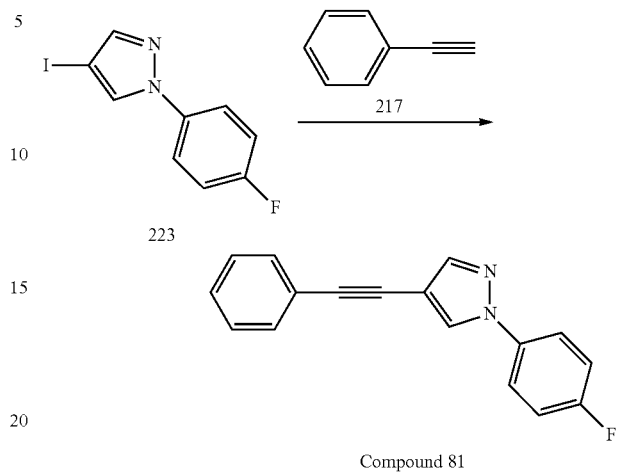

Compound 81

To a solution of 223 (100 mg, 0.347 mmol) and 217 (0.042 mL, 0.382 mmol) in 20 mL of Et₃N was added Pd(PPh₃)₂Cl₂ (12.18 mg, 0.017 mmol) and CuI (6.61 mg, 0.035 mmol). The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 81 (36 mg, yield: 39.5%).

LCMS: m/z 263 (M+H)⁺;

$^1$H NMR (400 MHz, CDCl₃): δ 8.04 (s, 1H), 7.86 (s, 1H), 7.71-7.60 (m, 2H), 7.54-7.47 (m, 2H), 7.38-7.31 (m, 3H), 7.23-7.13 (m, 2H).

Example Compound 82

Preparation of 2-((1-(4-fluorophenyl)-1H-pyrazol-4-yl)ethynyl)pyridine

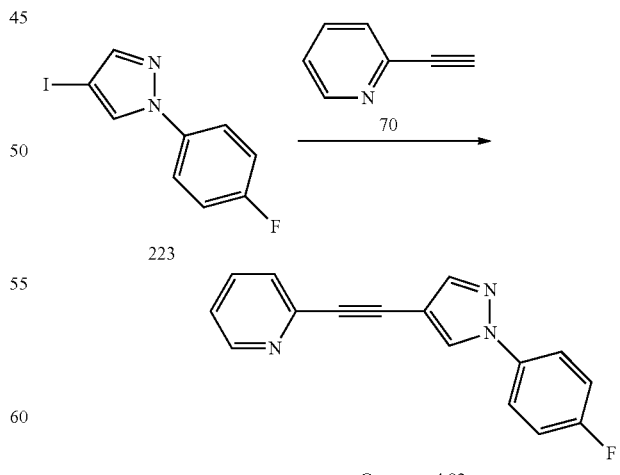

Compound 82

To a solution of 223 (100 mg, 0.347 mmol) and 70 (0.039 mL, 0.382 mmol) in 20 mL of Et₃N was added Pd(PPh₃)₂Cl₂ (12.18 mg, 0.017 mmol) and CuI (6.61 mg, 0.035 mmol).

The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 82 (24 mg, yield: 26.3%).

LCMS: m/z 264 (M+H)⁺;

¹H NMR (400 MHz, CDCl₃): δ 8.65-8.59 (m, 1H), 8.09 (s, 1H), 7.89 (s, 1H), 7.72-7.59 (m, 3H), 7.49 (m, 1H), 7.25-7.21 (m, 1H), 7.20-7.13 (m, 2H).

Example Compound 83

Preparation of 3-((1-(4-fluorophenyl)-1H-pyrazol-4-yl)ethynyl)pyridine

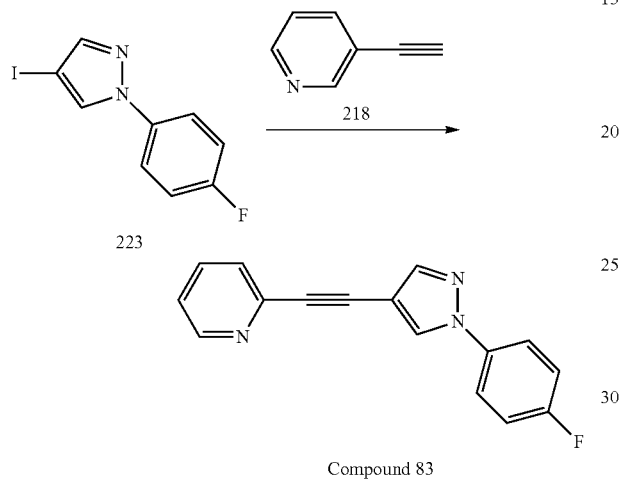

Compound 83

To a solution of 223 (100 mg, 0.347 mmol) and 218 (39.4 mg, 0.382 mmol) in 20 mL of Et₃N was added Pd(PPh₃)₂Cl₂ (12.18 mg, 0.017 mmol) and CuI (6.61 mg, 0.035 mmol). The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 83 (28 mg, yield: 30.6%).

LCMS: m/z 264 (M+H)⁺;

¹H NMR (400 MHz, CDCl₃) δ 8.75 (s, 1H), 8.56 (d, 1H), 8.08 (s, 1H), 7.87 (s, 1H), 7.80 (dt, J=7.9, 1.9 Hz, 1H), 7.71-7.60 (m, 2H), 7.35-7.27 (m, 1H), 7.22-7.13 (m, 2H).

Example Compound 84

Preparation of 4-((3-chlorophenyl)ethynyl)-1-(4-fluorophenyl)-1H-pyrazole

Compound 84

To a solution of 223 (100 mg, 0.347 mmol) and 219 (39.4 mg, 0.382 mmol) in 20 mL of Et₃N was added Pd(PPh₃)₂Cl₂ (12.18 mg, 0.017 mmol) and CuI (6.61 mg, 0.035 mmol). The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 84 (21 mg, yield: 20.390/%).

LCMS: m/z 297 (M+H)⁺;

¹H NMR (400 MHz, CDCl₃): δ 8.04 (s, 1H), 7.85 (s, 1H), 7.69-7.62 (m, 2H), 7.49 (s, 1H), 7.40-7.36 (m, 1H), 7.33-7.27 (m, 2H), 7.21-7.14 (m, 2H).

Example Compound 85

Preparation of 2-chloro-4-((1-(4-fluorophenyl)-1H-pyrazol-4-yl)ethynyl)pyridine

Compound 85

To a solution of 223 (100 mg, 0.347 mmol) and 7 (39.4 mg, 0.382 mmol) in 20 mL of Et₃N was added Pd(PPh₃)₂Cl₂ (12.18 mg, 0.017 mmol) and CuI (6.61 mg, 0.035 mmol). The mixture was protected under N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 85 (25 mg, yield: 12.09%).

LCMS: m/z 298 (M+H)⁺;

$^1$H NMR (400 MHz, CDCl$_3$) δ 8.37 (d, J=5.1, 0.8 Hz, 1H), 8.09 (s, 1H), 7.88 (s, 1H), 7.69-7.62 (m, 2H), 7.40 (s, 1H), 7.29-7.26 (m, 1H), 7.22-7.14 (m, 2H).

Example Compound 86

Preparation of 2-((1-(4-fluorophenyl)-H-pyrazol-4-yl)ethynyl)pyrimidine

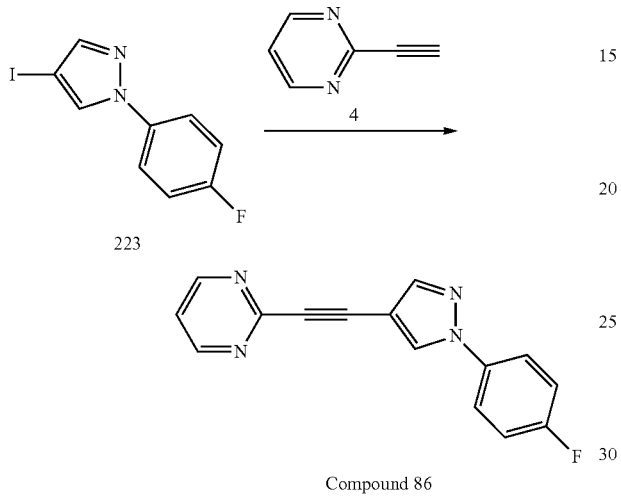

Compound 86

To a solution of 223 (200 mg, 0.694 mmol) and 4 (80 mg, 0.764 mmol) in 20 mL of Et$_3$N was added Pd(PPh$_3$)$_2$Cl$_2$ (24.37 mg, 0.035 mmol) and CuI (13.22 mg, 0.069 mmol). The mixture was protected under N$_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 86 (18 mg, yield: 9.80%).

LCMS: m/z 265 (M+H)$^+$;

$^1$H NMR (400 MHz, CDCl$_3$): δ 8.75 (d, J=4.9 Hz, 2H), 8.16 (s, 1H), 7.96 (s, 1H), 7.69-7.61 (m, 2H), 7.25-7.22 (m, 1H), 7.22-7.11 (m, 2H).

Example Compound 87

Preparation of 4-((1-(4-fluorophenyl)-1H-pyrazol-4-yl)ethynylpyridine

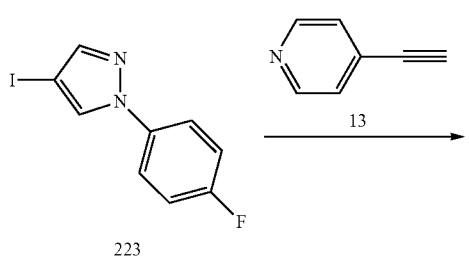

-continued

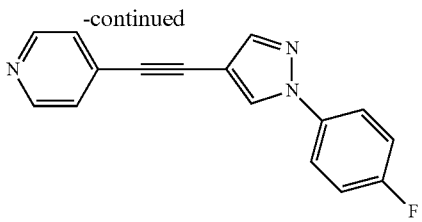

Compound 87

To a solution of 223 (100 mg, 0.347 mmol), 13 (39.4 mg, 0.382 mmol) in 20 mL of Et$_3$N was added Pd(PPh$_3$)$_2$Cl$_2$ (12.18 mg, 0.017 mmol) and CuI (6.61 mg, 0.035 mmol). The mixture was protected under N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 87 (20 mg, yield: 21.88%).

LCMS: m/z 264 (M+H)$^+$;

$^1$H NMR (400 MHz, CDCL$_3$): δ 8.61 (br, 2H), 8.10 (s, 1H), 7.79 (s, 1H), 7.68-7.64 (m, 2H), 7.38 (d, J=5.6 Hz, 2H), 7.21-7.16 (m, 2H).

Example Compound 88

Preparation of 2-((1-(4-fluorophenyl)-1H-pyrazol-4-yl)ethynyl)pyrazine

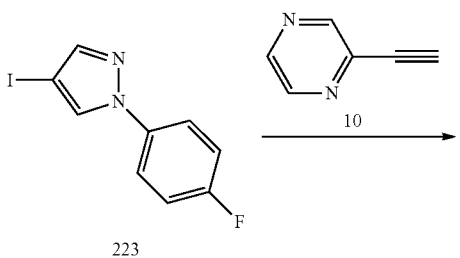

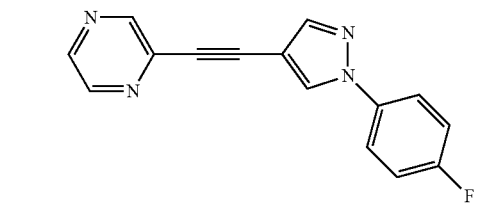

Compound 88

To a solution of 223 (100 mg, 0.347 mmol), 10 (36.1 mg, 0.347 mmol) in 20 mL of Et$_3$N was added Pd(PPh$_3$)$_2$Cl$_2$ (244 mg, 0.347 mmol) and CuI (66.1 mg, 0.347 mmol). The mixture was protected under N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 88 (20 mg, yield: 21.80%).

LCMS: m/z 265 (M+H)$^+$;

$^1$H NMR (400 MHz, CDCl$_3$): δ 8.74 (d, J=1.2 Hz, 1H), 8.58-8.57 (m, 1H), 8.49 (d, J=2.4 Hz, 1H), 8.13 (s, 1H), 7.93 (s, 1H), 7.68-7.64 (m, 2H), 7.18 (t, J=8.6 Hz, 2H).

Example Compound 89

Preparation of 4-(phenylethynyl)-1-(4-(trifluoromethoxy)phenyl)-1H-pyrazole

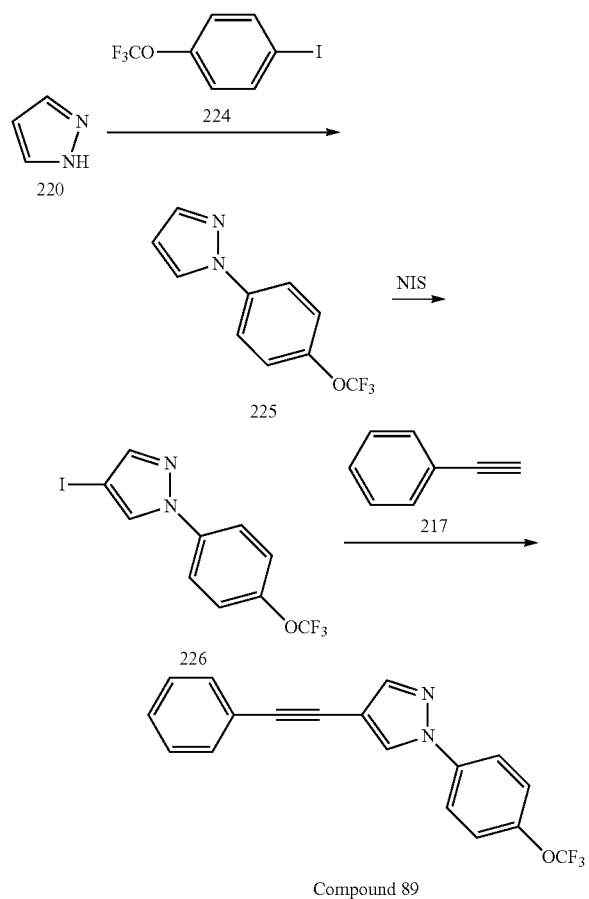

Compound 89

Experimental Section

Procedure for Preparation of 225

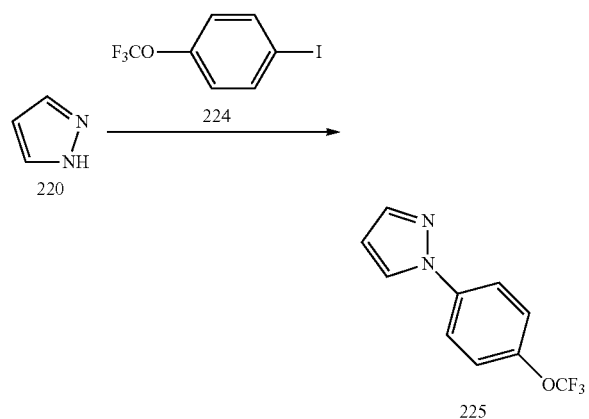

A mixture of 220 (0.613 g, 9.01 mmol), $Cs_2CO_3$ (4.40 g, 13.51 mmol), 224 (2.0 g, 9.01 mmol) and $Cu(OAc)_2$ (0.16 g) in 20 mL DMF. The mixture was heated at 120° C. for the appropriate time and subsequent cooling, the reaction mixture was diluted with saturated aqueous ammonium chloride. Products were isolated by extraction with EA. The organic layer was dried over anhydrous $Na_2SO_4$, filtered, and concentrated. Products 225 were purified by silica gel column chromatography (1.40 g, yield: 68%).

Procedure for Preparation of 226

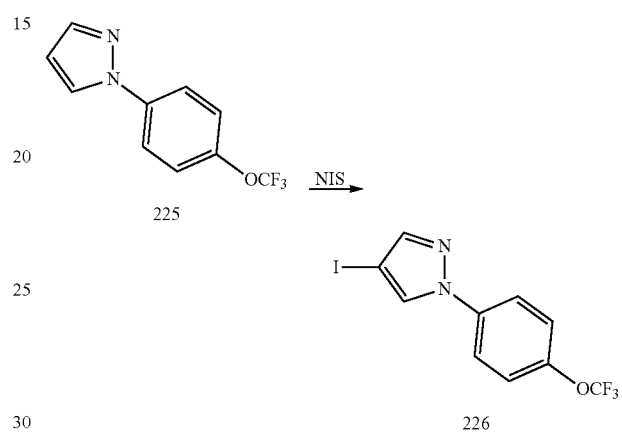

225 (1.0 g) and NIS (1.66 g) were added to AcOH (10 ml). The reaction mixture was heated at 120° C. via MW for 30 minutes. The reaction mixture was diluted with EA, washed with brine, then dried over $Na_2SO_4$, filtered, and concentrated. The residue was purified by column chromatography on silica gel to afford product 226 (0.70 g, yield: 45%).

Procedure for Preparation of Compound 89

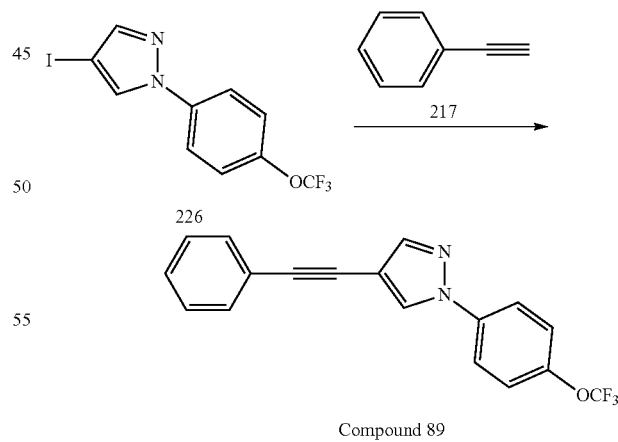

Compound 89

The solution of 226 (100 mg, 0.282 mmol), 217 (57.7 mg, 0.565 mmol) in 20 mL of $Et_3N$ was added $Pd(PPh_3)_2Cl_2$ (9.91 mg, 0.014 mmol) and CuI (5.38 mg, 0.028 mmol). The mixture was protected with $N_2$ atmosphere, then was heated at 70° C. for 4 h. TLC analysis showed complete conversion of starting material to a major product. The reaction mixture was then concentrated in vacuo. The crude product was purified by Prep-HPLC to give the target product Compound 89 (25 mg, yield: 27.0%).

LCMS: m/z 329 (M+H)$^+$;

$^1$H NMR (400 MHz, CDCl$_3$): δ8.09 (s, 1H), 7.87 (s, 1H), 7.74-7.72 (m, 2H), 7.53-7.50 (m, 2H), 7.36-7.32 (m, 5H).

Example Compound 90

Preparation of 2-((1-(4-(trifluoromethoxy)phenyl)-1H-pyrazol-4-yl)ethynyl)pyridine

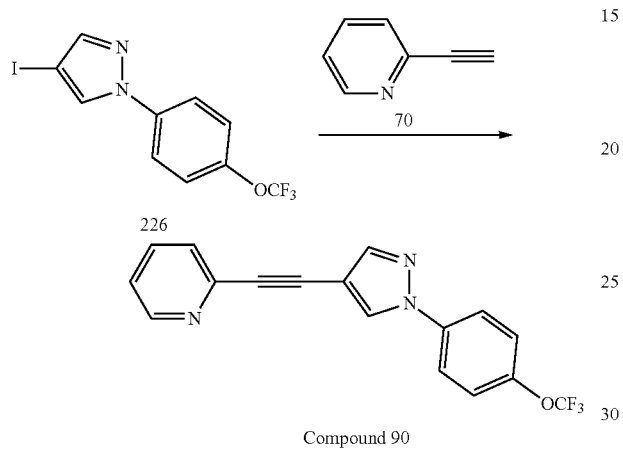

Compound 90

To a solution of 26 (100 mg, 0.282 mmol) and 70 (58.2 mg, 0.565 mmol) in 20 mL of Et$_3$N was added Pd(PPh$_3$)$_2$Cl$_2$ (9.91 mg, 0.014 mmol) and CuI (5.38 mg, 0.028 mmol). The mixture was protected under N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 90 (20 mg, yield: 21.6%).

LCMS: m/z 330 (M+H)$^+$;

$^1$H NMR (400 MHz, CDCl$_3$): δ8.65 (br, 1H), 8.15 (s, 1H), 7.92 (s, 1H), 7.72 (m, 3H), 7.52 (br, 1H), 7.34 (dd, J=9.0, 1.0 Hz, 2H), 7.27 (br, 1H).

Example Compound 91

Preparation of 3-((1-(4-(trifluoromethoxy)phenyl)-H-pyrazol-4-yl)ethynyl)pyridine

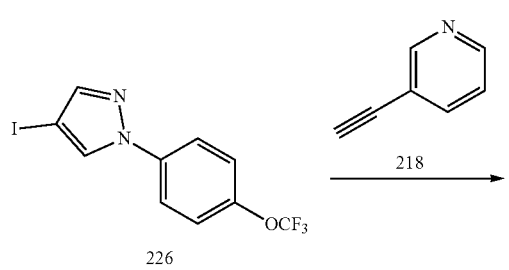

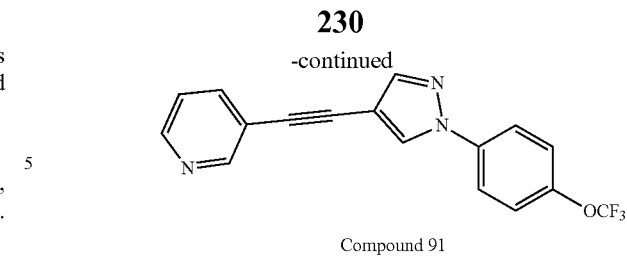

Compound 91

To a solution of 226 (100 mg, 0.282 mmol) and 218 (58.2 mg, 0.565 mmol) in 20 mL of Et$_3$N was added Pd(PPh$_3$)$_2$Cl$_2$ (9.91 mg, 0.014 mmol) and CuI (5.38 mg, 0.028 mmol). The mixture was protected under N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 91 (23 mg, yield: 24.73%).

LCMS: m/z 330 (M+H)$^+$;

$^1$H NMR (400 MHz, CDCl$_3$): δ 8.75 (d, J=1.2 Hz, 1H), 8.57-8.55 (m, 1H), 8.12 (d, J=0.4 Hz, 1H), 7.89 (s, 1H), 7.81 (d, J=8 Hz, 1H), 7.74-7.72 (m, 2H), 7.36-7.33 (m, 3H).

Example Compound 92

Preparation of 4-((3-chlorophenyl)ethynyl)-1-(4-(trifluoromethoxy)phenyl)-1H-pyrazole

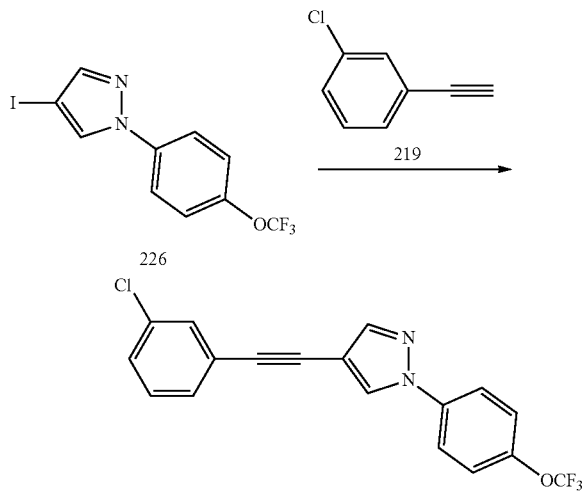

Compound 92

To a solution of 226 (100 mg, 0.282 mmol) and 219 (38.6 mg, 0.282 mmol) in 20 mL of Et$_3$N was added Pd(PPh$_3$)$_2$Cl$_2$ (9.91 mg, 0.014 mmol) and CuI (5.38 mg, 0.028 mmol). The mixture was protected under N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 92 (23 mg, yield: 22.45%).

LCMS: m/z 363 (M+H)$^+$;

$^1$H NMR (400 MHz, CDCl$_3$): δ 8.09 (d, J=0.4 Hz, 1H), 7.87 (s, 1H), 7.73 (d, J=9.6 Hz, 2H), 7.50 (d, J=1.6 Hz, 1H), 7.39-7.28 (m, 5H).

Example Compound 93

Preparation of 2-((1-(4-(trifluoromethoxy)phenyl)-1H-pyrazol-4-yl)ethynyl pyrimidine

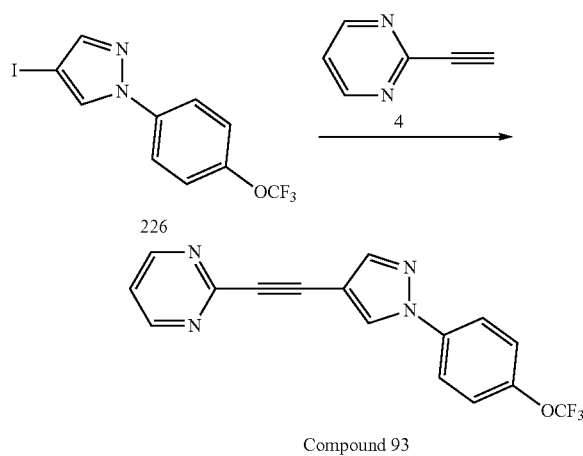

Compound 93

To a solution of 226 (100 mg, 0.282 mmol) and 4 (58.8 mg, 0.565 mmol) in 20 mL of Et₃N was added Pd(PPh₃)₂Cl₂ (9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 93 (20 mg, yield: 21.44%).

LCMS: m/z 331 (M+H)$^+$;

$^1$H NMR (400 MHz, CDCl₃): δ 8.76 (d, J=5.2 Hz, 2H), 8.21 (d, J=0.8 Hz, 1H), 7.98 (s, 1H), 7.73 (d, J=9.2 Hz, 2H), 7.36-7.34 (m, 2H), 7.26 (d, J=9.6 Hz, 1H).

Example Compound 94

Preparation of 4-((1-(4-(trifluoromethoxy)phenyl)-1H-pyrazol-4-yl)ethynyl)pyridine

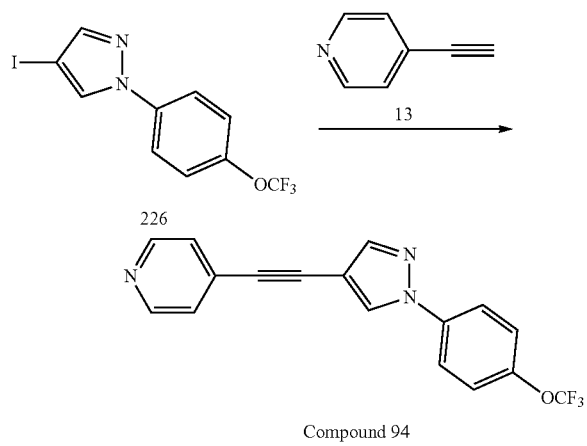

Compound 94

To a solution 226 (100 mg, 0.282 mmol) and 13 (58.2 mg, 0.565 mmol) in 20 mL of Et₃N was added Pd(PPh₃)₂Cl₂ (9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 94 (19 mg, yield: 20.43%).

LCMS: m/z 330 (M+H)$^+$;

$^1$H NMR (400 MHz, DMSO-d₆): δ 9.06 (s, 1H), 8.63-8.62 (m, 2H), 8.13 (s, 1H), 8.02-7.99 (m, 2H), 7.56 (d, J=8.0 Hz, 2H), 7.49-7.48 (m, 2H).

Example Compound 95

Preparation of 2-((1-(4-(trifluoromethoxy)phenyl)-1H-pyrazol-4-yl)ethynyl) pyrazine

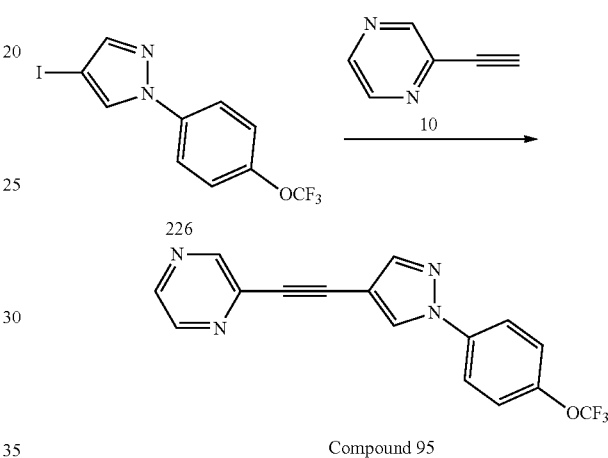

Compound 95

To a solution of 226 (100 mg, 0.282 mmol) and 10 (58.8 mg, 0.565 mmol) in 20 mL of Et₃N was added Pd(PPh₃)₂Cl₂ (9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 95 (20 mg, yield: 21.44%).

LCMS: m/z 331 (M+H)$^+$;

$^1$H NMR (400 MHz, CDCl₃): δ 8.78 (br, 1H), 8.60-8.51 (m, 2H), 8.18 (s, 1H), 7.95 (s, 1H), 7.76-7.72 (m, 2H), 7.35 (d, J=8.0 Hz, 2H).

Example Compound 96

Preparation of 3-fluoro-5-(5-methyl-3-(phenylethynyl)-1H-pyrazol-1-yl) benzonitrile

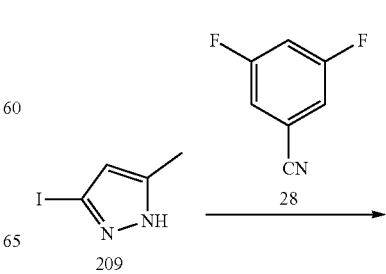

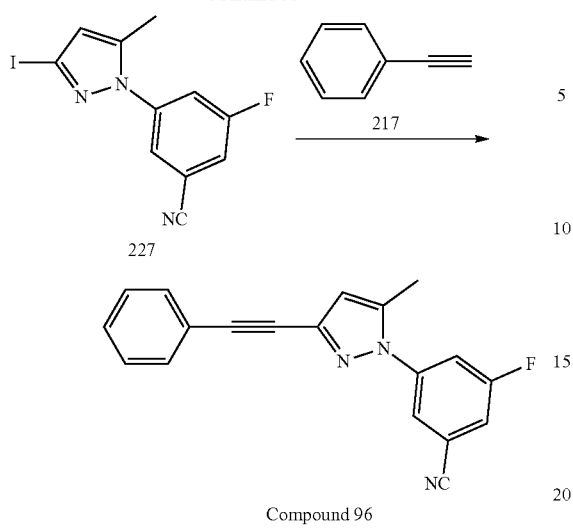

Compound 96

Experimental Section

Procedure of Preparation of 227

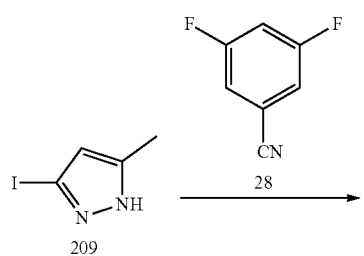

To a solution of compound 209 (2 g, 9.62 mmol) in DMF (20 mL) was added NaH (0.38 g of 60% dispersion in oil). The resulting mixture was stirred for 15 minutes at 60° C., then 28 (2.68 g, 19.23 mmol) was added, and the mixture was heated at 70° C. for another 45-60 minutes (tracking with TLC). The reaction mixture was diluted with EA, and washed with H₂O and saturated NaCl. The organic phase was dried over Na₂SO₄, filtered, and concentrated in vacuo to give crude product, which was purified via Prep-HPLC to give product 227 (1.45 g, yield: 46.26).

Procedure of Preparation of Compound 96

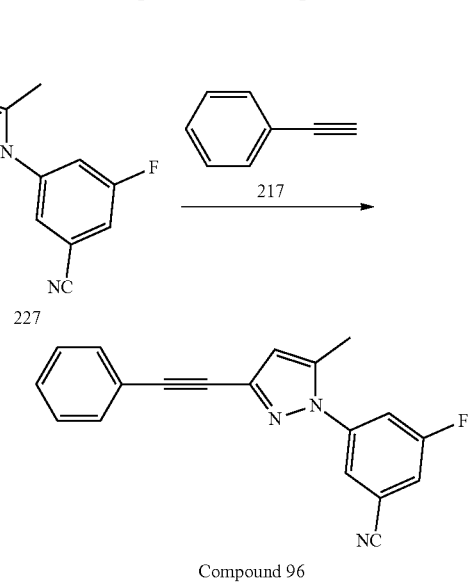

Compound 96

To a solution of 227 (100 mg, 0.306 mmol) and 217 (0.067 ml, 0.611 mmol) in 20 mL of Et₃N was added Pd(PPh₃)₂Cl₂ (10.73 mg, 0.015 mmol) and CuI (5.82 mg, 0.031 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 96 (29 mg, yield: 31.5%).

LCMS: m/z 302 (M+H)$^+$;

$^1$H NMR (400 MHz, CDCl₃): δ 7.67 (d, J=0.8 Hz, 1H), 7.58-7.56 (m, 3H), 7.38-7.35 (m, 4H), 6.45 (d, J=0.8 Hz, 1H), 2.46 (d, J=0.8 Hz, 3H).

Example Compound 97

Preparation of 3-fluoro-5-(5-methyl-3-(pyridin-2-ylethynyl)-1H-pyrazol-1-yl) benzonitrile

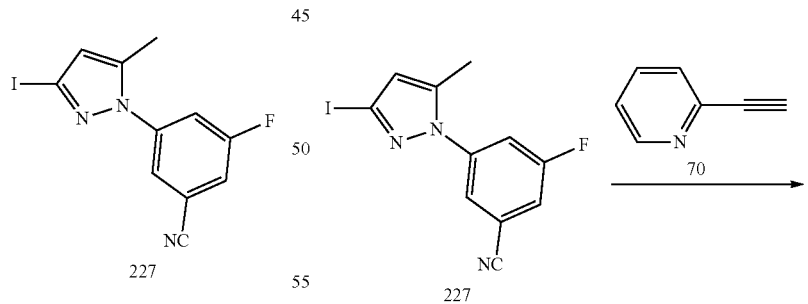

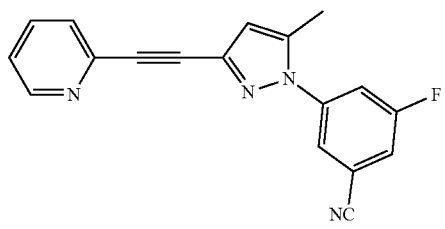

Compound 97

To a solution of 227 (100 mg, 0.306 mmol) and 70 (0.062 ml, 0.611 mmol) in 20 mL of Et₃N was added Pd(PPh₃)₂Cl₂ (10.73 mg, 0.015 mmol) and CuI (5.82 mg, 0.031 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 97 (21 mg, yield: 22.72%).

LCMS: m/z 303 (M+H)⁺;

¹H NMR (400 MHz, CDCl₃): δ 8.65-8.63 (m, 1H), 7.71-7.67 (m, 2H), 7.59-7.57 (m, 2H), 7.40 (d, J=7.6 Hz, 1H), 7.28 (d, J=7.6 Hz, 1H), 6.52 (d, J=0.8 Hz, 1H), 2.46 (d, J=0.8 Hz, 3H).

Example Compound 98

Preparation of 3-fluoro-5-(5-methyl-3-(pyridin-3-ylethynyl)-1H-pyrazol-1-yl) benzonitrile

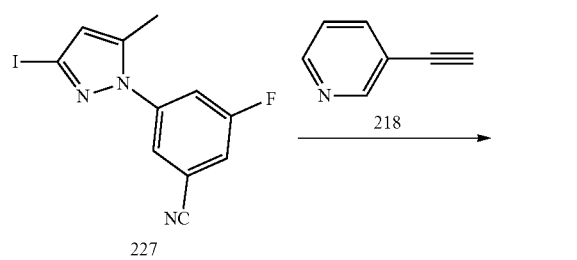

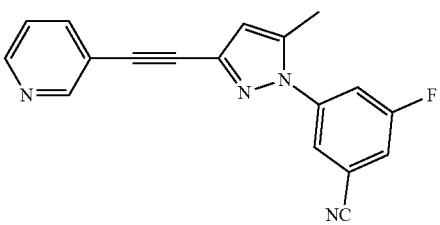

Compound 98

To a solution of 227 (100 mg, 0.306 mmol) and 218 (63.1 mg, 0.61 mmol) in 20 mL of Et₃N was added Pd(PPh₃)₂Cl₂ (10.73 mg, 0.015 mmol) and CuI (5.82 mg, 0.031 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 98 (21 mg, yield: 22.72%).

LCMS: m/z 303 (M+H)⁺;

¹H NMR (400 MHz, CDCl₃): δ 8.60-8.85 (m, 2H), 7.86 (d, 1H), 7.67 (s, 1H), 7.58 (m, 1H), 7.40 (m, 1H), 7.35 (br, 1H), 6.48 (s, 1H), 2.46 (s, 3H).

Example Compound 99

Preparation of 3-(3-((3-chlorophenyl)ethynyl)-5-methyl-1H-pyrazol-1-yl)-5-fluorobenzonitrile

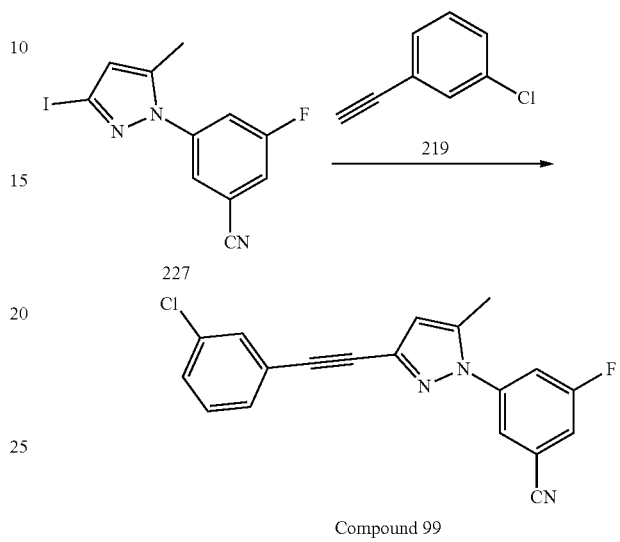

Compound 99

To a solution of 227 (100 mg, 0.306 mmol) and 2219 (0.075 ml, 0.611 mmol) in 20 mL of Et₃N was added Pd(PPh₃)₂Cl₂ (10.73 mg, 0.015 mmol) and CuI (5.82 mg, 0.031 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 99 (20 mg, yield: 19.48%).

LCMS: m/z 336 (M+H)⁺;

¹H NMR (400 MHz, CDCl₃): δ 7.67 (s, 1H), 7.59-7.55 (m, 2H), 7.4-7.29 (m, 4H), 6.45 (s, 1H), 2.46 (s, 3H).

Example Compound 100

Preparation of 3-(3-((2-chloropyridin-4-yl)ethynyl)-5-methyl-1H-pyrazol-1-yl)-5-fluorobenzonitrile

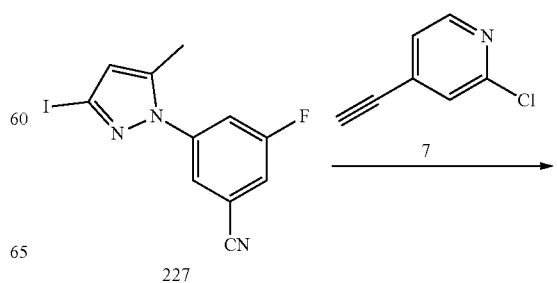

-continued

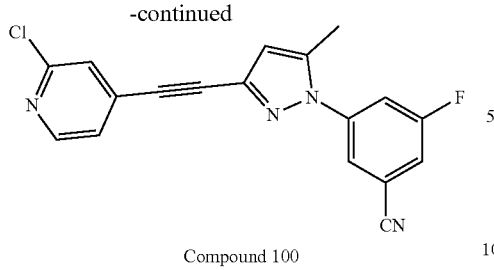

Compound 100

To a solution of 227 (100 mg, 0.306 mmol) and 7 (63.7 mg, 0.611 mmol) in 20 mL of Et$_3$N was added Pd(PPh$_3$)$_2$Cl$_2$ (10.73 mg, 0.015 mmol) and CuI (5.82 mg, 0.031 mmol). The mixture was protected with N$_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 100 (19 mg, yield: 18.46%).

LCMS: m/z 337 (M+H)$^+$;

$^1$H NMR (400 MHz, CDCl$_3$): δ 8.40-8.39 (m, 1H), 7.66 (s, 1H), 7.59-7.56 (m, 1H), 7.47 (s, 1H), 7.44-7.41 (m, 1H), 7.34-7.33 (m, 1H), 6.50 (s, 1H), 2.47 (s, 3H).

Example Compound 101

Preparation of 3-fluoro-5-(5-methyl-3-(pyrimidin-2-ylethynyl)-H-pyrazol-1-yl) Benzonitrile

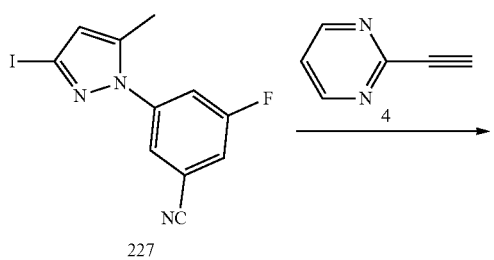

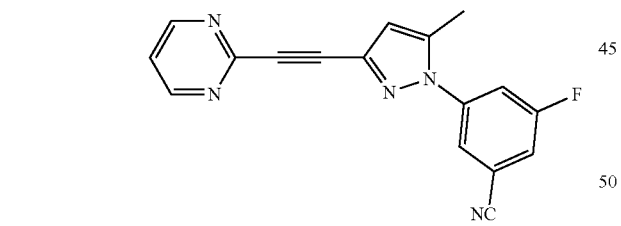

Compound 101

To a solution of 227 (100 mg, 0.306 mmol) and 4 (63.7 mg, 0.61 mmol) in 20 mL of Et$_3$N was added Pd(PPh$_3$)$_2$Cl$_2$ (10.73 mg, 0.015 mmol) and CuI (5.82 mg, 0.031 mmol). The mixture was protected with N$_2$ atmosphere, then was heated at 100° C. for 24 hours. TLC analysis showed complete conversion of starting material to a major product. The reaction mixture was then concentrated in vacuo. The crude product was purified by Prep-HPLC to give the target product Compound 101 (15 mg, yield: 16.2%).

LCMS: m/z 304 (M+H)$^+$;

$^1$H NMR (400 MHz, CDCl$_3$): δ 8.77 (d. J=4.9 Hz, 2H), 7.66 (s, 1H), 7.59 (dt, J=9.2, 2.2 Hz, 1H), 7.45-7.34 (m, 1H), 7.30-7.26 (m, 1H), 6.55 (s, 1H), 2.46 (s, 4H).

Example Compound 102

Preparation of 3-fluoro-5-(5-methyl-3-(pyridin-4-ylethynyl)-1H-pyrazol-1-yl) benzonitrile

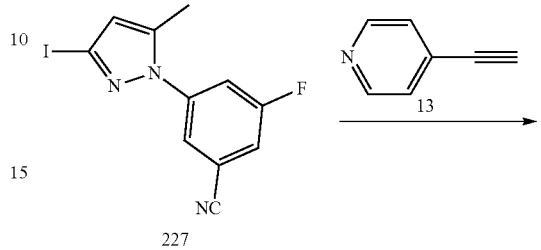

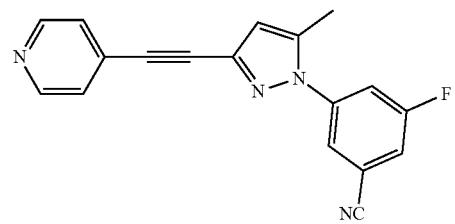

Compound 102

To a solution of 227 (100 mg, 0.306 mmol) and 13 (63.1 mg, 0.611 mmol) in 20 mL of Et$_3$N was added Pd(PPh$_3$)$_2$Cl$_2$ (10.73 mg, 0.015 mmol) and CuI (5.82 mg, 0.031 mmol). The mixture was protected with N$_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 102 (16 mg, yield: 17.31%).

LCMS: m/z 303 (M+H)$^+$;

$^1$H NMR (400 MHz, CDCl$_3$): δ 8.64 (br, 2H), 7.67-7.66 (m, 1H), 7.60-7.56 (m, 1H), 7.44-7.40 (m, 3H), 6.49 (d, J=1.2 Hz, 1H), 2.47 (d, J=0.8 Hz, 3H).

Example Compound 103

Preparation of 3-fluoro-5-(5-methyl-3-(pyrazin-2-ylethynyl)-1H-pyrazol-1-yl) Benzonitrile

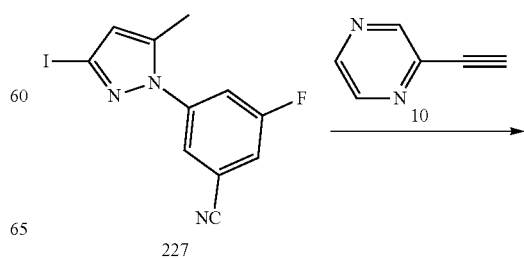

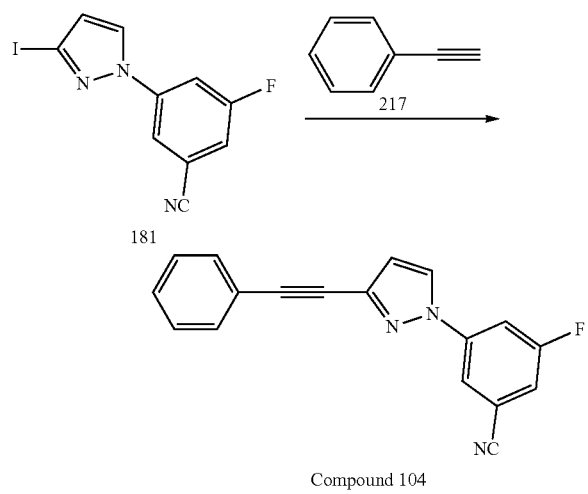

Compound 103

To a solution of 227 (100 mg, 0.306 mmol) and 10 (63.7 mg, 0.611 mmol) in 20 mL of Et₃N was added Pd(PPh₃)₂Cl₂ (10.73 mg, 0.015 mmol) and CuI (5.82 mg, 0.031 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 103 (18 mg, yield: 19.41%).

LCMS: m/z 304 (M+H)⁺;

¹H NMR (400 MHz, CDCl₃): δ 8.66-8.65 (m, 3H), 7.67 (s, 1H), 7.60-7.57 (m, 1H), 7.43-7.40 (m, 1H), 6.55 (s, 1H), 2.47 (s, 3H).

Example Compound 104

Preparation of 3-fluoro-5-(3-(phenylethynyl-1H-pyrazol-1-yl)benzonitrile

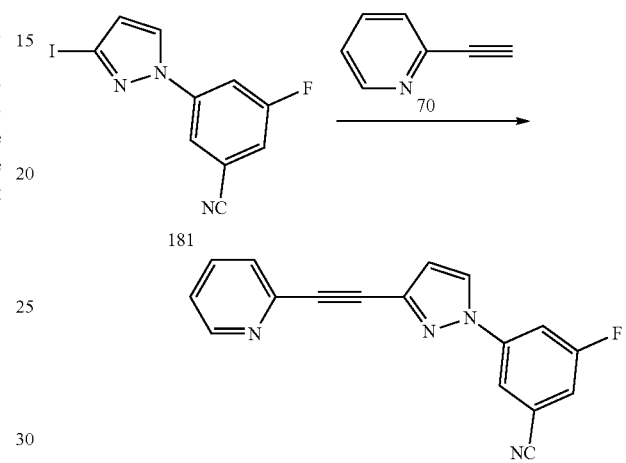

Compound 104

To a solution of 181 (100 mg, 0.319 mmol) and 217 (0.070 ml, 0.639 mmol) in 20 mL of Et₃N was added Pd(PPh₃)₂Cl₂ (11.21 mg, 0.01 mmol) and CuI (6.08 mg, 0.032 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 104 (28 mg, yield: 30.5%).

LCMS: m/z 288 (M+H)⁺;

¹H NMR (400 MHz, CDCl₃): δ 7.94 (d, J=2.8 Hz, 1H), 7.85 (d, J=0.8 Hz, 1H), 7.79 (d, J=9.2 Hz, 1H), 7.61-7.58 (m, 2H), 7.39-7.36 (m, 3H), 7.30-7.28 (m, 1H), 6.73 (d, J=1.4 Hz, 1H).

Example Compound 105

Preparation of 3-fluoro-5-(3-(pyridin-2-ylethynyl)-1H-pyrazol-1-yl)benzonitrile

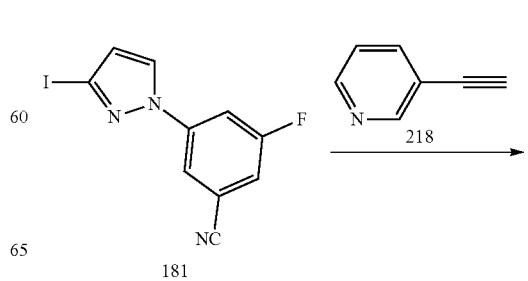

Compound 105

To a solution of 181 (100 mg, 0.319 mmol) and 70 (65.9 mg, 0.639 mmol) in 20 mL of Et₃N was added Pd(PPh₃)₂Cl₂ (11.21 mg, 0.016 mmol) and CuI (6.08 mg, 0.032 mmol). The mixture was protected with N₂ atmosphere, then was heated at 70° C. for 24 hours. TLC analysis showed to complete conversion of starting material to a major product. The reaction mixture was then concentrated in vacuo. The crude product was purified by Prep-HPLC to give the target product Compound 105 (18 mg, yield: 19.55%).

LCMS: m/z 289 (M+H)⁺;

¹H NMR (400 MHz, CDCl₃): δ 8.66 (br, 1H), 7.95 (d, J=2.4 Hz, 1H), 7.85 (s, 1H), 7.80-7.73 (m, 2H), 7.62 (d, J=8.4 Hz, 1H), 7.33-7.29 (m, 2H), 6.81 (d, J=2.4 Hz, 1H).

Example Compound 106

Preparation of 3-fluoro-5-(3-(pyridin-3-ylethynyl)-1H-pyrazol-1-yl)benzonitrile

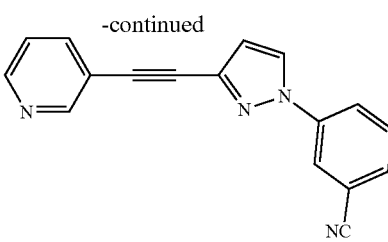

Compound 106

To a solution of 181 (100 mg, 0.319 mmol) and 218 (65.9 mg, 0.639 mmol) in 20 mL of Et₃N was added Pd(PPh₃)₂Cl₂ (11.21 mg, 0.016 mmol) and CuI (6.08 mg, 0.032 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 106 (15 mg, yield: 16.29%).

LCMS: m/z 289 (M+H)⁺;

¹H NMR (400 MHz, CDCl₃): δ 8.83 (s, 1H), 8.60 (d, J=3.6 Hz, 1H), 7.96 (d, J=2.8 Hz, 1H), 7.89 (d, J=8.0 Hz, 1H), 7.86-7.85 (m, 1H), 7.81-7.78 (m, 1H), 7.36-7.30 (m, 2H), 6.76 (d, J=2.8 Hz, 1H).

Example Compound 107

Preparation of 3-(3-((3-chlorophenyl)ethynyl)-1H-pyrazol-1-yl)-5-fluorobenzonitrile

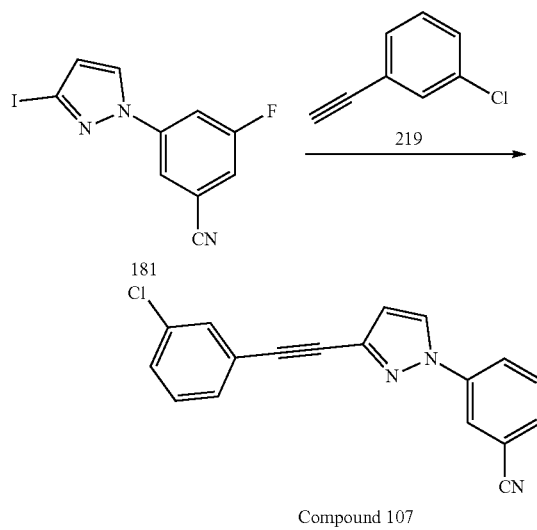

Compound 107

To a solution of 181 (100 mg, 0.319 mmol) and 219 (0.079 mL, 0.639 mmol) in 20 mL of Et₃N was added Pd(PPh)₂Cl₂ (11.21 mg, 0.016 mmol) and CuI (6.08 mg, 0.032 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 107 (25 mg, yield: 24.33%).

LCMS: m/z 322 (M+H)⁺;

¹H NMR (400 MHz, CDCl₃): δ 7.95 (d, J=2.4 Hz, 1H), 7.84 (s, 1H), 7.80-7.77 (m, 1H), 7.58-7.57 (m, 1H), 7.48-7.46 (m, 1H), 7.36-7.29 (m, 3H), 6.73 (d, J=2.8 Hz, 1H).

Example Compound 108

Preparation of 3-(3-((2-chloropyridin-4-yl)ethynyl)-1H-pyrazol-1-yl)-5-fluorobenzonitrile

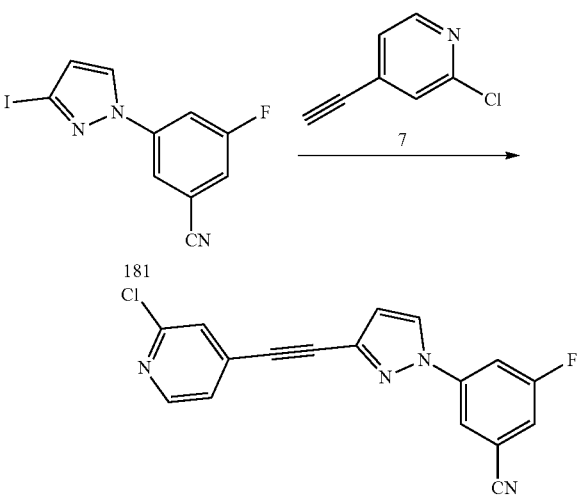

Compound 108

To a solution of 181 (100 mg, 0.319 mmol) and 7 (88 mg, 0.639 mmol) in 20 mL of Et₃N was added Pd(PPh₃)₂Cl₂ (11.21 mg, 0.016 mmol) and CuI (6.08 mg, 0.032 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 108 (15 mg, yield: 14.55%).

LCMS: m/z 323 (M+H)⁺;

¹H NMR (400 MHz, CDCl₃); δ 8.43-8.41 (m, 1H), 7.98 (d, J=2.8 Hz, 1H), 7.85 (d, J=0.8 Hz, 1H), 7.80-7.77 (m, 1H), 7.50 (d, J=0.8 Hz, 1H), 7.37-7.32 (m, 2H), 6.78 (d, J=2.8 Hz, 1H).

Example Compound 109

Preparation of 3-fluoro-5-(3-(pyrimidin-2-ylethynyl)-1H-pyrazol-1-yl)benzonitrile

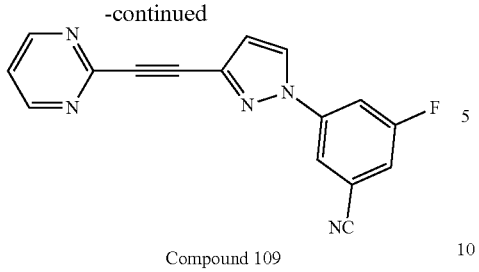

Compound 109

To a solution of 181 (100 mg, 0.319 mmol) and 4 (66.5 mg, 0.639 mmol) in 20 mL of Et$_3$N was added Pd(PPh$_3$)$_2$Cl$_2$ (11.21 mg, 0.016 mmol) and CuI (6.08 mg, 0.032 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 109 (20 mg, yield: 21.7%).

LCMS: m/z 290 (M+H)$^+$;

$^1$H NMR (400 MHz, CDCl$_3$): δ 8.79 (d, J=5.2 Hz, 2H), 7.96 (d, J=2.4 Hz, 1H), 7.84 (s, 1H), 7.80 (d, J=9.2 Hz, 1H), 7.31-7.29 (m, 2H), 6.84 (d, J=2.4 Hz, 1H).

Example Compound 110

Preparation of 3-fluoro-5-(3-(pyridin-4-ylethynyl)-H-pyrazol-1-yl)benzonitrile

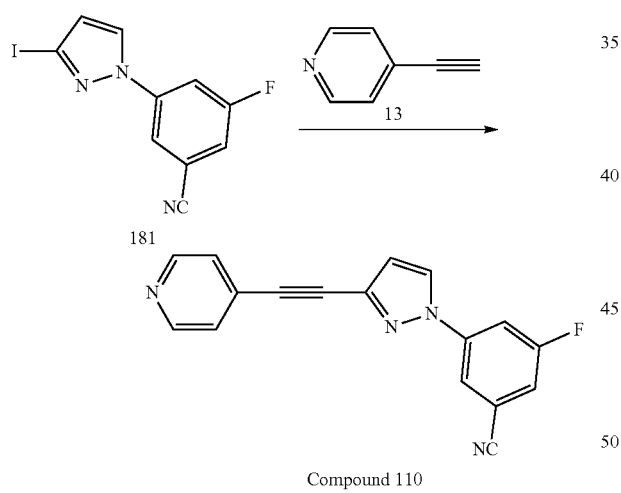

Compound 110

To a solution of 181 (100 mg, 0.319 mmol) and 13 (65.9 mg, 0.639 mmol) in 20 mL of Et$_3$N was added Pd(PPh$_3$)$_2$Cl$_2$ (11.21 mg, 0.016 mmol) and CuI (5.38 mg, 0.028 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 110 (30 mg, yield: 32.6%).

LCMS: m/z 289 (M+H)$^+$;

$^1$H NMR (400 MHz, CDCl$_3$) δ 8.65 (d, J=4.8 Hz, 2H), 7.97 (d, J=2.4 Hz, 1H), 7.86-7.85 (m, 1H), 7.80-7.78 (m, 1H), 7.47-7.45 (m, 2H), 7.33-7.31 (m, 1H), 6.78 (d, J=2.4 Hz, 1H).

Example Compound 111

Preparation of 3-fluoro-5-(3-(pyrazin-2-ylethynyl)-1H-pyrazol-1-yl)benzonitrile

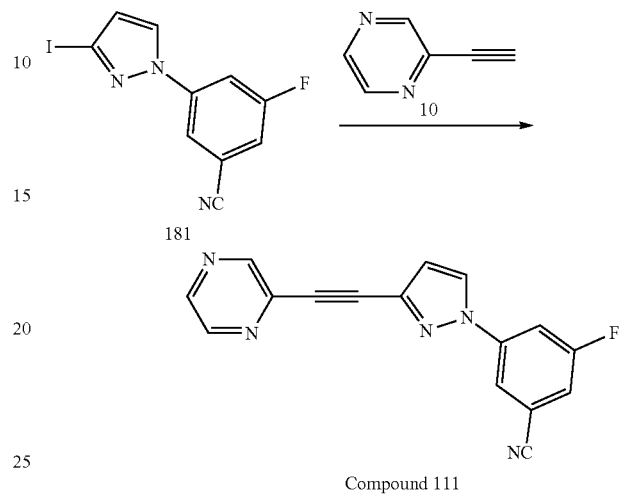

Compound 111

To a solution of 181 (100 mg, 0.319 mmol) and 10 (66.5 mg, 0.639 mmol) in 20 mL of Et$_3$N was added Pd(PPh$_3$)$_2$Cl$_2$ (11.21 mg, 0.016 mmol) and CuI (6.08 mg, 0.032 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 111 (18 mg, yield: 19.48%).

LCMS: m/z 290 (M+H)$^+$;

$^1$H NMR (400 MHz, CDCl$_3$): δ 8.84 (d, J=1.6 Hz, 1H), 8.63-8.62 (m, 1H), 8.55 (d, J=2.4 Hz, 1H), 7.97 (d, J=2.8 Hz, 1H), 7.85 (t, 1H), 7.79 (d, J=9.2 Hz, 1H), 7.34-7.32 (m, 1H), 6.83 (d, J=2.4 Hz, 1H).

Example Compound 112

Preparation of 2-((1-(4-fluorophenyl)-1H-pyrazol-3-yl)ethynyl)pyridine

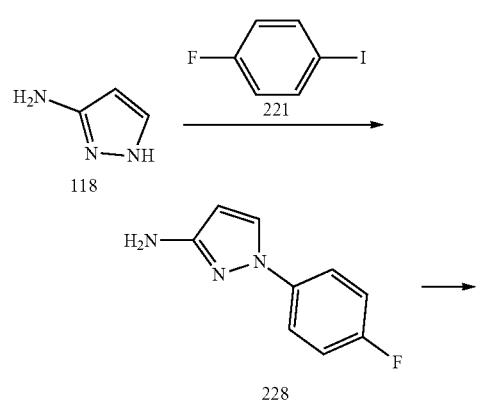

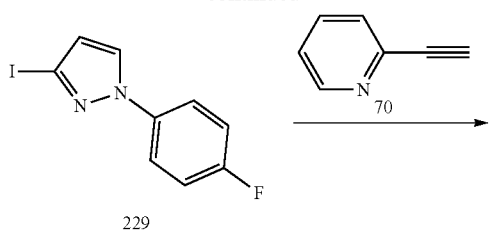

229

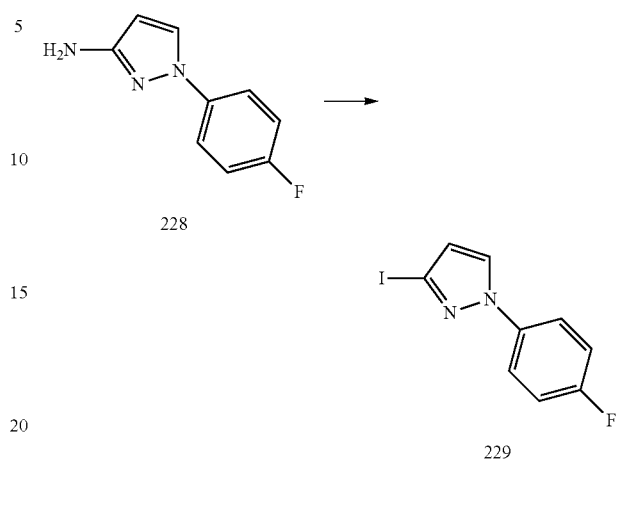

Procedure for Preparation of 229

228

229

To a solution of 228 (0.5 g, 2.82 mmol) in concentrated HCl solution (18 mL) was added a solution of $NaNO_2$ (0.195 g, 2.82 mmol) in water (2 mL) over 3 minutes at 0° C. A solution of KI (0.468 g, 2.82 mmol) in water (3 mL) was added to the reaction mixture over 5 minutes, resulting in nitrogen evolution. The reaction mixture was stirred for 5 minutes. Water was added, the aqueous mixture was extracted with EA, washed with $NaS_2O_3$ two times, dried over $Na_2SO_4$, and concentrated in vacuo. The crude residue was purified by flash chromatography to obtain the target product 229 (0.1 g, yield: 12.30%).

$^1$H NMR (400 MHz, $CDCl_3$): δ 7.67 (d, J=2.5 Hz, 1H), 7.61-7.09 (m, 2H), 7.17-7.09 (m, 2H), 6.62 (d, J=2.4 Hz, 1H).

Compound 112

Experimental Section

Procedure for Preparation 228

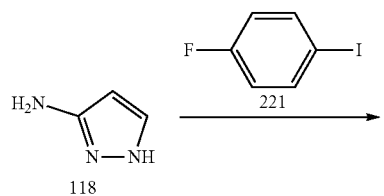

118    221

Procedure for Preparation Compound 112

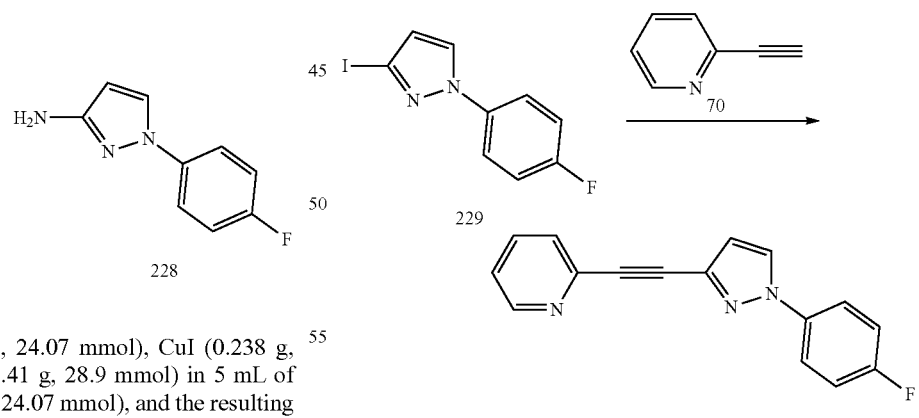

229

Compound 112

To a solution of 118 (2 g, 24.07 mmol), CuI (0.238 g, 2.407 mmol) and $Cs_2CO_3$ (9.41 g, 28.9 mmol) in 5 mL of DMF was added 221 (5.34 g, 24.07 mmol), and the resulting mixture was heated at 140° C. via MW irradiation for 30 minutes. The mixture was cooled to room temperature, and diluted with EA, washed with $H_2O$ (20 mL×3). The combined organic layer was washed with saturated NaCl and dried over $Na_2SO_4$, filtered, and concentrated in vacuo. The residue was purified by column chromatography on silica gel to afford 228 (1 g, yield: 23.45%). $^1$H NMR (400 MHz, DMSO-$d_6$): δ 8.09 (d, J=2.5 Hz, 1H), 7.75-7.61 (m, 2H), 7.28-7.16 (m, 2H), 5.73 (d, J=2.5 Hz, 1H), 5.07 (s, 2H).

To a solution of 229 (100 mg, 0.347 mmol) and 70 (0.070 ml, 0.694 mmol) in 20 mL of $Et_3N$ was added $Pd(PPh_3)_2Cl_2$ (12.18 mg, 0.017 mmol) and CuI (6.61 mg, 0.035 mmol). The mixture was protected with $N_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 112 (25 mg, yield: 27.4%).

LCMS: m/z 264 (M+H)+;

$^1$H NMR (400 MHz, CDCl$_3$): δ 8.64 (d, J=4.8 Hz, 1H), 7.86 (d, J=2.4 Hz, 1H), 7.72-7.67 (m, 3H), 7.61-7.59 (m, 1H), 7.30-7.27 (m, 1H), 7.19-7.14 (m, 2H), 6.75 (d, J=2.4 Hz, 1H).

Example Compound 113

Preparation of 1-(4-fluorophenyl)-3-(phenylethynyl)-1H-pyrazole

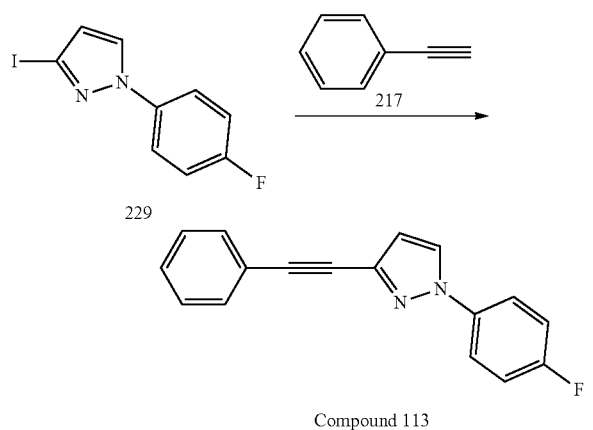

Compound 113

To a solution of 229 (75 mg, 0.260 mmol) and 217 (0.042 mL, 0.382 mmol) in 20 mL of Et$_3$N was added Pd(PPh$_3$)$_2$Cl$_2$ (9.14 mg, 0.013 mmol) and CuI (4.96 mg, 0.026 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 113 (20 mg, yield: 29.3%).

LCMS: m/z 263 (M+H)+;

$^1$H NMR (400 MHz, CDCl$_3$): δ 7.85 (d, J=2.5 Hz, 1H), 7.72-7.66 (m, 2H), 7.61-7.56 (m, 2H), 7.39-7.34 (m, 3H), 7.20-7.12 (m, 2H), 6.67 (d, J=2.5 Hz, 1H).

Example Compound 114

Preparation of 3-((1-(4-fluorophenyl)-1H-pyrazol-3-yl)ethynyl)pyridine

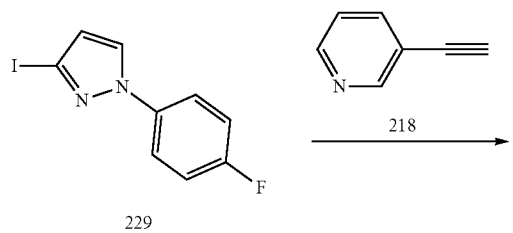

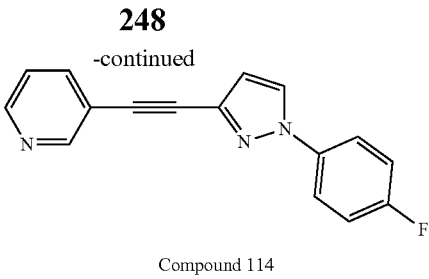

Compound 114

To a solution of 229 (100 mg, 0.347 mmol) and 218 (71.6 mg, 0.694 mmol) in 20 mL of Et$_3$N was added Pd(PPh$_3$)$_2$Cl$_2$ (12.18 mg, 0.017 mmol) and CuI (6.61 mg, 0.035 mmol). The mixture was protected with N$_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 114 (19 mg, yield: 20.79%).

LCMS: m/z 264 (M+H)+;

$^1$H NMR (400 MHz, DMSO-d$_6$): δ 8.83-8.61 (m, 3H), 8.03 (d, J=7.6 Hz, 1H), 7.95-7.90 (m, 2H), 7.51-7.49 (m, 1H), 7.42-7.37 (m, 2H), 6.89 (d, J=2.8 Hz, 1H).

Example Compound 115

Preparation of 3-((3-chlorophenyl)ethynyl)-1-(4-fluorophenyl)-1H-pyrazole

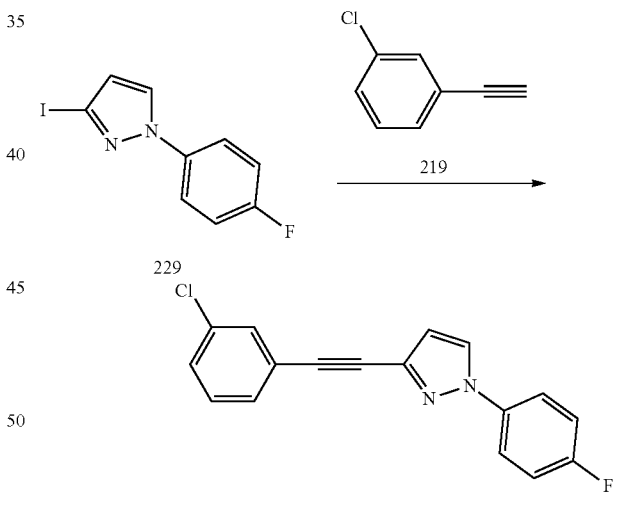

Compound 115

To a solution of 229 (100 mg, 0.347 mmol) and 219 (0.085 ml, 0.694 mmol) in 20 mL of Et$_3$N was added Pd(PPh$_3$)$_2$Cl$_2$ (12.18 mg, 0.017 mmol) and CuI (6.61 mg, 0.035 mmol). The mixture was protected with N$_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 115 (21 mg, yield: 20.39%).

LCMS: m/z 297 (M+H)+;

¹H NMR (400 MHz, CDCl₃): δ 7.86 (d, J=2.4 Hz, 1H), 7.71-7.67 (m, 2H), 7.57-7.56 (m, 1H), 7.46 (d, J=7.6 Hz, 1H), 7.33-7.29 (m, 2H), 7.19-7.14 (m, 2H), 6.67 (d, J=2.4 Hz, 1H).

Example Compound 116

Preparation of 2-chloro-4-((1-(4-fluorophenyl)-1H-pyrazol-3-yl)ethynyl)pyridine

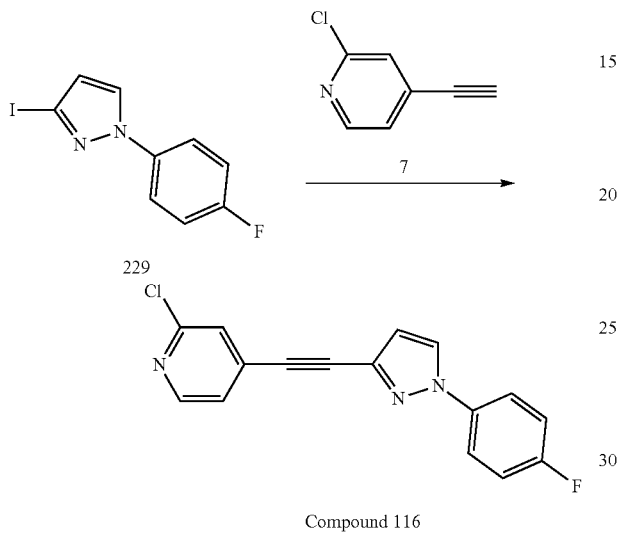

Compound 116

To a solution of 229 (100 mg, 0.347 mmol) and 7 (96 mg, 0.694 mmol) in 20 mL of Et₃N was added Pd(PPh₃)₂Cl₂ (12.18 mg, 0.017 mmol) and CuI (6.61 mg, 0.035 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 116 (20 mg, yield: 19.35%).

LCMS: m/z 298 (M+H)⁺;

¹H NMR (400 MHz, CDCl₃): δ 8.40-8.38 (m, 1H), 7.88 (d, J=2.8 Hz, 1H), 7.70-7.67 (m, 2H), 7.48 (d, J=0.8 Hz, 1H), 7.36-7.34 (m, 1H), 7.20-7.16 (m, 2H), 6.72 (d, J=2.4 Hz, 1H).

Example Compound 117

Preparation of 2-((1-(4-fluorophenyl)-1H-pyrazol-3-yl)ethynyl)pyrimidine

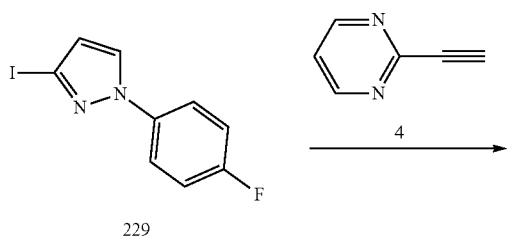

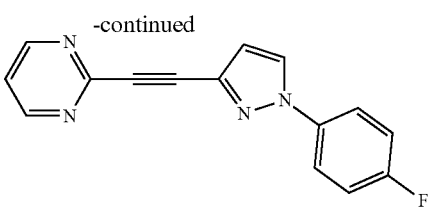

Compound 117

To a solution of 229 (100 mg, 0.347 mmol) and 4 (72.3 mg, 0.694 mmol) in 20 mL of Et₃N was added Pd(PPh₃)₂Cl₂ (12.18 mg, 0.017 mmol) and CuI (6.61 mg, 0.035 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 117 (18 mg, yield: 19.62%).

LCMS: m/z 265 (M+H)⁺;

¹H NMR (400 MHz, CDCl₃): δ8.77 (d. J=4.8 Hz, 2H), 7.87 (d, J=2.4 Hz, 1H), 7.71-7.68 (m, 2H), 7.28-7.26 (m, 1H), 7.19-7.15 (m, 2H), 6.79 (d, J=2.8 Hz, 1H).

Example Compound 118

Preparation of 4-((1-(4-fluorophenyl)-1H-pyrazol-3-yl)ethynyl)pyridine

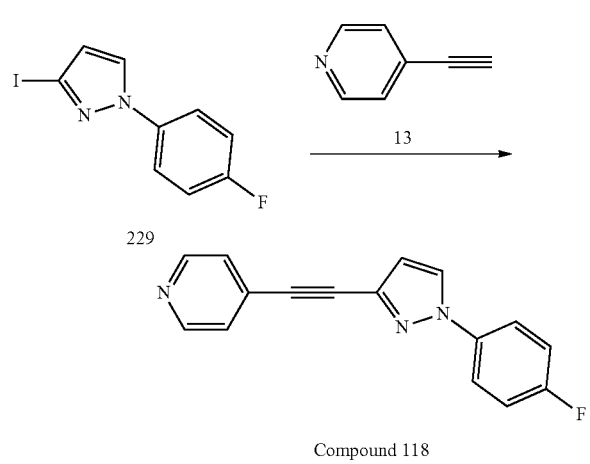

Compound 118

To a solution of 229 (100 mg, 0.347 mmol) and 13 (71.6 mg, 0.694 mmol) in 20 mL of Et₃N was added Pd(PPh₃)₂Cl₂ (12.18 mg, 0.017 mmol) and CuI (6.61 mg, 0.035 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 118 (20 mg, yield: 21.88%).

LCMS: m/z 264 (M+H)⁺;

¹H NMR (400 MHz, CDCl₃); δ 8.63 (br, 2H), 7.88 (d, J=2.4 Hz, 1H), 7.71-7.68 (m, 2H), 7.47 (d, J=5.2 Hz, 2H), 7.20-7.16 (m, 2H), 6.72 (d, J=2.4 Hz, 1H).

Example Compound 119

Preparation of 2-((1-(4-fluorophenyl)-H-pyrazol-3-yl)ethynyl)pyrazine

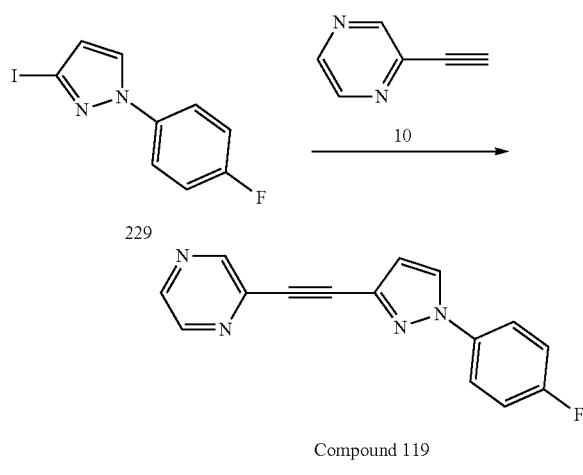

Compound 119

To a solution of 229 (100 mg, 0.347 mmol) and 10 (72.3 mg, 0.694 mmol) in 20 mL of Et₃N was added Pd(PPh₃)₂Cl₂ (12.18 mg, 0.017 mmol) and CuI (6.61 mg, 0.035 mmol). The mixture was protected with N₂ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 119 (23 mg, yield: 25.07%).

LCMS: m/z 265 (M+H)$^+$;

$^1$H NMR (400 MHz, CDCl₃): δ 8.82 (d, J=1.2 Hz, 1H), 8.61-8.60 (m, 1H), 8.52 (d, J=2.4 Hz, 1H), 7.88 (d, J=2.4 Hz, 1H), 7.71-7.68 (m, 2H), 7.20-7.15 (m, 2H), 6.77 (d, J=2.4 Hz, 1H).

Example Compound 120

Preparation of 3-(phenylethynyl-1-(4-(trifluoromethoxy)phenyl)-1H-pyrazole

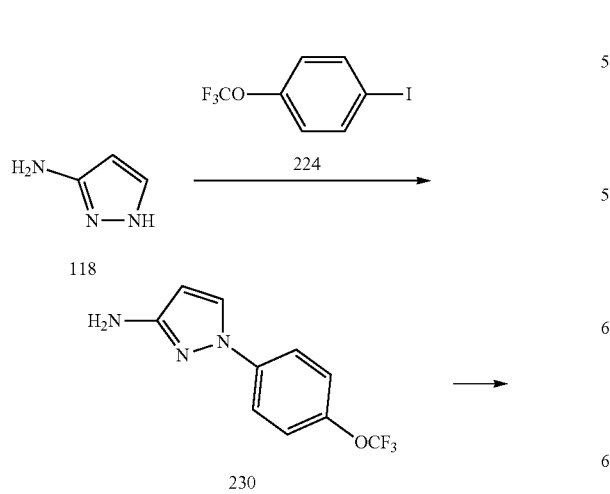

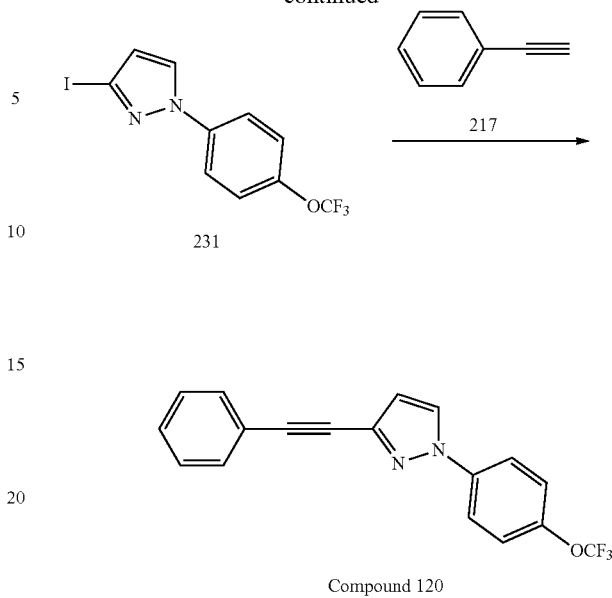

Compound 120

Experimental Section

Procedure for Preparation of 230

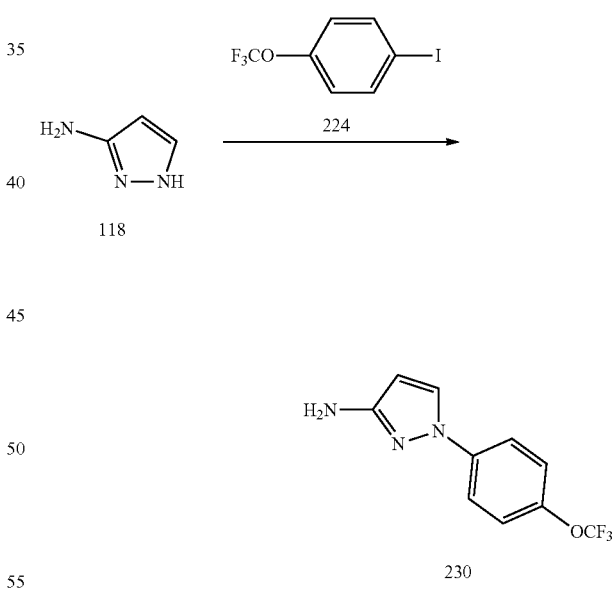

To a solution of 118 (2 g, 24.07 mmol), CuCl (0.238 g, 2.407 mmol) and Cs₂CO₃ (8.63 g, 26.5 mmol) in 5 mL of DMF was added 224 (6.93 g, 24.07 mmol) and the resulting mixture was heated at 130° C. via MW irradiation for 30 minutes. The mixture was cooled to room temperature, and diluted with EA, washed with H₂O (20 mL×3). The combined organic layer was washed with saturated NaCl and dried over Na₂SO₄, filtered, and concentrated in vacuo. The residue was purified by column chromatography on silica gel to afford 230 (1 g, yield: 17.08%).

Procedure for Preparation of 231

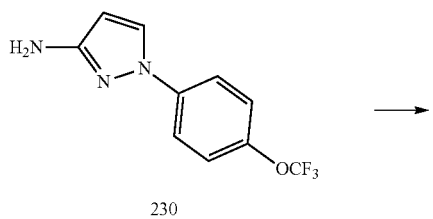

230

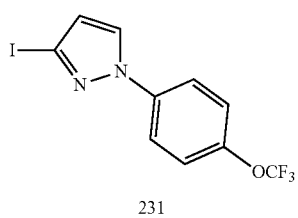

231

To a solution of 230 (0.5 g, 2.056 mmol) in concentrated HCl solution (10 mL) was added a solution of NaNO$_2$ (0.170 g, 2.467 mmol) in water (2 mL) over 3 minutes at 0° C. A solution of KI (0.444 g, 2.67 mmol) in water (3 mL) was added to the reaction mixture over 5 minutes, resulting in nitrogen evolution. The reaction mixture was stirred for 5 minutes. Water was added, the aqueous mixture was extracted with EA, washed with NaS$_2$O$_3$ two times, dried over Na$_2$SO$_4$, and concentrated in vacuo. The crude residue was purified by flash chromatography to give the product 231 (0.2 g, yield: 27.5%).

LCMS: m/z 355 (M+H)$^+$.

Preparation of Compound 120

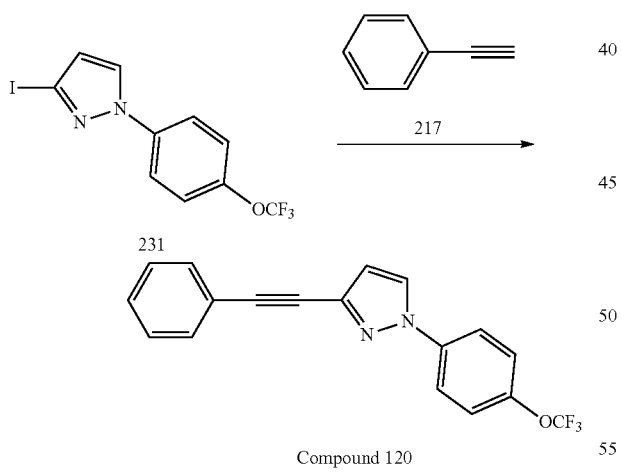

To a solution of 231 (100 mg, 0.282 mmol) and 217 (0.062 ml, 0.565 mmol) in 20 mL of Et$_3$N was added Pd(PPh$_3$)$_2$Cl$_2$ (9.91 mg, 0.014 mmol) and CuI (5.38 mg, 0.028 mmol). The mixture was protected with N$_2$ atmosphere, then was heated at 70° C. for 24 hours. TLC analysis showed complete conversion of starting material to a major product. The reaction mixture was then concentrated in vacuo. The crude product was purified by Prep-HPLC to give the target product Compound 120 (23 mg, yield: 24.81%).

LCMS: m/z 329 (M+H)$^+$;

$^1$H NMR (400 MHz, CDCl$_3$): δ 7.90 (d, J=2.4 Hz, 1H), 7.78-7.75 (m, 2H), 7.60-7.58 (m, 2H), 7.38-7.31 (m, 5H), 6.68 (d, J=2.4 Hz, 1H).

Example Compound 121

Preparation of 3-((1-(4-(trifluoromethoxy)phenyl)-1H-pyrazol-3-yl)ethynyl) pyridine

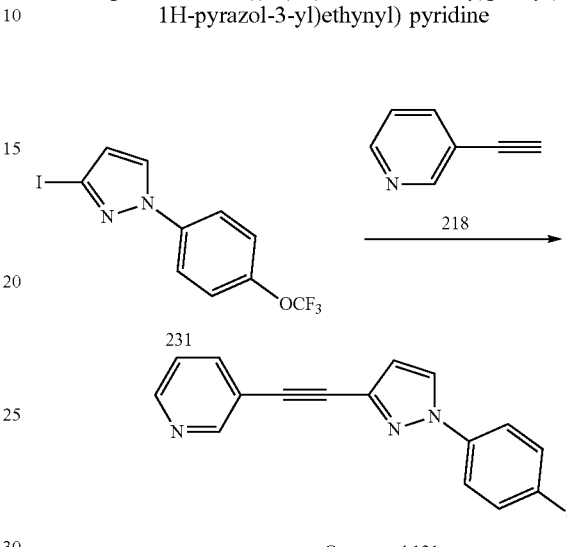

Compound 121

To a solution of 231 (100 mg, 0.282 mmol) and 218 (58.2 mg, 0.565 mmol) in 20 mL of Et$_3$N was added Pd(PPh$_3$)$_2$Cl$_2$ (9.91 mg, 0.014 mmol) and CuI (5.38 mg, 0.028 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by silica gel column chromatography to give the target product Compound 121 (18 mg, yield: 19.36%).

LCMS: m/z 330 (M+H)$^+$;

$^1$HNMR (400 MHz, CDCl$_3$): δ 8.82 (s, 1H), 8.58 (s, 1H), 7.92 (d, J=2.8 Hz, 1H), 7.88-7.85 (m, 1H), 7.78-7.74 (m, 2H), 7.34-7.29 (m, 3H), 6.71 (d, J=2.4 Hz, 1H).

Example Compound 122

Preparation of 3-((3-chlorophenyl)ethynyl)-1-(4-(trifluoromethoxy)phenyl)-1H-pyrazole

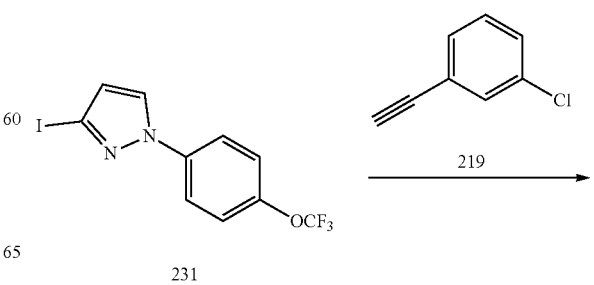

231

-continued

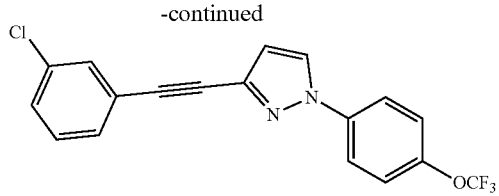

Compound 122

To a solution of 231 (100 mg, 0.282 mmol) and 219 (77 mg, 0.565 mmol) in 20 mL of Et₃N was added Pd(PPh₃)₂Cl₂ (9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 122 (22 mg, yield: 21.47%).

LCMS: m/z 363 (M+H)⁺;

¹H NMR (400 MHz, CDCl₃): δ 7.91 (d, J=2.4 Hz, 1H), 7.77-7.75 (m, 2H), 7.57 (d, J=1.2 Hz, 1H), 7.46 (d, J=7.2 Hz, 1H), 7.34-7.29 (m, 4H), 6.69 (d, J=2.4 Hz, 1H).

Example Compound 123

Preparation of 2-((1-(4-(trifluoromethoxy)phenyl)-1H-pyrazol-3-yl)ethynyl) pyrimidine

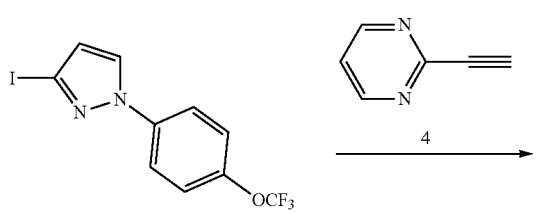

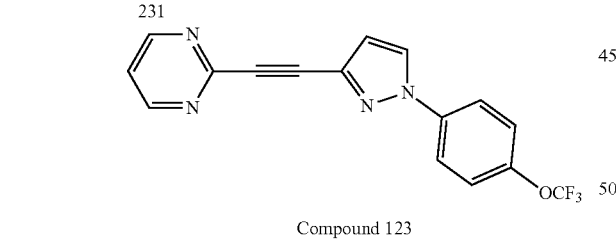

Compound 123

To a solution of 231 (100 mg, 0.282 mmol) and 4 (58.8 mg, 0.565 mmol) in 20 mL of Et₃N was added Pd(PPh₃)₂Cl₂ (9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 123 (22 mg, yield: 23.59%).

LCMS: m/z 331 (M+H)⁺;

¹H NMR (400 MHz, CDCl₃): δ 8.77 (d, 4.8 Hz, 2H), 7.92 (d, J=2.4 Hz, 1H), 7.78-7.76 (m, 2H), 7.34-7.32 (m, 2H), 7.29-7.26 (m, 1H), 6.80 (d, J=2.8 Hz, 1H).

Example Compound 124

Preparation of 4-((1-(4-(trifluoromethoxy)phenyl)-1H-pyrazol-3-yl)ethynyl) pyridine

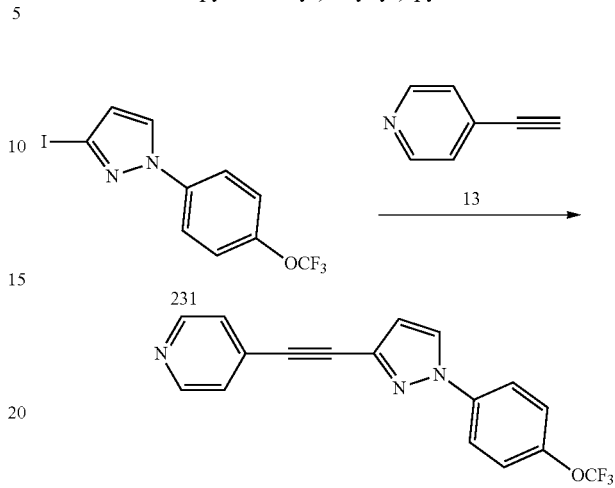

Compound 124

To a solution of 231 (100 mg, 0.282 mmol) and 13 (58.2 mg, 0.565 mmol) in 20 mL of Et₃N was added Pd(PPh₃)₂Cl₂ (9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 124 (19 mg, yield: 20.43%).

LCMS: m/z 330 (M+H)⁺;

¹H NMR (400 MHz, CDCl₃): δ 8.64 (s, 2H), 7.93 (d, J=2.4 Hz, 1H), 7.78-7.74 (m, 2H), 7.45 (d, J=5.2 Hz, 2H), 7.34 (d, J=8.4 Hz, 2H), 6.73 (d, J=2.4 Hz, 1H).

Example Compound 125

Preparation of 2-((1-(4-(trifluoromethoxy)phenyl)-1H-pyrazol-3-yl)ethynyl) pyrazine

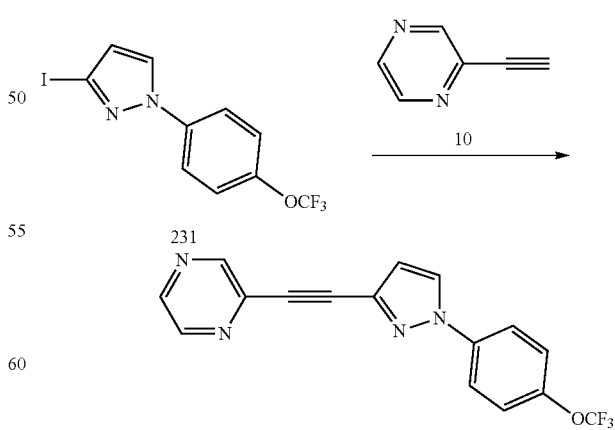

Compound 125

To a solution of 231 (100 mg, 0.282 mmol) and 10 (58.8 mg, 0.565 mmol) in 20 mL of Et₃N was added Pd(PPh₃)₂Cl₂

(9.91 mg, 0.014 mmol) and CuI (5.38 mg, 0.028 mmol). The mixture was protected with N₂ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 125 (23 mg, yield: 24.66%).

LCMS: m/z 331 (M+H)$^+$;

$^1$H NMR (400 MHz, CDCl$_3$): δ 8.83 (d, J=6.4 Hz, 1H), 8.62 (s, 1H), 8.54 (s, 1H), 7.93 (d, J=2.4 Hz, 1H), 7.79-7.75 (m, 2H), 7.35-7.33 (m, 2H), 6.79 (d, J=2.4 Hz, 1H).

Example Compound 126

Preparation of 2-((1-(4-fluorophenyl)-5-methyl-1H-pyrazol-3-yl)ethynylpyridine

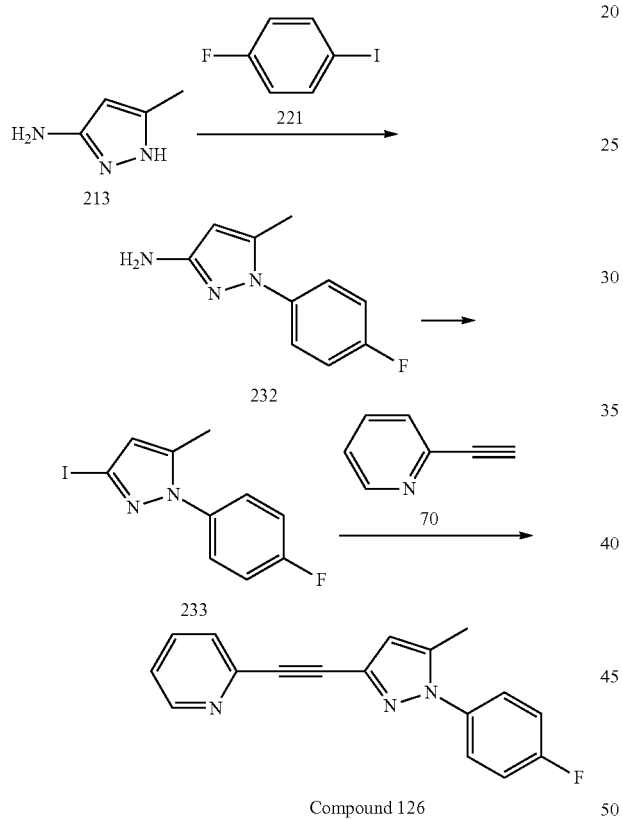

Compound 126

Experimental Section

Procedure for Preparation of 232

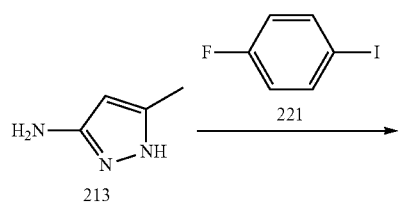

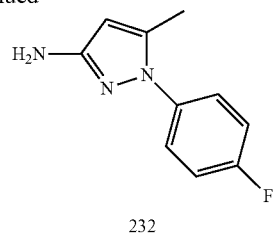

232

To a solution of 213 (1 g, 10.30 mmol), CuCl (0.102 g, 1.030 mmol), Cs₂CO₃ (4.03 g, 12.36 mmol) and quinolin-8-ol (0.149 g, 1.030 mmol) in 10 mL of t-BuOH was added 221 (2.286 g, 10.30 mmol), and the resulting mixture was heated at 130° C. via MW irradiation for 30 minutes. The mixture was cooled to room temperature, and diluted with EA, washed with H₂O (20 mL×3). The combined organic layer was washed with saturated NaCl and dried over Na₂SO₄, filtered, and concentrated in vacuo. The residue was purified by column chromatography on silica gel to afford 220 (0.5 g, yield: 25.4%).

Procedure for Preparation of 233

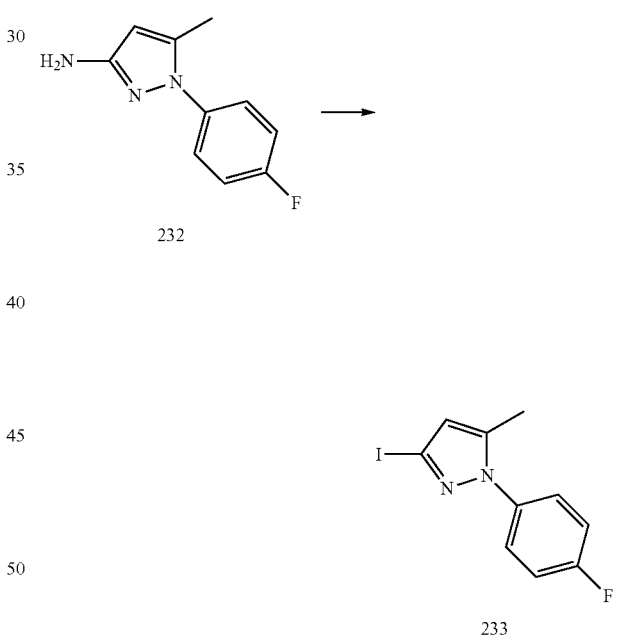

To a solution of 232 (1.2 g, 6.28 mmol) in concentrated HCl solution (18 mL) was added a solution of NaNO₂ (0.650 g, 9.41 mmol) in water (2 mL) over 3 minutes at 0° C. A solution of KI (1.302 g, 7.84 mmol) in water (3 mL) was added to the reaction mixture over 5 minutes, resulting in nitrogen evolution. The reaction mixture was stirred for 15 minutes. Water was added, the aqueous mixture was extracted with EA, washed with NaS₂O₃ for two times, dried over Na₂SO₄, and concentrated in vacuo. The crude residue was purified by flash chromatography to give product 233 (0.5 g, yield: 26.4%).

LCMS: m/z 303 (M+H)$^+$.

Preparation of Compound 126

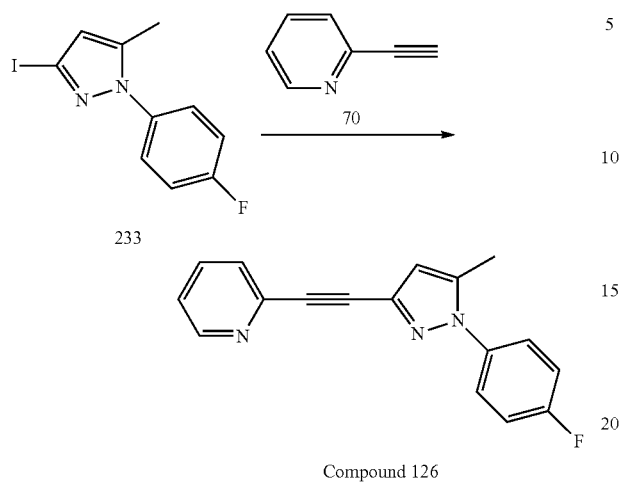

Compound 126

To a solution of 233 (100 mg, 0.331 mmol) and 70 (68.3 mg, 0.662 mmol) in 20 mL of Et$_3$N was added Pd(PPh$_3$)$_2$Cl$_2$ (11.62 mg, 0.017 mmol) and CuI (6.30 mg, 0.033 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 126 (25 mg, yield: 27.2%).

LCMS: m/z 278 (M+H)$^+$;

$^1$H NMR (400 MHz, CDCl$_3$): δ 8.61 (d, J=4.0, 1H), 7.68-7.66 (m, 1H), 7.56-7.54 (m, 1H), 7.46-7.43 (m, 2H), 7.25 (d, J=5.2 Hz, 1H), 7.19-7.15 (m, 2H), 6.47 (d, J=0.8 Hz, 1H), 2.32 (d, J=0.8 Hz, 3H).

Example Compound 127

Preparation of 3-((1-(4-fluorophenyl)-5-methyl-1H-pyrazol-3-yl)ethynyl)pyridine

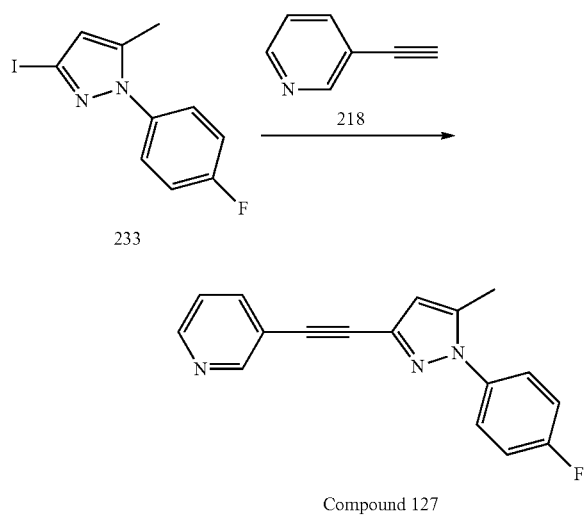

Compound 127

To a solution of 233 (100 mg, 0.331 mmol) and 218 (68.3 mg, 0.662 mmol) in 20 mL of Et$_3$N was added Pd(PPh$_3$)$_2$Cl$_2$ (11.62 mg, 0.017 mmol) and CuI (6.30 mg, 0.033 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 127 (23 mg, yield: 25.06%).

LCMS: m/z 278 (M+H)$^+$;

$^1$H NMR (400 MHz, CDCl$_3$): δ 8.80 (br, 1H), 8.56 (br, 1H), 7.84 (d, J=7.6 Hz, 1H), 7.47-7.43 (m, 2H), 7.31-7.28 (m, 1H), 7.20-7.16 (m, 2H), 6.43 (s, 1H), 2.33 (s, 3H).

Example Compound 128

Preparation of 2-((1-(4-fluorophenyl)-5-methyl-1H-pyrazol-3-yl)ethynyl)

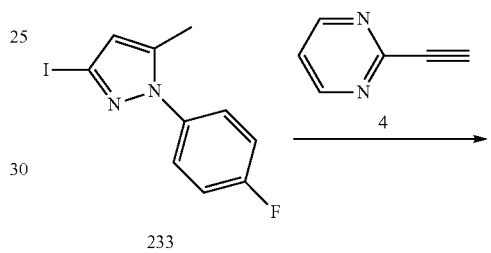

Compound 128

To a solution of 233 (100 mg, 0.331 mmol) and 4 (68.9 mg, 0.662 mmol) in 20 mL of Et$_3$N was added Pd(PPh)$_2$Cl$_2$ (11.62 mg, 0.017 mmol) and Cu (6.30 mg, 0.033 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 128 (17 mg, yield: 18.45%).

LCMS: m/z 279 (M+H)$^+$;

$^1$H NMR (400 MHz, CDCl$_3$): δ 8.75 (d, J=5.2 Hz, 2H), 7.47-7.43 (m, 2H), 7.25 (d, J=4.8 Hz, 1H), 7.17 (t, J=8.6 Hz, 2H), 6.51 (s, 1H), 2.33 (s, 3H).

Example Compound 129

Preparation of 2-((1-(4-fluorophenyl)-5-methyl-1H-pyrazol-3-yl)ethynyl)pyrazine

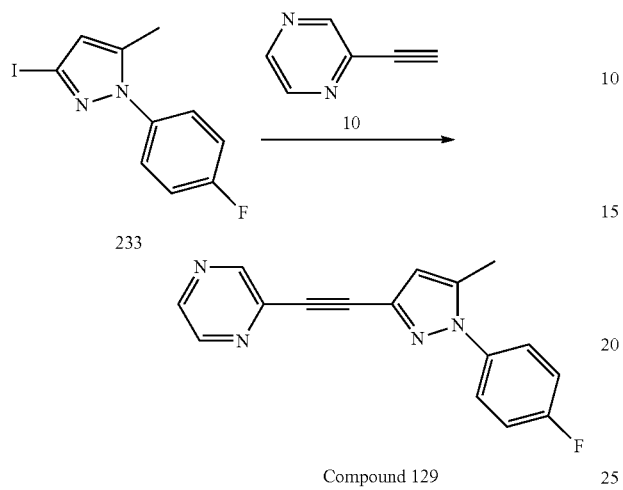

Compound 129

To a solution of 233 (100 mg, 0.331 mmol) and 10 (68.9 mg, 0.662 mmol) in 20 mL of Et$_3$N was added Pd(PPh$_3$)$_2$Cl$_2$ (11.62 mg, 0.017 mmol) and CuI (6.30 mg, 0.033 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 129 (25 mg, yield: 27.1%).

LCMS: m/z 279 (M+H)$^+$;

$^1$H NMR (400 MHz, CDCl$_3$): δ 8.79 (br, 1H), 8.59 (br, 1H), 8.51 (br, 1H), 7.47-7.43 (m, 2H), 7.20-7.16 (m, 2H), 6.50 (s, 1H), 2.34 (s, 3H).

Example Compound 130

Preparation of 4-((1-(4-fluorophenyl)-5-methyl-1H-pyrazol-3-yl)ethynyl) pyridine

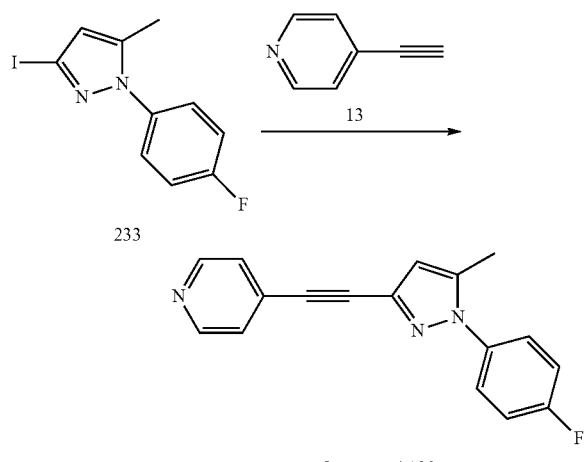

Compound 130

To a solution of 233 (100 mg, 0.331 mmol) and 13 (68.3 mg, 0.662 mmol) in 20 mL of Et$_3$N was added Pd(PPh$_3$)$_2$Cl$_2$ (11.62 mg, 0.017 mmol) and CuI (6.30 mg, 0.033 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 130 (25 mg, yield: 27.2%).

LCMS: m/z 278 (M+H)$^+$;

$^1$H NMR (400 MHz, CDCl$_3$): δ 9.5-8.0 (br, 2H), 7.45-7.42 (m, 4H), 7.19-7.15 (t, J=8.4 Hz, 2H), 6.43 (s, 1H), 2.32 (s, 3H).

Example Compound 131

Preparation of 2-chloro-4-((1-(4-fluorophenyl)-5-methyl-1H-pyrazol-3-yl)ethynyl) pyridine

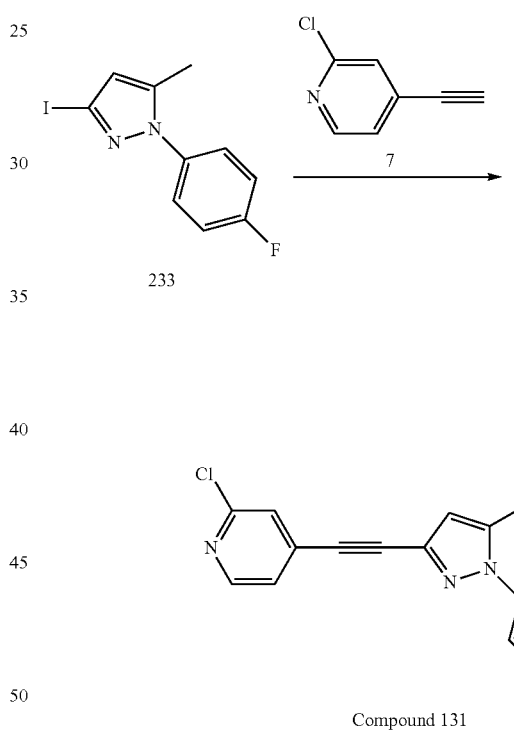

Compound 131

To a solution of 233 (100 mg, 0.331 mmol) and 7 (91 mg, 0.662 mmol) in 20 mL of Et$_3$N was added Pd(PPh$_3$)$_2$Cl$_2$ (11.62 mg, 0.017 mmol) and CuI (6.30 mg, 0.033 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 131 (21 mg, yield: 20.4%)

LCMS: m/z 312 (M+H)$^+$;

$^1$H NMR (400 MHz, CDCl$_3$): δ 8.37-8.36 (m, 1H), 7.46-7.42 (m, 3H), 7.32-7.30 (m, 1H), 7.18 (t, J=8.6 Hz, 2H), 6.44 (d, J=0.8 Hz, 1H), 2.33 (d, J=0.4 Hz, 3H).

Example Compound 132

Preparation of 3-((5-methyl-1-(4-(trifluoromethoxy)phenyl)-1H-pyrazol-3-yl) ethynyl)pyridine

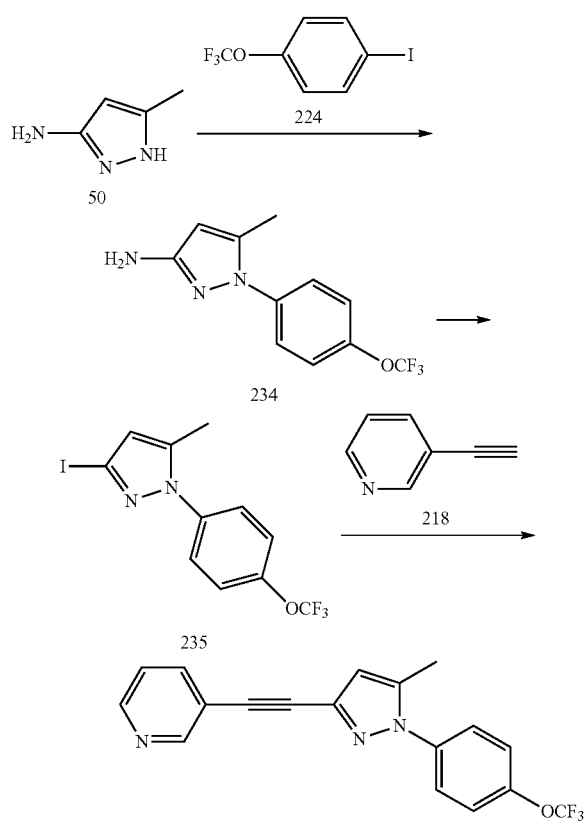

Experimental Section

Procedure for Preparation of 234

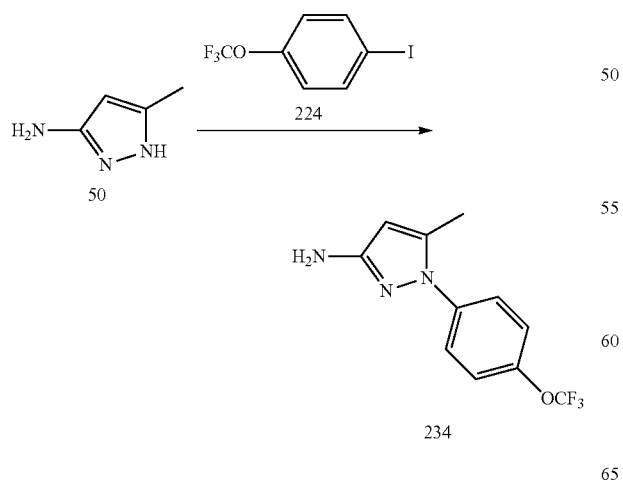

To a solution of 50 (1 g, 10.30 mmol), CuI (0.102 g, 1.030 mmol), Cs₂CO₃ (4.03 g, 12.36 mmol) and quinolin-8-ol (0.299 g, 2.059 mmol) in 5 mL of t-BuOH was added 224 (2.67 g, 9.27 mmol), and the resulting mixture was heated at 130° C. via MW irradiation for 30 minutes. The mixture was cooled to room temperature, and diluted with EA, washed with H₂O (20 mL×3). The combined the organic layer was washed with saturated NaCl and dried over Na₂SO₄, filtered, and concentrated in vacuo. The residue was purified by column chromatography on silica gel to afford 234 (0.4 g, yield: 15.10%).

Procedure for Preparation of 235

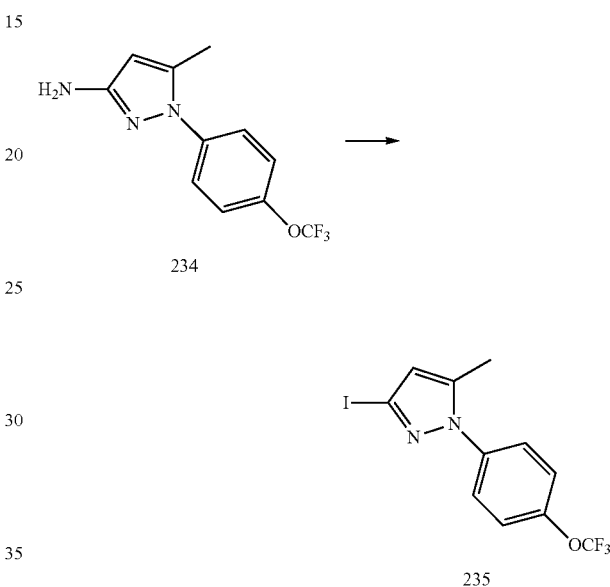

To a solution of 234 (1.3 g, 5.05 mmol) in concentrated HCl solution (15 mL) was added a solution of NaNO₂ (0.384 g, 5.56 mmol) in water (2 mL) over 3 minutes at 0° C. A solution of KI (1.007 g, 6.07 mmol) in water (3 mL) was added to the reaction mixture over 5 minutes, resulting in nitrogen evolution. The reaction mixture was stirred for 15 minutes. Water was added, the aqueous mixture was extracted with EA, washed with NaS₂O₃ two times, dried over Na₂SO₄, and concentrated in vacuo. The crude residue was purified by flash chromatography to give product 235 (0.6 g, yield: 32.3%).

LCMS: m/z 369 (M+H)⁺.

Preparation of Compound 132

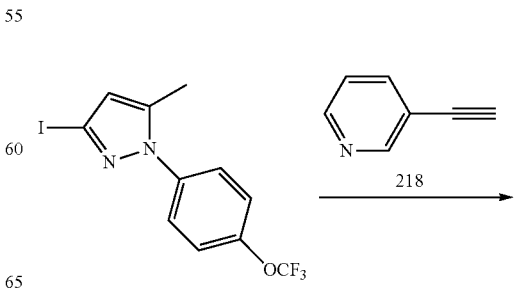

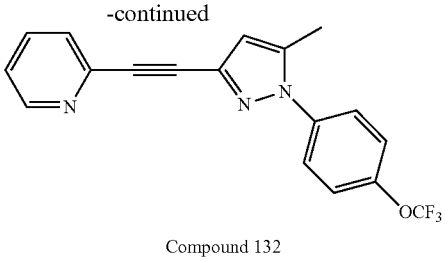

Compound 132

To a solution of 235 (100 mg, 0.272 mmol) and 218 (56.0 mg, 0.543 mmol) in 20 mL of Et$_3$N was added Pd(PPh$_3$)$_2$Cl$_2$ (9.53 mg, 0.014 mmol) and CuI (5.17 mg, 0.027 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 132 (22 mg, yield: 23.59%).

LCMS: m/z 344 (M+H)$^+$;

$^1$H NMR (400 MHz, DMSO-d$_6$): δ 8.80 (s, 1H), 8.64 (s, 1H), 8.00 (d, J=7.9 Hz, 1H), 7.78-7.70 (m, 2H), 7.56 (d, 2H), 7.53-7.43 (m, 1H), 6.64 (s, 1H), 2.37 (s, 3H).

Example Compound 133

Preparation of 2-((5-methyl-1-(4-(trifluoromethoxy)phenyl)-1H-pyrazol-3-yl) ethynyl)pyrimidine

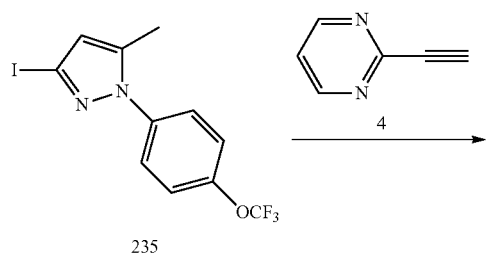

Compound 133

To a solution of 235 (100 mg, 0.272 mmol) and 4 (56.6 mg, 0.543 mmol) in 20 mL of Et$_3$N was added Pd(PPh$_3$)$_2$Cl$_2$ (9.53 mg, 0.014 mmol) and CuI (5.17 mg, 0.027 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 133 (24 mg, yield: 25.7%).

LCMS: m/z 345 (M+H)$^+$;

$^1$H NMR (400 MHz, CDCl$_3$): δ 8.76 (d, J=4.0 Hz, 2H), 7.54-7.52 (m, 2H), 7.35-7.32 (m, 2H), 7.25 (t, J=4.6 Hz, 1H), 6.52 (d, J=0.4 Hz, 1H), 2.37 (d, J=0.4 Hz, 3H).

Example Compound 134

Preparation of 2-((5-methyl-1-(4-(trifluoromethoxy)phenyl)-H-pyrazol-3-yl) ethynyl)pyrazine

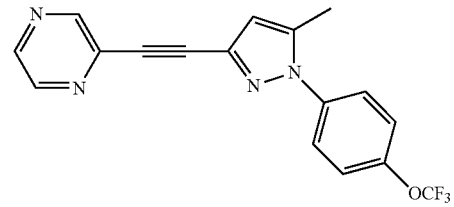

Compound 134

To a solution of 235 (100 mg, 0.272 mmol) and 10 (56.6 mg, 0.543 mmol) in 20 mL of Et$_3$N was added Pd(PPh$_3$)$_2$Cl$_2$ (9.53 mg, 0.014 mmol) and CuI (5.17 mg, 0.027 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 134 (23 mg, yield: 24.59%).

LCMS: m/z 345 (M+H)$^+$;

$^1$H NMR (400 MHz, CDCl$_3$): δ 8.78 (s, 1H), 8.58 (s, 1H), 8.50 (s, 1H), 7.53 (d, J=8.8 Hz, 2H), 7.35 (d, J=8.0 Hz, 2H), 6.51 (s, 1H), 2.38 (s, 3H).

Example Compound 135

Preparation of 2-chloro-4-((5-methyl-1-(4-(trifluoromethoxy)phenyl)-1H-pyrazol-3-yl)ethynyl)pyridine

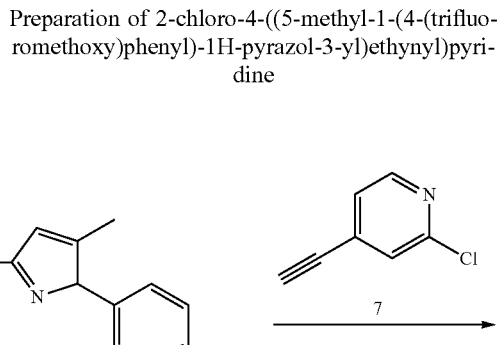

-continued

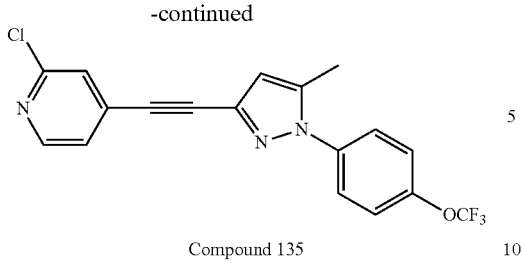

Compound 135

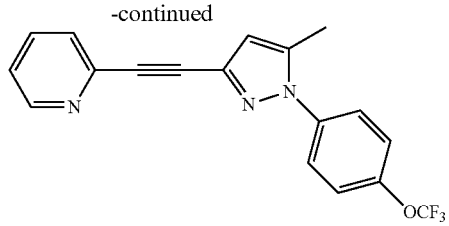

Compound 136

To a solution of 235 (100 mg, 0.272 mmol) and 7 (74.7 mg, 0.543 mmol) in 20 mL of Et$_3$N was added Pd(PPh$_3$)$_2$Cl$_2$ (9.53 mg, 0.014 mmol) and CuI (5.17 mg, 0.027 mmol). The mixture was protected with N$_2$ atmosphere, then was heated at 70° C. for 4 hours. TLC analysis showed complete conversion of starting material to major product. The reaction mixture was then concentrated in vacuo. The crude product was purified by Prep-HPLC to give the target product Compound 135 (22 mg, 21.44°% yield).

LCMS: m/z 378 (M+H)$^+$;

$^1$H NMR (400 MHz, CDCl$_3$): δ 8.35 (d, J=5.2 Hz, 1H), 7.52-7.50 (m, 2H), 7.43 (t, J=0.8 Hz, 1H), 7.35 (s, 1H), 7.32-7.30 (m, 2H), 6.44 (s, 1H), 2.36 (s, 3H).

Example Compound 136

Preparation of 2-((5-methyl-1-(4-(trifluoromethoxy)phenyl)-1H-pyrazol-3-yl)ethynyl)pyridine To a solution of 235 (100 mg, 0.272 mmol) and 70 (56.0 mg, 0.543 mmol) in 20 mL of Et$_3$N was added Pd(PPh$_3$)$_2$Cl$_2$ (9.53 mg, 0.014 mmol) and CuI (5.17 mg, 0.027 mmol). The mixture was protected with N$_2$ atmosphere, then was heated at 70° C. for 4 hours. TLC analysis showed complete conversion of starting material to a major product. The reaction mixture was then concentrated in vacuo. The crude product was purified by Prep-HPLC to give the target product Compound 136 (23 mg, yield: 24.66%).

LCMS: m/z 344 (M+H)$^+$;

$^1$H NMR (400 MHz, CDCl$_3$): δ 8.60 (d, J=4.4 Hz, 1H), 7.67-7.65 (m, 1H), 7.54-7.50 (m, 3H), 7.32 (d, J=8.0 Hz, 2H), 7.26-7.21 (m, 1H), 6.46 (s, 1H), 2.35 (s, 3H).

Example 8

Functional Calcium Clux Assay Methodology

For functional assays, HEK293 cells stably expressing recombinant rat mGluR5 were seeded in 384-well plates and dye loaded using Fluo-8. Cells were then washed to remove the un-incorporated dye. Antagonist evaluation was performed following a 15 min incubation of the test compound followed by the addition of submaximal concentration of glutamate. Intracellular calcium ([Ca$^{2+}$]$_i$) measurements were performed using a fluorometric imaging plate reader (FLIPR, Molecular Devices). The glutamate-evoked increase in [Ca$^{2+}$]$_i$ in the presence of the test compounds was compared to the response to glutamate alone (the positive control). Antagonist inhibition curves were fitted with a 4-parameter logistic equation giving IC$_{50}$ values, and Hill coefficients using an iterative nonlinear curve fitting algorithm.

The tables below provide IC50 data in this assay. In the activity column, A=IC$_{50}$>1,000 and ≤5,000 nM; B=IC$_{50}$>500 and ≤1,000 nM and C=IC$_{50}$≤500 nM.

TABLE 1

| # | Example Compound | Structure | IC50 value (FLIPR assay) |
|---|---|---|---|
| 1 | 18 | 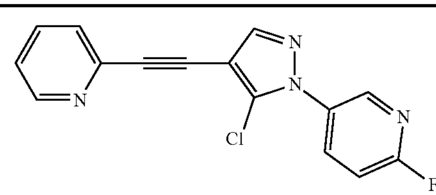 | C |
| 2 | 20 | 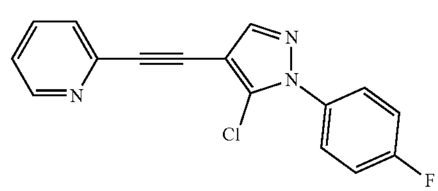 [SMILES: Fc1ccc(-n2ncc(C#Cc3ccccn3)c2Cl)cc1] | C |

TABLE 1-continued

| # | Example Compound | Structure | IC50 value (FLIPR assay) |
|---|---|---|---|
| 3 | 17 | 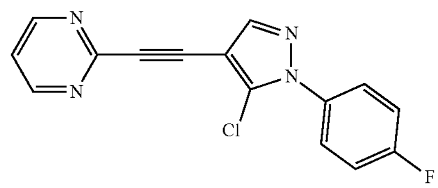 [SMILES: Fc1ccc(-n2ncc(C#Cc3ncccn3)c2Cl)cc1] | C |
| 4 | 1 | 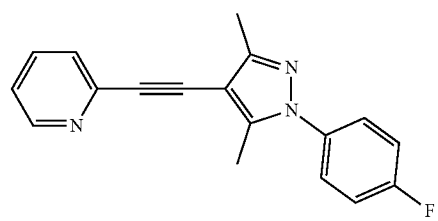 | C |
| 5 | 47 | 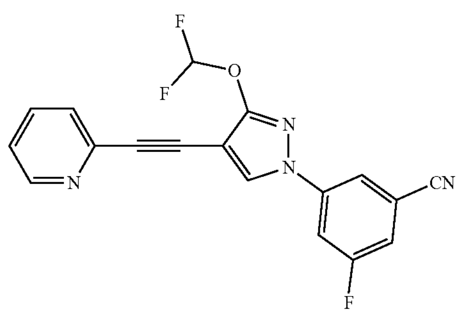 [SMILES: N#Cc1cc(F)cc(-n2cc(C#Cc3ccccn3)c(OC(F)F)n2)c1] | C |
| 6 | 51 | 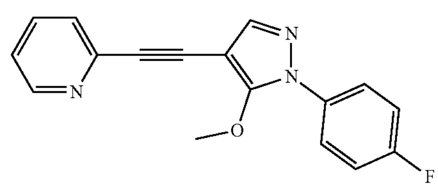 [SMILES: COc1c(C#Cc2ccccn2)cnn1-c1ccc(F)cc1] | C |
| 7 | 42 | 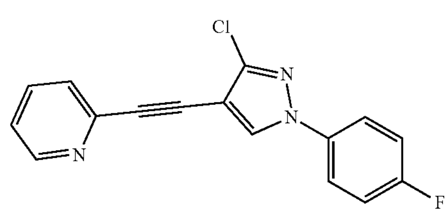 [SMILES: Fc1ccc(-n2cc(C#Cc3ccccn3)c(Cl)n2)cc1] | C |
| 8 | 36 | 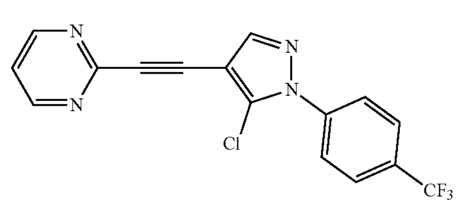 [SMILES: FC(F)(F)c1ccc(-n2ncc(C#Cc3ncccn3)c2Cl)cc1] | C |

TABLE 1-continued

| # | Example Compound | Structure | IC50 value (FLIPR assay) |
|---|---|---|---|
| 9 | 32 | 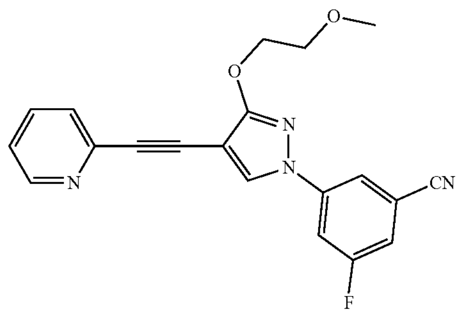 [SMILES: COCCOc1nn(-c2cc(F)cc(C#N)c2)cc1C#Cc1ccccn1] | C |
| 10 | 19 | 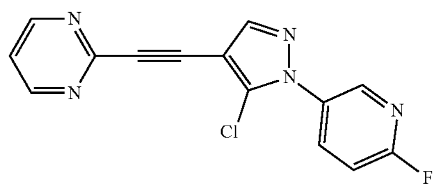 [SMILES: Fc1ccc(-n2ncc(C#Cc3ncccn3)c2Cl)cn1] | C |
| 11 | 62 | 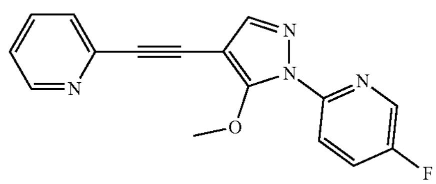 [SMILES: COc1c(C#Cc2ccccn2)cnn1-c1ccc(F)cn1] | C |
| 12 | 35 | 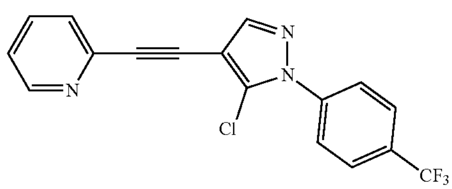 [SMILES: FC(F)(F)c1ccc(-n2ncc(C#Cc3ccccn3)c2Cl)cc1] | C |
| 13 | 22 | 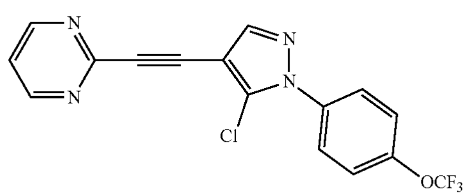 [SMILES: FC(F)(F)Oc1ccc(-n2ncc(C#Cc3ncccn3)c2Cl)cc1] | C |
| 14 | 50 | 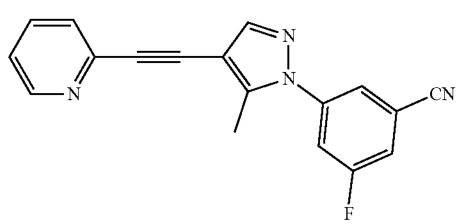 [SMILES: Cc1c(C#Cc2ccccn2)cnn1-c1cc(F)cc(C#N)c1] | C |
| 15 | 21 | 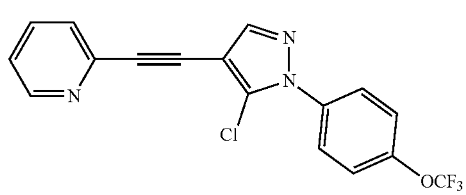 [SMILES: FC(F)(F)Oc1ccc(-n2ncc(C#Cc3ccccn3)c2Cl)cc1] | C |

TABLE 1-continued

| # | Example Compound | Structure | IC50 value (FLIPR assay) |
|---|---|---|---|
| 16 | 48 | 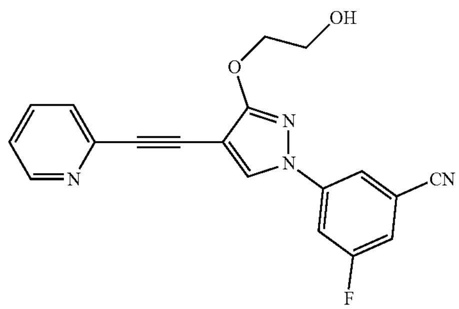 [SMILES: N#Cc1cc(F)cc(-n2cc(C#Cc3ccccn3)c(OCCO)n2)c1] | C |
| 17 | 23 | 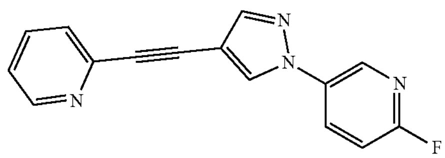 [SMILES: Fc1ccc(-n2cc(C#Cc3ccccn3)cn2)cn1] | C |
| 18 | 8 | 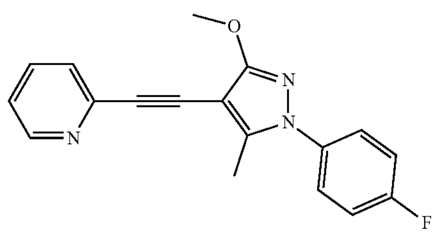 [SMILES: COc1nn(-c2ccc(F)cc2)c(C)c1C#Cc1ccccn1] | C |
| 19 | 33 | 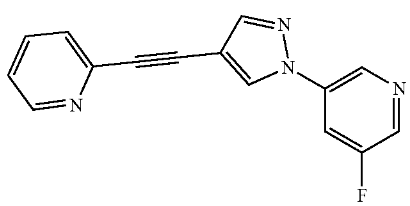 [SMILES: Fc1cncc(-n2cc(C#Cc3ccccn3)cn2)c1] | C |
| 20 | 24 | 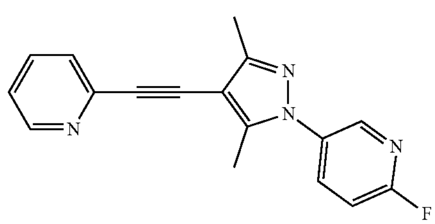 [SMILES: Cc1nn(-c2ccc(F)nc2)c(C)c1C#Cc1ccccn1] | C |
| 21 | 27 | 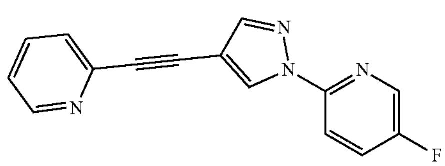 [SMILES: Fc1ccc(-n2cc(C#Cc3ccccn3)cn2)nc1] | C |
| 22 | 6 | 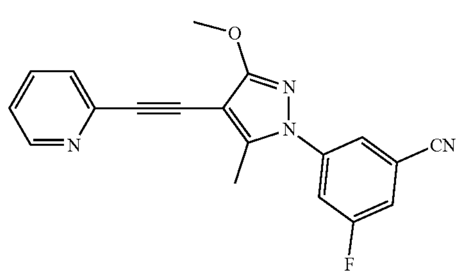 [SMILES: COc1nn(-c2cc(F)cc(C#N)c2)c(C)c1C#Cc1ccccn1] | C |

TABLE 1-continued

| # | Example Compound | Structure | IC50 value (FLIPR assay) |
|---|---|---|---|
| 23 | 66 | 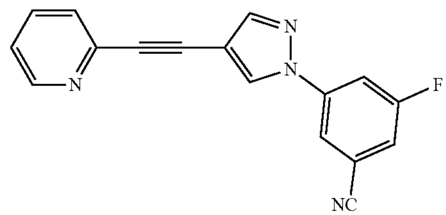 [SMILES: N#Cc1cc(F)cc(-n2cc(C#Cc3ccccn3)cn2)c1] | C |
| 24 | 52 | 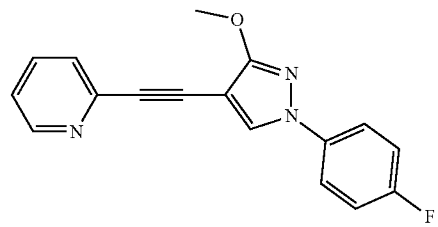 [SMILES: COc1nn(-c2ccc(F)cc2)cc1C#Cc1ccccn1] | C |
| 25 | 44 | 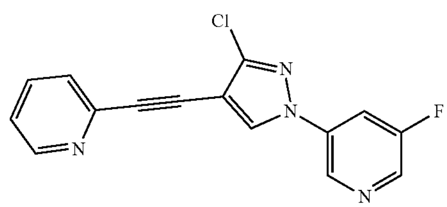 [SMILES: Fc1cncc(-n2cc(C#Cc3ccccn3)c(Cl)n2)c1] | C |
| 26 | 3 | 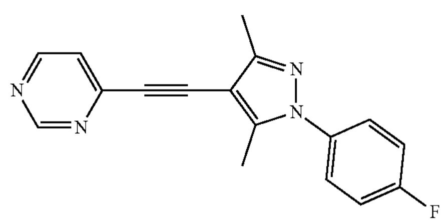 [SMILES: Cc1nn(-c2ccc(F)cc2)c(C)c1C#Cc1ccncn1] | C |
| 27 | 38 | 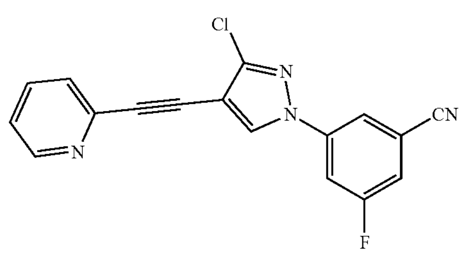 [SMILES: N#Cc1cc(F)cc(-n2cc(C#Cc3ccccn3)c(Cl)n2)c1] | C |
| 28 | 63 | 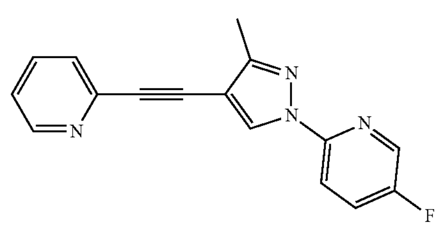 [SMILES: Cc1nn(-c2ccc(F)cn2)cc1C#Cc1ccccn1] | C |
| 29 | 43 | 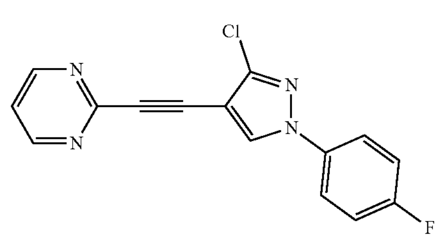 [SMILES: Fc1ccc(-n2cc(C#Cc3ncccn3)c(Cl)n2)cc1] | C |

TABLE 1-continued

| # | Example Compound | Structure | IC50 value (FLIPR assay) |
|---|---|---|---|
| 30 | 5 | 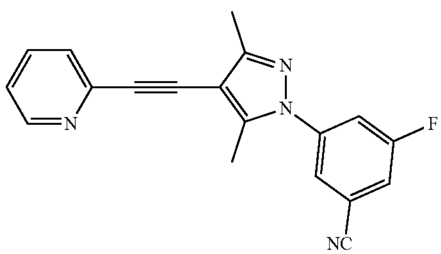 [SMILES: Cc1nn(-c2cc(F)cc(C#N)c2)c(C)c1C#Cc1ccccn1] | C |
| 31 | 28 | 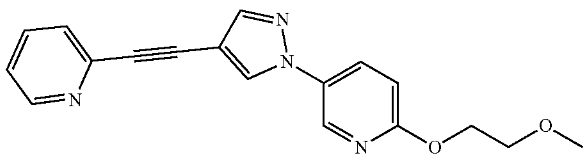 | C |
| 32 | 2 | 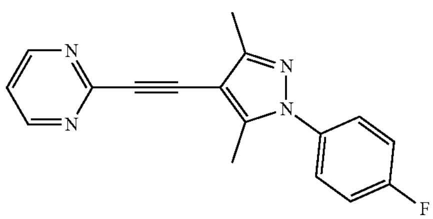 [SMILES: Cc1nn(-c2ccc(F)cc2)c(C)c1C#Cc1ncccn1] | C |
| 33 | 25 | 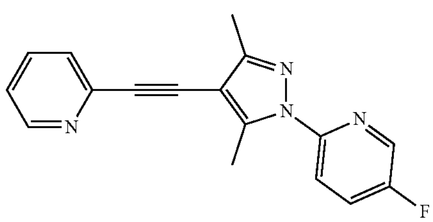 | C |
| 34 | 37 | 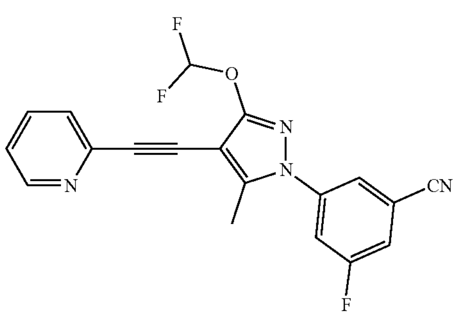 [SMILES: Cc1c(C#Cc2ccccn2)c(OC(F)F)nn1-c1cc(F)cc(C#N)c1] | C |
| 35 | 68 | 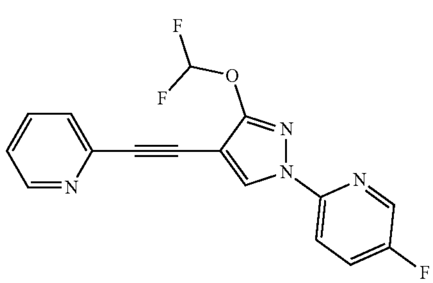 [SMILES: Fc1ccc(-n2cc(C#Cc3ccccn3)c(OC(F)F)n2)nc1] | C |

TABLE 1-continued

| # | Example Compound | Structure | IC50 value (FLIPR assay) |
|---|---|---|---|
| 36 | 54 | 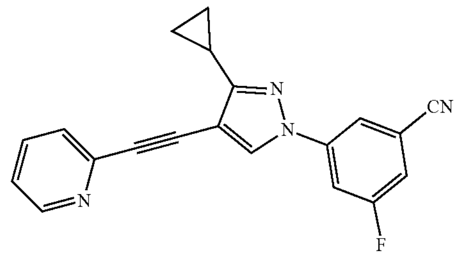 [SMILES: N#Cc1cc(F)cc(-n2cc(C#Cc3ccccn3)c(C3CC3)n2)c1] | C |
| 37 | 56 | 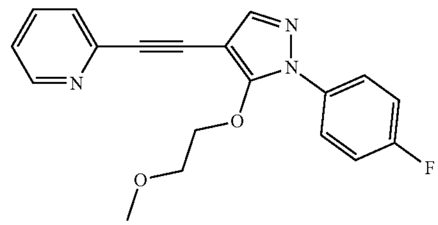 [SMILES: COCCOc1c(C#Cc2ccccn2)cnn1-c1ccc(F)cc1] | C |
| 38 | 49 | 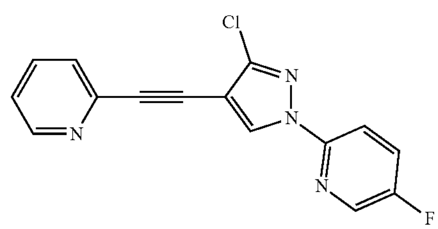 [SMILES: Fc1ccc(-n2cc(C#Cc3ccccn3)c(Cl)n2)nc1] | C |
| 39 | 39 | 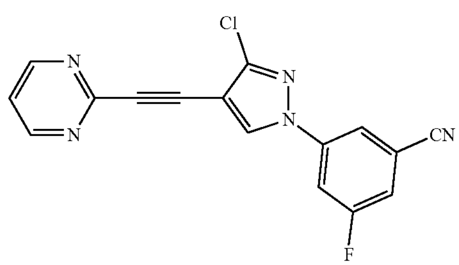 [SMILES: N#Cc1cc(F)cc(-n2cc(C#Cc3ncccn3)c(Cl)n2)c1] | C |
| 40 | 9 | 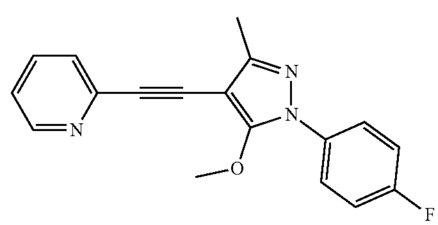 [SMILES: COc1c(C#Cc2ccccn2)c(C)nn1-c1ccc(F)cc1] | C |
| 41 | 55 | 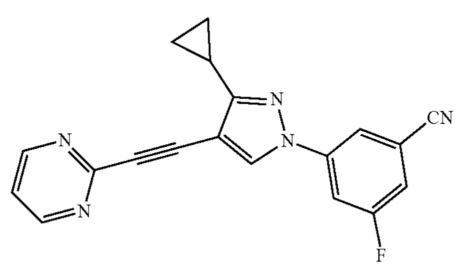 [SMILES: N#Cc1cc(F)cc(-n2cc(C#Cc3ncccn3)c(C3CC3)n2)c1] | C |

TABLE 1-continued

| # | Example Compound | Structure | IC50 value (FLIPR assay) |
|---|---|---|---|
| 42 | 4 | 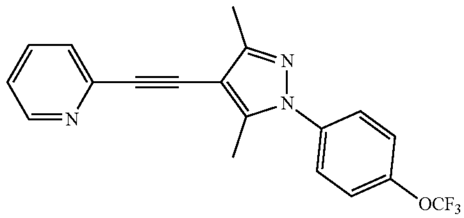 | C |
| 43 | 26 | 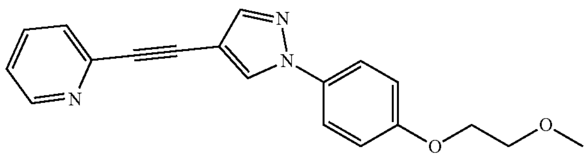 [SMILES: COCCOc1ccc(-n2cc(C#Cc3ccccn3)cn2)cc1] | C |
| 44 | 14 | 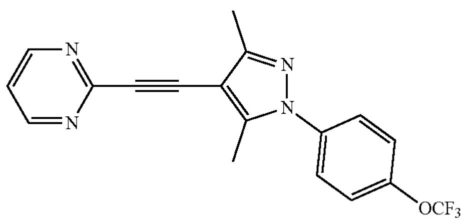 [SMILES: Cc1nn(-c2ccc(OC(F)(F)F)cc2)c(C)c1C#Cc1ncccn1] | C |
| 45 | 40 | 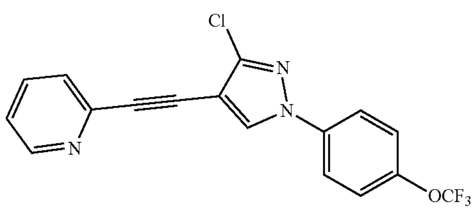 [SMILES: FC(F)(F)Oc1ccc(-n2cc(C#Cc3ccccn3)c(Cl)n2)cc1] | C |
| 46 | 29 | 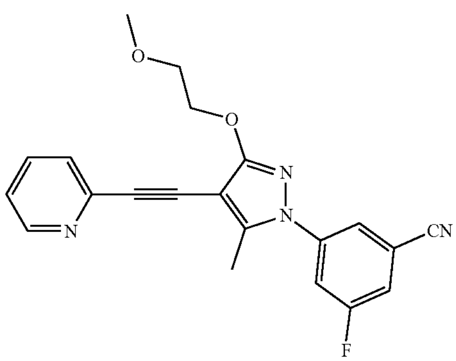 [SMILES: COCCOc1nn(-c2cc(F)cc(C#N)c2)c(C)c1C#Cc1ccccn1] | C |
| 47 | 7 | 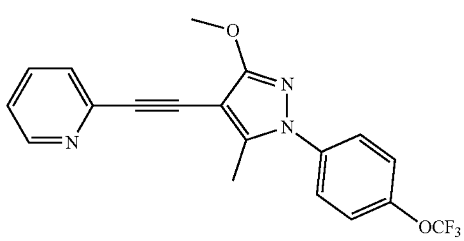 [SMILES: COc1nn(-c2ccc(OC(F)(F)F)cc2)c(C)c1C#Cc1ccccn1] | C |

TABLE 1-continued

| # | Example Compound | Structure | IC50 value (FLIPR assay) |
|---|---|---|---|
| 48 | 12 | 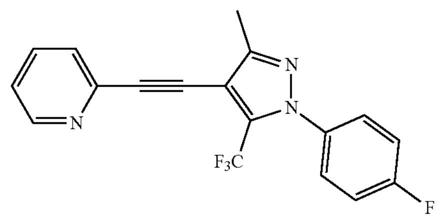 [SMILES: Cc1nn(-c2ccc(F)cc2)c(C(F)(F)F)c1C#Cc1ccccn1] | C |
| 49 | 34 | 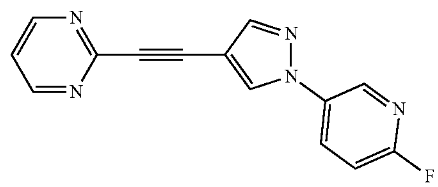 | C |
| 50 | 64 | 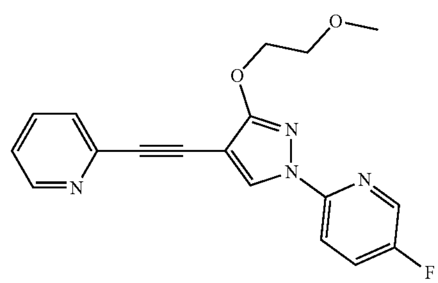 [SMILES: COCCOc1nn(-c2ccc(F)cn2)cc1C#Cc1ccccn1] | B |
| 51 | 46 | 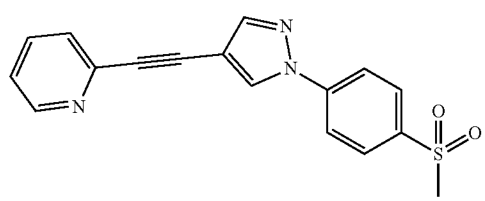 [SMILES: CS(=O)(=O)c1ccc(-n2cc(C#Cc3ccccn3)cn2)cc1] | B |
| 52 | 11 | 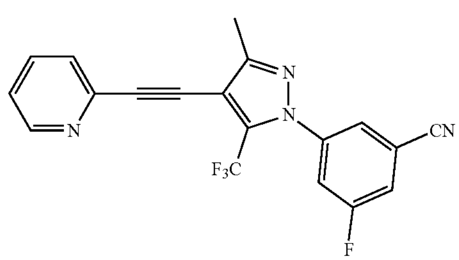 [SMILES: Cc1nn(-c2cc(F)cc(C#N)c2)c(C(F)(F)F)c1C#Cc1ccccn1] | A |
| 53 | 15 | 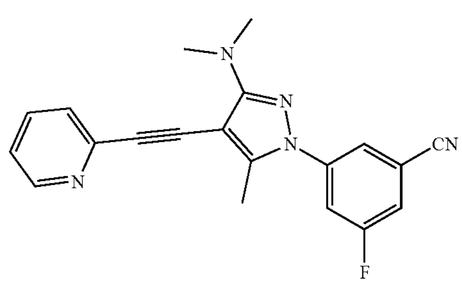 [SMILES: Cc1c(C#Cc2ccccn2)c(N(C)C)nn1-c1cc(F)cc(C#N)c1] | A |

TABLE 1-continued

| # | Example Compound | Structure | IC50 value (FLIPR assay) |
|---|---|---|---|
| 54 | 53 | 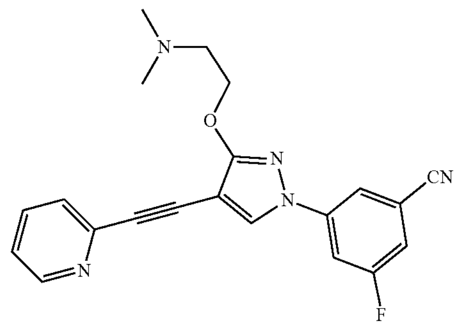 [SMILES: CN(C)CCOc1nn(-c2cc(F)cc(C#N)c2)cc1C#Cc1ccccn1] | A |
| 55 | 10 | 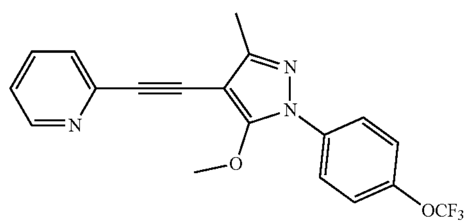 | A |
| 56 | 13 | 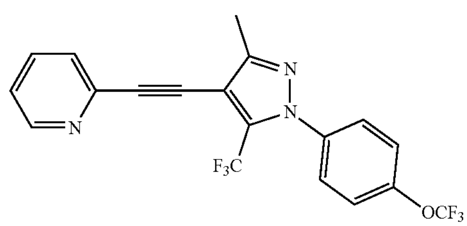 | A |
| 57 | 16 | 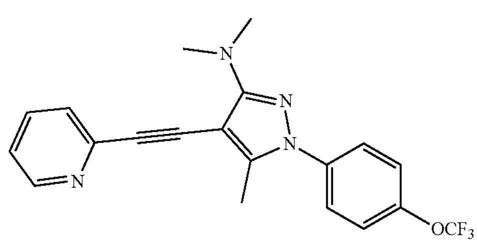 [SMILES: Cc1c(C#Cc2ccccn2)c(N(C)C)nn1-c1ccc(OC(F)(F)F)cc1] | A |
| 58 | 31 | 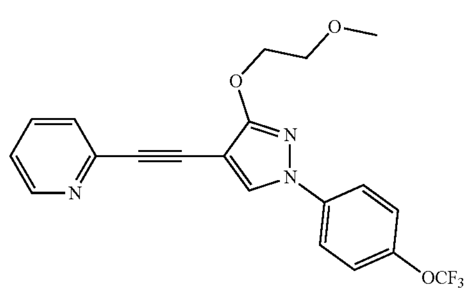 [SMILES: COCCOc1nn(-c2ccc(OC(F)(F)F)cc2)cc1C#Cc1ccccn1] | A |
| 59 | 58 | 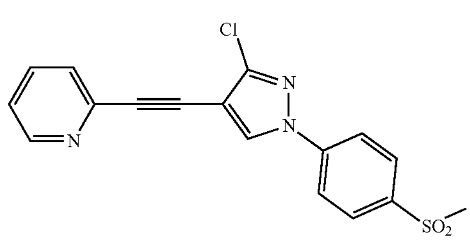 [SMILES: CS(=O)(=O)c1ccc(-n2cc(C#Cc3ccccn3)c(Cl)n2)cc1] | A |

TABLE 1-continued
| # | Example Compound | Structure | IC50 value (FLIPR assay) |
|---|---|---|---|
| 60 | 75 | 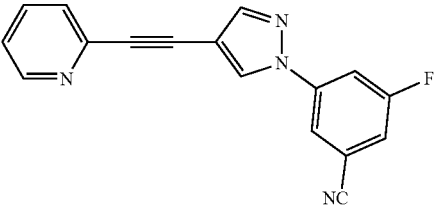 | C |
| 61 | 82 | 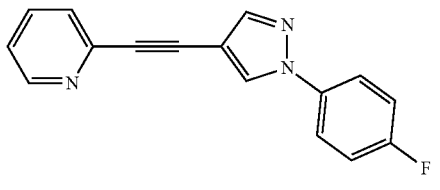 [SMILES: Fc1ccc(-n2cc(C#Cc3ccccn3)cn2)cc1] | C |
| 62 | 90 | 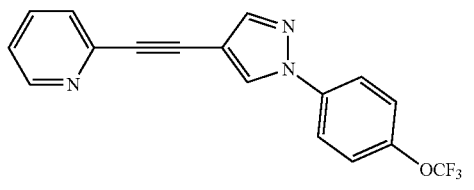 | C |
| 63 | 30 | 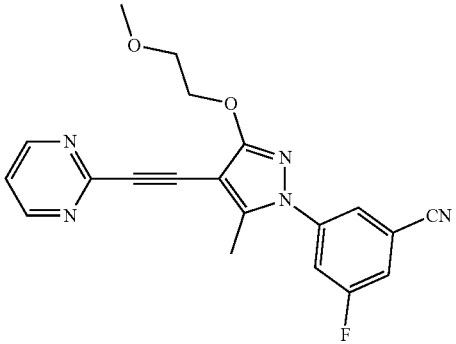 [SMILES: COCCOc1nn(-c2cc(F)cc(C#N)c2)c(C)c1C#Cc1ncccn1] | A |
| 64 | 57 | 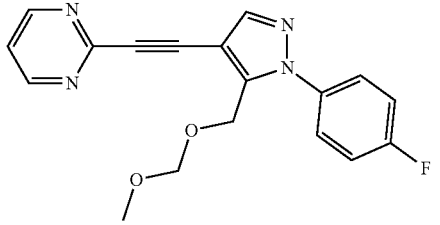 [SMILES: COCOCc1c(C#Cc2ncccn2)cnn1-c1ccc(F)cc1] | A |
| 65 | 41 | 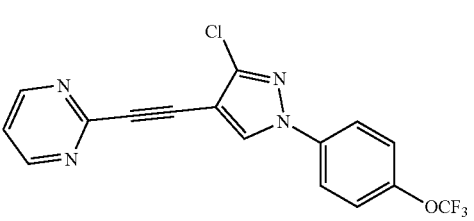 | A |

TABLE 1-continued
| # | Example Compound | Structure | IC50 value (FLIPR assay) |
|---|---|---|---|
| 66 | 45 | 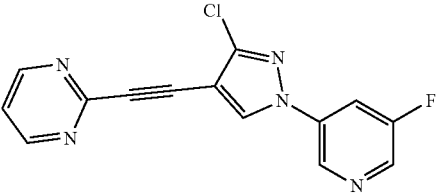 [SMILES: Fc1cncc(-n2cc(C#Cc3ncccn3)c(Cl)n2)c1] | A |
| 67 | 78 | 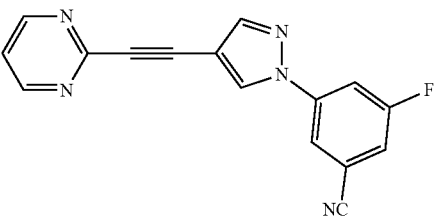 [SMILES: N#Cc1cc(F)cc(-n2cc(C#Cc3ncccn3)cn2)c1] | C |
| 68 | 86 | 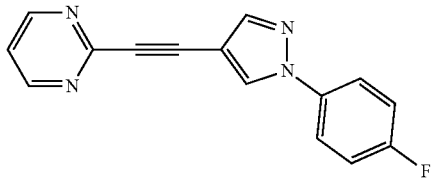 [SMILES: Fc1ccc(-n2cc(C#Cc3ncccn3)cn2)cc1] | C |
| 69 | 93 | 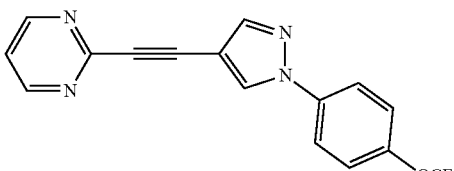 | C |
| 70 | 65 | 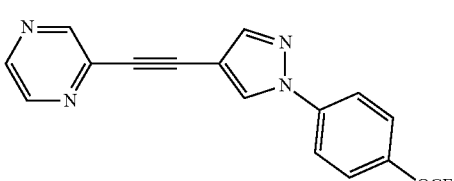 | A |
| 71 | 80 | 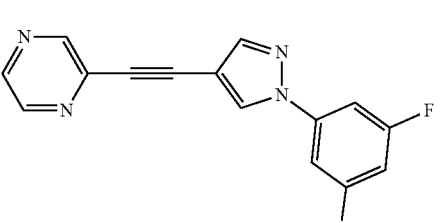 | A |
| 72 | 88 | 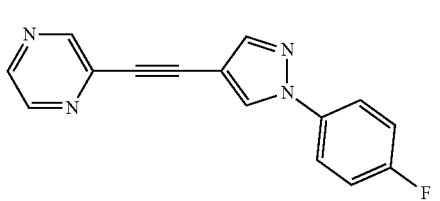 [SMILES: Fc1ccc(-n2cc(C#Cc3cnccn3)cn2)cc1] | C |

TABLE 1-continued

| # | Example Compound | Structure | IC50 value (FLIPR assay) |
|---|---|---|---|
| 73 | 95 | pyrazine-C≡C-pyrazole-N-(4-OCF$_3$-phenyl) | A |
| 74 | 74 | phenyl-C≡C-pyrazole-N-(3-F-5-CN-phenyl) | A |
| 75 | 81 | phenyl-C≡C-pyrazole-N-(4-F-phenyl) | C |
| 76 | 89 | phenyl-C≡C-pyrazole-N-(4-OCF$_3$-phenyl) | A |
| 77 | 76 | 3-pyridyl-C≡C-pyrazole-N-(3-F-5-CN-phenyl) | A |
| 78 | 83 | 3-pyridyl-C≡C-pyrazole-N-(4-F-phenyl) | C |
| 79 | 91 | 3-pyridyl-C≡C-pyrazole-N-(4-OCF$_3$-phenyl) | A |

TABLE 1-continued
| # | Example Compound | Structure | IC50 value (FLIPR assay) |
|---|---|---|---|
| 80 | 77 | 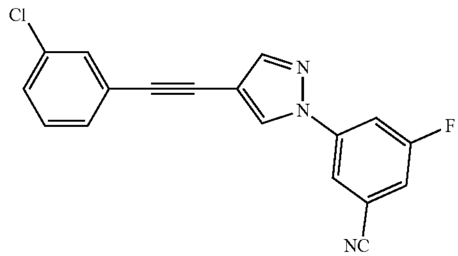 [SMILES: N#Cc1cc(F)cc(-n2cc(C#Cc3cccc(Cl)c3)cn2)c1] | B |
| 81 | 84 | 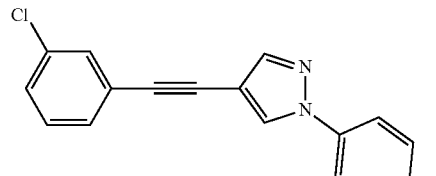 | C |
| 82 | 92 | 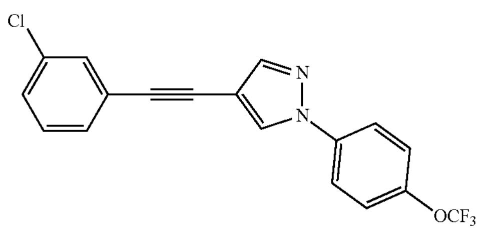 | C |
| 83 | 79 | 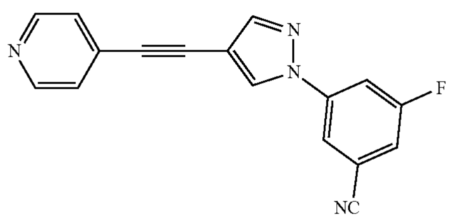 [SMILES: N#Cc1cc(F)cc(-n2cc(C#Cc3ccncc3)cn2)c1] | C |
| 84 | 87 | 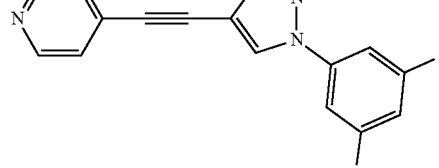 | C |
| 85 | 94 | 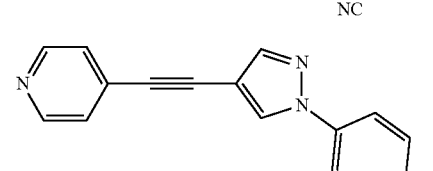 | B |
| 86 | 85 | 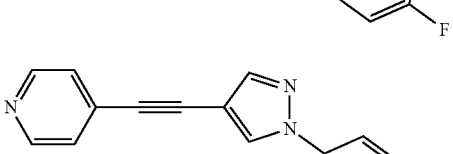 | C |

TABLE 2
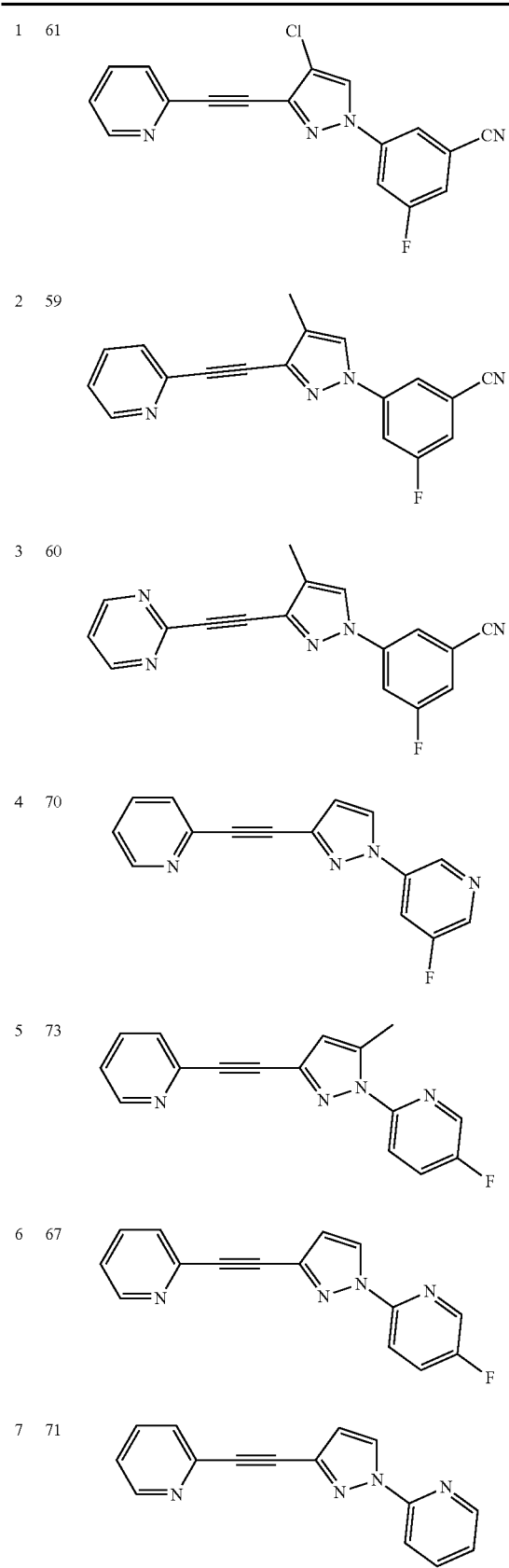
TABLE 2-continued
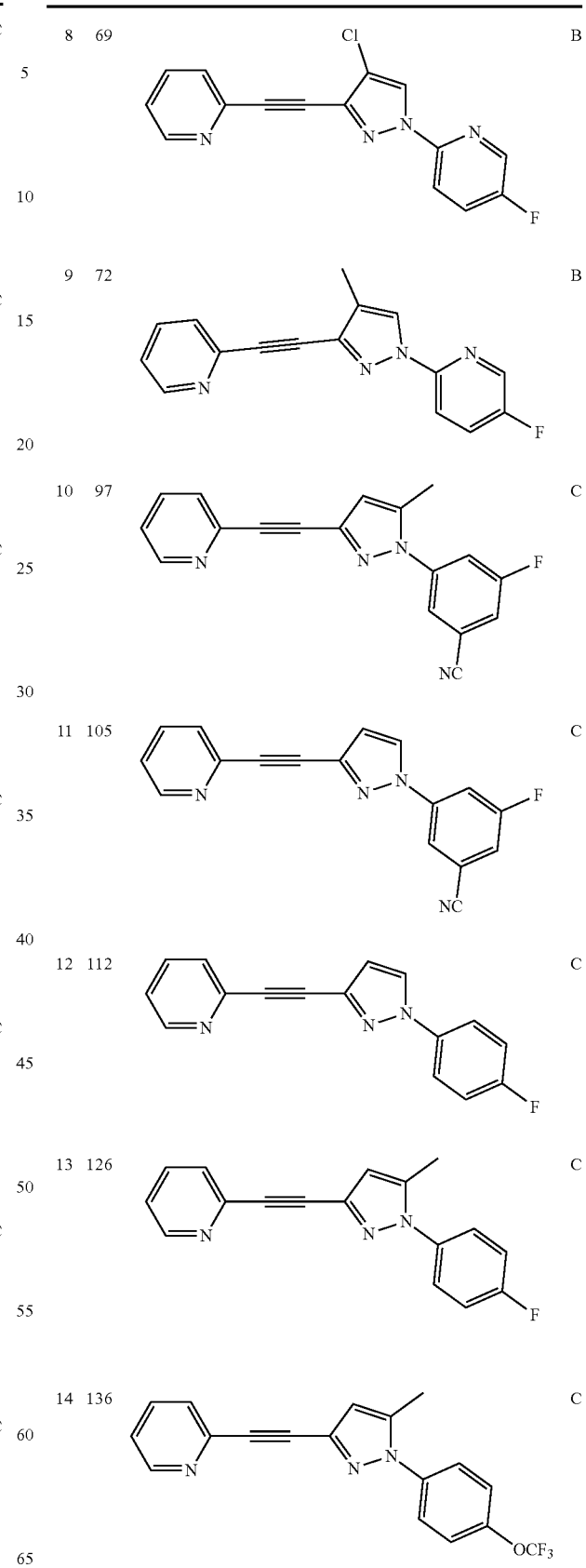

TABLE 2-continued
| 15 | 98 | 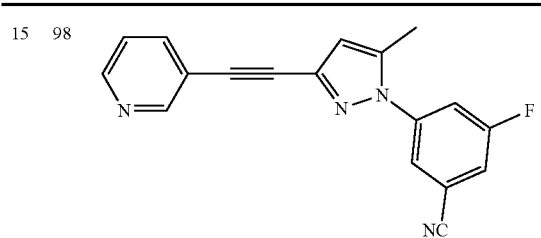 | C |
| 16 | 106 | 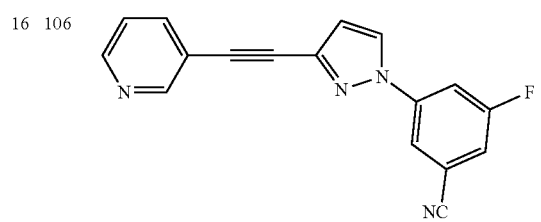 | A |
| 17 | 114 | 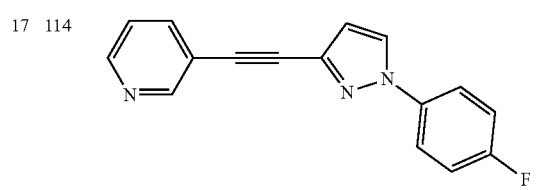 | A |
| 18 | 121 | 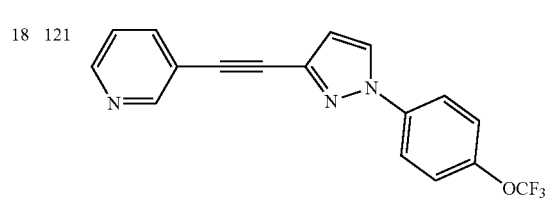 | A |
| 19 | 127 | 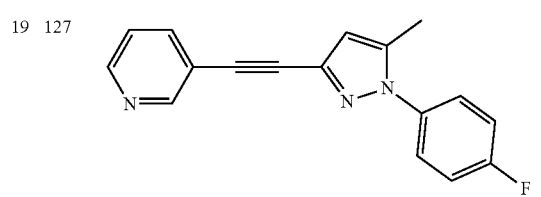 | A |
| 20 | 132 | 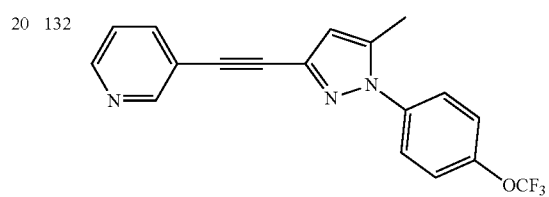 | A |
| 21 | 102 | 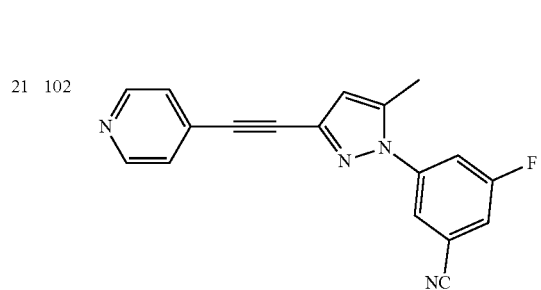 | C |
TABLE 2-continued
| 22 | 110 | 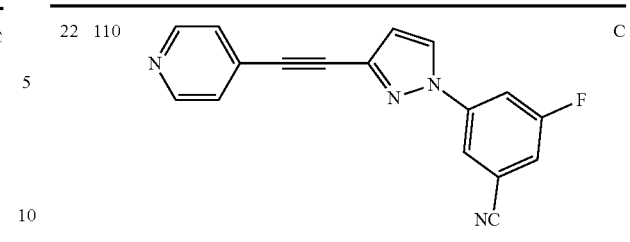 | C |
| 23 | 118 | 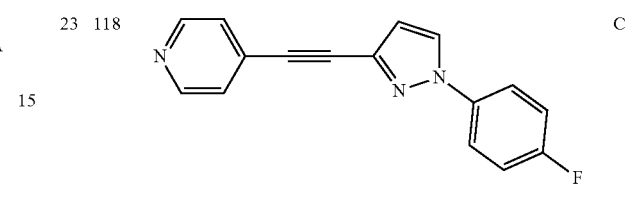 | C |
| 24 | 124 | 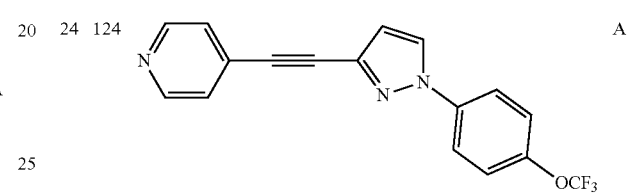 | A |
| 25 | 130 | 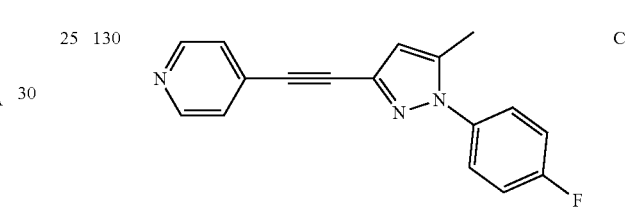 | C |
| 26 | 100 | 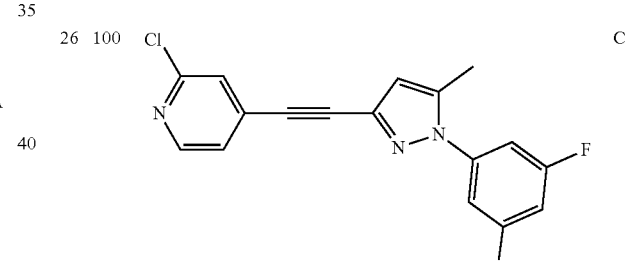 | C |
| 27 | 108 | 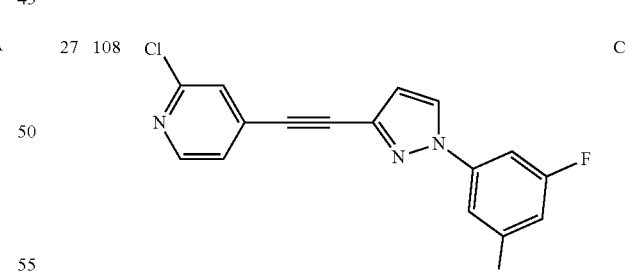 | C |
| 28 | 116 | 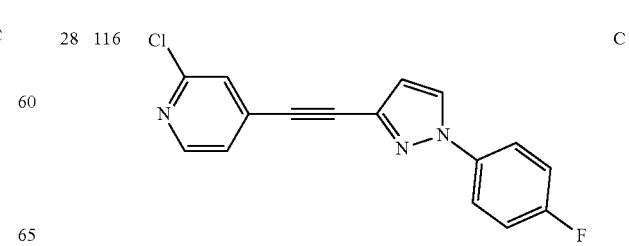 | C |

TABLE 2-continued
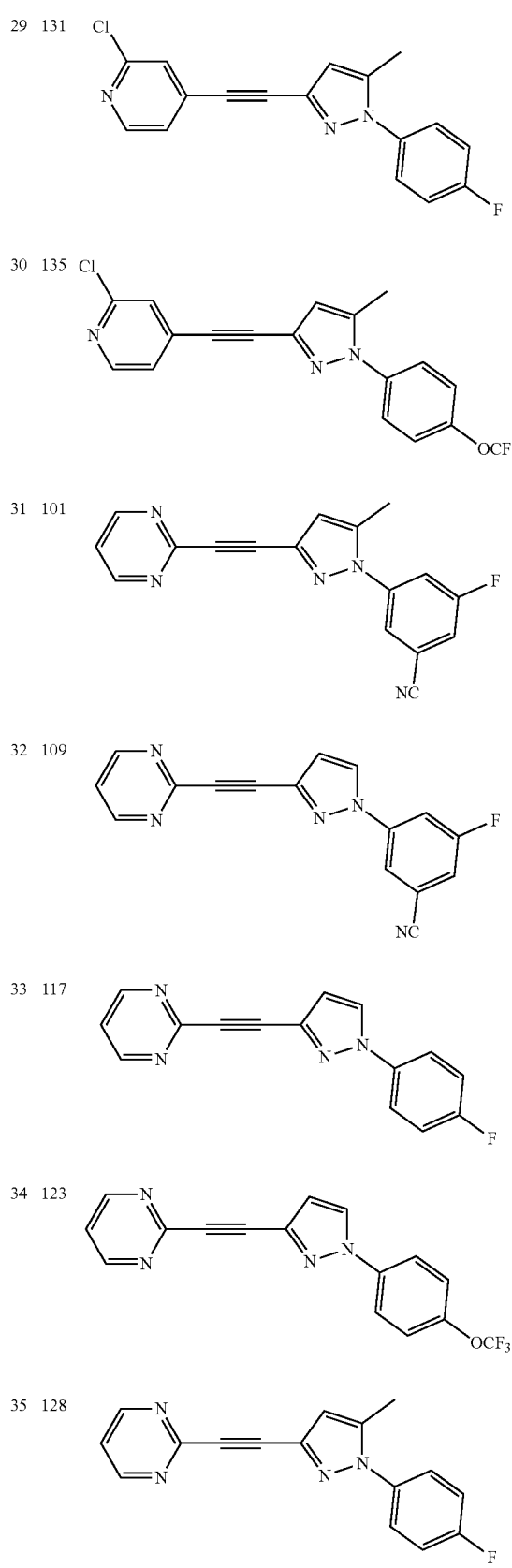
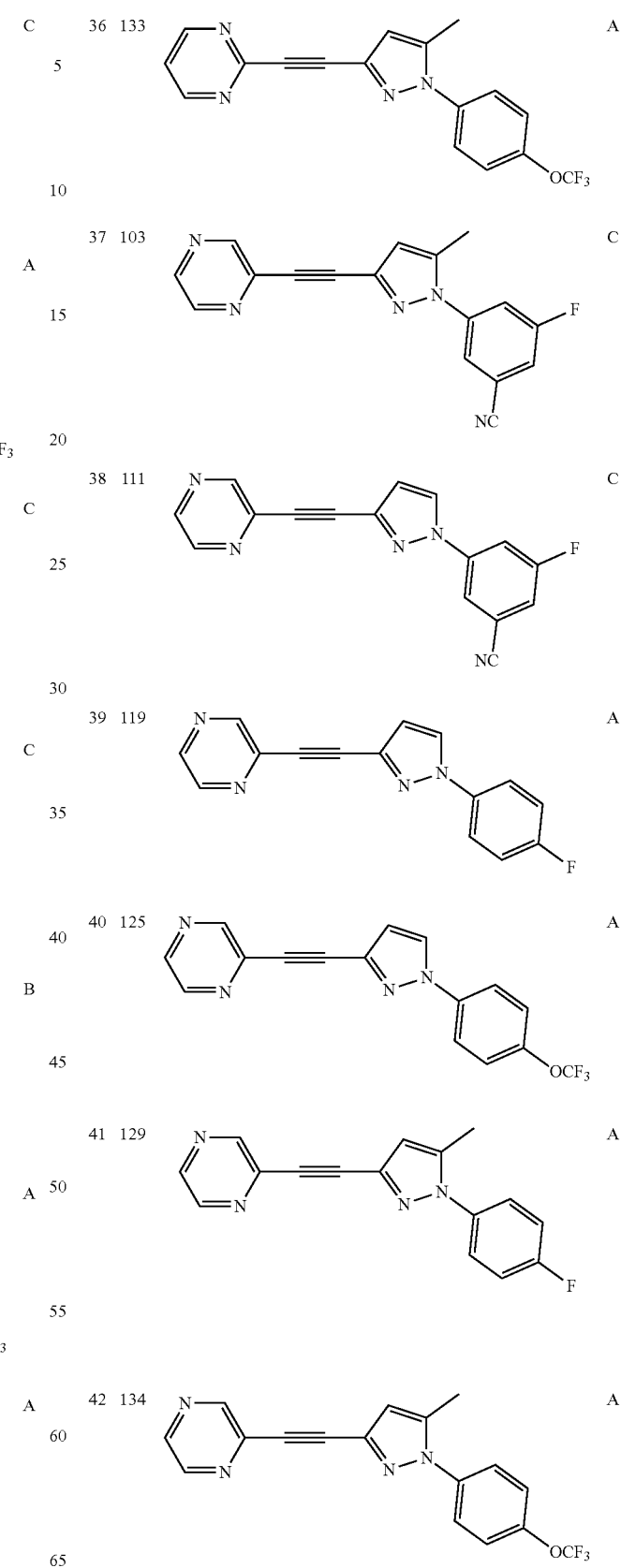

TABLE 2-continued

| 43 | 96 | (structure) | C |
| 44 | 104 | (structure) | A |
| 45 | 113 | (structure) | A |
| 46 | 120 | (structure) | A |
| 47 | 99 | (structure) | C |
| 48 | 107 | (structure) | C |
| 49 | 115 | (structure) | B |
| 50 | 122 | (structure) | A |

Example 9

Radioligand Binding Assay Using Membrane Preparations Expressing Rat mGluR5

The radiolabeled allosteric antagonist [$^3$H]-2-Methyl-6-(phenylethynyl)pyridine (MPEP, American Radiolabeled Chemical) was used to evaluate the ability of test compounds to interact with the MPEP site on mGluR5 as described in Rodriguez et al. [Mol Pharmacol 78:1105-1123, 2010]. Membranes were prepared from HEK293 cells expressing rat mGluR5. Radioligand binding assays were performed in 96-well plates (Corning) containing binding buffer (15 mM Tris pH 7.4, 120 mM NaCl, 100 mM KCl, 25 mM MgCl$_2$, 25 mM CaCl$_2$)) with a final assay volume of 250 μL and 40 μg membranes/well.

Saturation isotherms were determined by incubation in presence of 12 increasing concentrations of [$^3$H]-MPEP (0.1-100 nM), while competition experiments were performed with a fixed concentration (4 nM) of [$^3$H]-MPEP in presence of 12 increasing concentrations of test compound (1-30,000 nM). Incubations were performed at 4° C. for 1 h. Nonspecific binding was estimated using 100 μM MTEP. At the end of incubation, membranes were filtered over GF/C filter plates (Perkin Elmer) presoaked in 0.1% BSA for 2 h at room temperature. Filter plates were then washed 5 times with ice cold buffer (15 mM Tris, pH 7.4 plus 0.1% BSA) using the Packard Filtermate Harvester and dried overnight in a 37° C. oven. Fifty μL microscint 20 (PerkinElmer) were added to each well and the plates were incubated on an orbital shaker for 15 min before counting on a Microbeta Trilux for 2 min/well.

What is claimed is:
1. A compound of formula I:

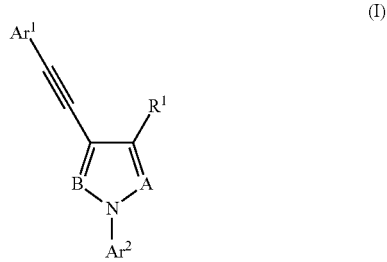

or a pharmaceutically acceptable salt thereof,
wherein:
one of A and B is CR, and the other is N;
R is —H, -halogen, -alkyl, -cycloalkyl, -haloalkyl, —OR$^2$, or —N(CH$_3$)$_2$, wherein R$^2$ is lower alkyl which may be optionally substituted with 1-3 substituents selected from the group consisting of -halogen, —OH, -alkoxy, and —N(CH$_3$)$_2$;

R$^1$ is —H, -halogen, -alkyl, -cycloalkyl, -haloalkyl, —OR$^{2'}$, or —N(CH$_3$)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is
a 5- to 10-membered mono- or bicyclic aryl ring, wherein the 5- to 10-membered mono- or bicyclic aryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form a 5-7 membered fused and optional substituted carbacyclic or heterocyclic ring;

Ar$^2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)—heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring.

2. The compound according to claim 1, of formula Ia, wherein:

(Ia)

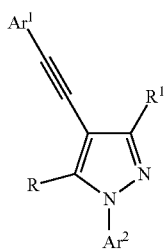

wherein:
R is —H, -halogen, -alkyl, -cycloalkyl, -haloalkyl, —OR$^2$, or —N(CH$_3$)$_2$, wherein R$^2$ is lower alkyl which may be optionally substituted with 1-3 substituents selected from the group consisting of -halogen, —OH, -alkoxy, and —N(CH$_3$)$_2$;

R$^1$ is —H, -halogen, -alkyl, -cycloalkyl, -haloalkyl, —OR$^{2'}$, or —N(CH$_3$)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is
a 5- to 10-membered mono- or bicyclic aryl ring, wherein the 5- to 10-membered mono- or bicyclic aryl ring is optionally substituted with 1-3 substituents independently selected from the group consisting of alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH— cycloalkyl, —C(O)N(cycloalkyl)$_2$, —C(O)NH— heterocycloalkyl, —C(O)N(heterocycloalkyl)$_2$, —C(O)NH-aryl, —C(O)N(aryl)$_2$, —C(O)NH— heteroaryl, —C(O)N(heteroaryl)$_2$, and substituted lower alkyl, wherein the substituents may combine to form a 5-7 membered fused and optionally substituted carbacyclic or heterocyclic ring;

Ar$^2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O— heterocycloalkyl, —C(O)O-aryl, —C(O)O-heteroaryl, —C(O)NH$_2$, —C(O)NH— alkyl, —C(O)N(alkyl)$_2$, —C(O)NH-cycloalkyl, —C(O)N(cycloalkyl)$_2$, —C(O)NH— heterocycloalkyl, —C(O)N(heterocycloalkyl)$_2$, —C(O)NH-aryl, —C(O)N(aryl)$_2$, —C(O)NH— heteroaryl, —C(O)N(heteroaryl)$_2$, and substituted lower alkyl wherein the substituents may combine to form an optionally substituted 5-7 membered fused carbacyclic or heterocyclic ring.

3. The compound according to claim 2 or a pharmaceutically acceptable salt thereof, wherein:
R is —H, -halogen, -alkyl, -cycloalkyl, -haloalkyl, —OR$^2$, or —N(CH$_3$)$_2$, wherein R$^2$ is lower alkyl which may be optionally substituted with 1-2 substituents selected from the group consisting of —OH and -alkoxy;

R$^1$ is —H, -halogen, -alkyl, -cycloalkyl, -haloalkyl, —OR$^{2'}$, or —N(CH$_3$)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is
a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, and —O-alkyl;

Ar$^2$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, —O-alkyl, —S-alkyl, —S(O)—alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$.

4. The compound according to claim 3 or a pharmaceutically acceptable salt thereof, wherein:

R is —H, -halogen, -alkyl, -cycloalkyl, -haloalkyl, —OR$^2$, or —N(lower alkyl)$_2$, wherein R$^2$ is lower alkyl which may be optionally substituted with 1-2 substituents selected from the group consisting of —OH and -alkoxy;

R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is a 6-membered aryl ring optionally substituted with 1, 2 or 3 substituents independently selected from the group consisting of lower alkyl, and halogen;

Ar$^2$ is a 5- or 6-membered mono-heteroaryl ring that contains 1, 2, or 3 heteroatoms independently selected from the group consisting of N, O and S, wherein the 5- or 6-membered mono-heteroaryl ring is optionally substituted with 1, 2 or 3 substituents independently selected from the group consisting of —C$_1$-C$_4$alkyl, —F, —Cl, —Br, —OH, —CN, nitro, —CF$_3$, —OCF$_3$, —O—C$_1$-C$_4$alkyl, —SCH$_3$, —S(O)—CH$_3$, —S(O$_2$)—CH$_3$, —O—C$_1$-C$_4$alkyl-O—C$_1$-C$_4$alkyl, —C(O)OCH$_3$, —C(O)NH$_2$, —C(O)NH(CH$_3$), —C(O)N(CH$_3$)$_2$, phenyl.

5. The compound according to claim 4 or a pharmaceutically acceptable salt thereof, wherein:

R is —H, -halogen, —C$_1$-C$_4$alkyl, —CF$_3$, —O—C$_1$-C$_4$alkyl, or —O—C$_1$-C$_4$alkyl-O—C$_1$-C$_4$alkyl;

R$^1$ is —H, -halogen, —C$_1$-C$_4$alkyl, —C$_3$-C$_6$cycloalkyl, -halo-C$_1$-C$_4$alkyl, —OR$^{2'}$, or —N(C$_1$-C$_4$alkyl)$_2$, wherein R$^{2'}$ is C$_1$-C$_4$alkyl which may be optionally substituted with 1-2 substituents selected from the group consisting of -halogen, —OH, —C$_1$-C$_4$alkoxy, and —N(CH$_3$)$_2$;

Ar$^1$ is phenyl optionally substituted with a substituent selected from the group consisting of lower alkyl, and halogen;

Ar$^2$ is pyridinyl optionally substituted with 1-2 substituents independently selected from the group consisting of —C$_1$-C$_4$alkyl, -halogen, —CN, —CF$_3$, —O—CF$_3$, —S(O$_2$)—C$_1$-C$_4$alkyl, and —O—C$_1$-C$_4$alkyl-O—C$_1$-C$_4$alkyl.

6. The compound according to claim 1, of formula Ib,

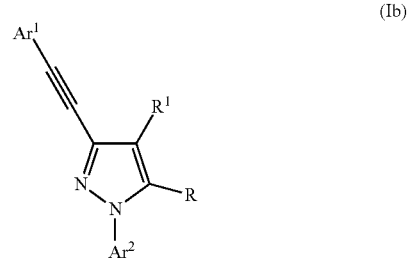

(Ib)

or a pharmaceutically acceptable salt thereof, wherein:

R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;

R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;

Ar$^1$ is
a 5- to 10-membered mono- or bicyclic aryl ring, wherein the 5- to 10-membered mono- or bicyclic aryl ring is optionally substituted with 1-3 substituents independently selected from the group consisting of alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form a 5-7 membered fused and optional substituted carbacyclic or heterocyclic ring;

Ar$^2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —O-alkyl-OH, —O-alkyl-O-alkyl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)— heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH$_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring.

7. The compound according to claim 6 or a pharmaceutically acceptable salt thereof, wherein:
R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;
R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;
Ar$^1$ is
  a 6-membered aryl ring, wherein the 6-membered aryl is optionally substituted with 1-3 substituents independently selected from the group consisting of -alkyl, -halogen, —OH, —CN, nitro, —CF$_3$, —O—CF$_3$, and —O-alkyl,
Ar$^2$ is a 5- or 6-membered mono-heteroaryl ring that contains 1-3 heteroatoms selected from the group consisting of N, O and S, wherein the 5- or 6-membered mono-heteroaryl ring is optionally substituted with 1-3 substituents independently selected from the group consisting of -alkyl, -halogen, —OH, —CN, nitro, —CF$_3$, —O—CF$_3$, —O-alkyl, —S-alkyl, —S(O)—alkyl, —S(O$_2$)-alkyl, —O-alkyl-O-alkyl, aryl, —C(O)O-alkyl, —C(O)NH$_2$, —C(O)NH-alkyl, and —C(O)N(alkyl)$_2$.

8. The compound according to claim 7 or a pharmaceutically acceptable salt thereof, wherein:
R is —H, -halogen, -alkyl, -cycloalkyl, -haloalkyl, —OR$^2$, or —N(lower alkyl)$_2$, wherein R$^2$ is lower alkyl which may be optionally substituted with 1-3 substituents selected from the group consisting of -halogen, —OH, -alkoxy, and —N(CH$_3$)$_2$;
R$^1$ is —H, -halogen, -alkyl, -cycloalkyl, -haloalkyl, —OR$^{2'}$, or —N(lower alkyl)$_2$, wherein R$^{2'}$ is lower alkyl which may be optionally substituted with 1-3 substituents selected from the group consisting of -halogen, —OH, -alkoxy, and —N(CH$_3$)$_2$;
Ar$^1$ is a 6-membered aryl ring optionally substituted with 1, 2 or 3 substituents independently selected from the group consisting of lower alkyl, and halogen;
Ar$^2$ is a 5- or 6-membered mono-heteroaryl ring that contains 1, 2, or 3 heteroatoms independently selected from the group consisting of N, O and S, wherein the 5- or 6-membered mono-heteroaryl ring is optionally substituted with 1, 2 or 3 substituents independently selected from the group consisting of —C$_1$-C$_4$alkyl, —F, —Cl, —Br, —OH, —CN, nitro, —CF$_3$, —OCF$_3$, —O—C$_1$-C$_4$alkyl, —SCH$_3$, —S(O)—CH$_3$, —S(O$_2$)—CH$_3$, —O—C$_1$-C$_4$alkyl-O—C$_1$-C$_4$alkyl, —C(O)OCH$_3$, —C(O)NH$_2$, —C(O)NH(CH$_3$), —C(O)N(CH$_3$)$_2$, and phenyl.

9. The compound according to claim 8 or a pharmaceutically acceptable salt thereof, wherein:
R is —H, -halogen, or —C$_1$-C$_4$alkyl;
R$^1$ is —H, -halogen, or —C$_1$-C$_4$alkyl;
Ar$^1$ is phenyl optionally substituted with a substituent selected from the group consisting of —C$_1$-C$_4$alkyl, and halogen;
Ar$^2$ is pyridinyl optionally substituted with 1-2 substituents independently selected from the group consisting of —C$_1$-C$_4$alkyl, -halogen, —CF$_3$, —O—CF$_3$, —CN, —S(O$_2$)—C$_1$-C$_4$alkyl, and —O—C$_1$-C$_4$alkyl-O—C$_1$-C$_4$alkyl.

10. A compound or a pharmaceutically acceptable salt thereof, wherein said compound is:
3-fluoro-5-(5-methyl-3-(phenylethynyl)-1H-pyrazol-1-yl)benzonitrile,
3-(3-((3-chlorophenyl)ethynyl)-5-methyl-1H-pyrazol-1-yl)-5-fluorobenzonitrile,
3-fluoro-5-(3-(phenyl ethynyl)-1H-pyrazol-1-yl)benzonitrile,
3-(3-((3-chlorophenyl)ethynyl)-1H-pyrazol-1-yl)-5-fluorobenzonitrile.

11. A pharmaceutical composition, comprising the compound according to claim 1, in free base or pharmaceutically acceptable salt form, in association with a pharmaceutical carrier or diluent.

12. A method for treating disorders associated with irregularities of glutamatergic signal transmission in the digestive tract, urinary tract or central nervous system disorders mediated in full or in part by mGlu5 receptors, the method comprising administering a compound according to claim 1, in free base or pharmaceutically acceptable salt form.

13. A method according to claim 12, wherein the disorder is Alzheimer's disease, Parkinson's disease, levodopa-induced dyskinesia in Parkinson's disease (PD-LID), Huntington's chorea, psychiatric disorder, schizophrenia, mood disorder, emotion disorder, attention deficit disorder, Fragile X syndrome, autism spectrum disorder (ASD), gastroesophageal reflux disease (GERD), drug addiction, or depression.

14. A method according to claim 12, wherein the disorder is acute or chronic neurological disorder, cognitive disorder, memory deficit, acute and chronic pain, drug or disease induced liver damage or failure, or urinary inconsistence.

* * * * *